(12) United States Patent
Brawn et al.

(10) Patent No.: US 12,138,471 B2
(45) Date of Patent: Nov. 12, 2024

(54) METHODS FOR TREATING DISORDERS AND FOR STIMULATING STEM CELLS BY ADMINISTERING LIGHT THERAPY

(71) Applicant: Biolux Group SA, Anieres (CH)

(72) Inventors: Peter Robert Brawn, Vancouver (CA); Ke Shyang See, George Town (MY)

(73) Assignee: Biolux Group SA, Geneva (CH)

( * ) Notice: Subject to any disclaimer, the term of this patent is extended or adjusted under 35 U.S.C. 154(b) by 180 days.

(21) Appl. No.: 17/309,538

(22) PCT Filed: Dec. 13, 2019

(86) PCT No.: PCT/CA2019/051810
§ 371 (c)(1),
(2) Date: Jun. 4, 2021

(87) PCT Pub. No.: WO2020/118449
PCT Pub. Date: Jun. 18, 2020

(65) Prior Publication Data
US 2022/0118274 A1 Apr. 21, 2022

Related U.S. Application Data

(60) Provisional application No. 62/779,615, filed on Dec. 14, 2018.

(51) Int. Cl.
*A61N 5/06* (2006.01)
(52) U.S. Cl.
CPC ......... *A61N 5/0613* (2013.01); *A61N 5/0603* (2013.01); *A61N 5/0616* (2013.01); *A61N 5/0618* (2013.01); *A61N 2005/0606* (2013.01); *A61N 2005/0659* (2013.01); *A61N 2005/0663* (2013.01)

(58) Field of Classification Search
CPC .. A61N 5/0613; A61N 5/0603; A61N 5/0616; A61N 5/0618; A61N 2005/0606; A61N 2005/0659; A61N 2005/0663; A61N 5/06–2005/073
See application file for complete search history.

(56) References Cited

U.S. PATENT DOCUMENTS

| 9,999,785 | B2 * | 6/2018 | Ovokaitys | A61N 5/0622 |
| 2011/0060266 | A1 * | 3/2011 | Streeter | A61N 5/0613 604/20 |
| 2013/0280671 | A1 * | 10/2013 | Brawn | A61C 7/00 433/29 |
| 2015/0343234 | A1 * | 12/2015 | Ovokaitys | A61K 41/00 604/20 |

* cited by examiner

*Primary Examiner* — Jonathan T Kuo
(74) *Attorney, Agent, or Firm* — Levine Bagade Han LLP

(57) ABSTRACT

The disclosure relates generally to methods for treating or slowing progression of a tumor, a neurodegenerative disease or a cognitive impairment, and for improving cognition, comprising administration of light therapy. The disclosure also relates to methods for activating oral stem cells, comprising administration of light therapy. Further provided herein are methods for improving cognition, comprising administering to the oral cavity of a subject in need thereof an effective amount of light. Additionally provided herein are methods for treating autism or Asperger's syndrome, comprising administering to the oral cavity of a subject in need thereof an effective amount of light.

19 Claims, 121 Drawing Sheets

TD3 Daily Questionnaire

Please answer the following questions based on the pain and aligner fit you felt this morning after brushing your teeth

• 1. Please indicate your initials.

2. If this questionnaire is not reflective of today's date, what date is it for?
(mm/dd/yyyy)

• 3. Assess the level of pain you feel after placing your aligner, for the more painful arch.

○ 1. None or almost no pain      ○ 2. Somewhat painful      ○ 3. Very painful

• 4. Assess the level of pressure you feel after placing your aligner, for the more tight fitting arch.

○ 1. None or almost no pressure      ○ 2. Moderate pressure      ○ 3. High level of pressure

• 5. Indicate your current aligner number.

At any point in the day, you may advance to the next aligner should you feel the fit is a level 1 (none or almost no pressure) and there are no air gaps between your aligner and teeth.

Schedule an appointment when you start aligner 7 but before you start aligner 8.
Schedule another appointment when you start aligner 12.

• 6. Approximately how many hours in the last day (24hrs) did you go WITHOUT wearing your aligners?

7. Comments:

[Done]

FIG. 143

| Control Group Individual Patient Data ||||
|---|---|---|---|---|
| Patient Indentification No | Tooth No. | Total Space T1 (mm) | Total Space T2 (mm) | Space Closure Time (days) |
| 1 | 24 | 2.92 | 2.25 | 168 |
| 2 | 14 | 7.56 | 2.1 | 140 |
| | 24 | 7.59 | 2.17 | 140 |
| 3 | 25 | 3.3 | 0.97 | 315 |
| 4 | 45 | 5.08 | 0.89 | 169 |
| 5 | 35 | 5.52 | 0.5 | 200 |
| | 45 | 5.29 | 0.39 | 200 |
| 6 | 14 | 3.65 | 0 | 71 |
| | 24 | 3.32 | 0 | 71 |
| | 34 | 6.53 | 2.22 | 126 |
| | 44 | 4.78 | 1.26 | 126 |
| 7 | 14 | 5.56 | 1.42 | 75 |
| | 24 | 5.33 | 0.99 | 75 |
| 8 | 45 | 5.58 | 2.27 | 156 |
| 10 | 14 | 5.34 | 1.33 | 176 |
| | 44 | 3.48 | 1.15 | 160 |
| 11 | 35 | 4.1 | 0.67 | 82 |
| | 45 | 2.44 | 1.05 | 42 |
| 12 | 24 | 3.05 | 1 | 127 |
| 13 | 34 | 7.21 | 1.26 | 259 |
| | 44 | 6.23 | 1 | 200 |
| 14 | 14 | 6.79 | 0.52 | 155 |
| | 24 | 5.49 | 1.44 | 196 |
| | 35 | 6.21 | 1.07 | 224 |
| | 45 | 4.82 | 0.36 | 126 |
| 15 | 14 | 6.2 | 1.49 | 207 |
| | 24 | 7.24 | 1.86 | 207 |
| | 35 | 7.68 | 2.77 | 207 |
| | 45 | 6.34 | 1.73 | 207 |
| 16 | 14 | 4.77 | 0.73 | 156 |
| | 24 | 6.23 | 1.6 | 221 |
| | 34 | 2.73 | 0.76 | 112 |
| | 44 | 4.83 | 0.88 | 158 |

FIG. 144A

| Control Group Individual Patient Data (continued) |||||
|---|---|---|---|---|
| Patient Indentification No. | Tooth No. | Total Space T1 (mm) | Total Space T2 (mm) | Space Closure Time (days) |
| 18 | 35 | 7.38 | 1.89 | 122 |
|  | 45 | 4.8 | 0.84 | 98 |
| 20 | 14 | 3.19 | 1.46 | 58 |
|  | 34 | 3.26 | 1.55 | 58 |
|  | 44 | 3 | 1.31 | 44 |
| 22 | 14 | 7.35 | 2.26 | 126 |
|  | 35 | 5.18 | 1.84 | 169 |
|  | 45 | 5.93 | 2.05 | 169 |
| 24 | 14 | 7.85 | 4.59 | 230 |
|  | 24 | 7.68 | 2.49 | 230 |
|  | 34 | 6.52 | 1.96 | 230 |
|  | 44 | 6.45 | 3.03 | 230 |
| 28 | 14 | 5.84 | 3.33 | 179 |
|  | 24 | 6.98 | 1.8 | 179 |
|  | 34 | 5.28 | 2.99 | 179 |
|  | 44 | 5.9 | 2.47 | 179 |
| 29 | 14 | 6.65 | 2.9 | 155 |
|  | 24 | 7.62 | 5.01 | 155 |
| 30 | 14 | 5.9 | 1.73 | 70 |
|  | 35 | 4.85 | 2.41 | 101 |
|  | 45 | 5.18 | 2.56 | 101 |

FIG. 144B

| Intra-Oral Group Individual Patient Data ||||
|---|---|---|---|
| Patient Indentification No. | Tooth No. | Total Space T1 (mm) | Total Space T2 (mm) | Space Closure Time (days) |
| 32 | 14 | 1.9 | 0 | 43 |
| | 24 | 5.28 | 1.13 | 84 |
| | 34 | 2.89 | 0.37 | 84 |
| | 44 | 3.81 | 0.84 | 84 |
| 33 | 15 | 3.96 | 0.43 | 166 |
| | 25 | 4.25 | 1.14 | 166 |
| 34 | 14 | 5.31 | 1.54 | 71 |
| | 24 | 3.56 | 1.76 | 71 |
| | 35 | 5.38 | 0.96 | 138 |
| | 45 | 5.68 | 2.78 | 138 |
| 36 | 34 | 4.5 | 2.28 | 81 |
| | 44 | 6.11 | 2.02 | 137 |
| 37 | 14 | 6.17 | 1.64 | 153 |
| | 24 | 5.58 | 1.29 | 90 |
| | 45 | 4.91 | 0.94 | 90 |
| 38 | 34 | 3.71 | 1.21 | 109 |
| | 44 | 3093 | 1.59 | 109 |
| 39 | 14 | 6.1 | 3.24 | 137 |
| | 24 | 4.86 | 1.47 | 137 |
| | 35 | 3.67 | 0.5 | 137 |
| | 45 | 4.6 | 1.58 | 137 |
| 40 | 14 | 2.665 | 0.8 | 28 |
| | 24 | 4.82 | 1.45 | 45 |
| | 35 | 7.13 | 1.91 | 112 |
| | 45 | 6.54 | 2.03 | 112 |
| 41 | 14 | 2.87 | 0.4 | 112 |
| 43 | 15 | 6.68 | 0.86 | 165 |
| | 25 | 7.8 | 1.73 | 165 |
| | 35 | 8.51 | 2.48 | 207 |
| | 45 | 7.51 | 0.79 | 207 |
| 44 | 34 | 4.29 | 2.26 | 116 |
| | 44 | 6.07 | 3.27 | 116 |
| 45 | 25 | 4.69 | 1.58 | 114 |
| | 35 | 4.83 | 1.85 | 185 |
| 46 | 15 | 4.22 | 0.63 | 112 |
| | 25 | 5.83 | 1.5 | 112 |
| | 34 | 4.91 | 1.29 | 112 |
| | 44 | 5.5 | 1.23 | 112 |
| 47 | 14 | 6.93 | 2.57 | 56 |
| | 24 | 7.8 | 2.57 | 56 |
| | 35 | 7.2 | 1.45 | 125 |
| | 45 | 5.93 | 0.5 | 125 |

FIG. 145A

| Intra-Oral Group Individual Patient Data (continued) ||||
|---|---|---|---|---|
| Patient Indentification No. | Tooth No. | Total Space T1 (mm) | Total Space T2 (mm) | Space Closure Time (days) |
| 48 | 14 | 6.93 | 1.23 | 168 |
|  | 24 | 6.28 | 2.75 | 84 |
|  | 35 | 7.28 | 1.56 | 183 |
|  | 45 | 6.04 | 1.72 | 140 |
| 49 | 34 | 5.13 | 1.23 | 70 |
|  | 44 | 3.84 | 1.116 | 70 |
| 51 | 14 | 2.7 | 1.21 | 28 |
|  | 24 | 5.76 | 2.76 | 42 |
|  | 34 | 5.74 | 1.74 | 96 |
|  | 44 | 3.81 | 1.07 | 72 |
| 52 | 35 | 4.17 | 2.98 | 64 |
|  | 45 | 6.25 | 3.87 | 64 |
| 53 | 15 | 7.42 | 2.62 | 238 |
|  | 25 | 7.15 | 3.87 | 238 |
|  | 35 | 7.82 | 4.42 | 238 |
|  | 45 | 7.58 | 2.39 | 238 |
| 55 | 14 | 6.23 | 2.22 | 84 |
|  | 24 | 5.14 | 1.43 | 84 |
|  | 45 | 4.83 | 1.38 | 84 |
| 56 | 35 | 7.48 | 1.49 | 111 |
|  | 45 | 8.53 | 2.84 | 111 |
| 59 | 35 | 5.71 | 4.39 | 56 |
|  | 45 | 4.36 | 2.92 | 56 |
| 60 | 14 | 6.28 | 2.83 | 187 |
|  | 24 | 6.77 | 3.87 | 187 |

FIG. 145B

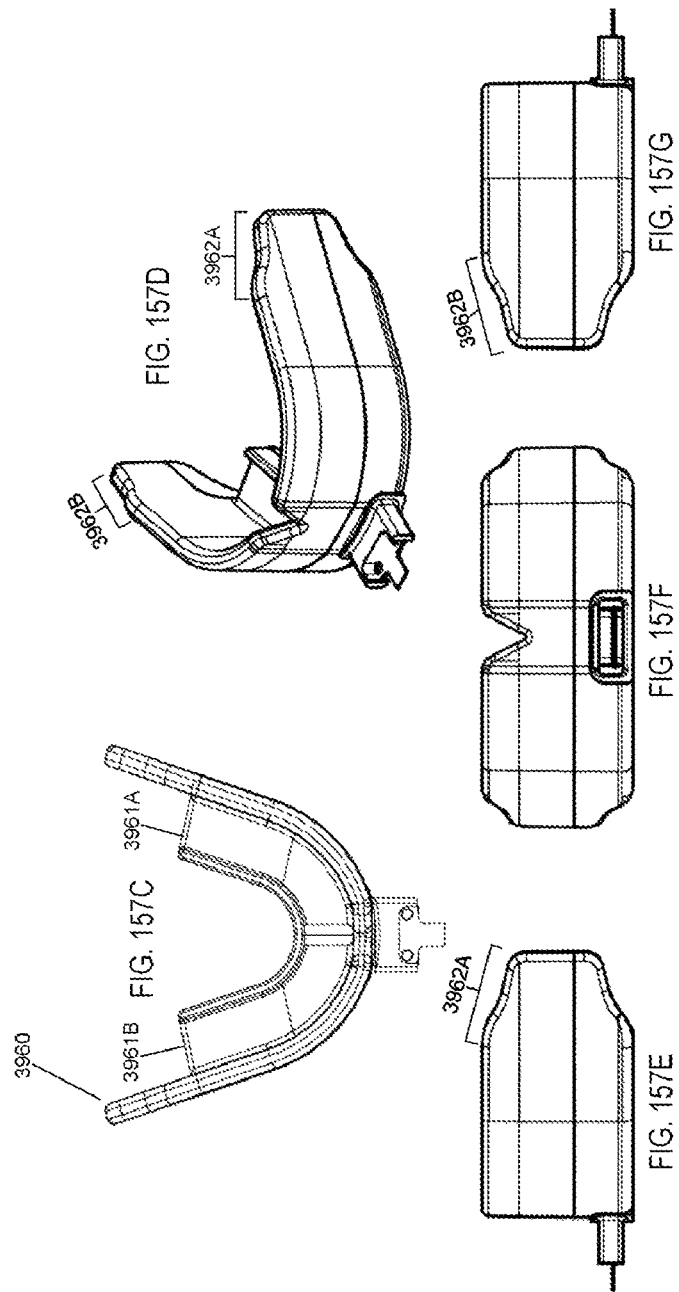

METHODS FOR TREATING DISORDERS AND FOR STIMULATING STEM CELLS BY ADMINISTERING LIGHT THERAPY

FIELD OF INVENTION

The disclosure relates generally to methods for treating or slowing progression of a tumor, a neurodegenerative disease or a cognitive impairment, and for improving cognition, comprising administration of light therapy. The disclosure also relates to methods for activating oral stem cells, comprising administration of light therapy.

BACKGROUND OF THE INVENTION

Despite considerable efforts expended on research and development of treatments, cancer remains one of the leading causes of death in many countries throughout the world. There remains a need for therapies that are less invasive than standard cancer treatments and that can be used on tumors that are inoperable.

SUMMARY OF THE INVENTION

The following summary is an explanation of some of the general inventive steps for the method and tools in the description. This summary is not an extensive overview of the invention and does not intend to limit the scope beyond what is described and claimed as a summary.

Provided herein are methods for treating or slowing progression of a tumor, comprising administering to the oral cavity of a subject in need thereof an effective amount of light.

Also provided herein are methods for treating or slowing progression of a neurodegenerative disorder or a cognitive impairment, comprising administering to the oral cavity of a subject in need thereof an effective amount of light.

Further provided herein are methods for improving cognition, comprising administering to the oral cavity of a subject in need thereof an effective amount of light. Additionally provided herein are methods for treating autism or Asperger's syndrome, comprising administering to the oral cavity of a subject in need thereof an effective amount of light.

Additionally, provided herein are methods for activating oral stem cells, comprising administering to the oral cavity of a subject in need thereof an effective amount of light.

Also provided herein are methods for enhancing a directional migration of oral stem cells, comprising administering to the oral cavity of a subject in need thereof an effective amount of light.

Further provided herein are methods for inducing proliferation or differentiation of oral stem cells, comprising administering to the oral cavity of a subject in need thereof an effective amount of light.

Also provided herein are methods for increasing the number of oral stem cells in blood vessels, comprising administering to the oral cavity of a subject in need thereof an effective Each of the aforementioned methods is a "method of the invention".

BRIEF DESCRIPTION OF THE FIGURES

FIG. 96A illustrates an accelerometer of the light therapy apparatus of FIG. 84 according to embodiments.

FIG. 96B illustrates a microcontroller of the light therapy apparatus of FIG. 84 according to embodiments.

FIG. 96C illustrates a switch of the light therapy apparatus of FIG. 84 according to embodiments.

FIG. 96D illustrates an induction coil for wireless charging of the light therapy apparatus of FIG. 84 according to embodiments.

FIG. 96E illustrates a temperature sensor of the light therapy apparatus of FIG. 84 according to embodiments.

FIG. 96F illustrates a capacitive sensor of the light therapy apparatus of FIG. 84 according to embodiments.

FIG. 143 is an image of a sample display screen of an external electronic device according to an embodiment.

FIGS. 144A, 144B, 145A, and 145B are tables of individual patient data during a space closure phase of orthodontic treatment for study group participants.

FIG. 152A—Baseline (Day 0); LIi is 8.80 mm. FIG. 152B—Day 13 1; LIi is 0.00 mm. FIG. 152C—Baseline (Day 0); LIi is 9.07 mm. FIG. 152D—Day 50; LIi is 0.00 mm.

FIG. 155 illustrates osteocalcin expression around first molars in the TM+PBM+VitD group (group 5) in response to intra-oral light therapy, vitamin D administration, and conventional tooth movement in rats.

FIG. 156A is a perspective view of a light therapy apparatus according to an embodiment.

FIG. 156B is a top view of the light therapy apparatus of FIG. 156A.

FIG. 156C is a back/posterior view of the light therapy apparatus of FIG. 156A.

FIG. 156D is a side view of the light therapy apparatus of FIG. 156A.

FIG. 157A is a perspective view of a portion of a light therapy apparatus according to an embodiment.

FIG. 157B is an exploded view of the portion of the light therapy apparatus of FIG. 157A.

FIG. 157C is a top view of a light therapy apparatus according to an embodiment.

FIG. 157D is a perspective view of the light therapy apparatus of FIG. 157C.

FIG. 157E is a first side view of the light therapy apparatus of FIG. 157C.

FIG. 157F is a rear view of the light therapy apparatus of FIG. 157C.

FIG. 157G is a second side view of the light therapy apparatus of FIG. 157C. FIGS. 157H-I show example views of a patient's mouth (upper dental arch and lower arch), with an overlaid outline of a light therapy apparatus disposed therein.

DETAILED DESCRIPTION OF THE INVENTION

Figure 1:
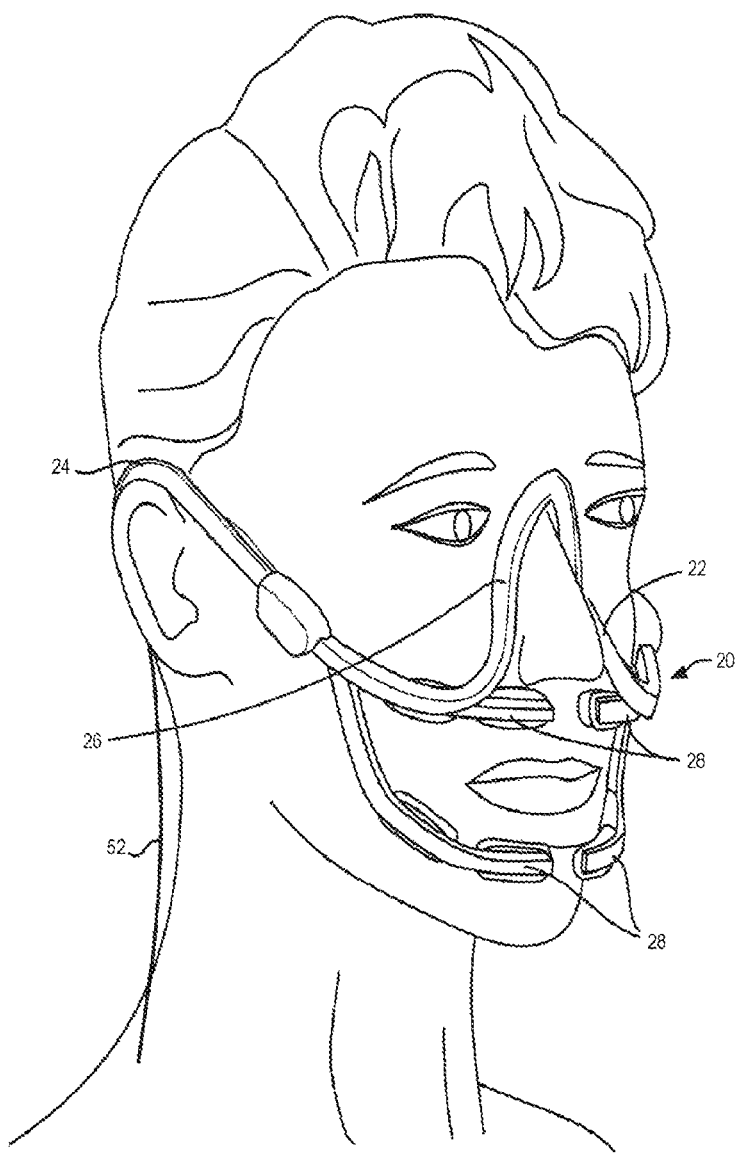
FIG. 1 is an isometric view of an embodiment of a light-therapy apparatus useful for providing light therapy to specified regions of a patient's maxillary or mandibular alveolar bone.

Provided herein are methods for treating or slowing progression of a tumor, a neurodegenerative disease or a cognitive impairment, for improving cognition and for treating autism, Asperger's syndrome, hyperprolactinemia or sexual dysfunction, comprising administering to the oral cavity of a subject in need thereof an effective amount of light.

Additionally provided herein are methods for activating oral stem cells, comprising administering to the oral cavity of a subject in need thereof an effective amount of light.

Definitions

The term "about" when immediately preceding a numerical value means±0% to I 0% of the numerical value, ±0% to 10%, ±0% to 9%, ±0% to 8%, ±0% to 7%, ±0% to 6%, ±0% to 5%, ±0% to 4%, ±0% to 3%, ±0% to 2%, ±0% to I %, ±0% to less than I %, or any other value or range of values therein. For example, "about 40" means±0% to 10% of 40 (i.e., from 36 to 44).

The term "subject" as used herein refers to any living subject that can receive medical treatment. A subject can be, for example, a mammal such as a human. The subject can be an adult subject or a child subject. The subject can be a male subject or a female subject. The terms "subject" and "patient" are used interchangeably herein.

The term "substantially rigid" as used herein to describe an apparatus, or a component thereof, means that the various dimensional parameters associated with the apparatus or component (e.g., length, depth, thickness, curvature, angle, etc.) remain about the same when the apparatus is manipulated and/or otherwise used as described herein.

The term "transparent" as used herein relates to an object's ability to transmit light therethrough. The transparency of an object is directly related to the absence of (or very low amounts of) scattering of light within the object. An object is said to be "substantially transparent" if the object allows visible light to be transmitted therethrough such that another object can be distinctly seen through the subject object. In another embodiment, an object is said to be "substantially transparent" if the object permits transmission of at least sixty percent of incident light in a visible range through a portion of the object, as measured by any applicable test, such as ASTM D-1746, ASTM D-1003 or the like. In yet other embodiments, an object is said to be "substantially transparent" if the object permits transmission of at least seventy percent of incident light in a visible range through a portion of the object. In yet other embodiments, an object is said to be "substantially transparent" if the object permits transmission of at least eighty percent of incident light in a visible range through a portion of the object. In yet other embodiments, an object is said to be "substantially transparent" if the object permits transmission of at least ninety percent of incident light in a visible range through a portion of the object. In yet other embodiments, an object is said to be "substantially transparent" if the object permits transmission of at least ninety-five percent of incident light in a visible range through a portion of the object. In yet other embodiments, an object is said to be "substantially transparent" if the object permits transmission of at least ninety-nine percent of incident light in a visible range through a portion of the object.

The term "directly" as used herein in connection with administration of light to a region or target, means that the light reaches the region or target without first reflecting from another region or target.

As used herein, "intra-orally administering" light means that the source of the light is within a subject's oral cavity.

As used herein, "extra-orally administering" light means that the source of the light is not within a subject's oral cavity.

In some embodiments, a light-therapy apparatus is an extra-oral light-therapy apparatus. In some embodiments, the extra-oral light therapy apparatus is removably coupled to the face, scalp or neck of the subject. In some embodiments, the extra-oral light therapy apparatus includes the one or more light emitters.

In some embodiments, a light therapy apparatus is an intra-oral light therapy apparatus. In some embodiments, the intra-oral light-therapy apparatus includes a mouthpiece that includes one or more light emitters. In some embodiments, the intra-oral light therapy apparatus includes a mouthpiece configured to fit within a subject's mouth. The intra-oral therapy apparatus also includes a mouthpiece including a bite tray and a flange coupled to the bite tray, and the one or more light emitters is disposed within the flange. In some embodiments, the method further includes disposing the mouthpiece into the subject's mouth.

Diseases and Disorders

Provided herein are methods for treating or slowing progression of a tumor, comprising administering to the oral cavity of a subject in need thereof an effective amount of light. In some embodiments, the tumor is a benign tumor. In some embodiments, the tumor is a malignant tumor. Also provided herein are methods for treating or slowing progression of cancer, comprising administering to the oral cavity of a subject in need thereof an effective amount of light.

In some embodiments, the methods of the invention reduce the size of a tumor, the number of tumors or the tumor load in a subject, as compared to the size of the tumor, the number of tumors or the tumor load in the subject before administration of the light. In some embodiments, the methods of the invention reduce risk of a subject's benign tumor becoming a malignant tumor. In some embodiments, the methods of the invention reduce risk of metastasis of a subject's cancer. In some embodiments, the methods of the invention reduce the prolactin level in the subject's blood. In some embodiments, the methods of the invention reduce the subject's tumor load and the prolactin level in the subject's blood.

In some embodiments, the light is administered to the subject's tumor. In some embodiments, the light is administered directly to the subject's tumor.

In some embodiments, the tumor is a brain, oral, skin, jaw or head-and-neck tumor.

In some embodiments, a brain tumor is a pituitary tumor, hypothalamic tumor, glioma or neurofibroma. In some embodiments, a pituitary tumor is a nonfunctional adenoma, prolactinoma, adrenocorticotropic hormone (ACTH)-producing tumor or a growth hormone-producing tumor. In some embodiments, a pituitary tumor is a craniopharyngioma, pituitary adenoma or Rathke's cleft cyst. In some embodiments, a pituitary tumor is a pituitary adenoma. In some embodiments, a pituitary adenoma is a pituitary macroadenoma. In some embodiments, the tumor is brain cancer. In some embodiments, the brain cancer is astrocytoma or glioblastoma multiforme. In some embodiments, a glioma is a brain stem glioma, ependymoma, glioblastoma multiforme, mixed glioma, oligodendroglioma or an optic nerve glioma. In some embodiments, an astrocytoma is an anaplastic astrocytoma, fibrillary astrocytoma or juvenile pilocytic astrocytoma.

In some embodiments, the tumor is skin cancer. In some embodiments, a skin cancer is a basal cell carcinoma, squamous cell carcinoma or melanoma.

In some embodiments, the tumor is oral cancer. In some embodiments, the oral cancer is mouth cancer or sinus cancer. In some embodiments, mouth cancer is located in or on the floor of the subject's mouth, or in or on the subject's gum, hard palate, alveolar mucosa, buccal mucosa, labial mucosa or tongue.

In some embodiments, the tumor is a tumor of the subject's jaw. The jaw tumor may be present on the mandible or maxilla, or both. In some embodiments, the jaw tumor is an ameloblastoma, keratocystic odontogenic tumor, odontoma, odontogenic myxoma or central giant cell granuloma. In some embodiments, the jaw tumor is a jaw cancer.

In some embodiments, provided herein are methods for treating or slowing progression of a pituitary adenoma, comprising administering light to the oral cavity of a subject in need thereof, wherein the light: (a) is administered to the subject's maxilla or the subject's mandible; (b) has a wavelength of about 850 nm; (c) has a power density of about 65 mW/cm 2; (d) has an energy density of about 20 J/cm2; and (e) is administered to each of the maxilla and the mandible for about 5 minutes to about IO minutes per day three times per week for a period of three months. In some embodiments, the administering is intra-orally administering. In some embodiments, light is administered to the subject's maxilla and the subject's mandible. In some embodiments, the light is intra-orally administered directly to the subject's maxilla or mandible. In some embodiments, the light is intra-orally administered directly to the subject's maxilla and mandible.

In some embodiments, the methods for treating or slowing progression of a pituitary adenoma further comprise extra-orally administering light to the subject's skin. In some embodiments, the extra-orally administered light to the subject's skin: (a) is administered to the subject's forehead; (b) has a wavelength ranging from about 660-670 nm; (c) has a power density of about 88 mW/cm 2; (d) has an energy density of about 40 J/cm2; and (e) is administered for about 15 minutes per day three times per week for a period of three months. In some embodiments, the light is administered directly to the subject's skin. In some embodiments, the light is administered directly to the subject's forehead.

In some embodiments, the subject's benign or malignant tumor or is inoperable, e.g., unresectable. In some embodiments, the benign or malignant tumor is too large to remove safely, or its removal would cause removing too much of an essential organ.

In some embodiments, the subject's benign or malignant tumor is impossible to remove without harming the subject because the tumor is intertwined with blood vessels and/or surrounding tissue. In some embodiments, the benign or malignant tumor metastasized and spread to one or more other sites of the subject's body. In some embodiments, surgical removal of the subject's benign or malignant tumor is impossible because the subject has another medical condition that limits the subject's ability to tolerate surgery. In some embodiments, the subject has one or more risk factors that render the subject a poor candidate for surgical removal of the subject's benign or malignant tumor. In some embodiments, a subject has declined surgical removal of the subject's benign or malignant tumor.

In some embodiments, a method of the invention further comprises treating the subject's tumor with surgery. In some embodiments, the subject's tumor is treated with surgery after the light administration. In some embodiments, the light administration reduces the size of the tumor before the tumor is treated with surgery. In some embodiments, the subject's tumor is treated with surgery before the light administration.

In some embodiments, light administration is used to treat a portion of the subject's tumor that is impossible to treat with surgery. In some embodiments, the subject has a plurality of tumors, and light administration is used to treat those tumors that are impossible to treat with surgery.

In some embodiments, a method of the invention further comprises administering to the subject an anti-tumor agent. The anti-tumor agent may be administered sequentially or concurrently with the light administration. In some embodiments, the anti-tumor agent is administered before the light administration. In some embodiments, the anti-tumor agent is administered after the light administration.

In some embodiments, the anti-tumor agent is an anti-cancer agent.

In some embodiments, the anti-tumor agent is a drug, a chemotherapeutic, a polypeptide, an antibody, a peptide, a small molecule, a nucleic acid or a gene therapy vector. In some embodiments, a gene therapy vector is a viral vector. In some embodiments, a gene therapy vector is a non-viral vector. In some embodiments, the anti-tumor agent is an immunotherapeutic agent. In some embodiments, the anti-tumor agent is an immune checkpoint inhibitor.

In some embodiments, the anti-tumor agent is a PD-I axis binding antagonist. A PD-I axis binding antagonist includes but is not limited to a PD-I binding antagonist, a PD-LI binding antagonist and a PD-L2 binding antagonist. Alternative names for "PD-I" include CD279 and SLEB2. Alternative names for "PD-LI" include B7-H1, B7-4, CD274, and B7-H. Alternative names for "PD-L2" include B7-DC, Btdc, and CD273. In some embodiments, PD-I, PD-LI, and PD-L2 are human PD-I, PD-LI and PD-L2. In some embodiments, the PD-I binding antagonist is a molecule that inhibits the binding of PD-I to its ligand binding partners. In a specific aspect the PD-I ligand binding partners are PD-LI and/or PD-L2. In another embodiment, a PD-LI binding antagonist is a molecule that inhibits the binding of PD-LI to its binding partners. In a specific aspect, PD-LI binding partners are PD-I and/or B7-1. In another embodiment, the PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or oligopeptide. In some embodiments, the PD-I binding antagonist is an anti-PD-I antibody (e.g., a human antibody, a humanized antibody, or a chimeric antibody). In some embodiments, the anti-PD-I antibody is selected from the group consisting of MDX-1106 (nivolumab, OPDIVO), Merck 3475 (MK-3475, pembrolizumab, KEYTRUDA®) and CT-011 (Pidilizumab). In some embodiments, the PD-I binding antagonist is an immunoadhesin (e.g., an immunoadhesin comprising an extracellular or PD-I binding portion of PD-LI or PD-L2 fused to a constant region (e.g., an Fe region of an immunoglobulin sequence). In some embodiments, the PD-I binding antagonist is AMP-224. In some embodiments, the PD-LI binding antagonist is anti-PD-LI antibody. In some embodiments, the anti-PD-LI binding antagonist is selected from the group consisting of YW243.55.S70, MPDL3280A, MEDI4736 and MDX-1105. MDX-1105, also known as BMS-936559, is an anti-PD-LI antibody described in WO2007/005874. Antibody YW243.55.S70 is an anti-PD-LI described in WO 2010/077634 A1. MDX-I 106, also known as MDX-1106-04, ONO-4538, BMS-936558 or nivolumab, is an anti-PD-1 antibody described in WO2006/121168. Merck 3475, also known as MK-3475, SCH-900475 or pembrolizumab, is an anti-PD-I antibody described in WO2009/1 14335. CT-011, also known as hBAT, hBAT-1 or pidilizumab, is an anti-PD-I antibody described in WO2009/10161 1. AMP-224, also known as B7-DCig, is a PD-L2-Fc fusion soluble receptor described in WO2010/027827 and WO2011/066342. In some embodiments, the anti-PD-I antibody is MDX-1106. Alternative names for "MDX-1106" include MDX-I 106-04, ONO-4538, BMS-936558 or nivolumab. In some embodiments, the anti-PD-I antibody is nivolumab (CAS Registry Number: 946414-94-4).

In some embodiments, the anti-tumor agent is a PARP (poly (ADP-ribose) polymerase) inhibitor (e.g., Olaparanib, Rucaparib, Niraparib, Cediranib, BMN673, Veliparib), Trabectedin, nab-paclitaxel (albumen-bound paclitaxel, ABRAXANE), Trebananib, Pazopanib, Cediranib, Palbociclib, everolimus, fluoropyrimidine (e.g., FOLFOX, FOLFIRI), IFL, regorafenib, Reolysin, Alimta, Zykadia, Sutent, Torisel (temsirolimus), Inlyta (axitinib, Pfizer), Afinitor (everolimus, Novartis), Nexavar (sorafenib, Onyx/Bayer), Votrient, Pazopanib, axitinib, IMA-901, AGS-003, cabozantinib, Vinflunine, Hsp90 inhibitor (e.g., apatorsin), Ad-GM-CSF (CT-0070), Temazolomide, IL-2, IFNa, vinblastine, Thalomid, dacarbazine, cyclophosphamide, lenalidomide, azacytidine, lenalidomide, bortezomid (VELCADE®), amrubicine, carfilzomib, pralatrexate, and/or enzastaurin.

In some embodiment, the anti-tumor agent is an antimetabolite. Antimetabolites include, but are not limited to, folic acid analogs; pyrimidine analogs such as fluorouracil, floxuridine, and cytosine arabinoside; purine analogs such as mercaptopurine, thiogunaine, and pentostatin; natural products such as vinblastine, vincristine, etoposide, tertiposide, dactinomycin, daunorubicin, doxurubicin, bleomycin, mithamycin, mitomycin C, L-asparaginase, and interferon alpha; platinum coordination complexes such as cis-platinum, and carboplatin; mitoxantrone; hydroxyurea; procarbazine; hormones and antagonists such as prednisone, hydroxyprogesterone caproate, medroxyprogesterone acetate, megestrol acetate, diethylstilbestrol, ethinyl estradiol, tamoxifen, testosterone propionate, fluoxymesterone, flutamide, and leuprolide, anti-angiogenesis agents or inhibitors such as angiostatin, retinoic acids, paclitaxel, estradiol derivatives, thiazolopyrimidine derivatives, and apoptosis prevention agents.

In some embodiments, the anti-tumor agent is N-acetyl cysteine (NAC), adriamycin, alemtuzumab, amifostine, arsenic trioxide, ascorbic acid, bendamustine, bevacizumab, bortezomib, busulfan, buthionine sulfoxime, carfilzomib, carmustine, clofarabine, cyclophosphamide, cyclosporine, cytarabine, dasatinib, datinomycin, defibrotide, dexamethasone, docetaxel, doxorubicin, etoposide, filgrastim, floxuridine, fludarabine, gemcitabine, interferon alpha, ipilimumab, lenalidomide, leucovorin, melphalan, mycofenolate mofetil, paclitaxel, palifermin, panobinostat, pegfilrastim, prednisolone, prednisone, revlimid, rituximab, sirolimus, sodium 2-mercaptoethane sulfonate (MESNA), sodium thiosulfate, tacrolimus, temozolomide, thalidomide, thioguanine, thiotepa or topotecan.

Also provided herein are methods for treating or slowing progression of a neurodegenerative disorder or a cognitive impairment, comprising administering to the oral cavity of a subject in need thereof an effective amount of light. In some embodiments, the neurodegenerative disorder is Alzheimer's disease, non-Alzheimer's dementia, amyotrophic lateral sclerosis, Batten disease, Parkinson's disease, Huntington's disease, Lewy body disease, ataxia telangiectasia, transmissible spongiform encephalopathy, supranuclear palsy, dementia pugilistica, frontotemporal dementia and parkinsonism linked to chromosome 17 (FTDP-17), Lytico-Bodig disease, tangle-predominant dementia, meningioangiomatosis, subacute sclerosing panencephalitis, lead encephalopathy, Hallervorden-Spatz disease, lipofuscinosis, Pick's disease, corticobasal degeneration, argyrophilic grain disease, multiple system atrophy, multiple sclerosis, neuroaxonal dystrophies, dentatorubralpallidoluysian atrophy (DRPLA), spinal-bulbar muscular atrophy (SBMA), spinocerebellar ataxia 1 (SCA 1), SCA 2, SCA 3, SCA 6, SCA 7, SCA 17, frontotemporal lobar degeneration (FTLD), familial encephalopathy with neuroserpin inclusion bodies (FENIB), familial British dementia (ABri) or familial Danish dementia (ADan).

In some embodiments, the transmissible spongiform encephalopathy (also known as a "prion disease") is Creutzfeldt-Jakob disease (CJD), variant CID (vCJD), kuru, fatal familial insomnia (FFI) or Gerstmann-Straussler-Scheinker disease (GSS).

In some embodiments, the cognitive impairment is dementia, substance-induced cognitive impairment, cognitive impairment following traumatic brain injury or a developmental cognitive disability.

Further provided herein are methods for improving cognition, comprising administering to the oral cavity of a subject in need thereof an effective amount of light. In some embodiments, the cognition is learning, plasticity, short term memory or long term memory. In some embodiments, the cognition is cortex-dependent or hippocampus-dependent cognition.

Additionally provided herein are methods for treating autism, an autism-spectrum disorder or Asperger's syndrome, comprising administering to the oral cavity of a subject in need thereof an effective amount of light. In some embodiments, the subject having autism or an autism-spectrum disorder also has fragile X syndrome (FXS).

Also provided herein are methods for treating hyperprolactinemia or sexual dysfunction, comprising administering to the oral cavity of a subject in need thereof an effective amount of intra-oral light. In some embodiments, hyperprolactinemia is associated with a prolactinoma or a pituitary tumor. In some embodiments, the sexual dysfunction is male sexual dysfunction. In some embodiments, the sexual dysfunction is female sexual dysfunction.

Oral Stem Cells

Provided herein are methods for activating oral stem cells, comprising administering to the oral cavity of a subject in need thereof an effective amount of light.

Also provided herein are methods for enhancing a directional migration of oral stem cells, comprising administering to the oral cavity of a subject in need thereof an effective amount of light. In some embodiments, the directional migration of oral stem cells is migration into blood vessels. Additionally provided herein are methods for increasing the number of oral stem cells in blood vessels, comprising administering to the oral cavity of a subject in need thereof an effective amount of light. In some embodiments, the blood vessels are in the subject's oral tissue, face or neck. In some embodiments, the oral tissue is gingiva, alveolar mucosa, buccal mucosa, labial mucosa, mandibular bone, maxillary bone or teeth. In some embodiments, light administration enhances migration of oral stem cells to the subject's tumor. In some embodiments, light administration enhances migration of stem cells to the subject's tumor and a reduction of the tumor size.

Further provided herein are methods for inducing proliferation or differentiation of oral stem cells, comprising administering to the oral cavity of a subject in need thereof an effective amount of light. In some embodiments, the oral stem cells differentiate into immune cells. In some embodiments, the immune cells are T-cells. In some embodiments, the immune cells are B-cells. In some embodiments, the immune cells are natural killer (NK) cells. In some embodiments, the immune cells target tumor cells. In some embodiments, light administration induces differentiation of oral stem cells into immune system cells that attack or inhibit the subject's tumor cells. In some embodiments, light administration induces differentiation of oral stem cells into immune system cells that assist the subject's existing immune system cells to attack or inhibit the subject's tumor cells. In some embodiments, light administration induces differentiation of oral stem cells into immune system cells that produce antibodies that attack or inhibit the subject's tumor cells.

In some embodiments, activated oral stem cells are stimulated to migrate through blood vessels and rehome at other sites in the subject's body. In some embodiments, the activated oral stem cells rehome at the site of the subject's tumor. In some embodiments, the activated oral stem cells rehome in the subject's brain. In some embodiments, the activated stem cells are stimulated to remove-amyloid from the brain of a subject with Alzheimer's disease. In some embodiments, the activated oral stem cells rehome in the subject's brain and differentiate into brain cells (for example, neurons or glial cells), thereby treating or slowing progression of the subject's neurodegenerative disorder or cognitive impairment. In some embodiments, the activated oral stem cells rehome at one or more sites where the subject has lost neuronal function and differentiate into cells that improve the subject's neuronal function. In some embodiments, the activated oral stem cells rehome in the subject's brain and differentiate into brain cells (for example, neurons or glial cells), thereby increasing the number of brain cells in the subject and improving the subject's cognition.

In some embodiments, the oral stem cells are adult stem cells.

In some embodiments, the oral stem cells are mesenchymal stem cells.

In some embodiments, the oral stem cells are dental stem cells or non-dental stem cells.

In some embodiments, the oral stem cells are dental pulp stem cells, stem cells of the apical papilla, periodontal ligament stem cells, dental follicle stem cells, tooth germ progenitor cells, oral epithelial stem cells, gingival-derived mesenchymal stem cells, inflamed periapical progenitor cells, periosteal stem cells, jaw bone marrow stem cells, alveolar bone marrow mesenchymal stem cells or salivary gland stem cells.

In some embodiments, the oral stem cells are in the oral mucosa of the subject. In some embodiments, the oral mucosa is the subject's hard palate, gingiva, dorsal surface of the tongue, ventral surface of the tongue, soft palate, buccal mucosa, labial mucosa oral veolar mucosa. In some embodiments, the oral stem cells are in the bone marrow of the subject's maxilla and/or mandible. In some embodiments, the oral stem cells are dental pulp stem cells.

In some embodiments, the oral stem cells are not cancer stem cells.

Light Administration

In some embodiments, the administering is intra-orally administering. In some embodiments, the administering is extra-orally administering.

In some embodiments, where the administering is intra-orally administering, the methods further comprise extra-orally administering to the subject an effective amount of light. In some embodiments, the extra-orally administering to the subject's oral cavity.

In some embodiments, where the administering is extra-orally administering, the methods further comprise intra-orally administering to the subject an effective amount of light.

In some embodiments, the extra-orally administering is to the subject's skin. In some embodiments, the extra-orally administering is to the subject's face. In some embodiments, the extra-orally administering is to the subject's forehead. In some embodiments, the extra-orally administering is to the subject's scalp. In some embodiments, the extra-orally administering is to the subject's neck.

In some embodiments, the extra-orally administering is directly to the subject's skin. In some embodiments, the extra-orally administering is directly to the subject's face. In some embodiments, the extra-orally administering is directly to the subject's forehead.

In some embodiments, the extra-orally administering is directly to the subject's scalp. In some embodiments, the extra-orally administering is directly to the subject's neck.

In some embodiments, the administering is directly to the subject's alveolar mucosa, buccal mucosa, labial mucosa, masticatory mucosa, tooth, gum or tongue. In some embodiments, the administering is directly to a region of the subject's oral or maxillofacial bone, muscle, or soft tissue, or one or more teeth. In some embodiments, the administering is directly to the maxillary bone, mandibular bone, or temporal bone, or other region of the subject.

In some embodiments, the administering is directly to one or more regions of a subject.

The region can be within the subject's mouth. The region can be all or a portion of the subject's maxillary bone, mandibular bone, or temporal bone of the skull. The region can be a temporomandibular joint, condyle, or glenoid fossa of the subject. The region can be the right temporomandibular joint, right condyle, or right glenoid fossa; left temporomandibular joint, left condyle, or left glenoid fossa; or both temporomandibular joints, both condyles, or both glenoid fossa of the subject.

In some embodiments, light is administered to a right temporomandibular joint without being administered to a left temporomandibular joint, a right condyle without being administered to a left condyle, a right glenoid fossa without being administered to aleft glenoid fossa, a left temporomandibular joint without being administered to a right temporomandibular joint, a left condyle without being administered to a right condyle, or a left glenoid fossa without being administered to a right glenoid fossa. The region can include a portion of the maxillary bone (e.g., portion of the subject's maxillary alveolar bone), a portion of the mandibular bone (e.g., portion of the subject's mandibular alveolarbone), or alveolus.

In some embodiments, in addition to being administered to a region of the subject's maxillary bone, mandibular bone, or temporal bone, light is administered to one or more other regions of the subject. Such regions can include, but are not limited to, one or more teeth (e.g., incisor, canine, premolar, or molar, such as a maxillary central incisor, maxillary lateral incisor, maxillary canine, maxillary first premolar, maxillary second premolar, maxillary first molar, maxillary second molar, maxillary third molar, mandibular central incisor, mandibular lateral incisor, mandibular canine, mandibular first premolar, mandibular second premolar, mandibular first molar, mandibular second molar, or mandibular third molar), a root of one or more teeth (e.g., wherein a root of a tooth can include a portion of one or more roots supporting the tooth, one root supporting the tooth, a plurality of roots supporting the tooth, or all of the roots supporting the tooth), tissue supporting one or more teeth, basal tissue, gingiva, periodontal ligaments, cementum, periodontium, a region of jaw bone or tissue, or at least a portion of the subject's other oral soft tissue or bone tissue. The region can be located on a left side or right side of the subject's face. In some embodiments, one or more regions are located on both the left and right side of the subject's face. In some embodiments, the region can be located on the front side of the subject's face. The region can include one, two, three, four, five, six, seven, eight, or more teeth, or tissue surrounding or supporting the teeth.

The region can include one or more roots of one, two, three, four, five, six, seven, eight, or more teeth, or periodontium of teeth. In other embodiments, light is not administered to a region outside the subject's maxillary bone, mandibular bone, or temporal bone. In some embodiments, light is not administered to a region outside the subject's oral or maxillofacial bone, muscle, or soft tissue, or one or more teeth. In some embodiments, the region includes the subject's skull, spine, pelvis or femur.

Light can be administered to regions that can include tissue (e.g., alveolar or basal tissue) surrounding or supporting any of the teeth specifically described with or without including the tooth itself Regions can include teeth or tissue supported by the maxillary bone or teeth supported by the mandibular bone. One or more regions can be adjacent to one another, continuous with one another, or separate from one another. Any discussion herein of regions or examples of regions can apply to any other region or examples of treatment regions provided herein.

In some embodiments, light irradiates a region that can include a portion of tissue (e.g., bone tissue, or soft tissue) or other regions within the subject's oral cavity without irradiating one or more other portions of the subject's oral cavity. In some embodiments, light is administered to one or both temporomandibular joint, condyle, or glenoid fossa of the subject. In some embodiments, light is administered to only one temporomandibular joint, only one condyle, or only one glenoid fossa of the subject. In some embodiments, light is administered to one or more temporomandibular joint, condyle, or glenoid fossa of the subject, without being administered to other regions of the subject's oral cavity, or without being administered to one or more of the subject's teeth, or without being administered to any of the subject's teeth. In some embodiments, light is administered to one or more roots of only one tooth root and to only one periodontium. Alternatively, light is administered to one or more roots of a plurality of teeth and to a plurality of periodontia. Light can be administered to one or more roots of all or less than all the teeth and periodontia in the subject's oral cavity. One or more selected teeth, roots or periodontia can be irradiated with light.

In some embodiments, light irradiates a region that can include a portion of tissue (e.g., bone tissue, or soft tissue) or other regions within the subject's oral cavity at a much greater intensity than it irradiates other portions of the subject's oral cavity. For example, light can irradiate a region at an intensity that is 3×, 5×, I O×, 20×, 50×, or 100× greater than the intensity that irradiates any another region. In some embodiments, the region is the subject's oral cavity or a portion thereof. In some embodiments, light irradiates a portion of a subject's oral or maxillofacial bone, muscle, or soft tissue, or one or more teeth at a greater intensity than that of light that irradiates another portion of the subject's oral or maxillofacial bone, muscle, or soft tissue, or one or more teeth. In one embodiment, light irradiates a portion of a subject's maxillary bone, mandibular bone, or temporal bone, such as the temporomandibular joint, condyle, or glenoid fossa, at a greater intensity than that of light that irradiates any of the subject's teeth. In some embodiments, this is achieved by applying to the subject, or adjusting within the subject, one or more intra-oral or extra-oral light-translucent or light-opaque masks that shield from light one or more non-regions. In some embodiments, light reaching a region has an intensity that is greater than a threshold value. In some embodiments, the threshold value has an intensity as discussed elsewhere herein.

The region can be close to a surface within the subject's mouth, or within a soft tissue or bone tissue. The region can be at a depth from the surface of the subject's skin, such as the subject's face. For example, the region can be about 1 nm, about 1 µm, about 10 µm, about 50 µm, about 100 µm, about 200 µm, about 300 µm, about 500 µm, about 750 µm, about 1 mm, about 2 mm, about 3 mm, about 4 mm, about 5 mm, about 7 mm, about 10 mm, about 15 mm, about 20 mm, about 25 mm, about 30 mm, about 40 mm, about 50 mm, about 60 mm, or about 70 mm from the surface of the subject's skin. Light can irradiate a region, which can have an area greater than, less than, or about 1 nm$^2$, about 1 µm$^2$, about 0.1 mm$^2$, about 0.2 mm$^2$, about 0.3 mm$^2$, about 0.4 mm$^2$, about 0.5 mm$^2$, about 0.7 mm$^2$, about 1 mm$^2$, about 10 mm$^2$, about 0.2 cm$^2$, about 0.5 cm$^2$, about 1 cm$^2$, about 2 cm$^2$, about 3 cm$^2$, about 5 cm$^2$, about 7 cm$^2$, about 10 cm$^2$, about 15 cm$^2$, about 20 cm$^2$, about 25 cm$^2$, about 30 cm$^2$, about 35 cm$^2$, about 40 cm$^2$, about 50 cm$^2$, about 60 cm$^2$, about 80 cm$^2$, about 100 cm$^2$, about 120 cm$^2$, about 140 cm$^2$, about 160 cm$^2$, about 180 cm$^2$ or about 200 cm$^2$. Light can irradiate one area, a plurality of areas, a point, or a plurality of points.

In some embodiments, light irradiates a particular area without irradiating with significant intensity surrounding areas. For example, light can irradiate a portion of maxillary bone, mandibular bone, or temporal bone without significant amounts of light irradiating teeth on that maxillary bone, mandibular bone, or temporal bone. In one embodiment, the light irradiates a temporomandibular joint, condyle, or glenoid fossa without significant amounts of light irradiating teeth on that maxillary bone, mandibular bone, or temporal bone or other regions of the maxillary bone, mandibular bone, or temporal bone. In another embodiment, light irradiates a particular tooth or set of teeth without significant amounts of light irradiating adjacent teeth. In one embodiment, irradiating a tooth comprises irradiating an exposed surface of the tooth, a tooth root, or a periodontium of the tooth.

In some embodiments, light is administered extra-orally to the subject. Light can be emitted from a light source that contacts the subject's skin. The light source can contact the skin of the subject. In some embodiments, the light source can contact the skin of the subject at the face, scalp, neck, torso, arms, or legs of the subject. In some embodiments, light is provided from a light-therapy apparatus, embodiments of which are described below. Light can be emitted from a light source that can include characteristics, features, components, or configurations of any of the light-therapy apparatus embodiments, as described below. The present methods can further comprise providing a light-therapy apparatus. For example, the methods of the invention can comprise administering light from a light-therapy apparatus. In some embodiments, light is provided from a helmet placed over the head of the subject. Light can be provided from any other source, and is not limited to a light-therapy apparatus as described herein.

In some embodiments, light is provided from a light source that can contact the subject's skin (e.g., scalp, face or neck). Similarly, light can be emitted from a plurality of light sources that can contact the subject's face. In one embodiment, one or more light sources contact skin of the subject's face overlying a region. For example, one or more light sources can contact skin of the subject's face overlying a portion of a maxillary bone, mandibular bone, or temporal bone, such as a temporomandibular joint, a condyle, or a glenoid fossa. In other words, in some embodiments, the one or more light sources are positioned directly over a right temporomandibular joint, a left temporomandibular joint, a right condyle, a left condyle, a right glenoid fossa, or a left glenoid fossa of the subject. The one or more light sources can contact the skin of the subject overlying a region where treatment of a tumor or activation of oral stem cells is intended to occur.

Light can be administered from a light source that can provide pressure on the subject's face. Light can pass through the subject's face to irradiate the region. The region can be located within a subject's oral cavity. In some embodiments, a light emitter is provided externally to the oral cavity. A portion of a subject's face, such as the cheek, skin over the jaw, lips, or chin can be located between the light emitter and the oral cavity. Light can be administered transcutaneously to a region that is located within the subject's oral cavity. The light can transcutaneously pass through the skin of the subject to irradiate the region. Light can pass through the cheek of the subject, the skin overlying the maxillary bone, mandibular bone, or temporal bone of the subject (such as skin overlying a temporomandibular joint of the subject, a condyle of the subject, a glenoid fossa of the subject), the chin of the subject, the lips of the subject, or any other region circumscribed or otherwise defined by the subject's face. In some embodiments, light irradiates a region by manually retaining one or more light sources providing light of one or more wavelengths to one or more regions of a subject. In some embodiments, light irradiates a region only transdermally through the skin of the subject. In some embodiments, light is administered only externally, and is not administered internally. For example, light can be administered only extra-orally, and not administered intra-orally. In some alternate embodiments, light is administered internally (e.g., intra-orally) or externally (e.g., extra-orally). In one embodiment, the patient to whom the light is administered has his or her mouth closed.

In other embodiments, the light source does not contact the patient's face or other skin. Extra-oral light can also be administered to the subject wherein a gap exists between a light source and skin of the subject's skin (e.g., scalp, face or neck). The light source can be in close proximity to the skin of the subject's scalp, face or neck without contacting the subject's scalp, face or neck. In some embodiments, light is administered from a light source that does not contact a subject's face when the subject's scalp, face or neck is relaxed but can contact the face if the subject flexes a portion of the subject's scalp, face or neck or tenses the scalp, face or neck. In some embodiments, a light source is about 1 mm or less, about 2 mm or less, about 3 mm or less, about 5 mm or less, about 7 mm or less, about 1 cm or less, about 1.5 cm or less, about 2 cm or less, about 2.5 cm or less, or about 3 cm or less away from a subject's scalp, face or neck while the subject's scalp, face or neck is relaxed or tensed. Light can be emitted from a light source located at a particular distance from a region. In some embodiments, the distance is about 0.1 mm or less, about 0.5 mm or less, about 1 mm or less, about 2 mm or less, about 3 mm or less, about 5 mm or less, about 7 mm or less, about 1 cm or less, about 1.5 cm or less, about 2 cm or less, about 2.5 cm or less, or about 3 cm or less. In some embodiments, a light source is about 0.1 mm, about 0.5 mm, about 1 mm, about 3 mm, about 5 mm, about 7 mm, about 1 cm, about 1.5 cm, about 2 cm and about 2.5 cm, about 2.75 cm, about 3 cm, about 3.5 cm, or about 4 cm away from the region to be treated by or irradiated by an effective amount of light.

In some embodiments, light is administered intra-orally to the subject. For example, the light source can be located within the subject. In some embodiments, the light source can include fiber optics that convey light within the subject. In some embodiments, the light source can be located within an orifice of the subject. For example, the light source can be located within the subject's oral cavity. In some embodiments, light is administered directly, i.e., nontransdermally, to a selected region or to a surface overlaying the selected region. In some embodiments, the light source is located outside the subject's oral cavity and the light is administered directly, i.e., non-transdermally, to a selected region or to a surface overlaying the selected region. In some embodiments, light is administered to a selected region through the subject's gums or soft tissue. Light need not be applied transdermally or through the subject's face. In some embodiments, the light source contacts the selected region or surface overlying the selected region. For example, the light source can contact a subject's tooth or gum. In some embodiments, light is directed at the selected region through soft tissue.

Light can be administered from a single light source. Alternatively, light can be administered from multiple light sources. Light can irradiate a continuous region or one or more discrete regions. Light can irradiate various regions from different directions.

For example, light can be administered from one or both of a right side of a subject's body (e.g., the right side of the subject's face) and from a left side of a subject's body (e.g., the left side of the subject's face). Light can be administered so that it is angled upward toward a region, or can be administered so that it is angled downward to toward a region. In some embodiments, light is administered from one or more stationary sources. For example, a light source can remain stationary during administration. In some embodiments, light is administered from one or more moving light sources. A light source can be displaced, can be angled, can be rotated, or any combination thereof. Light can be administered from a continuously moving source, or can be administered from a discretely or abruptly moving source.

Light can be administered from one or more light source capable of irradiating light having intended properties. A light source can emit light from one or more light emitters. In some embodiments, a light source comprises about 10 to about 15 emitters, about 15 to about 20 emitters, about 20 to about 30 emitters, about 30 to about 40 emitters, about 40 to about 50 emitters, about 50 to about 70 emitters, or about 70 emitters to about 100 emitters. For example, light can be administered from a light source, which can comprise one or more of the following emitters: a light-emitting diode (LED), which can be present in an array; and a laser, for example a vertical cavity surface emitting laser (VCSEL) or other suitable light emitter such as an Indium-Gallium-Aluminum-Phosphide (InGaAlP) laser, a Gallium-Arsenic Phosphide/Gallium Phosphide (GaAsP/GaP) laser, or a Gallium-Aluminum-Arsenide/Gallium-Aluminum-Arsenide (GaAlAs/GaAs) laser. In one embodiment the light source comprises a plurality of lasers. A plurality of light emitters can emit light at one or more different wavelengths.

Alternatively, one or more light emitters can emit light at the same wavelength for a light source. One or more light emitters can be arranged on a light source in any manner, such as a linear array or another arrangement described herein.

An effective amount of light has an intensity that is effective in the present methods. In one embodiment, the light intensity is at least about 10 mW/cm$^2$. In other embodiments, the light intensity is about 1 mW/cm$^2$ or greater, about 3 mW/cm$^2$ or greater, about 5 mW/cm$^2$ or greater, about 7 mW/cm$^2$ or greater, about 12 mW/cm$^2$ or greater, about 15 mW/cm$^2$ or greater, about 20 mW/cm$^2$ or greater, about 30 mW/cm$^2$ or greater, about 50 mW/cm$^2$ or greater, about 75 mW/cm$^2$ or greater, about 100 mW/cm$^2$ or greater, about 200 mW/cm$^2$ or greater, about 500 mW/cm$^2$ or greater, or about 1 W/cm$^2$ or greater. In other embodiments, the light intensity is about 20 mW/cm$^2$ or less, about 30 mW/cm$^2$ or less, about 50 mW/cm$^2$ or less, about 75 mW/cm$^2$ or less, about 100 mW/cm$^2$ or less, about 200 mW/cm$^2$ or less, about 500 mW/cm$^2$ or less, about 1 W/cm$^2$ or less, about 2 W/cm$^2$ or less, about 5 W/cm$^2$ or less, or about 10 W/cm$^2$ or less. In one embodiment the light intensity ranges from about 1 mW/cm$^2$ to about 10 W/cm$^2$. In another embodiment, the light intensity's lower range is about 3 mW/cm$^2$, about 5 mW/cm$^2$, about 7 mW/cm$^2$, about 12 mW/cm$^2$, about 15 mW/cm$^2$, about 20 mW/cm$^2$, about 30 mW/cm$^2$, about 50 mW/cm$^2$, about 75 mW/cm$^2$, about 100 mW/cm$^2$, about 200 mW/cm$^2$, about 500 mW/cm$^2$, or about 1 W/cm$^2$. In another embodiment, the light intensity's upper range is about 20 mW/cm$^2$, about 30 mW/cm$^2$ about 50 mW/cm$^2$, about 75 mW/cm$^2$, about 100 mW/cm$^2$, about 200 mW/cm$^2$, about 500 mW/cm$^2$, about 1 W/cm$^2$, about 2 W/cm$^2$, about 5 W/cm$^2$, or about 10 W/cm$^2$. Light can be administered having an intensity falling within a range determined by any of the intensities mentioned above.

In some embodiments the intensity is an average intensity. In some embodiments, the light has an intensity in the range of about 10 mW/cm$^2$ to about 60 mW/cm$^2$, or about 20 mW/cm$^2$ to about 60 mW/cm$^2$. In some embodiments, the light has an intensity in the range of about 20 mW/cm$^2$ to about 200 mW/cm$^2$.

In some embodiments, the peak light intensity can about 50 mW/cm 2 or greater. A peak wavelength is the wavelength at which the highest intensity of light is emitted. In some embodiments, light can be pulsed. In other embodiments, the output of light is continuous. In some embodiments, the light intensity can vary over time in a cyclical or non-cyclical fashion. The light intensity can vary with or without pulsing. In some embodiments, pulse width modulation can be used to effect a desired light intensity. If one or more wavelengths of light are administered, then each wavelength can be administered at its own intensity.

In some embodiments, an effective amount of light includes light having a wavelength that is within in a particular range, or light of a range of wavelengths. Either intra-orally or extra-orally administered light can be light having a wavelength that is within in a particular range, or light of a range of wavelengths. The light is not necessarily visible light. For example, the light can include infrared light or near-infrared light. The light can also be provided in the visible light region. In some embodiments, light can be administered having one or more wavelengths ranging from about 600 nm to about 1100 nm. In some embodiments, light can be administered having one or more wavelengths ranging from about 620 nm to about 1000 nm. In some embodiments, administered light has one or more wavelengths ranging from about 585 nm to about 665 nm, about 666 nm to about 814 nm, about 815 nm to about 895 nm, about 640 nm to about 680 nm, or about 740 nm to about 780 nm, or any given wavelength or range of wavelengths within those ranges, such as, for example, about 625 nm or about 855 nm, or about 605 nm to about 645 nm, or about 835 nm to about 875 nm. In some embodiments, the administered light has one or more wavelengths from about 605 nm to about 645 nm, or from about 835 nm to about 875 nm. In some embodiments, the administered light has one or more wavelengths from about 615 nm to about 635 nm, or from about 845 nm to about 865 nm. In some embodiments, the wavelengths of the administered light is about 625 nm or about 855 nm. In additional embodiments, the administered light has one or more wavelengths ranging from about 400 nm to about 1200 nm. In some embodiments, the administered light has one or more wavelengths ranging from about 700 nm to about 900 nm, from about 800 nm to about 1100 nm, or from about 900 nm to about 1000 nm. In particular embodiments, the administered light has one or more wavelengths ranging from about 500 nm to about 700 nm, about 585 nm to about 665 nm, about 605 nm to about 630 nm, about 620 nm to about 680 nm, about 666 nm to about 814 nm, about 815 nm to about 895 nm, about 820 nm to about 890 nm, about 640 nm to about 680 nm, or about 740 nm to about 780 nm. In some embodiments the administered light has one or more wavelengths in one or both of the following wavelength ranges: about 820 to about 890 nm and about 620 to about 680 nm. In some embodiments, the administered light has one or more wavelengths in the ranges of about 820 to about 890 nm and about 620 nm to about 680 nm.

In some embodiments, the administered light has one or more wavelengths in the ranges of about 815 to about 895 nm and about 585 to about 665 nm. In some embodiments, the administered light has one or more wavelengths ranging from about 600 to about 1200 nm. The administered light can alternatively have one or more wavelengths in one or more of the following ranges: about 613 nm to about 624 nm, about 667 nm to about 684 nm, about 750 nm to about 773 nm, about 812 nm to about 846 nm. In one embodiment, the light wavelength's lower range is about 400 nm, about 450 nm, about 500 nm, about 550 nm, about 585 nm, about 595 nm, about 605 nm, about 613 nm, about 615 nm, about 620 nm, about 624 nm, about 625 nm, about 640 nm, about 650 nm, about 667 nm, about 680 nm, about 710 nm, about 740 nm, about 750 nm, about 770 nm, about 812 nm, about 815 nm, about 820 nm, about 835 nm, about 845 nm, or about 860 nm. In another embodiment, the light wavelength's upper range is about 585 nm, about 605 nm, about 624 nm, about 630 nm, about 635 nm, about 645 nm, about 655 nm, about 660 nm, about 665 nm, about 680 nm, about 684 nm, about 700 nm, about 725 nm, about 755 nm, about 773 nm, about 780 nm, about 795 nm, about 815 nm, about 830 nm, about 846 nm, about 855 nm, about 865 nm, about 875 nm, about 890 nm, about 895 nm, about 935 nm, about 975 nm, about 1000 nm, about 1050 nm, about 1100 nm, or about 1200 nm.

The wavelengths of light administered can be limited to any of the ranges or limits described above. Additionally, the wavelengths of light administered with a sufficient intensity to be an effective amount can be limited to any of the ranges or limits described above.

For example, in some embodiments, light administered to a region does not have wavelengths exceeding one or more of the following: about 585 nm, about 605 nm, about 624 nm, about 630 nm, about 635 nm, about 645 nm, about 655 nm, about 660 nm, about 665 nm, about 680 nm, about 684 nm, about 700 nm, about 725 nm, about 755 nm, about 773 nm, about 780 nm, about 795 nm, about 815 nm, about 830 nm, about 846 nm, about 855 nm, about 865 nm, about 875 nm, about 890 nm, about 895 nm, about 905 nm, about 910 nm, about 915 nm, about 920 nm, about 935 nm, about 975 nm, about 1000 nm, about 1050 nm, about 1100 nm, or about 1200 nm. For example, no light exceeding about 585 nm, about 605 nm, about 624 nm, about 630 nm, about 635 nm, about 645 nm, about 655 nm, about 660 nm, about 665 nm, about 680 nm, about 684 nm, about 700 nm, about 725 nm, about 755 nm, about 773 nm, about 780 nm, about 795 nm, about 815 nm, about 830 nm, about 846 nm, about 855 nm, about 865 nm, about 875 nm, about 890 nm, about 895 nm, about 905 nm, about 910 nm, about 915 nm, about 920 nm, about 935 nm, about 975 nm, about 1000 nm, about 1050 nm, about 1100 nm, or about 1200 nm can be administered to a selected region. In some examples, light administered to a region does not have wavelengths below one or more of the following: about 400 nm, about 450 nm, about 500 nm, about 550 nm, about 585 nm, about 595 nm, about 605 nm, about 613 nm, about 615 nm, about 620 nm, about 624 nm, about 625 nm, about 640 nm, about 650 nm, about 667 nm, about 680 nm, about 710 nm, about 740 nm, about 750 nm, about 770 nm, about 812 nm, about 815 nm, about 820 nm, about 835 nm, about 845 nm, or about 860 nm. For example, no light below about 400 nm, about 450 nm, about 500 nm, about 550 nm, about 585 nm, about 595 nm, about 605 nm, about 613 nm, about 615 nm, about 620 nm, about 624 nm, about 625 nm, about 640 nm, about 650 nm, about 667 nm, about 680 nm, about 710 nm, about 740 nm, about 750 nm, about 770 nm, about 812 nm, about 815 nm, about 820 nm, about 835 nm, about 845 nm, or about 860 nm is administered to a selected region.

In some embodiments, the light administered does not comprise a wavelength of about 600 nm or less. In some embodiments, the light administered does not comprise a wavelength of about 1000 nm or greater. In some embodiments, the light administered does not comprise a wavelength of about 600 nm or less and does not comprise a wavelength of about 1000 nm or greater.

In some embodiments, light administered to a region with a sufficient intensity to be an effective amount in the present methods does not have wavelengths exceeding one or more of the following: about 585 nm, about 605 nm, about 624 nm, about 630 nm, about 635 nm, about 645 nm, about 655 nm, about 660 nm, about 665 nm, about 680 nm, about 684 nm, about 700 nm, about 725 nm, about 755 nm, about 773 nm, about 780 nm, about 795 nm, about 815 nm, about 830 nm, about 846 nm, about 855 nm, about 865 nm, about 875 nm, about 890 nm, about 895 nm, about 905 nm, about 910 nm, about 915 nm, about 920 nm, about 935 nm, about 975 nm, about 1000 nm, about 1050 nm, about 1100 nm, or about 1200 nm. For example, no light having a sufficient intensity to be an effective amount in the present methods and exceeding about 585 nm, about 605 nm, about 624 nm, about 630 nm, about 635 nm, about 645 nm, about 655 nm, about 660 nm, about 665 nm, about 680 nm, about 684 nm, about 700 nm, about 725 nm, about 755 nm, about 773 nm, about 780 nm, about 795 nm, about 815 nm, about 830 nm, about 846 nm, about 855 nm, about 865 nm, about 875 nm, about 890 nm, about 895 nm, about 905 nm, about 910 nm, about 915 nm, about 920 nm, about 935 nm, about 975 nm, about 1000 nm, about 1050 nm, about 1100 nm, or about 1200 nm can be administered to a selected region. In some examples, light administered to a region with a sufficient intensity to be an effective amount in the present methods does not have wavelengths exceeding one or more of the following: about 400 nm, about 450 nm, about 500 nm, about 550 nm, about 585 nm, about 595 nm, about 605 nm, about 613 nm, about 615 nm, about 620 nm, about 624 nm, about 625 nm, about 640 nm, about 650 nm, about 667 nm, about 680 nm, about 710 nm, about 740 nm, about 750 nm, about 770 nm, about 812 nm, about 815 nm, about 820 nm, about 835 nm, about 845 nm, or about 860 nm. For example, no light having a sufficient intensity to be an effective amount in the present methods and below about 400 nm, about 450 nm, about 500 nm, about 550 nm, about 585 nm, about 595 nm, about 605 nm, about 613 nm, about 615 nm, about 620 nm, about 624 nm, about 625 nm, about 640 nm, about 650 nm, about 667 nm, about 680 nm, about 710 nm, about 740 nm, about 750 nm, about 770 nm, about 812 nm, about 815 nm, about 820 nm, about 835 nm, about 845 nm, or about 860 nm is administered to a selected region.

In some embodiments, the light administered does not comprise a wavelength of about 600 nm or less having a sufficient intensity to be an effective amount for the present methods. In some embodiments, the light administered does not comprise a wavelength of about 1000 nm or greater having a sufficient intensity to be an effective amount for the present methods. In some embodiments, the light administered does not comprise a wavelength of about 600 nm or less having a sufficient intensity to be an effective amount for the present methods and does not comprise a wavelength of about 1000 nm or greater having a sufficient intensity to be an effective amount for the present methods.

In some embodiments, light is administered at one, two, or more of the light ranges described. In some embodiments, light is not administered outside of one, two, or more of the light ranges described. In some embodiments, light is not administered with a sufficient intensity to constitute an effective amount in the present methods outside of one, two, or more of the light ranges described. In other embodiments, administered light has other wavelengths, as desired for a particular application. In some embodiments, light having a first set of characteristics (e.g., wavelength, intensity, pulsing, timing) is administered to a first region, and light with a second set of characteristics is administered to a second region. The first region and the second region can be the same region, can partially overlap, or cannot overlap. The first set of characteristics can be the same as the second set of characteristics, can partially overlap with the second set, or can all be different from the second set. In one embodiment, one region of a bone (e.g., a maxillary bone, mandibular bone, or temporal bone) receives light within a first wavelength range, while another region of the bone receives light within a second wavelength range. The first and second wavelengths can overlap. Alternatively, the first and second wavelengths do not overlap.

Although examples of light wavelength ranges are provided below for different applications, light having any other light wavelength value, which can include those described above, can be administered for those applications.

In some embodiments, the light is administered to substantially the entirety of a patient's body. In some embodiments, the light can be administered to substantially the entirety of a patient's oral or maxillofacial bone, muscle, or soft tissue, or one or more teeth, such as the patient's maxillary and mandibular bone. Alternatively, using a light-therapy apparatus or other suitable apparatus, light of one or more particular wavelengths can be administered to different selected regions of a patient's oral tissue, maxillary and mandibular alveolar bone, or teeth, in order to treat a tumor or activate stem cells in one or more regions of a patient's mouth. For example, one or more regions in which it is desired that the stem cells not be activated or in which no tumor is present, can be optionally screened or masked such that they receive no light.

Alternatively, in one or more regions in which it is desired that the stem cells not be activated or in which no tumor is present do not receive light as light emitters over such regions are turned off Regions in which it is desired that stem cells be activated or a tumor be treated can be administered with light having a wavelength in the range of about 585 nm to about 665 nm, in the range of about 605 nm to about 645 nm, about 615 nm to about 635 nm, or about 625 nm. Regions in which it is desired that stem cells be activated or a tumor be treated can be administered with light having a wavelength in the range of about 815 nm to about 895 nm, about 835 nm to about 875 nm, about 845 nm to about 865 nm, or about 855 nm. Tumor treatment or stem cell activation can be selectively regulated by administering an effective amount of light having one wavelength to one or more selected regions of a patient's oral tissue, maxillary bone, mandibular bone, temporal bone, and by administering an effective amount of light having a different wavelength to one or more different selected regions of the oral tissue or bone.

In some embodiments, light is administered within a narrow range of wavelengths (e.g., 50 nm or less, 30 nm or less, 20 nm or less, 10 nm or less, 5 nm or less), or at a single wavelength. In some embodiments, light is administered at a limited wavelength range (e.g., 1000 nm or less, 700 nm or less, 600 nm or less, 500 nm or less, 400 nm or less, 300 nm or less, 250 nm or less, 200 nm or less, 150 nm or less, 100 nm or less, or 75 nm or less). In some embodiments, the light administered does not include wavelengths beyond the narrow or limited range of wavelengths. The narrow or limited range of wavelengths can have any of the upper or lower limits of wavelength as described previously. In some embodiments, however, the light administered does not include light with a sufficient intensity to constitute an effective amount having wavelengths beyond the narrow or limited range of wavelengths.

In some embodiments, light is emitted at one, two, or more peak wavelengths of emission. A peak wavelength is the wavelength at which the highest intensity of light is emitted. In some embodiments, light is administered at a range of wavelengths that includes a peak wavelength having the highest intensity within the range.

In some embodiments, a peak wavelength is at about 620 nm, about 640 nm, about 650 nm, about 655 nm, about 660 nm, about 665 nm, about 670 nm, about 680 nm, about 690 nm, about 800 nm, about 820 nm, about 830 nm, about 835 nm, about 840 nm, about 845 nm, about 850 nm, about 860 nm, about 870 nm, about 890 nm, about 910 or about 930 nm. In some embodiments, the administered light does not have wavelengths that vary from the peak wavelength by more than about I nm, about 2 nm, about 3 nm, about 5 nm, about I0 nm, about 15 nm, about 20 nm, about 30 nm, about 40 nm, about 50 nm, about 75 nm, about 100 nm, about 150 nm, about 200 nm, about 250 nm, about 300 nm, about 400 nm, or about 500 nm.

Where two or more light wavelengths are administered, the light can be administered at any ratio of each wavelength's intensity. For example, light administered at a first wavelength can have an intensity that is about I.Ix, 1.2x, 1.3x, 1.5x, 1.7x, 2.0x, 2.5x, 3.0x, 3.5x, 4.0x, 5.0x, I Ox, 12x, 15x, 20x, 30x, 50x, lOOx that of light administered at a second wavelength. In some embodiments, the administered light is emitted from one or more light emitters, in another embodiment, from one or more light emitters having a first set of properties and, optionally, from a second set of light emitters having a second set of properties. In other embodiments, the number of light emitters having a first set of characteristics exceeds that of the light emitters having a second set of characteristics. For example, the number of light emitters having the first set of characteristics can be about I. Ix, 1.2x, 1.3x, 1.5x, 1.7x, 2.0x, 2.5x, 3.0x, 3.5x, 4.0x, 5.0x, 10x, 12x, 15x, 20x, 30x, 50x, 100x the number of light emitters having the second set of characteristics, or vice versa.

The light can optionally be substantially monochrome. When light is "substantially monochrome" it consists of a single wavelength or comprises other wavelengths that are emitted at an intensity that is ineffective in the present methods.

In some embodiments, a substantially monochromatic light is emitted at a narrow range of wavelengths without being emitted at other wavelengths outside the range or without an effective intensity of light being emitted at other wavelengths outside the range. In some embodiments, a substantially monochromatic light is emitted within an about 5 nm or less, about IO nm or less, or about 20 nm or less wavelength range without being emitted at other wavelengths outside the range or without an effective intensity of light being emitted at other wavelengths outside the range. Administering light from light emitters that emit at multiple wavelengths can allow for irradiation over multiple wavelengths or greater selectivity and precision in administration. The light can optionally comprise incoherent light. In some embodiments, light is administered at a single frequency, light can have a phase that drifts relatively quickly, a pulse of light waves can have an amplitude that changes quickly, or a light wave can encompass a broad range of frequencies.

Light can be administered directly from a light emitter. Light can be emitted and can travel directly through a patient's skin, such as the patient's face, to a region. In another embodiment, the light is administered intra-orally to a region of the oral tissue (e.g., alveolar mucosa, buccal mucosa, labial mucosa, masticatory mucosa, tooth, gum or tongue). In some embodiments, light is modified by optics before reaching the patient's face or traveling through the patient's skin. For example, light can be diffused, focused, parallel, reflected, redirected, or filtered after it is emitted and before it reaches the patient's face or travels through the patient's skin. In one embodiment, light of one or more wavelengths is selectively blocked or partially filtered before reaching the patient's face or a region. In some embodiments, light diverges or converges from an emission source before reaching the region. For example, light can diverge in a beam having an included angle 8 in the range of about 45-60°. The emitted light diverge to have an included angle 8 of O to about 15°, 0 to about 30°, 0 to about 45°, 0 to about 60°, 0 to about 75°, 0 to about 90°, or 0 to about 120°.

Light that irradiates the region can optionally have the same or about the same characteristics as light that is emitted. In some embodiments, light that reaches the region does not have the same characteristics as the light that is emitted. One or more of the light characteristics can optionally be altered prior to administration or when it passes through the face of the patient. One or more of the light characteristics can optionally be altered when it passes through optics, such as one or more lenses or mirrors. For example, one or more of the light characteristics can be altered in the range of about ±20% or less, about ±15% or less, about ±10% or less, about ±5% or less, about ±3% or less, about ±1% or less, about ±0.5% or less, or about ±0.1% or less. An effective dosage of light can have an energy density that irradiates from a light source. For example, an effective dosage of irradiated light can be from about 24 J/cm$^2$ to about 200 J/cm$^2$. The effective dosage of irradiated light can be administered once or repetitively. In some other embodiments, the effective dosage has an irradiated light energy density that is from about 30 J/cm$^2$ to about 100 J/cm$^2$. In other embodiments, the dosage of light is about 5 J/cm$^2$ or less, about 10 J/cm$^2$ or less, about 20 J/cm$^2$ or less, about 30 J/cm$^2$ or less, about 50 J/cm$^2$ or less, about 75 J/cm$^2$ or less, about 100 J/cm$^2$ or less, about 125 J/cm$^2$ or less, about 150 J/cm$^2$ or less, about 175 J/cm$^2$ or less, or about 200 J/cm$^2$ or less. The dosage of light can be about 1 J/cm$^2$ or more, about 5 J/cm$^2$ or more, about 20 J/cm$^2$ or more, about 25 J/cm$^2$ or more, about 30 J/cm$^2$ or more, about 40 J/cm$^2$ or more, about 50 J/cm$^2$ or more, about 60 J/cm$^2$ or more, about 75 J/cm$^2$ or more, about 100 J/cm$^2$ or less, about 125 J/cm$^2$ or more, about 150 J/cm$^2$ or more, or about 175 J/cm$^2$ or more. In some embodiments, the light has an energy density ranging from about 5 J/cm$^2$ to about 50 J/cm$^2$. The dosage of irradiated light can be in a range bounded by any of the energy density values described above. The dosage of light can be increased, for example, by using a light source that emits light having a relatively higher average intensity, or by increasing the duration of administration of light.

An effective dosage of light can have an energy density that reaches a region, such as the mandibular bone, maxillary bone, or temporal bone. For example, an effective dosage of light that reaches a region can be from about 0.5 J/cm$^2$ to about 100 J/cm$^2$. The effective dosage of light that reaches the region can be administered once or repetitively. In some other embodiments, the effective dosage has an irradiated light energy density that is from about 1 J/cm$^2$ to about 50 J/cm$^2$. In other embodiments, the dosage of light is about 0.5 J/cm$^2$ or less, about 1 J/cm$^2$ or less, about 2 J/cm$^2$ or less, about 5 J/cm$^2$ or less, about 10 J/cm$^2$ or less, about 15 J/cm$^2$ or less, about 20 J/cm$^2$ or less, about 30 J/cm$^2$ or less, about 40 J/cm$^2$ or less, about 50 J/cm$^2$ or less, about 70 J/cm$^2$ or less, about 80 J/cm$^2$ or less, about 90 J/cm$^2$ or less, or about 100 J/cm$^2$ or less. The dosage of light can be about 0.5 J/cm$^2$ or more, about 1 J/cm$^2$ or more, about 2 J/cm$^2$ or more, about 3 J/cm$^2$ or more, about 5 J/cm$^2$ or more, about 10 J/cm$^2$ or more, about 15 J/cm$^2$ or more, about 20 J/cm$^2$ or more, about 30 J/cm$^2$ or more, about 40 J/cm$^2$ or more, about 50 J/cm$^2$ or less, about 60 J/cm$^2$ or more, about 70 J/cm$^2$ or more, or about 80 J/cm$^2$ or more. The dosage of light that reaches the region can be in a range bounded by any of the energy density values described above.

The duration over which the effective dosage, which is optionally repetitive, is administered can range from about 10 minutes to about 40 minutes. In some embodiments, the dosage is administered over a period of time equaling about 30 seconds or more, about 1 minute or more, about 2 minutes or more, about 3 minutes or more, about 5 minutes or more, about 7 minutes or more, about 10 minutes or more, about 15 minutes or more, about 20 minutes or more, about 25 minutes or more, about 30 minutes or more, about 40 minutes or more, about 50 minutes or more, about 1 hour or more, about 1 hour 15 minutes or more, about 1 hour 30 minutes or more, or about 2 hours or more. In other embodiments, the dosage is administered over a period of time equaling about 3 minutes or less, about 5 minutes or less, about 10 minutes or less, about 15 minutes or less, about 20 minutes or less, about 25 minutes or less, about 30 minutes or less, about 35 minutes or less, about 40 minutes or less, about 50 minutes or less, about 1 hour or less, about 1 hour 15 minutes or less, about 1 hour 30 minutes or less, about 2 hours or less, or about 4 hours or less. In some embodiments, the dosage is administered over a period from about 5 to about 10 minutes. Alternatively, the dosage can be administered in a range of time within any of the time values described above. Such light therapy can include light emission that has been provided externally, such as, for example, extra-orally. In some embodiments, one or more internal, such as, for example, intra-oral, light blocking masks or shades can be used. An internal or oral mask can block one or more wavelengths of light, or can reduce the intensity of one or more wavelengths of light, from reaching a region covered by the internal or oral mask. This can include an upper arch (e.g., maxillary teeth), lower arch (e.g., mandibulary teeth), right side of the mandibular bone, left side of the mandibular bone, right side of the maxillary bone, left side of the maxillary bone, right side of the temporal bone, or the leftside of the temporal bone, such as the right temporomandibular joint, left temporomandibular joint, right condyle, left condyle, right glenoid fossa, or left glenoid fossa. A mask can be provided for any oral or maxillofacial bone, muscle, or soft tissue, or one or more teeth. Accordingly in other embodiments the methods further comprise applying an intra-oral or extra-oral shade or mask to the patient. The intra-oral or extra-oral shade or mask can be applied prior to or concurrently with the administration of light.

Any time period (or "duration") can be provided between dosages. For example, the time period between dosages can be on the order of seconds, minutes, hours, days, weeks, months, quarter of a year, or years.

The effective dosage, which in some embodiments is repetitive, can be administered with any desired frequency, e.g., four times daily, three times daily, twice daily, daily, every second day, weekly, biweekly, monthly, or quarterly. In some embodiments, dosage is administered at regular intervals (e.g., daily), while in other embodiments, the dosage is not administered at regular intervals (e.g., administration can occur 2 times a week at any time during the week). In one embodiment, light is administered in the morning and at night. Light can be administered throughout the time period that a patient is undergoing tumor or cancer treatment or stem cell activation. In some embodiments, a patient undergoes chemotherapy in addition to undergoing light therapy. Light therapy can occur prior to, subsequent to, or concurrently with chemotherapy. Light can be administered throughout the time period that a patient is undergoing chemotherapy, or following chemotherapy treatment. It can be desirable to administer light with greater frequency, e.g. four times daily, three times daily, twice daily, daily or every second day, while a patient is undergoing chemotherapy. When a patient is in remission, light treatments of reduced frequency, e.g. weekly, biweekly, monthly, or quarterly, can be used to minimize inconvenience to the patient.

Light can be administered for any length of time. In some embodiments, light is administered on the order of weeks, months, quarters, or years. Administration of light, which can include regular, irregular, continuous or discontinuous administration of light, can be on the order of days, weeks, months, quarters, or years. In some embodiments, light is administered over a plurality of days, weeks, months, quarters, or years. In some embodiments, light is administered over a plurality of sessions. In some embodiments, one or more hours, days, weeks, months, quarters, or years occur between sessions. In some embodiments, light is administered daily three times per week for a period of three months.

If the light emitters are pulsed, then their duty cycle can be adjusted as desired; e.g., light can be administered with a duty cycle of about 10%, about 20%, about 30%, about 40%, about 50%, about 60%, about 70%, about 80%, or about 90%. The pulsing can occur with any frequency. For example, light can be pulsed every picosecond, nanosecond, microsecond, millisecond, second, multiple seconds, or minutes.

Frequencies can include, but are not limited to, about 1 mHz, about 10 mHz, about 50 mHz, about 100 mHz, about 500 mHz, about 1 Hz, about 2 Hz, about 5 Hz, about 10 Hz, about 15 Hz, about 20 Hz, about 25 Hz, about 30 Hz, about 35 Hz, about 40 Hz, about 50 Hz, about 70 Hz, about 100 Hz, about 200 Hz, about 500 Hz, or about 1 kHz. Any of the aforementioned characteristics of light emission (e.g., whether the light is on or off, continuous or pulsed, duty cycle, frequency, intensity, wavelength) can be varied or maintained. Where the light is emitted from a source having a controller, any characteristics of light emission can be varied or maintained in accordance with instructions from its controller.

Where the light is emitted from one or more lights, light can be controlled so that the number of lights that are on or off at a given period can be individually controllable. For example, in some embodiments, a light source is turned on or off relative to other light sources. Various light sources can be modulated individually (e.g., one or more properties of a particular light source can be varied) or otherwise individually controlled, to expose individual sections of a patient to a desired energy density. In some embodiments, light sources can be modulated individually, to expose individual sections of a patient's oral tissue, bone or other regions to a desired energy density. In some embodiments, light sources can be modulated individually, to expose individual sections of a patient's oral or maxillofacial bone, muscle, or soft tissue, or one or more teeth, such as a maxillary bone, mandibular bone, temporal bone, or other regions to a desired energy density. This can be desirable when it is desirable to administer light to different regions. Thus, the position of light being administered can be varied. In another embodiment, different types of light sources are turned on or off relative to other light emitters. For example, at some times, light emitted in a first wavelength range can be turned on while light emitted in a second wavelength range can be turned off, vice versa, or both types of light emitters can be turned on or off. Thus, the wavelength of light being administered can be varied. In some embodiments, the intensity of light being administered is varied (e.g., by turning some light sources on or off, or varying the intensity emitted by the light sources).

In some embodiments, where infrared light is administered to a region, a visible light is also emitted. In one embodiment, the visible light is bright, e.g., uncomfortable for a patient to look at. The bright visible light can deter users or patients from looking into a light source when it is operating, can provide a perceptible indication that a light is being emitted, and can be useful in properly positioning a light source. The visible light can be, but is not necessarily, of a wavelength range that is beneficial in the present methods, including for light therapy, tumor treatment or stem cell activation. In some embodiments, the ratio of the intensities of the visible and infrared components of the light is 1 part or less visible light to 5 parts or more infrared light. In other embodiments, the ratio of the intensities of visible and infrared components is about 1 part or more visible light to 5 parts or more infrared light, 1 part or more visible light to 3 parts infrared light, 1 part or more visible light to 2 parts infrared light, 1 part or more visible light to 1 part infrared light, 2 parts or more visible light to 1 part infrared light, 3 parts or more visible light to 1 part infrared light, 5 parts or more visible light to 1 part infrared light, 10 parts or more visible light to 1 part infrared light, or substantially no infrared light. In some embodiments, light is emitted within a range that includes wavelengths less than an order of magnitude relative to one another. Alternatively, the range can include wavelengths emitted at one, two, three or more orders of magnitude relative to one another.

The region and desired light characteristics can vary from patient to patient. A physician, dentist, other health-care provider or patient can determine a light treatment regimen for a patient.

In some instances, it is desirable to administer light to less than all regions of the patient's oral tissue or bone. For example, in some instances, it can be desirable to administer light to less than all regions of the patient's maxillary or mandibular bone.

Administering light to selected regions of the patient's oral or maxillofacial bone, muscle, or soft tissue, or muscle, or one or more teeth can comprise causing light to irradiate one or more selected regions of the patient's oral or maxillofacial bone, muscle, or soft tissue, or one or more teeth, such as tooth roots through the bone.

It can also be desirable to administer light of different wavelengths to different regions of the patient's oral or maxillofacial bone, such as a maxillary bone, mandibular bone, or temporal bone or teeth, if it is desired to differentially treat the patient's soft tissue, brain regions, teeth or oral or maxillofacial bone, such as the maxillary bone, mandibular bone, or temporal bone. For example, if a tumor is located on the right side of the patient's brain, the right side of the patient can receive light treatment while the left side does not. In another example, light of a first wavelength can be administered to a first region and light of a second wavelength can be administered to a second region. The first and second wavelengths can include any wavelengths described elsewhere herein, such as about 585 nm to about 665 nm, about 666 nm to about 814 nm or about 815 nm to about 895 nm.

Light can be administered over an area (also referred to herein as a "light irradiation area"). For example, in some embodiments, light is administered to a region with an area. In some such embodiments, light characteristics remain uniform over the area. For example, light intensity can be uniform over the area. In other embodiments, however, light characteristics vary over the area. For example, light intensity can vary over the area.

Light can be administered to a light irradiation area of any size and shape. For example, a region, such as a specified region of the patient's maxillary bone, mandibular bone, or temporal bone can have any size or shape. The light irradiation area can have one or more dimensions (e.g., length, width, diameter) that range from about 1 to about 80 mm, or from about 1 to about 70 mm. In some embodiments, the light irradiation area has one or more dimensions (e.g., length, width, diameter) that range from about 1 to about 3 mm, about 3 to about 5 mm, about 5 to about 7 mm, about 7 to about 10 mm, about 10 to about 15 mm, about 15 to about 20 mm, about 20 to about 25 mm, about 25 to about 30 mm, about 30 to about 35 mm, about 35 to about 40 mm, about 40 to about 50 mm, about 50 to about 60 mm, or about 60 to about 80 mm.

A light irradiation area can have any shape, which can include, but is not limited to, a substantially rectangular shape, square shape, triangular shape, hexagonal shape, octagonal shape, trapezoidal shape, circular shape, elliptical shape, crescent shape, cylindrical shape or half-circle. In some embodiments, the dimensions of a light source is about the same as dimensions for a light irradiation area. In other embodiments, the dimensions of a light source is greater than the dimensions of a light irradiation area. Alternatively, the dimensions of a light source can be less than the dimensions of the light irradiation area. The relative areas of a light source and light irradiation area can depend on any angle, which can be a parallel, convergence, or divergence angle, at which light is emitted.

In some embodiments, an effective dosage of light is provided in a treatment regimen.

The treatment regimen can be used in the methods of the invention.

In one embodiment, a typical treatment regimen provides a dose of light daily. Each of the daily doses of light can be administered over a period lasting from a few minutes to about an hour. For example, daily ½ hour doses of light can be effective and are not unduly inconvenient for patients. A single daily dose can be as effective as dividing the same dose into multiple sessions administered at different times during the day. Some treatment regimens can comprise administering light in 5 treatments per week for 12 weeks. Each treatment can last ½ hour and irradiate the tissues of a patient's jaw with light having wavelengths of 660 nm and 840 nm. The 660 nm light can have an intensity of about 20 mW/cm$^2$ at the skin's surface. The 840 nm light can have an intensity of about 10 mW/cm$^2$ at the skin's surface. In some embodiments, these treatment regimens enhance bone density.

Other treatment regimens can comprise administering light in daily treatments for 21 days. Each treatment lasts between 20 minutes and one hour and illuminates the tissues of a patient's jaw with light having a wavelength of 618 nm and an intensity of 20 mW/cm$^2$ at the skin's surface. In some embodiments, these treatment regimens accelerate healing of bone grafts.

Another treatment regimen can include a twice-daily administration of light for six months. In one embodiment the light is administered from a light-therapy apparatus. Light can be administered at a wavelength of about 660 nm or about 840 nm, or at both wavelengths. The intensity of the light can be about 20 mW/cm$^2$ at the skin's surface. Subsequent to the first 6 month period, a second 6 month period can be provided where light is administered once every other day. The administration of light can optionally become less frequent or be administered at a lower intensity as treatment progresses. The present methods can further comprise controlling temperature of the patient's skin (such as the patient's face) or of any light source that contacts or is close to a patient's skin or a region. For example, the method can comprise cooling, heating, or maintaining the temperature at a patient's face. A patient's face can be contacted with a temperature control mechanism, which can cause the removal or provision of heat. In some embodiments, heat can be generated by the light source. In some embodiments, the temperature of the light source can be controlled. A temperature control mechanism can communicate with the light source. Heat can be removed from or provided to the light source. Any embodiments for temperature regulation described herein can be used within the method. The method can further comprise measuring a temperature at a patient's face or at a light source. Temperature regulation can optionally occur in response to one or more temperature measurements made.

Light Therapy Apparatuses and Systems

In some embodiments, the administering is via one or more light-therapy apparatuses. The light-therapy apparatuses are useful for administering an effective amount of light (for example, to the oral or maxillofacial bone, muscle, or soft tissue or to one or more teeth of a patient) and, accordingly, useful in the methods of the invention.

In some embodiments, the light therapy apparatuses are useful for intra-orally administering light. In some embodiments, the light therapy apparatus are useful for extra-orally administering light. Light-therapy apparatuses and systems as described herein can be applied to treat a variety of conditions as described elsewhere herein.

A light therapy system is provided and comprises a light-therapy apparatus. A light therapy system can also optionally comprise an oral appliance, such as an orthodontic appliance, or oral or tooth mask. In some embodiments, the orthodontic appliance can be a functional appliance. Any orthodontic appliance, including any functional appliance, as described anywhere above, can be part of the light therapy system. An oral or tooth mask can block or partially filter one or more wavelength of light from a region covered by the mask. For example, a tooth mask can cover one or more teeth. The tooth mask can cover one or more mandibular or maxillary tooth. An oral mask can cover any region of the mouth. For example, an oral mask can cover one or more teeth, or one or more portion of the gums. An oral mask or tooth mask can be formed of a transparent, translucent, or opaque material. An oral mask or tooth mask can block all wavelengths, reduce the intensity of all wavelengths, filter only some wavelengths, or reduce the intensity of only some wavelengths. In some embodiments, an oral mask or tooth mask can alter one or more light characteristics.

A light therapy system can also optionally comprise an external controller or a computer (or any other device described below) in communication with a controller. Any embodiments of a light-therapy apparatus as described herein can be incorporated within the light therapy system. The light-therapy apparatus can optionally comprise one or more support features that can engage with a portion of a patient's face or head. In another embodiment the light-therapy apparatus engages with the mouth of the patient. The light-therapy apparatus can also comprise one or more light sources, wherein the one or more light sources can each comprise one or more light emitters. The light therapy system can also comprise a controller that controls the operation of the light-therapy apparatus. The controller can control the wavelength, intensity or duration of light emitted by the light-therapy apparatus or the position of its components. The controller can control any other light characteristics. The controller can be integral to or separate from the light-therapy apparatus. The light therapy system provides light and, accordingly, is useful in the present methods.

In some embodiments, a light therapy system comprises one or more other appliances. For example, a functional appliance can be installed within or external to an oral cavity of the patient. In another embodiment, an oral mask or tooth mask can be applied within the oral cavity of the patient. A light therapy system can comprise oral appliances or inserts that are within the oral cavity of the patient.

The light-therapy apparatus can be fixed or movable with respect to the functional appliance, oral or tooth mask, or any other appliance.

Figure 2:
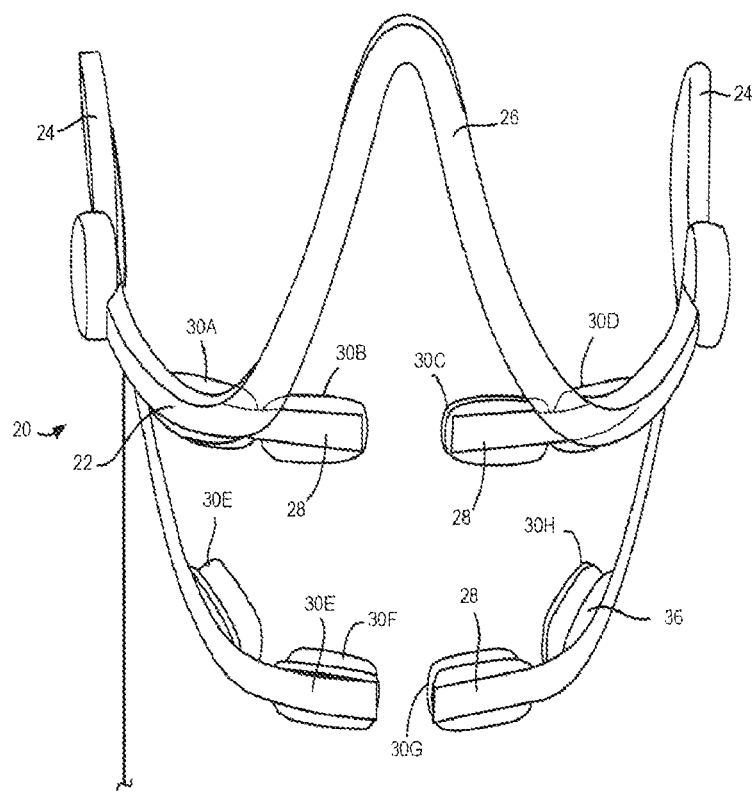
FIG. 2 is a front view of the embodiment shown in FIG. 1.
Figure 3:
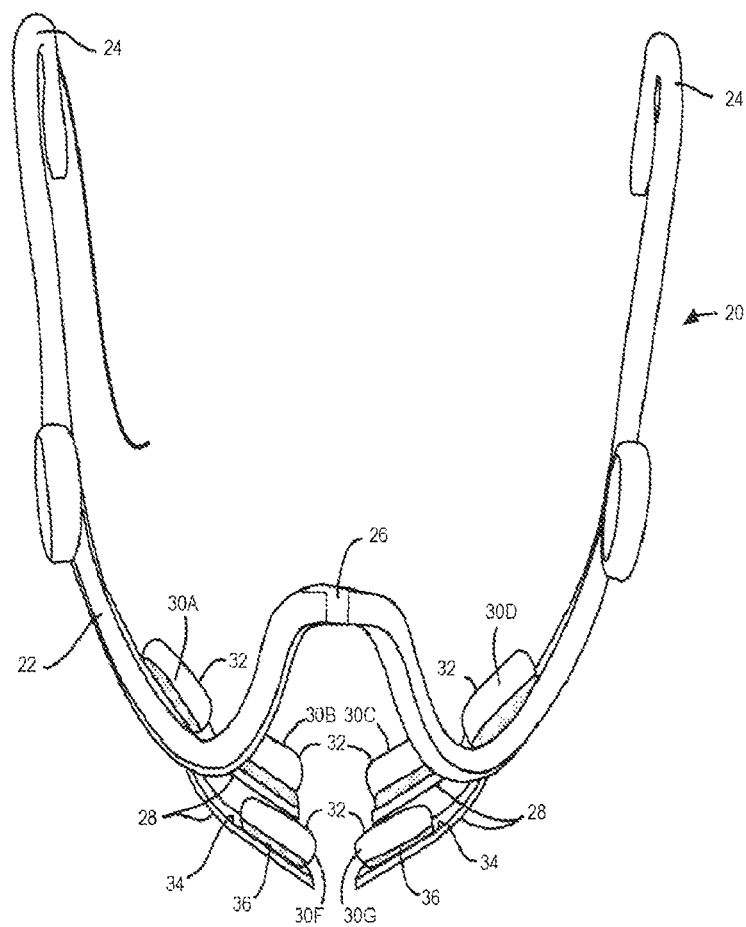
FIG. 3 is a top view of the embodiment shown in FIG. 1.
Figure 4:
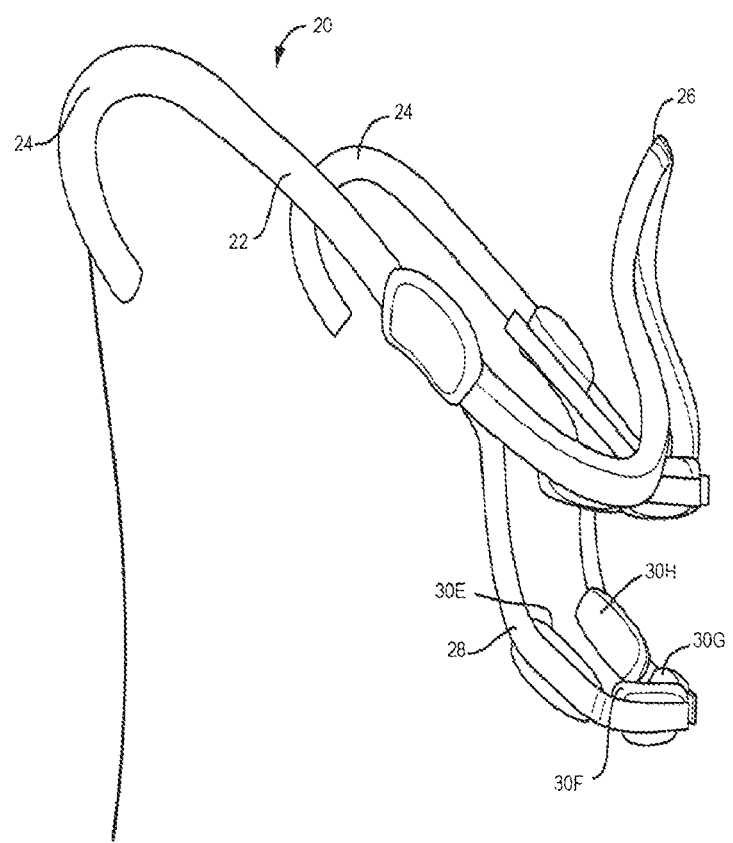
FIG. 4 is a right isometric view of the embodiment shown in FIG. 1.

An embodiment of a light-therapy apparatus 20 is shown in FIGS. 1-4. FIG. 1 is an isometric view of an embodiment of a light-therapy apparatus useful for providing light to one or more specified regions of a patient's maxillary or mandibular bone. FIG. 2 is a front view of the embodiment shown in FIG. 1. FIG. 3 is a top view of the embodiment shown in FIG. 1. FIG. 4 is a right isometric view of the embodiment shown in FIG. 1. The light-therapy apparatus can be useful for providing light to any region described anywhere above.

Light-therapy apparatus 20 has a frame 22 which is sized and/or shaped to engage with one or more features of a patient's face. Features of a patient's face can include, but are not limited to, the patient's ears, nose, nostrils, mouth, lips, chin, jaw, cheek, brow, or forehead. The light-therapy apparatus 20 can have a frame 22 that optionally engages with other features of a patient's head or portion of their anatomy. For example, the frame can engage with the crown of the patient's head, the top or back of the patient's head, the neck, or shoulders.

In the illustrative embodiment illustrated in FIGS. 1-4, frame 22 is shaped to provide ear-engaging portions 24, a nose-engaging portion 26, and support arms 28. A frame can engage with features of a patient's face by conforming to the shape of the feature, wrapping around the feature, overlying the feature, grasping the feature, adhering to the feature or providing pressure or weight to the feature. In some embodiments, frame 22 is formed as an integral unit. In other embodiments, frame 22 is formed from two or more separate pieces of material, which are suitably joined to provide frame 22.

In some embodiments, frame 22 comprises more than one type of material; for example, support arms 28 can be made from a material that is different from other portions of frame 22. Alternatively, the frame 22 can be formed of the same type of material.

Support arms 28 can be disposed so that they are overlying and contacting a patient's face, directly over the patient's jawbone when light-therapy apparatus 20 is worn in a use configuration by a patient. Portions 24 and 26 facilitate retention of light-therapy apparatus 20 on the facial area of a patient, while support arms 28 support a plurality of light sources 30 (also shown as light sources 30A-30H in some figures), as discussed below. Support arms 28 can also facilitate engagement of light-therapy apparatus 20 on the facial region of a patient, e.g., by providing a biasing force inwardly against a patient's face. Other suitable configurations of frame 22 in addition to the illustrated embodiment are useful for securing light-therapy apparatus 20 to a patient's face and to support light sources 30 at the desired locations and with the desired orientations. The frame can support one or more light sources so that they contact the patient's face. The frame can be positioned so that the light source contacts the skin of a portion of the face overlying the region.

The frame 22 can comprise one or more support arms 28 that can be formed of an elongated portion. The support arms can be straight, curved, or bent in order to engage with a patient's face as desired. In some embodiments, the frame 22 comprises other shaped portions that can comprise surfaces that can be flat, curved, or bent, that can cover one or more portion of the face. In one embodiment, the frame 22 can be curved over the bridge of a patient's nose, or curved around their ears. The frame can curve around the mouth or around a portion of the mouth.

FIG. 2 provides an example of a frame 22 where four elongated support arms extend around the mouth. For example, one, two or more support arms can be provided below the mouth. The support arms can be configured to lie over the patient's face, directly above the patient's jaw. One, two or more elongated support arms can be provided above the mouth or below the nose. The support arms can form two tracks, an upper track above the mouth, and a lower track below the mouth. In another embodiments, only one track is provided, which can be above the mouth, below the mouth, or in line with the mouth. Alternatively, additional tracks can be provided; for example, multiple support arm tracks can be provided above the mouth, below the mouth, or in line with the mouth. The support arms can lie over a right side or a left side of the patient's face. In some embodiments, an elongated support arm can form a continuous piece lying over both a right side and left side of a patient's face. Alternatively, separate elongate portions can be provided for a right side and left side of a patient's face.

Elongate portions can optionally overlie a central region of the patient's face. In some embodiments, elongate portions do not overlie a central region of the patient's face. Any discussion herein of elongated support arms can also apply to support arms or other portions of the frame 22 that can have other shapes. Any arrangement of support arms can be applied to any of the light-therapy apparatus embodiments discussed herein.

In some embodiments, a support arm can comprise a support feature.

In some embodiments, at least one of a right side of the support or left side of the support can comprise a support feature. In some embodiments, both the right and left side of the support can comprise support features. A support feature can allow one or more component of the light-therapy apparatus to removably engage with the support. In some embodiments, the support feature can allow the one or more components to move relative to the support while being engaged with the support. In some embodiments, the one or more components can comprise a light emitter, a light source, a secondary support, a hinge, or a light assembly. The support feature can be a track. In some embodiments, a track can comprise a slot, channel, groove, or other female feature which can be configured to accept a protrusion, ridge, or any other male feature, which can be provided on a component, such as a light source, a secondary support, a hinge, or a light assembly. In one embodiment, the track can be formed on an inner surface portion of the support (e.g., side of the support closer to a patient's face when in use). Alternatively, the track can be provided on an outer surface portion of the support (e.g., side of the support further from the patient's face when in use). In some embodiments, the track can be provided through the support. Alternatively, a support feature, such as a track, can have male features that can engage with a female feature of a component. Interlocking features can be provided between the support and one or more component.

FIGS. 8A-8D show another embodiment of a light-therapy apparatus 80. The light-therapy apparatus 80 can have a frame 82 which is sized and/or shaped to engage with features of a patient's face. The frame 82 can optionally be shaped to engage with features of a patient's head or another portion of the patient's anatomy. Alternatively, the frame 82 is not shaped to engage with other features of the patient's head or other portions of the patient's anatomy.

In some embodiments, the frame 82 can be shaped to provide ear engaging portions, a nose engaging portion 86, and support arms 88. In some embodiments, the frame 82 can be formed as an integral unit. For example, the ear engaging portions, the nose engaging portion, and the support arms can be formed of a continuous integral unit. In one instance, the ear engaging portions, the nose engaging portion, and the support arms can form a single continuous elongated piece. In other embodiments, frame 82 can be formed from two or more separate pieces of material, which are suitably joined to provide frame 82. In some embodiments, one support arm per side of the face can be provided. Alternatively, multiple support arms per side of the face can be provided. One or more support arm can be engaged with the nose engaging portion or ear engaging portion.

Support arms 88 can be disposed so that they are adjacent to a patient's face overlying the jawbone or so that they are in the proximity of a patient's jawbone when light-therapy apparatus 80 is worn in a use configuration by a patient. In some embodiments, the support arms can be positioned so that one more light source 81 can contact the patient's face over the patient's jawbone or contact any other selected region of a patient's face. In some embodiments, the support arms can be configured to position one or more light source over one or more temporomandibular joint, condyle, or glenoid fossa of the patient. The light source can be positioned over a right temporomandibular joint, a left temporomandibular joint, a right condyle, a left condyle, a right glenoid fossa, or a left glenoid fossa of the patient. Portions, such as an ear engaging portion, nose engaging portion 26, or any other portion of a frame that can engage with features of a patient's face, can facilitate retention of light-therapy apparatus 80 on the facial area of a patient, while support arms 88 supports one or a plurality of light sources 81 (also shown as light sources 81A-81D in some figures), as discussed below. Support arms 88 can also facilitate engagement of light-therapy apparatus 80 on the facial region of a patient, e.g., by providing a biasing force inwardly against a patient's face. Other suitable configurations of frame 82 in addition to the illustrated embodiment could be used to secure light-therapy apparatus 80 to a patient's face and to support light sources 81 at the desired locations and with the desired orientations. Other features, configurations, or components, as described in other embodiments, can be incorporated within this embodiment.

A frame, for any embodiment of a light-therapy apparatus, can be constructed from any suitable material; for example, lightweight plastic, steel, aluminum, copper, copper clad materials (such as aluminum or steel), nickel, titanium, silver, iron, other suitable metal or plastic, tubular plastic, plastic composite embedded with metal particles, graphite, graphite-epoxy, or any combinations or alloys thereof. The frame or portions of frame can optionally comprise a resin covering or suitable padding to cushion a patient's face. The frame can be made from flexible material, or from material which is thermally conductive. If a frame is made from a thermally conductive material such as, for example, aluminum, the frame can be capable of dissipating heat from one or more light sources, described below.

A frame can be made from a material which provides the frame with flexibility or which permits the frame to be conformed to the anatomical features of a particular patient's face. The frame or other components of the light-therapy apparatus can be bent in one or two dimensions. They can be moldable to conform to contours of the patient's face. A physician, dentist, orthodontist, therapist, technician or other individual, including a patient, can initially "fit" a particular light-therapy apparatus to a particular patient by adjusting and conforming that particular light-therapy apparatus to the anatomical features of that particular patient to provide an individualized fit. The material of which the frame is constructed can be sufficiently resilient to retain the individualized fit over the course of orthodontic therapy for that particular patient, and yet sufficiently flexible to permit that particular light-therapy apparatus to be re-adjusted (e.g. in response to complaints of discomfort from a patient) or adjusted to fit a different patient.

Any description, components, features, details of an embodiment of a light-therapy apparatus can be applied to any other embodiment of a light-therapy apparatus, and vice versa. For example, modifications to any device of FIGS. 1-4 (e.g., a frame 22 or light source 30 as provided in FIGS. 1-4) can be made to any of FIGS. 8A-8D (e.g., frame 82 or light source 81 in FIGS. 8A-8D), FIG. 9, FIG. 14, FIG. 17, or FIG. 18.

Providing a flexible frame 22 can also facilitate light source 30 contacting the cheek of a patient by support arms 28 (i.e., support arms 28 can bias light source 30 against the desired region of light administration on a patient's face, directly over his or her jawbone). In some embodiments, the morphology of the frame or the support arms, can cause the light source to contact a portion of a patient's face when the light-therapy apparatus is in use, e.g., when the light-therapy apparatus is worn by a patient. Other features can bias the light source, e.g., by providing pressure, to contact a portion of the patient's face, including but not limited to, elastic components, springs, inflatable portions, moving mechanical portions. Such bias can be provided when the patient's face is relaxed or when the patient's face is tensed. Bias of light source 30 on the cheek of a patient can depress the soft tissue, which can increase the effective transmission of light through the tissue. Thus, in some embodiments, it can be desirable for a light source to contact the skin of a patient's face or depress the skin of the patient's face. In other embodiments, a gap can be provided between a light source and a skin of the patient's face. The frame can be configured to provide the gap between the light source and the patient's face. The light source can be in close proximity to the skin of the patient's face without contacting the patient's face. In some embodiments, the light source does not contact a patient's face when the patient's face is relaxed but can contact the face if the patient flexes a portion of the patient's face or tenses the face. In some embodiments, a light source can be about 1 mm or less, 2 mm or less, 3 mm or less, 5 mm or less, 7 mm or less, 1 cm or less, 1.5 cm or less, 2 cm or less, 2.5 cm or less, 3 cm or less, or any distance described anywhere above, away from a patient's face while the patient's face is relaxed.

In some embodiments, the light source can contact a translucent or transparent material, such as a gel or solid film that contacts the patient's face. The frame can be configured so that the translucent or transparent material contacts the patient's face when the apparatus is in use. In some embodiments, the light source can comprise an exterior surface formed of a translucent or transparent material, such as a gel or solid film that contacts the patient's face. One or more light emitters of the light source can contact that exterior surface. Alternatively, a gap can be provided between the light emitters and the exterior surface. In some embodiments, the translucent or transparent material filters light of one or more particular wavelengths. In some other embodiments, the material dissipates heat generated by operation of the light source.

In some embodiments, a light emitter provided on a light source can be positioned at a distance from a region. The frame can be configured so that the light source is at a distance from the region. The region can be within a patient's oral cavity. In some embodiments, the light emitter can be provided external to the oral cavity. A portion of a patient's face, such as the cheek, lips, or chin can be lie between the light emitter and the oral cavity when the device is in use. A light emitter can be positioned at about 0.1 mm or less, about 0.5 mm or less, about I mm or less, about 2 mm or less, about 3 mm or less, about 5 mm or less, about 7 mm or less, about I cm or less, about 1.5 cm or less, about 2 cm or less, about 2.5 cm or less, about 3 cm or less, or any distance described anywhere above, from a region.

Optionally, regions of greater flexibility than the remainder of frame can be provided between light sources or at other suitable locations on frame, to allow frame to be bent to provide a better fit around the facial area. Regions of greater flexibility can be provided, for example, by forming the region of greater flexibility from a portion of material that is thinner than the remainder of frame, by forming the region of greater flexibility from a material that is more flexible than the remainder of frame, or by providing hinge-like members (e.g., a thin crease or other bend line set into the material of which frame is constructed) within the frame. Other examples of how flexibility can be provided, can include using a bendable material, using a stretchable elastic material, using a spring, including multiple components that can slide or move relative to one another, that can unfold relative to one another, using telescoping features, including one or more joint (e.g., ball and socket, hinges), or having parts that can lock to one another at different size options. The frame can be adjustable to fit patients with different sized or shaped heads. In some embodiments, a frame size can be selected based on the size or shape of a patient's head.

In some embodiments, at least one light source 30 is secured to frame 22 in order to emit light towards a patient when light-therapy apparatus 20 is in the use position. Light source 30 is disposed extra-orally, i.e., outside of a patient's oral cavity, when light-therapy apparatus 20 is in the use position. When in use, the light source irradiates through the skin of a patient's face. Light can reach a region that is within a patient's oral cavity by transcutaneously irradiating through the skin. In some embodiments, when in use, light from a light source 30 is not configured to directly irradiate into the oral cavity, and reaches the oral cavity only through the skin. In one embodiment, light can reach a region only transdermally.

A light-therapy apparatus can have one or more light source capable of emitting light in the wavelengths discussed below or described anywhere above. The light provided by the light source is not necessarily visible light—any desired wavelength can be used. For example, light emitted by the light source can comprise infrared light or near-infrared light. The light source can also irradiate in the visible light region. For example, the light source can be configured to irradiate light falling within or ranging from about 400 nm to about 1200 nm. In some embodiments, the light source can be configured to irradiate light falling within or ranging from about 600 nm to about 1100 nm. In particular embodiments, the light source can be configured to irradiate light falling within or ranging from about 500 to about 700, about 585 nm to about 665 nm, about 605 nm to about 630 nm, about 620 nm to about 680 nm, about 815 nm to about 895 nm, about 815 to about 895 nm, about 820 nm to about 890 nm, about 640 nm to about 680 nm, or about 740 nm to about 780 nm. In some embodiments, the wavelengths can fall within or range from about 605 nm to about 645 nm, or from about 835 nm to about 875 nm. In some embodiments, the wavelengths can fall within or range from about 615 nm to about 635 nm, or from about 845 nm to about 865 nm. In some embodiments, the wavelengths can be about 625 nm or about 855 nm. In some embodiments, the wavelengths can fall within or range from about 700 nm to about 900 nm, from about 800 nm to about 1100 nm, or from about 900 nm to about 1000 nm. In some embodiments, a light source can be configured to emit light at one, two, or more of the light ranges described. In some embodiments, a light source does not emit light outside one, two, or more of the light ranges described. In other embodiments, light emitters can be configured to irradiate light having other wavelengths, as desired for a particular application. The light sources described herein can emit light at any of the wavelengths described anywhere above.

In some embodiments a light source can be capable of emitting light at one, two, or more peak wavelengths of emission. A peak wavelength can be the wavelength at which the highest intensity of light is emitted. In some embodiments, light can be emitted at a range of wavelengths and the peak wavelength can be the wavelength with the highest intensity within the range. In some embodiments, a peak wavelength can be provided at about 620 nm, about 640 nm, about 650 nm, about 655 nm, about 660 nm, about 665 nm, about 670 nm, about 680 nm, about 690 nm, about 800 nm, about 820 nm, about 830 nm, about 835 nm, about 840 nm, about 845 nm, about 850 nm, about 860 nm, about 870 nm, about 890 nm, about 910 nm, about 930 nm, about 950 nm, about 970 nm, about 990 nm, about 1010 nm, about 1030 nm, about 1050 nm, about 1070 nm, or about 1090 nm. The light sources described herein can emit light having any of the wavelength characteristics described anywhere above.

A light source can be any suitable light source, which can comprise one, two, three, four, five, six, seven, eight, or more light emitters. In some embodiments, a light source comprises about 10 to about 15 emitters, about 15 to about 20 emitters, about 20 to about 30 emitters, about 30 to about 40 emitters, about 40 to about 50 emitters, about 50 to about 70 emitters, or about 70 emitters to about 100 emitters. For example, a light source can comprise a light-emitting diode (LED) (e.g., gallium arsenide (GaAs) LED, aluminium gallium arsenide (AlGaAs) LED, gallium arsenide phosphide (GaAsP) LED, aluminium gallium indium phosphide (AlGaInP) LED, gallium(III) phosphide (GaP) LED, indium gallium nitride (InGaN) I gallium(III) nitride (GaN) LED, or aluminium gallium phosphide (AlGaP) LED), which can be present in an array; or a laser, for example a vertical cavity surface emitting laser (VCSEL) or other suitable light emitter such as an Indium-Gallium-Aluminum-Phosphide (InGaAIP) laser, a Gallium-Arsenic Phosphide/Gallium Phosphide (GaAsP/GaP) laser, or a Gallium-Aluminum-Arsenide/Gallium-Aluminum-Arsenide (GaAIAs/GaAs) laser. In one embodiment the light source comprises a plurality of lasers. A plurality of light emitters capable of emitting light at several different wavelengths can be used for light source 30.

Alternatively, one or more light emitters capable of emitting light at the same wavelength can be used for the light source. One or more light emitters can be arranged on a light source many manner. For example, a plurality of light emitters can be arranged in one or more rows or columns. The rows or columns can form an array, or a staggered set of rows or columns, concentric shapes. Light emitters can be provided from any commercially available source, and can include but are not limited to Optowell XH85vcsel, ULM Vcsel, or Osram MID LED.

A light source 30 can be of any size and shape useful to irradiate through a patient's face a specified region of the patient's maxillary or mandibular alveolar bone. For example, in some embodiments, the light source 30 can have a height of about 9-10 mm along a vertical axis tangential to a patient's face, and a width in the range of about 15-18 mm along a horizontal axis tangential to a patient's face, as measured when light-therapy apparatus 20 is in the use configuration. One or more dimensions of a light source range from about 1-70 mm. In some embodiments, one or more dimensions of a light source range from about 1-3 mm, about 3-5 mm, about 5-7 mm, about 7-10 mm, about 10-15 mm, about 15-20 mm, about 20-25 mm, about 25-30 mm, about 30-35 mm, about 35-40 mm, about 40-50 mm, or about 50-60 mm.

A light source can have any shape, which can include, but is not limited to, a substantially rectangular shape, square shape, triangular shape, hexagonal shape, octagonal shape, trapezoidal shape, circular shape, elliptical shape, crescent shape, cylindrical shape or half-circle. A light source can have rounded or pointed corners. In some embodiments, the dimensions of a light source can be about the same as dimensions for a region area. In other embodiments, the dimensions of a light source can be greater than the dimensions of a region area. Alternatively, the dimensions of a light source can be less than the dimensions of the region area. The relative areas of a light source and region can depend on a parallel, convergence, or divergence angle at which light is emitted.

In some embodiments, each of the light sources within a light-therapy apparatus can be the same size or shape. In other embodiments, the light sources can have different sizes or shapes. Light source size or shape can be selected to administer a desired distribution of light to a region. A light source can have one type of light emitter.

Alternatively, a light source can have two, three, four, five, or more different types of light emitters. Each light source can have a different light emitter or combination of light emitters, or can have the same light emitter or combination of light emitters. For example, each light source can have LEDs emitting light within the range of about 585 nm to about 665 nm, and LEDs emitting light within the range of about 815 nm to about 895 nm. In another embodiment, a first light source can have LEDs emitting from about 585 to about 665 nm, while a second light source can have LEDs emitting from about 815 to about 895 nm.

In some embodiments, one or more light source can comprise a substrate supporting the one or more light emitters. For example, one or more light source can comprise an array of light emitters mounted on a flexible sheet of material that will hold a shape when it is bent. The flexible material can advantageously comprise a metal sheet that can serve as a heat sink or thermal path to a heat sink. The flexible sheet can be molded to conform to the contours of a patient's face while the light-therapy apparatus is being fitted or is in use. The substrate can also comprise a cushioned material that can contact a patient's face without causing discomfort.

In some embodiments, light emitters of different characteristics (e.g., wavelength, intensity, pulsing, size), can be provided for a light source. In some embodiments, the different light emitters can be evenly interspersed within a light source. For example, light emitters of a first wavelength can be evenly interspersed within light emitters of a second wavelength. Alternatively, different light emitters can be localized. For example, light emitters of a first wavelength can be provided within a first region of a light source, and light emitters of a second wavelength can be provided within a second region of the light source.

A plurality of light sources 30 can be disposed on frame 22 to administer light of the desired wavelength substantially uniformly to desired regions of a patient's face, so as to irradiate, in one embodiment through the face, the patient's maxillary or mandibular bone, such as the maxillary or mandibular alveolar bone, one or more temporomandibular joint, one or more condyle, one or more glenoid fossa, or any other region as described elsewhere herein. Any number of light sources can be disposed on a frame. For example, one, two, three, four, five, six, seven, eight, nine, ten, eleven, twelve, thirteen, fourteen, fifteen, sixteen, seventeen, eighteen, nineteen, twenty, or more light sources can be provided for a light-therapy apparatus. The light sources can be distributed along any portion of the frame. In some embodiments, the same number of light sources can be provided on the right side and the left side of the frame. Alternatively, different numbers of light sources can be provided the right and left sides of the frame. One, two, three or more light sources can be positioned to administer light to a region. In some embodiments, the light administered by light sources to a particular region can be the same for each light source, or can vary.

One or more of the light sources can be removable. In some embodiments, all of the light sources are removable, while in other embodiments, one or more of the light sources are not removable. In some embodiments, none of the light sources are removable. Different types of light sources can be used to provide a desired light with a desired distribution to a region. For example, different light sources can be used for different applications, such as different stages of orthodontic or orthopedic treatment. For example, a first light source providing light at a first wavelength range can be used for one purpose, and a second light source providing light at a second wavelength range can be used for the same or for a different purpose. Or a first light source having a first size or shape can be used instead of or in conjunction with a second light source having a second size or shape. Additional light sources can be added or removed. Different light sources can be added or removed during the course of a treatment disclosed herein, or during the course of slowing progression of one or more abnormal conditions disclosed herein.

Each individual light source 30 can be separately configured or separately controllable, to provide light of a specified wavelength or intensity to a specific region of a patient's jawbone, or any other region for a desired period. In one embodiment the light is provided through the patient's face.

In some embodiments, one or more groups or subgroups of light sources can be separately configured or separately controllable, while all light sources belonging to the group or subgroup provide light of the same wavelength or intensity. In another implementation, all light sources belonging to a light-therapy apparatus can be controlled together.

In some embodiments, a light-therapy apparatus can be configured to administer light to only some regions of the patient's oral tissue or maxillary or mandibular alveolar-bone. The light-therapy apparatus can also be capable of providing light of different wavelengths to different regions of the patient's oral tissue or maxillary or mandibular alveolar bone. For example, light of a first wavelength can be administered to a first region and light of a second wavelength can be administered to a second region. The first and second wavelengths can include any wavelengths described elsewhere herein, such as about 585 nm to about 665 nm, and about 815 nm to about 895 nm, respectively.

In some embodiments, light can be administered to a region that can include a portion of tissue (e.g., bone tissue, or soft tissue) or other regions within the patient's oral cavity without being administered to other portions of the patient's oral cavity. In some embodiments, light can be administered to a region that can include a portion of tissue (e.g., bone tissue, or soft tissue) or other regions within the patient's oral cavity at a much greater intensity than it is administered to other portions of the patient's oral cavity. For example, 3×, 5×, 10×, 20×, 50×, or 100× greater intensity of light can be administered to a region, than another portion of the patient's oral cavity. In some embodiments, this is achieved by applying to the patient one or more intraoral or extra-oral light-translucent or light-opaque masks that shield from light one or more non-regions. In some embodiments, light reaching a region can have an intensity that is greater than a threshold value. In some embodiments, the threshold value can be at an intensity as discussed elsewhere herein.

A patient can position light-therapy apparatus 20 herself or himself to accurately and repeatedly illuminate a desired location in the patient's dental and maxillofacial areas when light-therapy apparatus 20 is in a use position. Consistent positioning of light-therapy apparatus 20 during the course of a patient's treatment can make therapy more effective and repeatable, and ease of use of light-therapy apparatus 20 can facilitate patient compliance with a given treatment regimen.

In the embodiment illustrated in FIGS. 1-4, a plurality of light sources 30A, 30B, 30C, 30D, 30E, 30F, 30G, and 30H are disposed at symmetrical locations about frame 22. In other embodiments, a plurality of light sources 30 can be disposed asymmetrically about frame 22, the position of light sources 30 on frame 22 can be adjustable, or one or more than one light source 30 can be removable, to permit light-therapy apparatus 20 to be configured to administer, in one embodiment through the patient's face, light to a specific region or regions of a patient's maxillary or mandibular bone, such as specific regions of the patient's maxillary or mandibular alveolar bone, temporomandibular joint, condyle, or glenoid fossa. For example, each light source 30 can be configured to illuminate the bone surrounding a specific number of teeth, for example two or three teeth, at a specific location.

Figure 7A:
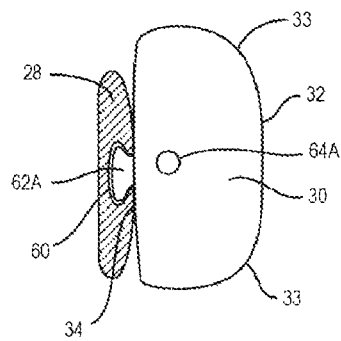
FIG. 7A is a partial cross-sectional view of a support arm of an embodiment of a light-therapy apparatus showing the engagement between a track engaging ridge on a light source and a track formed in the support arm.

In use, light is emitted from an inner surface 32 of one or more light source 30 extra-orally towards a desired area. As used herein, the term "inner surface" refers to the surface of an element that is closest to the facial regions of a patient when light-therapy apparatus 20 is in the use position. Inner surface 32 can have rounded edges 33, as shown for example in FIGS. 7A and 7B, and can comprise a clear resin window covering the light emitters, to provide greater comfort for a patient when light-therapy apparatus 20 is in the use position and when the light emitter's contact the patient's face. Any suitable light emitter can be used for the one or more light source 30. In some embodiments, light is emitted by arrays of discrete LEDs. The LEDs can be arranged in any of a wide variety of patterns. For example, the LEDs can be arranged in staggered parallel rows to maximize the density of LEDs in the LED array. The LEDs can be arranged to achieve substantially uniform optical intensity over the light-emitting inner surface 32 of one or more light source 30. Alternatively, the LEDs can be clustered or distributed to provide varying optical intensities over an area of a light source. In some embodiments, each array can comprise 5 to about 20 LEDs or other light emitters. In some embodiments, each array can comprise about 20 to about 50 or more LEDs or other light emitters. In other embodiments, light from one or more light source 30 can be emitted by one or more than one VCSEL. A plurality of VCSELs can be disposed in an array on a light source 30. The VCSELs can be disposed in aligned or staggered parallel rows. In another embodiment, a combination of different types of light emitters, such as LEDs and VCSELs can be provided for the same light source.

A light-therapy apparatus can be configured to provide light with a desired light intensity. In one embodiment the average light intensity produced by a light source 30 is at least about 10 mW/cm$^2$. In other embodiments, the average light intensity produced by a light source is be about 1 mW/cm$^2$ or greater, about 3 mW/cm$^2$ or greater, about 5 mW/cm$^2$ or greater, about 7 mW/cm$^2$ or greater, about 12 mW/cm$^2$ or greater, about 15 mW/cm$^2$ or greater, about 20 mW/cm$^2$ or greater, about 30 mW/cm$^2$ or greater, about 50 mW/cm$^2$ or greater, about 75 mW/cm$^2$ or greater, about 100 mW/cm$^2$ or greater, about 200 mW/cm$^2$ or greater, about 500 mW/cm$^2$ or greater, or about 1 W/cm$^2$ or greater. In other embodiments, the average light intensity produced by a light source can be about 20 mW/cm$^2$ or less, about 30 mW/cm$^2$ or less, about 50 mW/cm$^2$ or less, about 75 mW/cm$^2$ or less, about 100 mW/cm$^2$ or less, about 200 mW/cm$^2$ or less, about 500 mW/cm$^2$ or less, about 1 W/cm$^2$ or less, or about 2 W/cm$^2$ or less. In some embodiments, a light source 30 has an average intensity that is, or can be adjusted to be, in the range of about 10 mW/cm$^2$ to about 60 mW/cm$^2$, or about 20 mW/cm$^2$ to about 60 mW/cm$^2$. In some embodiments, the output of light source 30 is pulsed. In such embodiments, the peak light intensity can be significantly higher than about 50 mW/cm$^2$. In other embodiments, the output of light is continuous. In some embodiments, the light intensity can vary overtime in a cyclical or non-cyclical fashion. The light intensity can vary with or without pulsing. In some embodiments, the light intensity can vary with pulse width modulation. Any other light intensity described anywhere above can be provided by the light-therapy apparatus.

The light emitters can be controllable so that the number of lights that are on or off at a given period can be individually controllable. For example, each light emitter can be on or off relative to other light emitters. This can be desirable when it is desirable to administer light to different regions. Thus, the light-therapy apparatus can alter the position of light being administered. In another embodiment, each light emitter can be on or off relative to other light emitters. For example, at some times, light emitters emitting in a first wavelength range can be on while light emitters emitting in a second wavelength range can be off, vice versa, or both types of light emitters can be on or off Thus, the wavelength of light being administered can be varied. In some embodiments, the intensity of light being administered can be varied (e.g., by turning some light emitters on or off, or varying the intensity emitted by the light emitters). If the light emitters are pulsed, their duty cycle can be adjustable; e.g., light emitters can be capable of having a duty cycle of about 10%, about 20%, about 30%, about 40%, about 50%, about 60%, about 70%, about 80%, or about 90%. The light emitters can be capable of pulsing can occur with any frequency. For example, light emitters can be pulsed on the order of every picosecond, nanosecond, microsecond, millisecond, second, multiple seconds, or minutes. Light emitters can provide light with frequencies of about 1 mHz, about 10 mHz, about 50 mHz, about 100 mHz, about 500 mHz, about 1Hz, about 2 Hz, about 5 Hz, about 10 Hz, about 15 Hz, about 20 Hz, about 25 Hz, about 30 Hz, about 35 Hz, about 40 Hz, about 50 Hz, about 70 Hz, about 100 Hz, about 200 Hz, about 500 Hz, or about 1 kHz. The light-therapy apparatus can be controllable so that any of the aforementioned characteristics of light emission (e.g., whether the light is on or off, continuous or pulsed, duty cycle, frequency, intensity, wavelength) can be varied or maintained in accordance with instructions from a controller.

The light-therapy apparatus can be capable of emitting light with varying intensities. Any ratio of intensities can be provided for light emitted at any of the wavelengths. For example, light emitted at a first wavelength can have about a 1.1×, 1.2×, 1.3×, 1.5×, 1.7×, 2.0×, 2.5×, 3.0×, 3.5×, 4.0×, 5.0×, 10×, 12×, 15×, 20×, 30×, 50×, 100× intensity compared to a light emitted at a second wavelength. In some embodiments, the same number of light emitters having a first set of characteristics and a second set of characteristics can be provided. In other embodiments, more light emitters having a first set of characteristics can be provided than light emitters having a second set of characteristics. For example, about 1.1×, 1.2×, 1.3×, 1.5×, 1.7×, 2.0×, 2.5×, 3.0×, 3.5×, 4.0×, 5.0×, 1 O×, 12×, 15×, 20×, 30×, 50×, 100× light emitters having the first set of characteristics can be provided as light emitters having the second set of characteristics. One or more light source 30 can comprise optical elements such as one or more lenses or reflectors to focus and direct light from the light source 30 onto a selected area. Any type of optical lens or reflector can be used. For example, an optical lens can be used to collimate the light, diffuse the light, or focus the light. In some embodiments, one or more Fresnel lenses or telecentric lenses can be used. Any type of reflector can be used. A lens can be provided to cause light divergence, or light convergence. For example, one or more mirrors can be incorporated. The mirrors can be used to assist with scattering, redirecting, or focusing the light. Such optical elements can be suitably encapsulated in plastic or similar material, which can be transparent, translucent or opaque. The plastic or other encapsulating material can form an exterior surface of a light source. The light emitters or optical elements can be provided within an interior portion of the light source. Alternatively, encapsulating materials need not provided, and the optical elements or the light emitters can be provided as an exterior surface of a light source. In some embodiments, there can be a gap between a light emitter and an encapsulating material. A gap can exist between a light emitter and an exterior surface of the light source.

An exterior surface of a light source can contact a patient's face. For example, an encapsulating material for a light source can contact a patient's face. In other examples, optics, such as a lens optionally contacts the patient's face. In some embodiments, a light emitter can contact the face directly, while in other embodiments, the light emitter does not contact the face directly.

Figure 5:
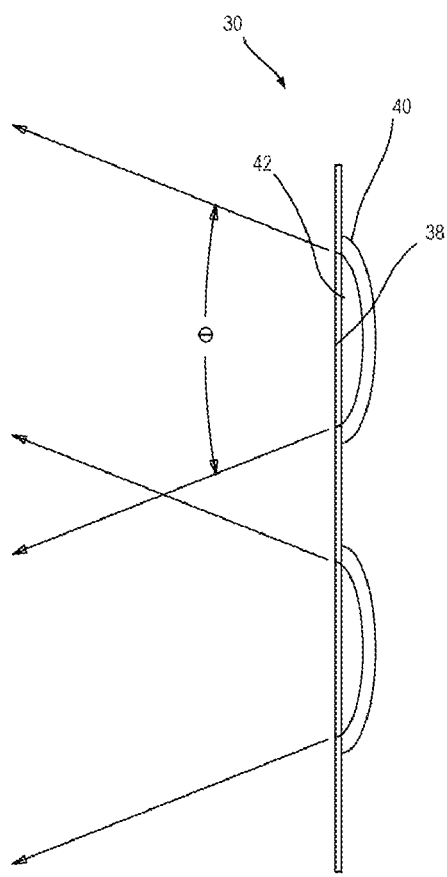
FIG. 5 is a schematic cross-sectional view through a portion of a light source having a light emitter and a reflector.

FIG. 5 shows a portion of a light source 30. In the illustrated embodiment, a light emitter 38 (which can, for example, comprise a junction in a light-emitting diode or other light-emitting semiconductor device) is located adjacent to a reflective backing 40. A curved light-reflecting recess 42 is provided adjacent to light emitter 38. Light from light emitter 38 is reflected in recess 42 to form a beam. The beams from all light emitters of alight source 30 can combine to illuminate the selected tissues. The area covered by the beam will depend upon the tissues which it is desired to treat. In some embodiments, the beam of light emitted by a light source 30 diverges to cover an area of tissue larger than the area of the light-emitting part of a light source 30. In other embodiments the emitted light converges to provide increased light intensity at the location of the tissues that it is desired to treat. In some embodiments, the emitted light diverges in a beam having an included angle 8 in the range of about 450 to about 60°. The emitted light can form a diverging to have an included angle 8 of 0° to about 15°, 0° to about 30°, 0° to about 45°, 0° to about 60°, 0° to about 75°, 0° to about 90°, or 0° to about 120°.

Since LEDs and other light emitters can emit heat when they are operated, it can be desirable to provide a suitable mechanism for dissipating the heat to prevent any parts of light-therapy apparatus 20 that are proximate to a patient's skin from getting too hot. In some embodiments, heat is dissipated by passive cooling, such as, for example, provision of appropriate heat sinks or permitting air to flow freely around light sources Heat sinks 36 are an example of passive cooling. Heat sinks can be in thermal communication with one or more light source. In one embodiment, one or more light source can comprise thermally-conductive LED wafers mounted on a suitable heat sink. Heat from the LED wafers can be conducted into the heat sink and dissipated (see, e.g., FIGS. 9B, 9C and 9D as shown and as described below).

In some embodiments, one or more light source 30 can include a forced air, liquid, or solid state cooling system. In one embodiment, a heat sink has pins projecting from its face that is away from LED arrays. A fan causes air to flow past pins to carry away excess heat. Other fluids, such as other gases, or water or other liquids, can be driven past the pins to assist with carrying away excess heat.

A cooling system allows for administration of light without the danger of potential burns to the patient and allows for greater efficiency and control of the apparatus. A cooling system can be installed on light-therapy apparatus 20 in any suitable manner. The cooling system can be in thermal contact with one or more light source. In some embodiments, a cable recess (illustrated as 64A or 64B in FIGS. 7 A and 7B) can be provided within one or more light source 30 to accommodate aspects of a cooling system or cables that can be used with or form part of light-therapy apparatus 20.

In one embodiment, as shown in FIGS. 8A-8D, a cooling mechanism 83 can be provided. In one embodiment, the cooling mechanism can contact one or more light source 81, and can be formed of a conductive material. The cooling mechanism can conduct heat from the one or more light source and dissipate the heat to the surroundings. The cooling mechanism can function as a heat spreader or heat sink. The cooling mechanism can have an increased surface area by including one or more open region 83a disposed between one or more solid region 83b. A fluid is optionally forced through the cooling mechanism.

In one embodiment that can use either passive or active cooling, or both, support arms 28 can be constructed from milled aluminum, and one or more light source 30 can be constructed so as to be engageable with a track formed on the inner surface 34 of support arms 28, as shown for example in FIG. 7 A One or more light source 30 can be engageable with a track 60 formed in the inner surface 34 of support arms 28 via a track-engaging ridge 62A formed on the one or more light source 30. Track 60 and track-engaging ridge 62A can have any suitable complementary configuration and orientation to retain one or more light source 30 against support arms 28 and oriented toward a wearer's face when light-therapy apparatus 20 is in the use position. One or more light source 30 can be slideable within track 60, to facilitate the positioning of light source 30. One or more light source 30 can alternatively be coupled to support arms 28 in any other suitable manner, such as by a clip, clamp, adhesive, thermally conductive adhesive, hook and loop fastener, or any other connection mechanism. In some embodiments, one or more light source 30 can be integrally formed with support arms 28.

In some embodiments, the track can have a fixed position relative to the rest of the frame. In one embodiment, a track can be a shaped feature within the frame. In other embodiments, the track can be adjustable to the rest of the frame. For example, the track can be formed of a material that can allow a user to bend the track to a desired configuration, and can stay at that configuration. In other embodiments, adjustment features, such as hinges, joints, or other moving parts can allow a user to adjust a track position.

One or more light source can slide along a length of the track. Alternatively, light sources can be attached or removed at different points along the track. In some embodiments, light sources can be attached or removed only at certain locations along the track (e.g., discrete portions that accept the light sources). Alternatively, one or more light source can be attached or removed at any point along the track. Thus, one or more light source can be displaced.

In some embodiments, one or more light sources can be applied to the frame so that they have a fixed orientation. Alternatively, the one or more light sources can be rotatable relative to the frame. Depending on the dimensions of a light source, this can allow variation in the region receiving light. One or more light source can be rotatable about one or more axis. For example, one or more light source can be rotatable about a first axis that is about parallel, i.e., ranging from +18° to −18° of being parallel, with the support arm, about a second axis that is perpendicular to the support arm, or about a third axis that is perpendicular to both the first and second axis. In some embodiments, one or more light source can be supported by a hinge, pivot, or other configuration that can allow one axis of rotation. In other embodiments, multiple hints, pivots, or other mechanisms can be provided that can allow for two or more axes of rotation. In another embodiment, one or more light source can be supported by a ball and socket joint that can provide multiple degrees of freedom. The orientation of one or more light source relative to the frame can be manually adjusted. A user can turn one or more light source to a desired orientation. Alternatively, the orientation of one or more light source can be remotely controlled. For example, one or more actuator can be provided that can cause one or more light source to turn to a desired orientation. Actuators can operate based on a signal received from a controller. The signal can be received via a wired connection or wirelessly, as discussed elsewhere herein.

In another embodiment, as shown in FIGS. 8A-8D, one or more light source 81 can be configured to slide along a support arm 88. For example, a support arm on the right side of the face and a support arm on the left side of the face can comprise a track 85 that can enable a light assembly to slide along the track. The track can be parallel to the support arm. Alternatively, the track can be provided at some non-parallel angle to the support arm. In some embodiments, the track or support arm can have a substantially horizontal orientation when the apparatus is in use. A light assembly can comprise one or more light source 81, temperature control system 83 or vertical track 87. In some embodiments, one or more light assembly can be provided on a right support arm or one or more light assembly can be provided on a left support arm. In some embodiments, a support arm does not comprise a light assembly. A track on a support arm can be about horizontal, i.e., ranging from +18° to −18° of being horizontal. In alternate embodiments, the track can have any other orientation, which can comprise a vertical track, slanted travel, or curved track. In some embodiments, one, two, three, or more tracks can be provided on a support arm. The position of a light assembly relative to a support arm can be manually adjusted. For example, a user can push the light assembly to a desired position along the support arm. Alternatively, the position of the light assembly can be remotely controlled. For example, one or more actuator can be provided that can cause the light assembly to move to a desired position. Actuators can include, but are not limited to, motors, solenoids, linear actuators, pneumatic actuators, hydraulic actuators, electric actuators, piezoelectric actuators, or magnets. Actuators can cause the light assembly to move based on a signal received from a controller.

In some embodiments a vertical track 87 can be provided. The vertical track can be about perpendicular, i.e., ranging from +9° to −9° of being perpendicular, to a track along a support arm 88. Any description herein of the vehicle track can be applied to any other secondary track of any orientation that can be in communication with a track on a support arm. The vertical track can be adjustable relative to a track on the support arm. For example, the vertical track can slide along the track along the support arm. In some embodiments, the vertical track can be removable or attachable to the support arm, such as on the track along the support arm. In some embodiments, the vertical track can be attachable at one or more location along the support arm. Such locations can be discrete or continuous. One, two, three, four, or more vertical tracks can be attachable to the support arm simultaneously. The position of a vertical track relative to a support arm can be manually adjusted. For example, a user can push the vertical track to a desired position along the support arm. Alternatively, the position of the light assembly can be remotely controlled. For example, one or more actuator can be provided that can cause the light assembly to move to a desired position. The actuator can respond to a signal from a controller. The vertical track is optionally rotatable relative to the support arm. For example, the vertical track can be rotatable so that it is no longer vertically oriented, but can be horizontally oriented, or provided at a slant. The vertical track can be rotated manually. Alternatively, one or more actuator can be provided that can cause the vertical track to rotate to a desired position. The actuator can respond to one or more signal from a controller.

One or more light source 81 can be configured to slide along a vertical track. Alternatively, one or more light source can be attachable or removable from the vertical track at discrete or continuous locations. The position of one or more light source relative to a vertical track can be manually adjusted. For example, a user can push one or more light source to a desired position along the vertical track. Alternatively, the position of one or more light source can be remotely controlled. For example, one or more actuator can be provided that can cause one or more light source to move to a desired position. One or more light source can have a fixed orientation relative to the vertical track. Alternatively, it can be rotatable about a first axis, second axis, or third axis, such as those previously described. One or more light source can be manually oriented, or can have an actuator that orients the light source in response to a signal received from a controller. In one embodiment, one or more light source can be attached to a vertical bar 89 that can allow the light source to rotate about the bar within a limited range. This can allow the light source to have a desired position relative to a patient's face when in use. In one embodiment, two light sources can be provided along a vertical track. In alternate embodiments of the invention, the vertical track need not be perpendicular to a support arm and vertical. For example, a secondary track can be provided at any angle relative to the support arm (e.g., at about 15 degrees, about 30 degrees, about 45 degrees, about 60 degrees, about 75 degrees, or about 90 degrees relative to the support arm). In some embodiments, the secondary track can have a fixed orientation relative to the support arm. Alternatively, the secondary track can be rotatable relative to the support arm.

In some embodiments, one or more light source can rotate or move relative to the secondary track. For example, a hinge, pivot, ball and socket joint, or other type of mechanism can be provided that can allow one or more light source to rotate relative to the second track. In some embodiments, one or more light source can rotate within a limited range. In some embodiments, the relative position of one or more light source can be adjusted manually. For example, one or more light source can contact a patient's face and the position of the light source can conform to the contours of the patient's face. For example, the relative angle of the light source can conform to the patient's face. In other embodiments, one or more actuator can be provided to adjust the position of one or more light source. An actuator can operate in response to a signal received from a controller. In some embodiments, the position of one or more light source can be locked so that once a desired configuration for the light source has been set, it is not be adjusted manually. Alternatively, one or more light source can be responsive to force, so that a patient or other individual can be able to adjust the position of the light source.

In some embodiments, a third track, or fourth track can be provided. In one embodiment, a third track can be provided on a secondary track, or a fourth track can be provided on a third track. The support arm can comprise any number of tracks that provide various degrees of flexibility in the locations of one or more light source. In other embodiments, the support arm comprises one or more other components or configurations which can comprise but are not limited to bars, notches, slides, elastics, or holes.

A heat sink 36 can interpose one or more light source 30 and inner surface 34 of support arms 28. Heat sink 36 can, for example, be made of copper, aluminum, or other suitable thermally conductive material, to enhance dissipation of heat from light source

Figure 7B:
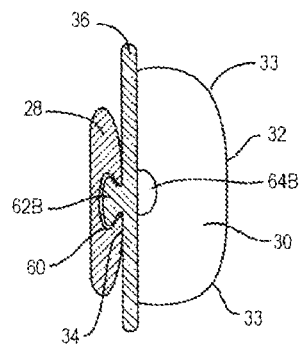
FIG. 7B is a partial cross-sectional view of a support arm of an embodiment of a light-therapy apparatus showing the engagement between a track engaging ridge on a heat sink and a track formed in the support arm.
Figure 8A:
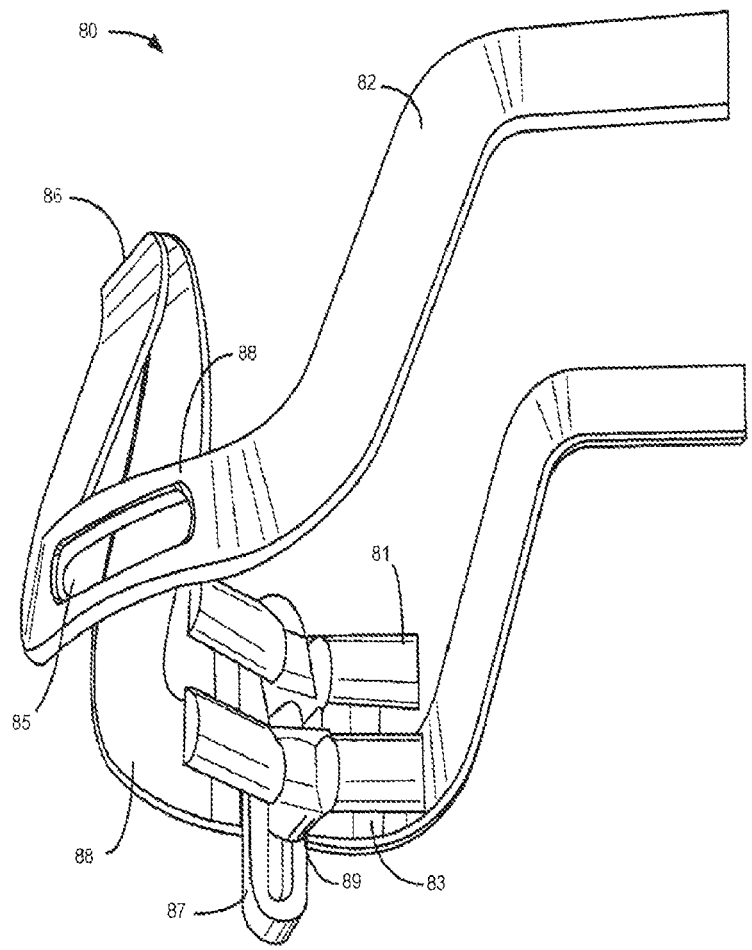
FIG. 8A shows a first view of a light-therapy apparatus in accordance with an embodiment.
Figure 8B:
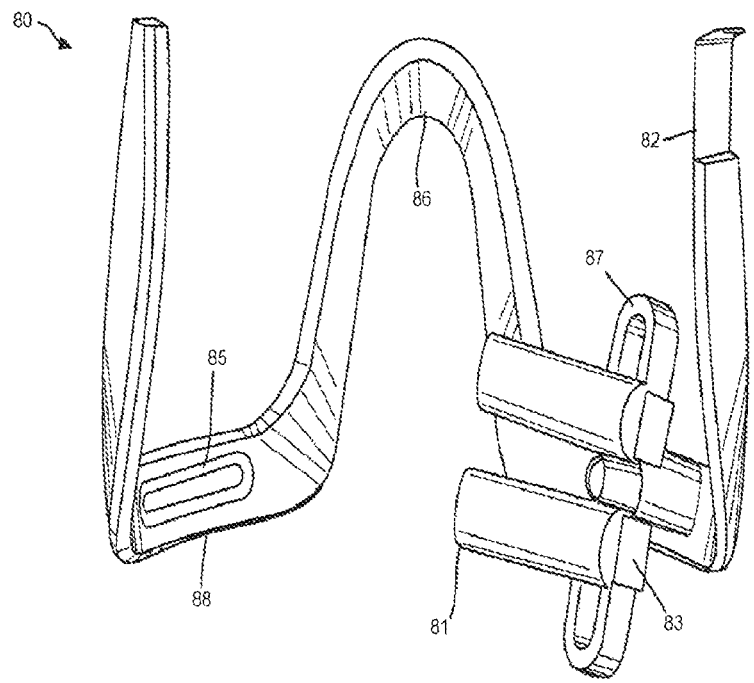
FIG. 8B is a rear view of the light-therapy apparatus of FIG. 8A.
Figure 8C:
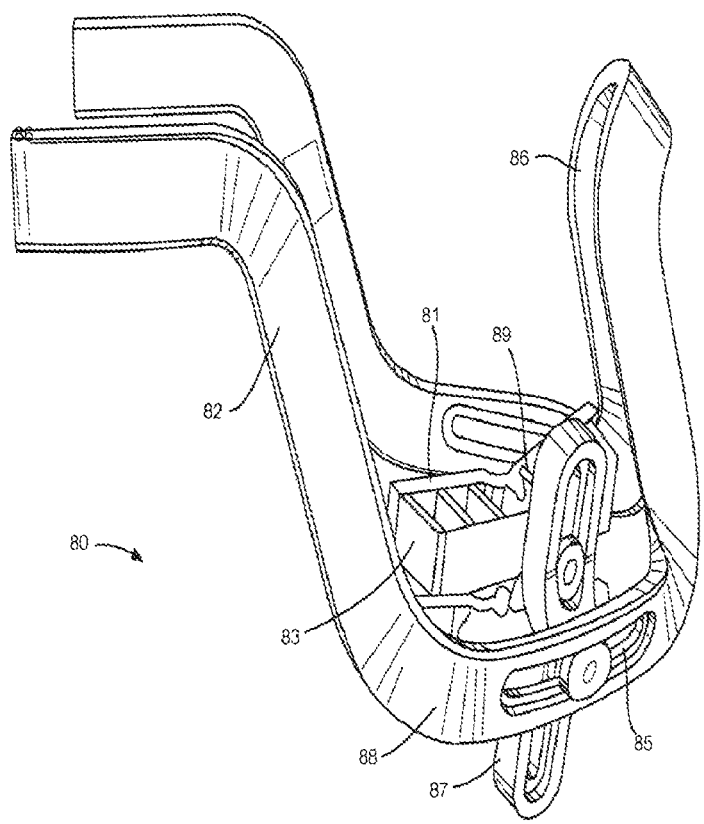
FIG. 8C is a side view of the light-therapy apparatus of FIG. 8A.
Figure 8D:
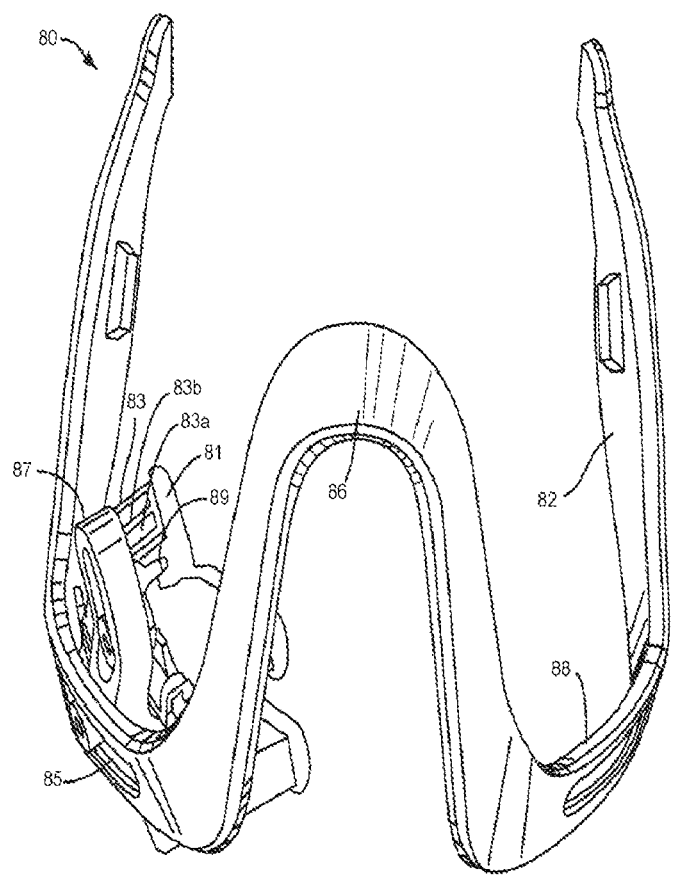
FIG. 8D is a front view of the light-therapy apparatus of FIG. 8A.
Figure 9A:
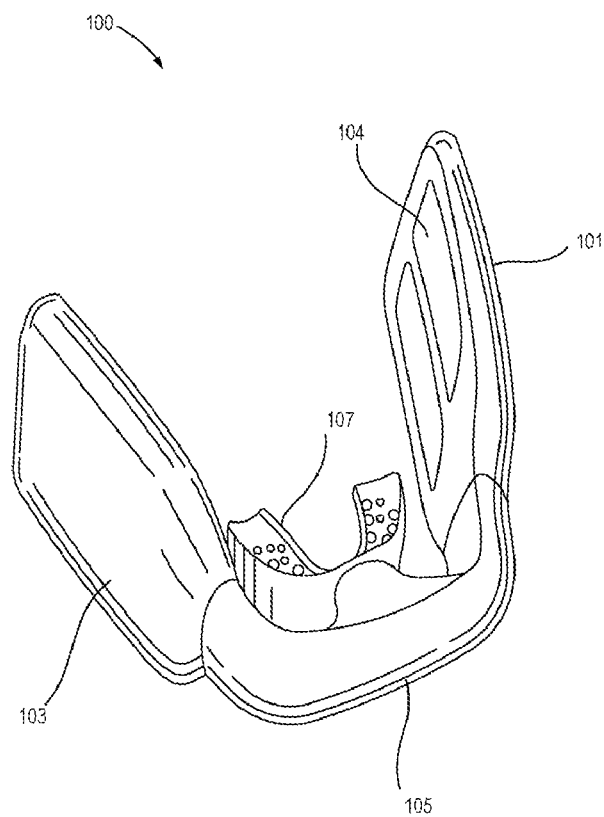
FIG. 9A is a perspective view of a light-therapy apparatus having an intra-oral tray, an extra-oral bridge, and left and right side extra-oral LED arrays.
Figure 9B:
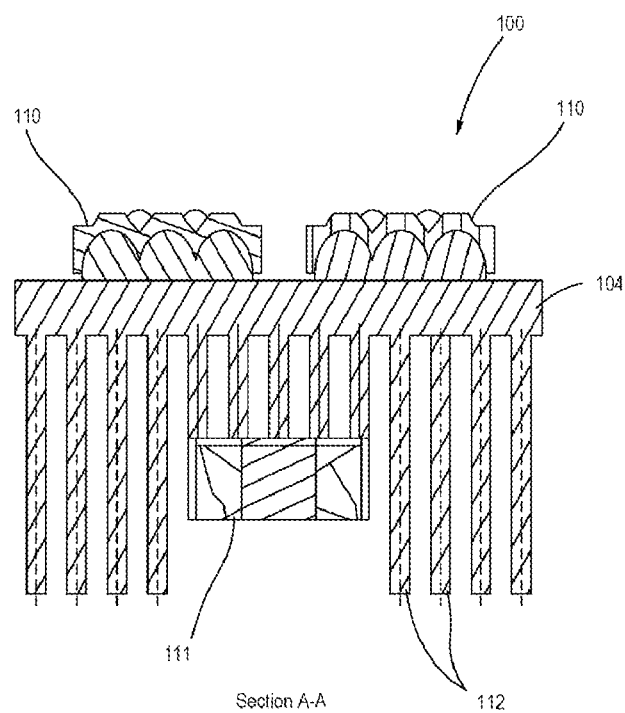
FIGS. 9B, 9C and 9D are respectively a cross-section, a front side elevation and a rear elevation of a light source having a cooling fan, a heat sink and two arrays of light emitters.
Figure 9C:
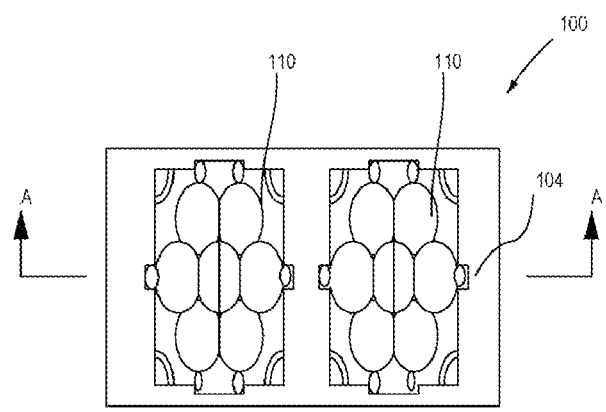
Figure 9D:
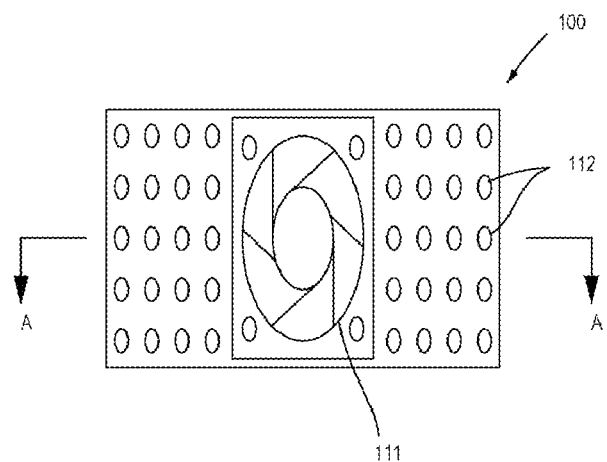

30. With reference to FIG. 7B, heat sink 36 can be engageable with track 60 formed in the inner surface 34 of support arms 28 via a track-engaging ridge 62B formed on heat sink 36. Track 60 and track-engaging ridge 62B can have any suitable complementary configuration and orientation to retain heat sink 36 against support arms 28, and to retain light source 30 oriented toward a wearer's face when light-therapy apparatus 20 is in the use position. Heat sink 36 can alternatively be coupled to support arms 28 in any suitable manner, rather than via engagement with track 60 through optional track-engaging ridge 62B. For example, heat sink 36 can be coupled to light source 30 by a clip, clamp, adhesive, thermally conductive adhesive, hook and loop fastener, or any other connection mechanism. In some embodiments, heat sink 36 can be integrally formed with either or both of light source 30 or support arms 28. In some embodiments, a heat sink can be coupled to each light source.

A gas, liquid, or solid state cooling system can be provided on support arms 28 to maintain light source 30 at a suitable temperature, or passive cooling means can be employed as previously described. In some embodiments, the temperature of the inner surface 32 of light source 30 can be maintained below a temperature of about 41° C., in one embodiment, from about 20° C. to about 35° C. A cable recess, illustrated for example as 64A or 64B (FIGS. 7A and 7B) can be provided in light source 30 to accommodate cables for carrying electricity to light source 30 or components of a gas or liquid cooling system. An optional sensor or a controller 50 as described below can be provided, to automatically switch off any light source if the temperature of inner surface 32 or some other designated portion of that particular light source 30 exceeds a predetermined value.

The temperature of a light source can be varied or maintained to maintain or approach a desired temperature. For example, a cooling system can be used to reduce the temperature of a light source and prevent it from becoming too hot. In some situations, a temperature control system can be provided that can prevent a light source from being too cold or too hot. A desired temperature range can be preset. The desired temperature range can be fixed or adjustable. In some embodiments, a desired temperature range can range about ±10° C., about ±7° C., about ±5° C., or about ±3° C. of the ambient air temperature, or range about ±10° C., about ±7° C., about ±5° C., or about ±3° C. of the skin temperature of the user wearing the apparatus.

In some embodiments, light-therapy apparatus 20 is disposed and supported exclusively or substantially external to a mouth of a patient. A light-therapy apparatus which is supported exclusively or substantially external to a mouth of a patient can facilitate the use of that light-therapy apparatus optionally with one or more of a wide variety of intra-oral orthodontic devices. For example, orthodontic appliances, such as those disclosed herein, can be provided as intra-oral orthodontic devices. In other embodiments, a portion of light-therapy apparatus 20 can be disposed within a mouth of a patient, to assist in securing or positioning light-therapy apparatus 20 on a patient's face or head. For example, bite wings or an intra-oral tray which is supported in position by having a patient hold the intra-oral tray between her or his upper and lower teeth can be coupled to light-therapy apparatus 20 to assist in retaining or supporting the apparatus. An example of a suitable intra-oral tray is described in PCT publication numbers WO2009/000075 and WO 2006/087633, both of which are incorporated by reference herein in their entirety. In some embodiments, an intra-oral device can comprise one or more light sources or be capable of intra-orally administering light to a region. In some embodiments, light can be administered to a region intra-orally or extra-orally or both. In other embodiments, light is administered to a region only extra-orally, and is not administered to a region intra-orally. In some embodiments, light can only be administered to a region transdermally through the skin of the patient. FIGS. 9A-9D and 10-13 show an illustrative light-therapy apparatus 100 that comprises an extra-oral light source 104 having a right side 101 and a left side 103 (as viewed from the front of the apparatus), an extra-oral bridge 105, and an intra-oral tray 107. Intra-oral tray 107 registers to a patient's teeth. A light source 104 is rigidly connected to intra-oral tray 107 by extra-oral bridge 105. Alternatively, some flexibility can be provided between the intra-oral tray and the extra-oral bridge. Therefore, a patient can position a light source 104 accurately and repeatedly to illuminate a desired location in the patient's dental or maxillofacial areas by inserting intra-oral tray 107 into his or her mouth and biting intra-oral tray 107 so that it registers to at least some of the patient's teeth. This stabilizes light-therapy apparatus 100 and positions a light source 104 at a desired position. The consistent alignment and targeting of light from the light source 104 during subsequent treatments makes the treatments more repeatable.

Figure 11:
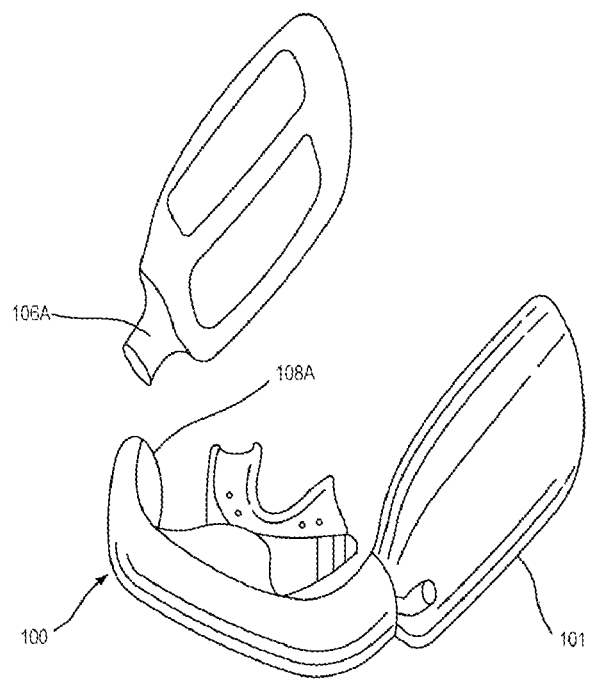
FIG. 11 is a view from the front-left side of the light-therapy apparatus of FIG. 9A with a portion of the extra-oral LED array detached.
Figure 12:
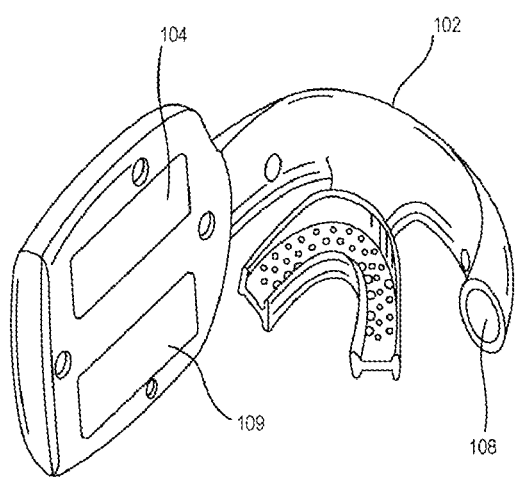
FIG. 12 is a view from the rear right side of a portion of the light-therapy apparatus of FIG. 9A.
Figure 13:
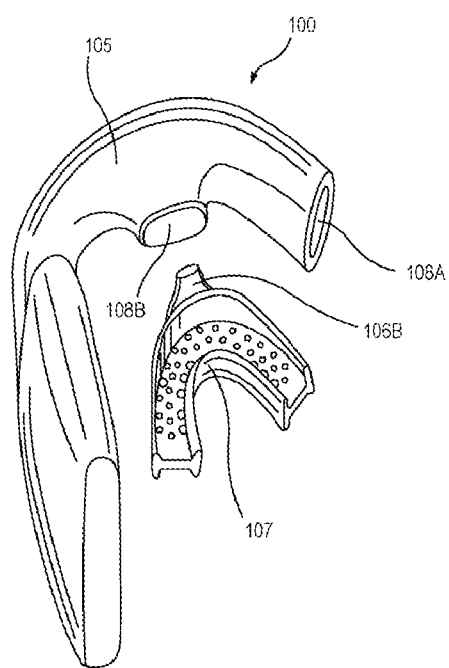
FIG. 13 is a view from the left rear side of a portion of the light-therapy apparatus FIG. 9A with the intra-oral tray detached.

In the illustrated embodiment, extra-oral bridge 105 is removable from an extra-oral light source 104 and intra-oral tray 107. Providing a light-therapy apparatus l00 having major components that are detachably connectable to one another adds versatility. A design which permits the major components of the light-therapy apparatus to be disassembled and reassembled while preserving alignment of extra-oral light source 104 to intra-oral tray 107 has the advantage that the apparatus can be disassembled for storage or transportation and then used immediately after assembly. FIG. 11 shows light-therapy apparatus 100 with extra-oral light source left side 103 detached from extra-oral bridge 105.

Extra-oral bridge 105, extra-oral light source right side 101, and extra-oral light source left side 103 can be secured together via a suitable connector. For example, extra-oral bridge 105, the extra-oral light source right side 101, and the extra-oral light source left side 103 can be connected by inserting male connector portions 106A of the extra-oral light source right and left sides 101 and 103 into corresponding female connector portions 108A of extra-oral bridge 105 (see FIG. 11). Suitably, the suitable connector allows extra-oral light source right and left sides 101 and 103 to be detached from extra-oral bridge 105 for ease of use and flexibility.

Figure 10:
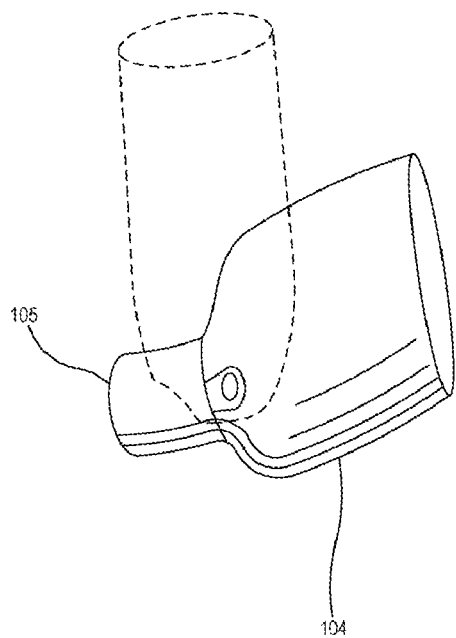
FIG. 10 is a side view of a portion of the light-therapy apparatus of FIG. 9A with the end of the extra-oral bridge attached to the extra-oral LED array and with the extra-oral LED array in a first orientation and a second orientation (shown in broken lines) with respect to the extra-oral bridge.

In some embodiments, extra-oral light source right and left sides 101 and 103 are rotatable between a sagittal orientation (as shown in FIG. 10) and a vertical orientation (indicated in dotted outline in FIG. 10). Light source right and left sides 101 and 103 can be locked at a desired angle of rotation by any suitable mechanism. This permits light source right and left sides 101 and 103 to be arranged so that the light that they emit fully covers the desired treatment areas.

Intra-oral tray 107 can be connected to extra-oral bridge 5 by way of another suitable connector. In the embodiment illustrated in FIG. 13, a male portion 106B of intra-oral tray 7 is removably received in a female portion 108B of extra-oral bridge 105. Where intra-oral tray 7 is removable from extra-oral bridge 105, extra-oral bridge 105 can be reused for other patients (after suitable sterilization). Intra-oral tray 107 can be disposed of after it is no longer required by a patient. In some embodiments, extra-oral bridge 105 is non-removably attached to intra-oral tray 107.

Intra-oral tray 107 can be inserted into a patient's mouth and can be suitably shaped to fit around a patient's teeth. Intra-oral tray 107 can register with a few selected teeth (for example, intra-oral tray 107 can comprise a bite tab) or can fit around the patient's full set of teeth. In one embodiment, the intra-oral tray 107 comprises a frame of a plastic or other suitable material that can serve as a skeleton for a settable material. The intra-oral tray frame can be perforated to aid retention of the settable material. The intra-oral tray frame can comprise extra-oral bridge 105 or a connector to connect to extra-oral bridge 105. The intra-oral tray can be optionally provided, and other securing means for an extra-oral bridge can be provided. For example, frames, as described elsewhere herein, can support an extra-oral bridge or extra-oral light source relative to the patient's face. Prior to being used in the administration of light, a frame for intra-oral tray 107 can be filled with a suitable settable material (for example a clear vinyl siloxane gel or similar material) which sets around the patient's teeth and subsequently allows repeatable alignment of intra-oral tray 107 in the patient's mouth. Where intra-oral tray 107 could being the path of light as it travels from light source 104 to selected tissues, the material of intra-oral tray 107 should be transparent to the light.

Extra-oral bridge 105 can conform around the jaw line of a patient. The light source right and left sides 101 and 103 can be respectively positioned on the right and leftsides of a patient's face along the patient's jaw line. Extra-oral bridge 105 can be adjustable to permit alignment of light source left and right sides 101 and 103 with selected areas to be irradiated. Light source left and right sides 101 and 103 are extra-oral (outside of the patient's oral cavity). Light can pass from left and right sides 101 and 103 through tissues of the patient's lips and cheeks into selected areas on the patient's gums or in the patient's jaws. Light can be administered transcutaneously through the patient's face to any region as disclosed herein.

In some embodiments, one or more light source 104 emits light toward the patient. Any light source, with any configuration of light emitters as described anywhere else herein can be used. In some embodiments, a light source 104 has an inner surface 109 (see FIG. 12) that is placed near or against the patient's skin adjacent to the tissues that it is desired to treat. In some embodiments, one or more light source can contact the patient's face. The one or more light source can contact the portion of the face overlying a desired region. Light is emitted is from inner surface 109 toward the area of treatment. In some embodiments, left and right sides 101 and 103 of light source 4 each have a length similar to a significant fraction of the length of a human jaw. For example, left and right sides 1 and 3 can each have a length of about 20 mm to about 90 mm in some embodiments and about 25 to about 45 mm or about 60 mm in some embodiments. A light source can have any other dimensions, including those disclosed herein. In cases where a light source 104 is intended to treat or prevent a localized condition, then light source 104 can be smaller in extent. In some embodiments, light source 104 has optics that emit light in the form of diverging beams. The light source is usable with optics as described anywhere above. In such cases, light source 104 can be somewhat smaller than the area of tissues to be treated because light from light source 104 can diverge as it passes through the tissues of the patient's lips and cheeks before reaching the tissues of the jaw and or gums.

Light source 104 can be wide enough to irradiate both upper and lower jaws of a patient simultaneously although in some embodiments light source 104 can be narrower. For example, light source 104 has a width in the range of about 12 mm to about 40 mm in some embodiments (e.g. about 15 to about 17 mm in some embodiments).

In some embodiments, a light source irradiates only an upper jaw or a lower jaw, or portions thereof.

In some embodiments, the light source 104 comprises thermally-conductive LED wafers mounted on a suitable heat sink. In use, heat from the LED wafers can be conducted into the heat sink and dissipated. For example, referring to FIGS. 9B, 9C and 9D, light source 104 can comprise one or more arrays 110 of LEDs that are mounted to a heat sink 104. Heat sink 104 can have pins 112 projecting or otherwise extended from its face and away from LED arrays 110. A fan 111 can be used to cause air to flow past pins 112 to carry away excess heat. In some embodiments, the light source can comprise any suitable mechanism described herein for dissipating the heat to prevent one or more portions of light-therapy apparatus 100 that are proximate to a patient's tissue from getting so hot as to burn the tissue or cause significant patient discomfort.

While the invention is described herein as usefully employing LEDs, other light emitters such as lasers could suitably be employed. The character of the light emitted by light source right and left sides 101 and 103 will depend upon the nature of the LEDs or other light emitters in light source 104. It is generally desirable that the emitted light comprise light in the wavelength range of 620 nm to 1000 nm. In some embodiments the emitted light comprises light having a wavelength in at least one of the following wavelength ranges: about 820 to about 890 nm or about 620 to about 680 nm. In some embodiments, light having a wavelength in the ranges of about 820 to about 890 nm and about 620 to about 680 nm can be provided. Light having wavelengths corresponding to or falling within one or more of the following ranges can be particularly effective: about 613 nm to about 624 nm, about 667 nm to about 684 nm, about 750 nm to about 773 nm, about 812 nm to about 846 nm, or any other wavelengths described elsewhere herein. The range about 613 nm to about 624 nm corresponds to a band at which reduced cytochrome c oxidase absorbs light. The range about 812 nm to about 846 nm corresponds to a band at which oxidized cytochrome c oxidase absorbs light. Light sources can be configured to provide light of any other wavelength as described anywhere above.

Figure 14:
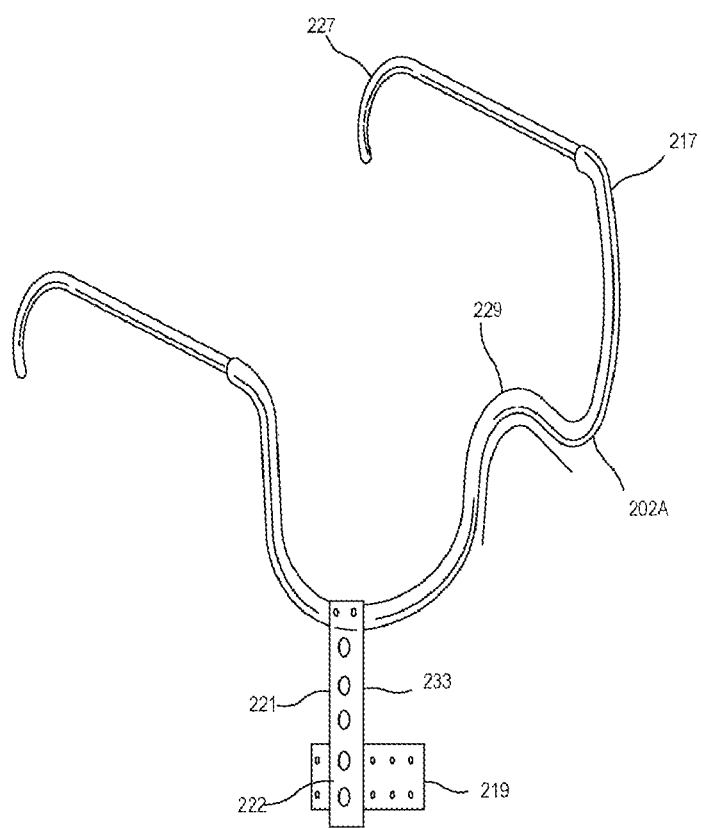
FIG. 14 is a perspective view of a light-therapy apparatus according to an embodiment in which an LED array is supported by a head-set.
Figure 15:
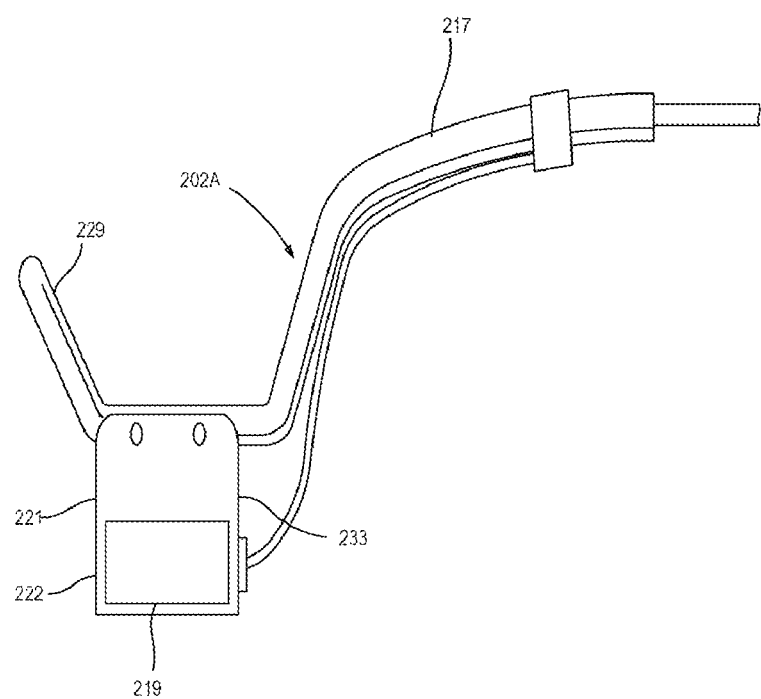
FIG. 15 is a side view of the light-therapy apparatus of FIG. 14.

FIGS. 14 and 15 show a light-therapy apparatus 202A having a head-set style arrangement. Light-therapy apparatus 202A comprises a head-set 217 and at least one extra-oral light source 219 mounted to head-set 217 by way of a suitable connector 221. Head-set 217 can have the general form of a frame for eyeglasses. In the illustrated embodiment, headset 217 has arms 227 that fit above and around the patient's ears and a frame 229 that fits over the bridge of the patient's nose. Head-set 217 can also comprise lenses (not shown). Suitably, the lenses can be made of a material that blocks radiation at wavelengths emitted by light source 219 so that the patient's eyes are protected from the radiation. Light source 219 can comprise an array of LEDs or other light emitters.

When head-set 217 has been adjusted to fit an individual patient, frame 229 registers with the bridge of the patient's nose and arms 227 sit on the patient's ears. Head-set 217 is configured to sit on the patient's head in the same way each time it is put on. Head set 217 can be adjusted for fit by adjusting arms 227 which can be made of a firm, resilient material that allows for some flexibility for a better and more secure fit for individual users. In some embodiments, arms 227 can also be adjusted horizontally along their axis. Frame 229 can also be adjustable, for example, by bending to allow for a better and more secure fit. An elastic keeper such as an elastic strap can be provided to hold head-set 217 in place during use.

Figure 16:
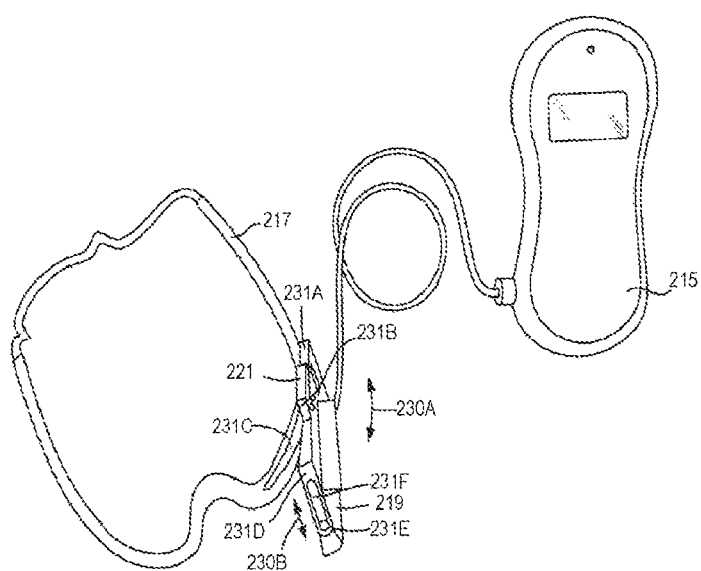
FIG. 16 is a perspective view of a light-therapy apparatus according to an embodiment in which an LED array is supported by a head-set.

In the embodiment shown in FIG. 16, connector 221 permits the position of light source 219 to be adjusted both along a horizontal axis 230A and a vertical axis 230B relative to head-set 217. A yoke 231A is mounted to head-set 217 by screws 231B which pass through slot 231C. The position of light source 219 in horizontal direction 230A can be adjusted by loosening screws 231B, sliding yoke 231A to a desired position along slot 231C and retightening screws 231B. Light source 219 is connected to arms 231D of yoke 231A by screws 231E which pass through slots 231F. The vertical position of light source 219 can be adjusted by loosening screws 231E, sliding light source 219 up or down along slots 231F to a desired vertical position and then retightening screws 231E. Any other mechanism, including those described elsewhere herein, can be used to allow the light source position to be altered vertically or horizontally.

In the illustrated embodiment slot 231C is curved when viewed from above. Slot 231C generally follows the curvature of a typical maxillary bone such that light source 219 can effectively be applied against the patient's skin for a range of positions of light source 219 along slot 231C. Since the lower portions of people's faces are typically narrower than upper portions, connector 221 can hold light source 219 so that it is tilted with its lower edge projecting more in the direction of the patient than its upper edge. In some embodiments the angle of tile of light source 219 is adjustable. Head-set 217 can be adjusted so that light source 19 is biased against the patient's face when head set 217 is being worn by a patient. When the apparatus is in use, the light source can be contacting the patient's face. The light source can contact the region of the face overlying the region, thereby administering light transdermally to the region.

Many alternative designs for connector 221 can be provided. For example, connector 221 can comprise a bar, rod or similar device that can be clamped or otherwise fastened to head-set 217 and a clip or similar mechanism that fastens light source 219 to the bar, rod or similar device.

Figure 17:
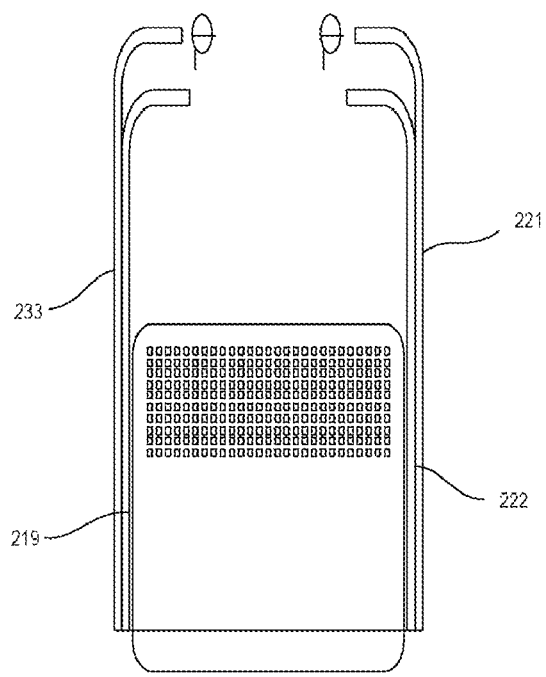
FIG. 17 is a front view of at least one LED array, and a connector detached from the head-set.

As shown in FIG. 17, in some embodiments light source 219 can be removably detached from headset 217. This can be convenient for storage or transportation of light-therapy apparatus 202A. When the apparatus is in use, the light source can contact a patient's face.

In another embodiment, head-set 217 comprises an adjustable strap (not shown) which fits around the crown of a patient's head for securing the extra-oral light-therapy apparatus 202A. The adjustable strap can also fit around a patient's chin and extend back to the crown and around the crown of a patient's head. The adjustable strap can be made of a flexible, elastic woven material.

Figure 18:
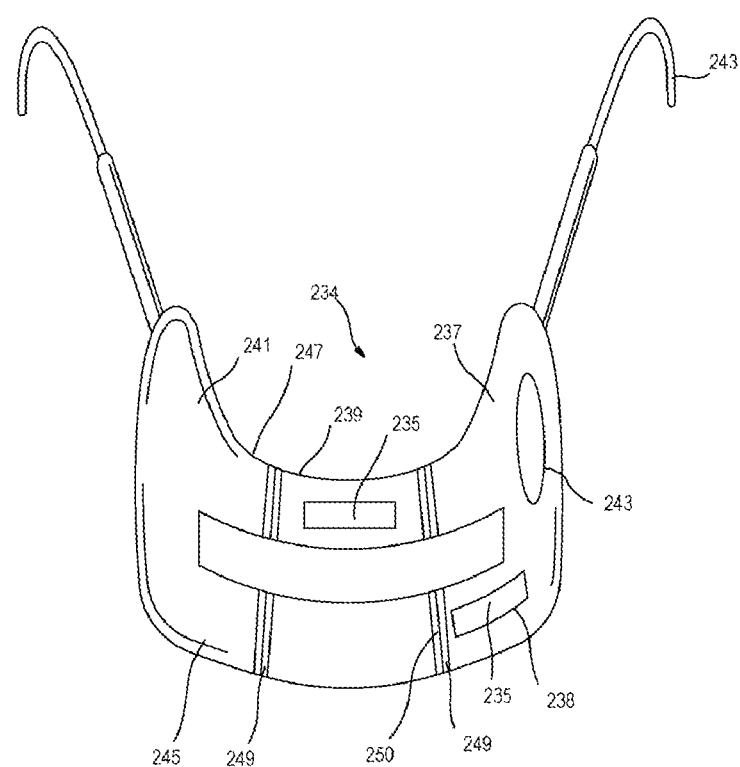
FIG. 18 is a front view of an external light-therapy apparatus having two LED arrays, a hinge-like member, and an attaching means.
Figure 19:
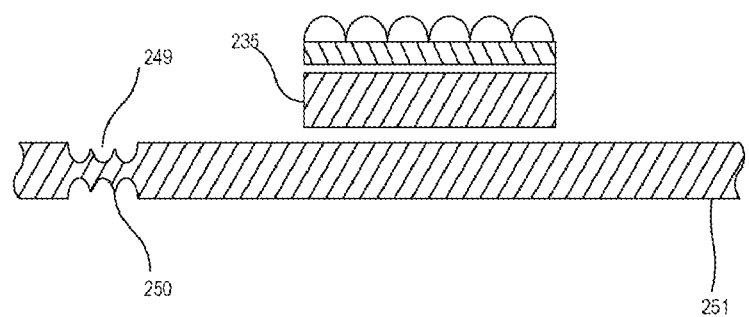
FIG. 19 is a cross-sectional view of an LED array mounted onto a substrate.

FIG. 18 shows a light-therapy apparatus 234 comprising at least one light source 235. Light source 235 comprises at least one light emitter, for example an LED array, mounted on a thin molded substrate 251 (FIG. 19). More than one array of light emitters can be provided in light source 235. For example, the light source 235 shown in FIG. 18 has two arrays of LEDs. Arrays 236 of light emitters can be arranged in lower level 245 and an upper level 247. The upper and lower levels can be separately controlled. The upper and lower levels respectively irradiate tissues of the upper and lower jaws. An attaching means 243 is provided for securing the apparatus to the area of treatment.

A power source and controller, which can comprise a programmable controller 215 as described above, operate light source 235 to emit light according to a desired protocol. In the illustrative apparatus 234 shown in FIG. 18, light source 235 has a right section 237, a center section 239 and a left section 241. Right section 237 and the left section 241 are respectively supported on the right and left sides of a patient's face. One or more light sources can contact a patient's face when the apparatus is worn by the patient. A light source 235 as shown in FIG. 18 can be supported by way of any suitable attaching means including: a head-set 217 as described above; an intra-oral tray 107 which can comprise a full tray or one or more bite tabs as described above; an adhesive such as double-sided adhesive tape; a strap or set of straps; or supporting or attachment mechanisms.

The LED arrays can be removably attached to light source 235 by suitable connectors 238 such as ribbon connectors or can be more permanently integrated into light source 235 as illustrated in FIG. 19. Providing removable, repositionable LED arrays on a light source 235 permits LED arrays to be arranged on light source 235 so as to optimally illuminate selected tissues. LED arrays can be concentrated to illuminate selected tissues while areas of light source 35 that overlie non-selected tissues do not need to have any LED arrays.

Figure 20:
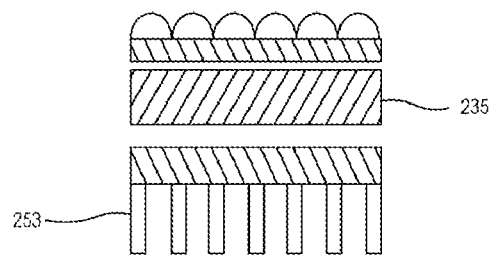
FIG. 20 is a cross-sectional view of an LED array detached from the substrate.

FIG. 20 shows a cross-section of an LED array 236 of external light-therapy apparatus 234 detached from substrate 251. A clip or similar attaching means 253 allows the at least one LED array 236 to be mounted onto substrate 251. Substrate 251 can serve as a heat sink as described above. Substrate 251 can be made of aluminum or similar metal that is a good heat conductor. Substrate 251 can be moldable (i.e., flexible in one or two dimensions so that it can be formed to follow contours of a patient's face and, once formed, retains its shape).

Hinge-like members 249 can be provided between arrays 236 to allow light source 235 to be bent to provide a better fit around the facial area. Hinge-like member 249 can comprise a thin crease 250 or other bend line set into the substrate material, as illustrated in FIG. 19. Hinge-like member 249 allows the center section 239 to fit around a patient's mouth and the right section 237 and the left section 241 to fit around a patient's face.

The apparatus can be applied by fitting a support to a patient. The support can comprise a head-set, intra-oral tray, a bite tab, one or more straps, one or more nose piece, one or more ear piece, or any other support or attachment mechanism. When the support has been fitted so that it can be repeatably worn by the patient one or more light sources can be attached to the support at locations where light from the light sources can illuminate a treatment area.

A treatment regimen can then be established. The physician, dentist, or therapist at her or his office or a patient at her or his home can optionally employ the apparatus in one or more methods of the invention.

Other embodiments, configurations, components, steps, or features can be incorporated in the invention. See, e.g., U.S. Patent Publication No. 2007/0248930 and U.S. Patent Publication No. 2006/0200212, which is hereby incorporated by reference in its entirety. To calibrate the light-therapy apparatus, a sensor useful for measuring optical proximity (not shown) can be provided, positioned at a location that will be adjacent to, or substantially adjacent to, the skin of a patient (e.g., of an extra-oral light therapy apparatus) when the light-therapy apparatus is in the use position. The sensor can measure the optical proximity, for example, by measuring optical power reflected from the skin of the patient, with the sensor positioned in close proximity to one or more of the light therapy emitters. In some embodiments, the optical geometry (i.e., the position of the optoelectronic components, such as the sensor and the light therapy emitters) is selected such that the sensor's signal level declines, in some embodiments rapidly, with distance between the optoelectronic components and the skin of the patient. In some embodiments, if the value measured is outside of a predetermined range (e.g. because light-therapy apparatus has been displaced from a patient's head), the sensor can automatically pause a treatment or the emission of light from light source. Pausing treatment or the emission of light if light-therapy apparatus is displaced from a patient's head can minimize the risk of accidental injury, e.g., due to exposure of a patient's eyes to light from light source.

In some embodiments, depending on a signal from the optical proximity sensor, a controller can determine whether one or more light characteristic is to be maintained or adjusted (e.g., increased or decreased). Light characteristics can include, but are not limited to, light intensity, light wavelength, light coherency, light range, peak wavelength of emission, continuity, pulsing, duty cycle, frequency, duration, or whether a light emitter is on or off The light source can be configured to emit light that is substantially monochrome in some embodiments, although this is not mandatory. Providing light emitters that emit at multiple wavelengths allows for irradiation over multiple wavelengths for greater biological activity and greater selectivity and precision in administration. The light source can emit incoherent light, although this is not mandatory. In some examples, light can be provided at a single frequency, light can have a phase that drifts quickly, pulse of light waves can have an amplitude that changes quickly, or a light wave with a broad range of frequencies can be provided. The light can be administered continuously or pulsed at suitable frequencies and duty cycles. The light source can be configured to administer any of these light characteristics as described anywhere above.

In some embodiments a light source emits light that comprises infrared light, and the light source also emits light that comprises visible light. The visible light, particularly where bright, deters users from looking into light source 30 when it is operating, provides a perceptible indication that the apparatus is operating, and can be useful in properly positioning the light-therapy apparatus 20 described above with reference to FIGS. 1-7B. The visible light can be, but is not necessarily, in a wavelength range that is beneficial for light therapy. In some embodiments, the ratio of the intensities of the visible and infrared components of the light is 1 part or less visible light to 5 parts or more infrared light. In some embodiments, a light source can comprise light emitters emitting light over a range of wavelengths. In some embodiments, the range can comprise wavelengths less than an order of magnitude. Alternatively, the range can comprise wavelengths emitted at one, two, three or more orders of magnitude.

Figure 6:
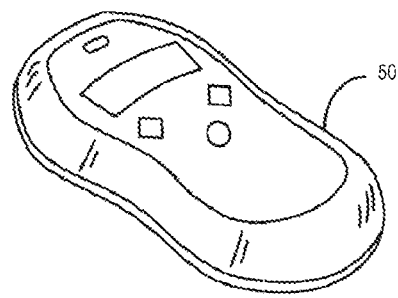
FIG. 6 is a top view of a programmable controller for use with a light-therapy apparatus.

FIG. 6 illustrates an example of a programmable controller 50 of a type that can be used to control the operation of light-therapy apparatus 20. Although controller 50 is described in this exemplary embodiment as being programmable, it is not necessary that controller 50 be programmable. For example, a controller can have controls that allow various parameters to be set, such as light wavelength, light intensity, light pulsing, light duty cycle, light frequency, or light duration, and can appropriately activate light emitters of one or more light sources 30 in response to an appropriate signal. A controller can control light emissions with any light characteristics, which can comprise those described anywhere above. Each of the light sources, e.g. light sources 30A-30H shown in FIG. 2, can be regulated independently by one or more controllers 50. A physician, dentist, therapist, technician or other professional can set those controls or program controller 50 so that an appropriate treatment is delivered when a patient initiates delivery of the treatment. Alternatively, the patient who is receiving the treatment might set controls. In some embodiments, the controls can comprise preset programs that can be suited to particular situations. In other embodiments, one or more parameter can be individually adjusted or entered.

In some embodiments, as shown in FIG. 6, a programmable controller can be a handheld device. Alternatively, the programmable controller can be part of another device or in communication with another device, such as a computer, which can include a personal computer, server computer, or laptop computer; personal digital assistants (PDAs) such as a Palm-based device or Windows CE device; phones such as cellular phones or location-aware portable phones (such as GPS); a roaming device, such as a network-connected roaming device; a wireless device such as a wireless email device or other device capable of communicating wireless with a computer network; or any other type of network device that can communicate over a network. Any discussion herein of computers or any other devices can apply to other devices, including controllers. A device can have a memory that can include tangible computer readable media that can include code, logic, instructions to perform any steps, calculations, algorithms, or execute programs or pre-stored instructions.

Programmable controller 50 can be a separate, remote unit or can be directly connected to or integrated with a light source 30. The programmable controller can connected to or integrated with any portion of the light-therapy apparatus, which can include a local controller, actuation mechanism, frame, or any other part of the controller. [0346] A cable (not shown) can be provided to connect light-therapy apparatus 20 to programmable controller 50, a source of electricity for light source 30, or a suitable heating or cooling system. In some embodiments, wired communication can be provided between the programmable controller and the light-therapy apparatus. In other embodiments, the programmable controller and the light-therapy apparatus can communicate wirelessly. Examples of wireless signals can include, but are not limited to, radio-frequency (e.g., RFID) signals, bluetooth, or control-area-network (CAN) messages.

In some embodiments, controller 50 can comprise a microprocessor, data store, power supply, clock and associated electronic circuitry. A power source can include an external power source or an internal power source. For example, power can be provided by an electric plug. The plug might be in communication with a grid/utility, generator, or energy storage system. In some embodiments, the power source might be a renewable power source. The power source can be an energy storage system, such as a battery, ultracapacitor, or fuel cell. In some embodiments, the power source can be portable.

Control parameters are stored in the data store. A controller can comprise a memory that can include tangible computer readable media that can include code, logic, instructions to perform any steps, calculations, algorithms, or execute programs or pre-stored instructions. Programmable controller 50 operates light source 30 according to the parameters in the data store. The parameters can specify one or more of: treatment duration; wavelength or wavelengths of light emitted by light emitters 38; light intensity of particular wavelength or wavelength ranges during the treatment; whether light emitters 38 operate continuously or are pulsed; if light emitters 38 are pulsed, the rate at which light emitters 38 are pulsed; if light emitters 38 are pulsed, the duty cycle at which light emitters 38 are pulsed, light coherency of the light emitters 38, or any other light characteristic as described anywhere above. The light emitters within the same light source can have the same light parameters. Alternatively, there can be light emitters of different light parameters within the same light source.

If light-therapy apparatus 20 has sets of light emitters 38 having different characteristics (e.g. sets of LEDs that emit light at different wavelengths or sets of light sources 30 that illuminate selected tissues in different locations) then separate control parameters can be provided for different sets of the light emitters 38 or light sources 30. In some embodiments, different sets of parameters are specified for different segments (intervals) of a light treatment. For example, light therapy treatments can be defined for a set of intervals each lasting from a few seconds to a few hundred seconds or a fraction of an hour. Different parameters can be specified for each of the intervals. The intervals are not necessarily equal in length. In some embodiments, a clock of a controller can assist in determining whether a predefined time interval has passed.

In some embodiments, different sets of parameters can be specified for different areas of light-therapy apparatus 20. In some cases, some light sources 30 of light-therapy apparatus 20 can be turned off because the treatment plan for a patient does not require light of particular wavelength or light at all wavelengths to be administered at locations corresponding to those parts of the light-therapy apparatus 20. For example, with reference to FIG. 2, programmable controller 50 can be programmed such that only light sources 30A, 30B, 30C and 30D are activated for a particular treatment regime in which it is desired that light therapy be administered only to a patient's upper teeth.

Alternatively, programmable controller 50 can be programmed such that only light sources 30A, 30D, 30E and 30H are activated for a particular treatment regime in which it is desired that light be administered only to a patient's molars. Various other combinations and permutations of the activation of various light sources disposed about light-therapy apparatus 20 in any suitable configuration can be devised and implemented, depending on the desired application. In some embodiments, light-therapy apparatus 20 is configured (i.e. light sources 30 are positioned and oriented) so as to provide substantially uniform illumination of substantially the entire maxillary and mandibular alveolar bone or teeth of a patient. The light-therapy apparatus can be configured to provide substantially uniform illumination to other regions of the patient. The regions can optionally be limited to alveolar bone or basal bone.

A physician, dentist, therapist, assistant, technician, or other professional can program a patient's treatment regimen into programmable controller 50. This can be done, for example, with the aid of suitable software running on a computer that is in data communication with programmable controller 50 or by way of a suitable user interface built into programmable controller 50. In some embodiments, programming a treatment regimen can include specifying desired values for one or more parameter of light treatment. Programming a treatment regimen can also comprise specifying timing associated with the one or more parameters of light treatment. For example, a treatment regimen can be programmed so that for the first several minutes, light is provided at a first wavelength, and for the next several minutes, light is provided at a second wavelength. In some embodiments, default values can be provided. A user can be able to adjust the default values to create a customized light treatment regimen. In other embodiments, no default values are provided and a user can enter different parameter values.

Programmable controller 50 can have one or more pre-set programs built in. As an alternative to, or as an aid to programming controller 50, the physician, dentist, therapist or other professional can select a pre-set program that is appropriate for controlling light-therapy apparatus 20 to administer light to a patient. Such pre-set programs can be provided for particular types or stages of orthodontic treatment. In some embodiments, a pre-set program can be selected, and a user can modify the pre-set program as desired. For example, a user can be able to deviate from a pre-set program by adjusting any of the following: timing, light wavelength, light intensity, light pulsing or continuous, light duty cycle, light frequency, which lights are on or off, location of light source, or any other parameter that is discussed elsewhere herein.

In some embodiments, a program can be determined prior to using the light-therapy apparatus. For example, after a user has created or selected a program, the light-therapy apparatus can be used, and one or more light source can emit light. In some embodiments, once a program is being implemented or a light-therapy apparatus is in use, the light treatment regimen is not be altered. In other embodiments, a light treatment regimen can be altered while the light-therapy apparatus is in use. For example, while light is being emitted, the light intensity can be adjusted, the light pulsing or continuous characteristics, the light wavelength, light selection, or location of the light source relative to a patient's face can be adjusted. The treatment regimen can be adjusted via the controller or a device in communication with the controller. In some embodiments, a patient wearing a light-therapy apparatus can adjust the treatment regimen. In other embodiments, physician, dentist, therapist, technician, assistant, or other professional can adjust the treatment regimen.

A user can interact with a user interface to program a controller, select a program or adjust a value of a program. Any user interface known in the art can be utilized. For example, a programmable controller can comprise one or more button, pointing device (e.g., mouse, joystick, trackball), keyboard, switch, knob, dial, touchscreen, or video display. The user interface can be provided to the controller directly, or can be provided to a device (e.g., computer) that can be in communication with the controller. A controller can comprise a display that can provide information to the user about selected parameters, timing or pre-set programs.

Programmable controller 50 can maintain a log of treatments that have been administered. For example, controller 50 can log the date and time that each treatment was initiated, the duration of the treatment, and whether or not the treatment was completed. The date and time can be logged based on a clock associated with the programmable controller. One or more timestamp can be provided indicating timing. The log can indicate parameters associated with the treatment. The log can be stored within a memory of the programmable controller. Alternatively, the log can be stored within a memory of a device in communication with the programmable controller, such as a computer.

The log can be accessed by a user to view log data. In one embodiment, the log can be accessed by a physician, dentist, technician, or patient who uses the light-therapy apparatus. A user can access the log directly from a controller or a device in communication with the controller. A user can access the log from any device that can be in communication with a device that stores the log data. The controller or devices can communicate directly with one another or over a network. The network can include a local area network, or a wide area network, such as the Internet.

This log can be subsequently reviewed by a physician, dentist or other medical professional to evaluate whether or not the patient has complied with a prescribed treatment regimen. The log can be displayed to a screen or other video display of a device. The log can track the times and durations of light therapy treatments administered by light-therapy apparatus 20 and can also track other features such as operating temperatures, operational status, treatment parameters, timing, or any combination thereof.

In some embodiments, a programmable controller 50 has a button or other suitable user patient interface that allows a patient to initiate a treatment according to previously-set parameters in the data store. In some embodiments, the patient interface is very simple such that minimal instruction is required to explain to a patient how to use light-therapy apparatus 20. Programmable controller 50 can comprise an audible or visual indicator that generates a signal to remind a patient that it is time for a treatment (or that a scheduled treatment is overdue).

In some embodiments, a treatment regimen can be pre-selected or programmed at the same device (e.g., controller, computer) through which a patient can initiate a treatment. Alternatively, a treatment regimen can be pre-selected or programmed at a different device (e.g., controller, computer) through which a patient can initiate a treatment. In some embodiments, communications can be provided between the controller and another device (e.g., computer) that can allow one or more treatment program to be delivered to the controller. In some embodiments, two-way communications can be provided between the controller and another device. In other embodiments, one-way communications can be provided from the other device to the controller or vice versa.

A patient can use light-therapy apparatus 20 at home or in another location by operating programmable controller 50 to initiate delivery of a treatment. The patient can use the light-therapy apparatus while at an appointment with a medical professional, or at a laboratory or clinic. Alternatively, a patient can use this apparatus while not at an appointment with a medical professional, or at a laboratory or clinic. The patient can use this apparatus while the patient is mobile or traveling.

Programmable controller 50 can comprise circuitry that monitors temperature at one or more locations in light source 30. The circuitry can monitor a signal modulated by a temperature sensor in light source 30. In some embodiments, the temperature sensor can be a thermocouple, thermistor, or resistance temperature sensor (RTD). In other embodiments, programmable controller 50 can monitor e.g. the current and voltage driving light emitters (e.g., LEDs, lasers) in light source 30. The current/voltage relationship can be temperature-dependent. Thus, by monitoring the current/voltage relationship programmable controller 50 can determine whether the light emitter (e.g., LED, laser) is at an undesirably high temperature. A temperature sensor can also be used to determine whether a light source or light assembly, or any component thereof is at an undesirably high temperature. Furthermore, the temperature sensor can determine whether a light emitter, light source, or light assembly has an undesirably low temperature. A temperature sensor can be used to determine whether any part of a light-therapy apparatus falls within a desired temperature range.

Programmable controller 50 can shut off or reduce current to any particular light source (e.g. one or more of light sources 30A-30H) when it detects that the temperature of that light source is undesirably high (or is trending towards being undesirably high). The programmable controller can also shut off or reduce current to any particular light emitter (e.g., one or more light emitter can be provided for a light source) if the controller detects that the temperature at that light emitter is undesirably high. Alternatively, the programmable controller can shut off or reduce current to a group or subgroups of light emitters or light sources if the temperature of a particular light emitter or light source is too high. For example, the programmable controller can shut off or reduce current to all light sources if a temperature is too high.

If light-therapy apparatus 20 is provided with a cooling apparatus, controller 50 can increase the operation of the cooling apparatus when it detects that the temperature of light source 30 is above a desired level. If increasing operation of the cooling apparatus does not bring the temperature of a light source or light emitter or any other portion of a light-therapy apparatus to a desired level, one or more light emitters or light sources can be shut off or reduced.

Figure 21A:
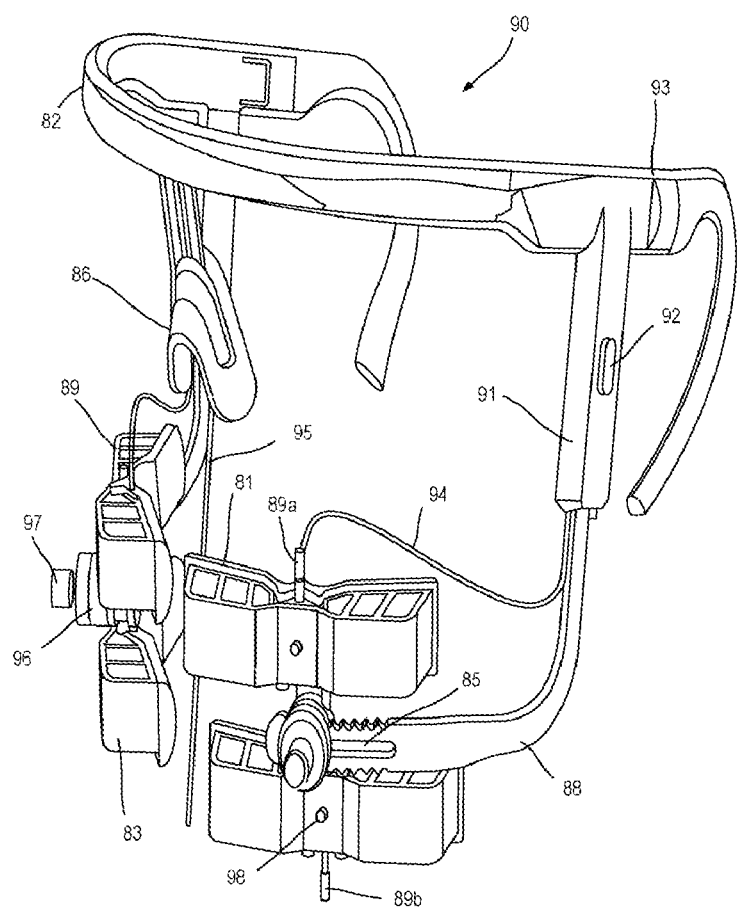
FIG. 21A is a perspective view of a light-therapy apparatus in accordance with another embodiment of the invention.

Shut-off or current reducing steps can occur automatically when a temperature threshold is reached. In some embodiments, a user can define the temperature threshold. In other embodiments the temperature threshold can be pre-set. In some embodiments, an alarm or alert can be provided when a temperature threshold is reached, and a user can manually shut off or reduce current to a light source or light emitter. In some embodiments, a temperature measurement can be displayed to a user. FIG. 21A is a perspective view of a light-therapy apparatus in accordance with another embodiment of the invention. The light-therapy apparatus can optionally have one or more ear pieces 90 configured to fit around the patient's ear. The length of the earpieces can be adjustable relative to the frame 82. In some embodiments, an ear switch 93 or mechanism can be used to allow the ear piece to adjust relative to the frame. In some embodiments, a vertical portion 91 of the frame can extend downwards from the frame. A support arm 88 can extend downwards from the vertical portion of the frame. In some embodiments, the support arm is adjustable relative to the vertical portion of the frame. The support arm can move up or down relative to the vertical portion of the frame. A support switch 92 or other mechanism can be used to allow the support arm to adjust relative to the vertical portion of the frame. A vertical hinge 89 can connect to a secondary support 96 that can slide along the support arm in a track 85. A screw 97 or other mechanical feature can be used to maintain or adjust the position of the secondary support relative to the track. The screw can be loosened to allow the secondary support to slide along the track 85 or tightened to keep the secondary support in place.

Figure 21B:
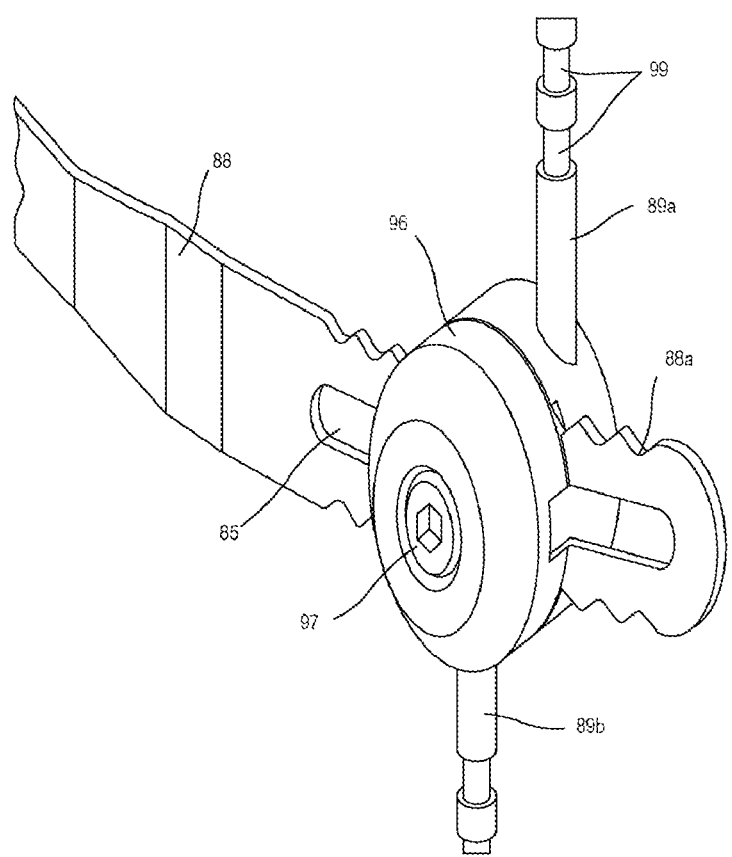
FIG. 21B shows a close up of an example of how a light source is supported in the light-therapy apparatus.

In some embodiments, an upper vertical hinge 89a can be provided above the secondary support and a lower vertical hinge 89b can be provided below the secondary support. One or more light source 81 can be provided on the vertical hinge. In some embodiments, at least one light source is provided on the upper vertical hinge 89a and at least one light source is provided on the lower vertical hinge 89b. The light source can slide up and down the vertical hinge, or rotate on a vertical axis relative that is parallel to the vertical hinge. In some embodiments, a screw 98 or other mechanical feature can be used to maintain or adjust the position of the light source relative to the vertical hinge. The screw can be loosened to allow the light source to slide or rotate relative to the vertical hinge, or tightened to keep the light source in place. One or more wire 94 can be connected to a light source 81. The wire conveys signals to the light sources to control the light emitted from the light source. A wire 95 can connect the head set to a controller 52. The wire can provide electrical signals that can provide power to the light source, or instructions on when specific light sources should be on or off. FIG. 21B shows a close up of an example of how a light source is supported in the light-therapy apparatus. A secondary support 96 can be positioned along a track 85 on a support arm 88. A screw 97 or other mechanical feature can allow the secondary support to maintain or adjust its position along the track. In some embodiments, a support arm can have one or more ridges 88a along the length of the track. The ridges can allow the secondary support to slide or snap into certain positions along the length of the track. One or more vertical hinge 89a, 89b can extend from the secondary support. In some embodiments, a vertical hinge can extend upwards 89a or can extend downwards 89b from the secondary support. Alternatively, a vertical hinge can extend upwards only, or downwards only. One or more grooves 99 or indentations can be provided on the vertical hinge. The grooves can provide positions for a light source to be affixed to the vertical hinge.

Figure 22A:
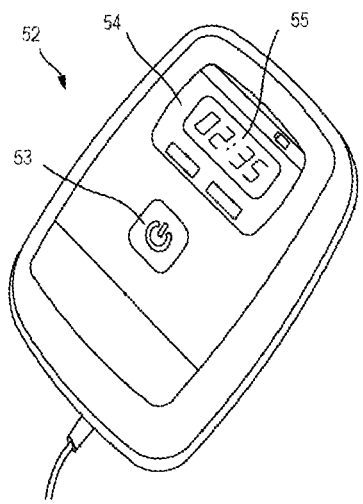
FIG. 22A shows an obverse view of a controller in accordance with another embodiment of the invention.

FIG. 22A shows an obverse view of a controller 52 in accordance with another embodiment of the invention. The controller can have a power button 53. The controller can have one or more display screen 54. The display screen can have one or more indicia The indicia can be of time, battery level, wavelengths of light, settings, intensity, or any other information associated with the operation of a light therapy apparatus.

Figure 22B:
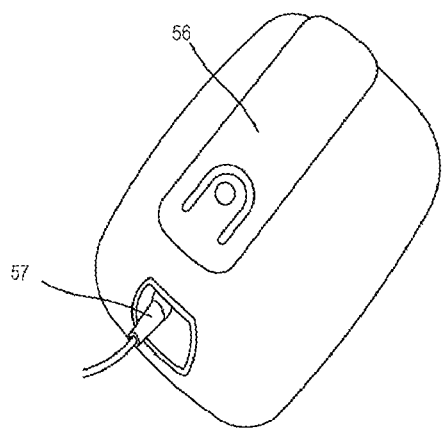
FIG. 22B shows a reverse view of the controller.

FIG. 22B shows a reverse view of the controller. The controller can have a clip 56 that allows a patient to clip the controller onto an article of clothing. The controller can also have one or more wire connector 57 can connect to the light therapy apparatus or one or more power source.

In some embodiments, a light therapy kit comprising a light-therapy apparatus as described herein and instructions is useful in the methods of the invention. The kit can further comprise a light source that is separate from the light-therapy apparatus. The light sources can be disposable, so that they can be easily replaced after a given amount of use. In some embodiments, a light-therapy apparatus and light sources can be individually packaged or can be packaged together.

The kit can also comprise a programmable controller as described herein. The kit can further comprise any components useful for the controller to operate. For example, the kit can comprise a component to power the controller or light-therapy apparatus. The kit can also comprise a component that allows the controller to operably connect with a light-therapy apparatus.

The kit can also comprise software, an algorithm, or a set of computer readable media that can provide instructions to a controller. The software, algorithm, or set of computer readable media can be provided on a memory medium. The memory medium can be a removable or portable, such as a CD, USB flash drive, or external hard drive. The kit can be conveniently packaged and can be commercially available. The kit can also comprise written instructions for use or maintenance of items therein.

In use, a physician, dentist, therapist or other professional can program a patient's prescribed treatment regimen into a programmable controller 50 (see FIG. 6, for example). Programmable controller 50 (or controller 52 in FIGS. 21 and 22) controls parameters of a light therapy treatment to be administered by light-therapy apparatus 20. For example, controller 50 can control the duration of the treatment, wavelength or wavelengths of light administered, light intensity, pulse frequency, or any other light or treatment characteristics. Programmable controller 50 runs a patient's prescribed treatment regimen causing the at least one light source 30 to emit pulsed or continuous light of specified wavelengths according to the prescribed parameters onto the treatment area of a patient's maxillary or mandibular alveolar bone. The treatment area can include any other regions discussed elsewhere herein. This can include oral tissue, alveolar bone, basal bone, or teeth. Light can be administered mostly only to the treatment area. Light-therapy apparatus 20 can provide effective, stabilized repeatable, accurate, programmable, and consistent light therapy for a desired treatment to specifically administer light of a desired wavelength or wavelengths to a particular treatment region at a substantially uniform intensity. Scattering of light as it enters a patient's soft tissues can also cause the beam of light to diverge, resulting in uniform illumination of the patient's soft or hard tissue.

In accordance with another aspect of the invention, a light-therapy apparatus can be used in a method of administering light to a region of a patient's oral tissue. The methods can comprise providing a light-therapy apparatus comprising a support sized and/or shaped to engage with features of the patient's face and one or more light source supported by the support, engaging the support with one or more features of the patient's face, determining whether the position of one or more light source needs to be adjusted in order to administer a desired intensity of light to the region, depending on said determination, varying or maintaining the position of the one or more light source, and administering light to the region.

The light-therapy apparatus can optionally be an apparatus as described in any of the embodiments anywhere above. The light-therapy apparatus can comprise a support that can be engaged with one or more features of the patient's face. For example, the light-therapy apparatus can engage with features of a patient's face by conforming to the shape of the feature, wrapping around the feature, overlying the feature, grasping the feature, adhering to the feature or providing pressure or weight to the feature. For example, the light-therapy apparatus can comprise an ear-engaging portion that can wrap around the back of the patient's ear. In another embodiment, the light-therapy apparatus can comprise a nose-engaging portion that can rest on the bridge of the patient's nose.

A method for administering light to a region can also comprise determining whether the position of one or more light source needs to be adjusted in order to administer a desired intensity of light to the region. Such determination can be made manually or automatically. For example, the patient or a medical professional can determine the position of a light source when the light-therapy apparatus is worn. The patient or medical professional can determine the relative position of the light source to a desired region. The light-therapy apparatus comprises one or more sensors. In some embodiments, the sensor can be a temperature sensor or an optical proximity sensor. In another embodiment, a sensor can determine the relative position of the light source with respect to the region. Determining whether a light characteristic needs to be adjusted in order to administer a desired light to the region can be based on the one or more signals from the one or more sensors.

Depending on said determination, the position of the one or more light source can be varied or maintained. The position of the light can be varied manually or automatically. For example, a patient or medical professional can manually move a light source. In another embodiment, one or more actuator can be provided in communication with a controller. The controller can provide one or more signal to the actuator, thereby causing the actuator to move or maintain its position. The light source can be displaced, rotated, or tilted to provide a desired intensity of light to a region. In some embodiments, the light source can be pressed against the patient's face above the region, and the position of the light source can be set to that location. In some embodiments, after the position of a light source is adjusted, the light source can remain at that position in the absence of any outside force. In some embodiments, a light source can be locked into a position after it is adjusted, so that the light source can remain in that position even if a force is exerted on it.

In some embodiments, after a light has been set to a desired position, the method can comprise administering light to the region. In some other embodiments, light can be administered before or while the light is being set to a desired position. In some embodiments, a light-therapy apparatus can be engaged with the patient, the light source can be positioned, and the light can be administered without removing the light-therapy apparatus from the patient. In some embodiments, the light-therapy apparatus can be engaged with the patient, the light source can be positioned, and the light-therapy apparatus can be removed from the patient. This can be a series of steps for fitting the light-therapy apparatus to the patient. The light-therapy apparatus can subsequently be re-engaged with the patient and light can be administered to the patient. This can include steps for administering the light to the patient, after fitting the light-therapy apparatus to the patient. The light sources can already be positioned to administer light to the region. In some embodiments, light can be administered to the patient on multiple occasions following a single fitting.

In some embodiments, the method can comprise varying the position of one or more light sources by adjusting the position of the light along the length of the support. The method the method can also comprise varying the position of one or more light by rotating the light source about an axis. The axis can be vertical, horizontal, or provided at any other orientation.

In some embodiments, light therapy apparatuses can be provided which are particularly suitable for intra-oral administration of light to one or more regions within a patient's oral cavity or mouth, such as a region of the patient's maxillary or mandibular alveolar bone. An intra-oral light therapy apparatus can incorporate one or more features or components of one or more embodiment of a light source or light therapy apparatus described herein. In one embodiment an intra-oral light therapy apparatus irradiates light having one or more characteristics of light described above.

Examples of intra-oral light therapy devices can include a laser beam delivered by an optical fiber to a point of irradiation. In one embodiment, a low-energy laser source, such as a gallium-aluminum-arsenide laser can be used. See, e.g., Kawasaki, et al., "Effects of Low-Energy Laser Irradiation on Bone Remodeling During Experimental Tooth Movement in Rats," Lasers in Surgery and Medicine 26:282-291 (2000); Cruz, et al., "Effects of Low-Intensity Laser Therapy on the Orthodontic Movement Velocity of Human Teeth: A Preliminary Study," Lasers in Surgery and Medicine 35: 117-120 (2004); Abi-Ramia, et al., "Effects of LowLevel Laser Therapy and Orthodontic Tooth Movement on Dental Pulp in Rats," Angle Orthodontist, 80(1): 116-122 (2010), which are hereby incorporated by reference in their entirety. Additional examples of intra-oral light emitting devices include U.S. Patent Publication No. 2007/0121786, U.S. Patent Publication No. 2008/0113313, U.S. Patent Publication No. 2009/0011380, U.S. Patent Publication No. 2009/0323370, which are hereby incorporated by reference in their entirety.

Other examples of intra-oral light therapy devices can include an oral tray that fits over one or more tooth or gums. In another embodiment, an oral tray need not fit over one or more tooth, but can be contoured to fit within a patient's oral cavity. Light from a light source can be transmitted to one or more teeth, or gum or mucosal tissue overlying one or more tooth root, via the oral tray. In some embodiments, the tray reflects or conveys light from a natural source (e.g., sun) or man-made source (e.g., lasers, LEDs, or light sources having any of the characteristics previously mentioned). In some embodiments, a light source is embedded within the tray or attached to the tray. In other embodiments, the intra-oral therapy devices comprise a cap-like structure that can fit over one or more tooth, or gum or mucosal tissue overlying one or more tooth root. The cap-light structure can transmit light from a distal light source. Alternatively, the cap-like structure comprises a light source provided therein. In some embodiments, the intra-oral light therapy devices are handheld devices that can provide or direct light to one or more tooth, or gum or mucosal tissue overlying one or more tooth root. The light can be provided from a proximal or distal light source. In some embodiments, the handheld devices comprise or otherwise utilize fiber optics. The light-providing portion of the handheld device can be held adjacent to a tooth, gums, or mucosal tissue overlying a tooth root. In some embodiments, the light providing portion of the handheld device can be located within a patient's oral cavity. See, e.g., U.S. Pat. No. 2,884,926; U.S. Patent Publication No. 2008/0255498; U.S. Patent Application No. 2006/0085052; U.S. Patent Publication No. 2008/0032252, which are hereby incorporated by reference in their entirety.

In some embodiments, a light therapy apparatus as described above is useful for administering light intra-orally. Thus, a light therapy apparatus can be configured to provide light extra-orally or intra-orally or both. An intra-oral light therapy apparatus can be used in conjunction with an extra-oral light therapy apparatus as described above.

Apparatuses and Methods for Intra-Oral Light Therapy

In one aspect, the invention provides an intra-oral apparatus, which comprises a housing, an emitter and electronic circuit. The housing is configured to fit within a patient's mouth. The emitter is at least partially encased within the housing, and is configured to emit an effective amount of a light to a region associated with the alveolar soft tissue when the housing is disposed within the mouth. The electronic circuit is operatively coupled to the emitter, and is configured to control the emitter when the housing is disposed within the mouth and the apparatus is in use during use in the methods of the invention. The apparatus is useful for treating or slowing progression of a tumor, a neurodegenerative disease or a cognitive impairment. In some embodiments, the apparatus is useful for improving cognition. In some embodiments, the apparatus is useful for treating autism, Asperger's syndrome, hyperprolactinemia or sexual dysfunction. In some embodiments, the apparatus is useful for activating oral stem cells.

In one or more embodiments, the invention provides apparatuses that comprise a mouthpiece configured to fit within a patient's mouth. The mouthpiece comprises a bite tray and a flange coupled to the bite tray. The flange spans from a first end of the bite tray to a second end of the bite tray. The flange is substantially rigid with respect to the bite tray, such that an angle formed between an inner face of the flange and an upper surface of the bite tray when the mouthpiece is disposed within the mouth is substantially unchanged, i.e., stays about the same angular value. The apparatus also comprises light emitters disposed within the flange. The light emitters are configured to emit light to the patient's oral tissue when the mouthpiece is disposed within the mouth. In one or more embodiments, the light emitters are a single row of light emitters such as LEDs.

In one or more embodiments, an apparatus comprises a housing, an emitter and an electronic circuit. The housing is configured to fit within a patient's mouth. The emitter is optically coupled to the housing, and is configured to emit an effective amount of a light to the alveolar soft tissue when the housing is disposed within the mouth. The electronic circuit is operatively coupled to the emitter, and is configured to control the emitter when the housing is disposed within the mouth and the apparatus is in use during treatment.

The invention provides systems, including a first portion and a second portion. The first portion is configured to be disposed within a patient's mouth. A first emitter coupled to the first portion is configured to emit an effective amount of a light at a first wavelength to the alveolar soft tissue when the first portion is disposed within the mouth. An electronic circuit is operatively coupled to the first emitter, and is configured to control the first emitter when the first portion is disposed within the mouth and the apparatus is in use during a first stage of an orthodontic treatment. The first stage begins at a time TO. The second portion is different from the first portion, and is configured to be disposed within the patient's mouth. A second emitter is coupled to the second portion and is configured to emit an effective amount of a light at a second wavelength, different than the first wavelength, to the alveolar soft tissue when the second portion is disposed within the mouth. The electronic circuit is operatively coupled to the second emitter, the electronic circuit configured to control the second emitter when the second portion is disposed within the mouth and the apparatus is in use during a second stage of the orthodontic treatment. The second stage is subsequent to the first stage, and begins at a time T>O.

In one or more embodiments, the methods comprise receiving, each day for a predetermined number of days, an indication associated with contact between an orthodontic appliance and a tissue within an oral cavity of a patient. The orthodontic appliance is one of one or more orthodontic appliances that is removably coupled to the teeth of the patient. A treatment period associated with each orthodontic appliance from the plurality of orthodontic appliances is determined based on the indication. The methods further comprise producing a signal associated with the treatment period.

In one or more embodiments, the methods comprise disposing a first orthodontic appliance within an oral cavity of a patient such that the first orthodontic appliance is removably coupled to the teeth of the patient. A period specific to the patient is determined. The first orthodontic appliance is maintained within the oral cavity for the period. The methods further comprise disposing a second orthodontic appliance within the oral cavity of the patient after the period such that the second orthodontic appliance is removably coupled to the teeth of the patient.

The systems are useful for administering light therapy to alveolar soft tissue of a patient.

In one or more embodiments, an apparatus comprises a mouthpiece configured to fit within a patient's mouth. The mouthpiece comprises a bite tray and a flange coupled to the bite tray. The flange comprises a top edge continuously spanning from a first end of the bite tray to a second end of the bite tray without a notch present therein.

The flange is substantially rigid with respect to the bite tray. The apparatus also comprises a light emitter disposed within the flange. The light emitter is configured to emit light to the patient's oral tissue when the mouthpiece is disposed within the mouth. In one or more embodiments, an apparatus comprises a mouthpiece configured to fit within a patient's mouth. The mouthpiece comprises a bite tray and a flange coupled to the bite tray. The flange spans from a first end of the bite tray to a second end of the bite tray. The flange is substantially rigid with respect to the bite tray and has a height of about 1 cm, of about 1.2 cm, of about 1.5 cm, of about 1.8 cm, of about 2.1 cm, of about 2.4 cm, of about 2.7 cm or of about 3 cm, including all values, ranges and subranges in between. The apparatus also comprises a light emitter disposed within the flange. The light emitter is configured to emit light to the patient's oral tissue when the mouthpiece is disposed within the mouth.

In one or more embodiments, an apparatus comprises a mouthpiece configured to fit within a patient's mouth. The mouthpiece comprises a bite tray and a flange coupled to the bite tray. The flange spans from a first end of the bite tray to a second end of the bite tray. The flange is substantially rigid with respect to the bite tray. The apparatus also comprises a single row of light emitters disposed within the flange. The row of light emitters spans from a first end of the flange proximal to the first end of the bite tray to a second end of the flange proximal to the second end of the bite tray. The row of light emitters is configured to emit light to the patient's oral tissue when the mouthpiece is disposed within the mouth.

In one or more embodiments, a method for orthodontic treatment of a patient with reduced periodontal bone support comprises disposing a mouthpiece of a light-therapy apparatus into a patient's mouth. The mouthpiece including a bite tray, a single flange, and a light emitter. The flange is coupled to the bite tray and spans from a first end of the bite tray to a second end of the bite tray. The disposing can comprise exerting a force, via the flange, on one or more teeth of the patient. The methods also comprise administering to the patient an effective amount of light from the light emitter.

Intra-Oral Light Treatment Apparatuses

One or more embodiments described herein relate to exposing the oral tissue (e.g., alveolar mucosa, buccal mucosa, labial mucosa, masticatory mucosa, tooth, gum or tongue) to light (e.g., light having an intensity from about 10 to about 200 mW/cm$^2$).

One or more embodiments described herein include an intra-oral light-therapy apparatus configured to administer light to one or more portions of the patient's alveolar soft tissue. In one or more embodiments, as disclosed herein, an apparatus can be used to administer light to a patient for I minute to 60 minutes per day. In other embodiments, the apparatus can contact a patient's oral mucosa for minutes, hours, day, weeks, months, or years, and one or more of the apparatus's emitters can irradiate light during at least some time during that period.

In one or more embodiments, an apparatus is configured to contact and/or be conformal with the oral tissue of any human subject; in other embodiments, an apparatus can be configured to be conformal with the oral tissue of a specific human subject. For example, the apparatus can be configured to be conformal with any human patient's, or to a specific human patient's, particular dental geometry, for example, using information obtained from CT scans (e.g., cone beam CT scans), models of the patient's jaw, intra-oral digital scanned models, and/or photographs of the patient's jaw. More specifically, the placement of LEDs within an apparatus to be positioned within the patient's mouth can be custom designed, using CAD/CAM design applications, for example, based on information obtained from one or more of the foregoing methods. In other embodiments, a standardized apparatus can be selected from one or more apparatuses configured to conform generally to human patients' oral anatomical features. In some such embodiments, the standardized apparatus can be adjusted to conform to a specific human patient's features. As used herein, the phrases "conforms to" and "conformal with" refer to the property of the apparatus contacting, and adopting the same or substantially the same shape as, a surface of a wearer/patient of the apparatus. For example, when the light therapy apparatus is worn by a user, the flanges of the light therapy apparatus may contact the alveolar mucosa of the user, and deform to mimic or substantially mimic the shape of the alveolar mucosa of the user. The deformation can be facilitated, for example, by a material property of the material from which the flanges are composed, and can include protruding in one or more regions thereof and/or recessing in one or more regions thereof. The light therapy apparatus can further be configured such that, when the light therapy apparatus is removed from the user's mouth, the flanges of the light therapy apparatus return or substantially return to their original shape.

In one or more embodiments, an apparatus is configured to deflect, bend and/or deform to conform to the oral anatomy of a patient. For example, in one or more embodiments, an apparatus comprises a mouthpiece configured to transition between a first configuration when the mouthpiece is outside of the patient's mouth and a second configuration when the mouthpiece is inside of the patient's mouth. Further, in one or more embodiments, an apparatus comprises a mouthpiece and a light emitter. In one or more embodiments, the mouthpiece is configured to fit within a patient's mouth and comprises a bite tray and a flange coupled to the bite tray. In one or more embodiments, an inner face of the flange forms a first angle with an upper surface of the bite tray, for example, when the mouthpiece is outside of the patient's mouth. In one or more embodiments the flange is deflectable with respect to the bite tray such that a second angle is formed between the inner face of the flange and the upper surface of the bite tray when the mouthpiece is disposed within the patient's mouth. In one or more embodiments, the light emitter is disposed within the flange and is configured to emit light to the patient's oral tissue when the mouthpiece is disposed within the mouth. In other embodiments, an apparatus is configured to be substantially rigid, and to resist deformation. For example, in one or more embodiments, an apparatus comprises a mouthpiece configured to maintain its configuration when the mouthpiece is outside of the patient's mouth and when the mouthpiece is inside of the patient's mouth.

In one or more embodiments, a method of the invention comprises disposing a mouthpiece of a light-therapy apparatus into a patient's mouth. In one or more embodiments, the mouthpiece comprises one or more of a bite tray, a flange, and a light emitter. In one or more embodiments, the flange is coupled to the bite tray and optionally comprises the light emitter therein. In one or more embodiments, the flange is configured to move with respect to the bite tray during the disposing such that an angle between an inner face of the flange and an upper surface of the bite tray has a first value before the disposing and a second value after the disposing. In one or more embodiments, the method further comprises administering to the patient in need thereof an effective amount of light from the light emitter.

In one or more embodiments, the apparatus is configured to administer light therapy based on a customized dosage, e.g., a dosage that is customized for a particular patient. Younger patients may have less dense bone than older patients. Density of the patient's bone can be measured, for example, using computed tomography (CT), in one or more embodiments, cone beam CT, prior to light therapy administration. In one or more embodiments, the patient's bone density can be measured by irradiating the patient's teeth and measuring the amount of light that penetrates the teeth (e.g., using an apparatus similar to or such as that depicted in FIG. 18A) Once the patient's bone density is determined, an optimal dosage of light can be determined for achieving the desired result.

In one or more embodiments, the apparatus can comprise a bite pad to improve patient comfort when the apparatus is in contact with the patient's alveolar soft tissue and/or for positioning of the apparatus in a patient's mouth.

In one or more embodiments, the apparatus is useful in combination with an appliance that exerts a force on the patient's teeth and/or on muscular tissue such as buccal and labial cheeks, tongue, etc. In one or more embodiments, the apparatus of the invention is useful in combination with more than one appliance that exerts a force on one or more teeth of the patient of about 1 g, about 5 g, about 10 g, about 50 g, about 100 g, about 200 g, about 300 g, about 400 g, about 500 g, about 600 g, about 700 g, about 800 g, about 900 g, about 1000 g, about 1100 g or about 1200 g, including all values, ranges and subranges in between. Exerting one or more forces to the gum region, including on one or more of the patient's teeth, and intra-orally administering light to a patient's alveolar soft tissue can increase the rate of tooth movement, increase the rate of healing of oral tissue and provide other orthodontic benefits. In one or more embodiments, one or more of the forces exerted is a heavy force. In one or more embodiments, one or more of the appliances exerting a force is a functional appliance. Heavy forces and functional appliances are disclosed herein.

In one or more embodiments, the appliance, such as an incremental position adjustment appliance as disclosed herein is made from a material that enables the appliance to conform to the shape of the patient's teeth and/or other oral tissue.

Examples of suitable materials include, but are not limited to, polymers such as polyurethane, silicone (including soft silicone), thermoplastics, and/or the like.

In other embodiments, the apparatus is useful in combination with an orthodontic appliance, such as, but not limited to, an aligner.

In one or more embodiments, a method for orthodontic treatment comprises disposing a mouthpiece of a light-therapy apparatus into a patient's mouth. The mouthpiece comprises a bite tray, a flange, and a light emitter. In one or more embodiments, the flange is coupled to the bite tray and optionally comprises the light emitter therein. In one or more embodiments, the flange is configured to move with respect to the bite tray during the disposing such that an angle between an inner face of the flange and an upper surface of the bite tray has a first value before the disposing and a second value after the disposing. In other embodiments, the flange is configured to be substantially rigid with respect to the bite tray during the disposing such that an angle between an inner face of the flange and an upper surface of the bite tray is substantially unchanged i.e., stays about the same angular value, from before the disposing to after the disposing. In one or more embodiments, the method further comprises administering to the patient an effective amount of light from the light emitter.

In one or more embodiments, an apparatus is configured to detect and/or send a signal when a mouthpiece is disposed within a patient's mouth. In this manner, the apparatus can initiate and/or control delivery of any of the methods of light therapy disclosed herein. For example, in one or more embodiments, a light-therapy apparatus comprises one or more of a mouthpiece, a bill and an electronics assembly. In one or more embodiments, the mouthpiece is configured to be disposed within a mouth of a patient, and comprises a series of light emitters therein. In one or more embodiments, the series of light emitters is a single row of light emitters, such as, for example, a single row of LEDs. In one or more embodiments, the series of light emitters is configured to emit light to alveolar soft tissue of the patient. In one or more embodiments, the bill is coupled to an anterior end of the mouthpiece, and configured to be disposed externally to the mouth when the mouthpiece is disposed within the mouth. In one or more embodiments, the least a portion of the electronics assembly is disposed within the bill. In one or more embodiments, the electronics assembly is configured to control operation of the light emitters. In one or more embodiments, the electronics assembly is further configured to send a first signal to cause a first light emitter to emit light. In one or more embodiments, the electronics assembly is configured to receive a second signal from a second light emitter, the second signal associated with the light emitted from the first light emitter. The electronics assembly is configured to detect when the mouthpiece is disposed within the mouth based on the second signal. In some embodiments, the electronics assembly is self-contained. Alternatively or in addition, in some embodiments, the electronics assembly is one or more of: hermetically sealed, waterproof, or water-resistant.

Figure 23:
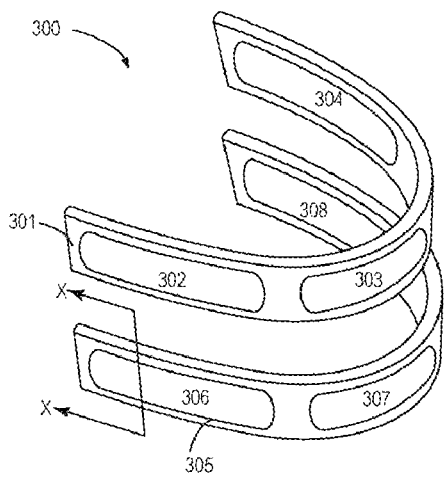
FIGS. 23 and 24 are perspective views of intra-oral light-therapy apparatuses according to an embodiment of the invention.
Figure 24:
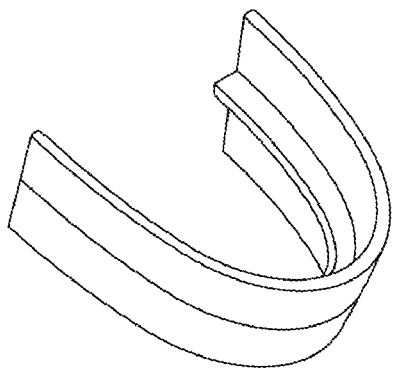

FIGS. 23 and 24 are schematic diagrams of embodiments of intra-oral light-therapy apparatuses of the invention. As shown in FIG. 23, an apparatus 300 comprises an upper panel 301 having subpanels 302, 303, and 304, and a lower panel 305 having subpanels 306, 307, and 308. Panels 302, 303, and 304 are configured to be disposed near the root area of one or more teeth of the upper jaw. In one or more embodiments, subpanels 302, 303, and 304 can be configured to be disposed adjacent to the upper buccal alveolar soft tissue. For example, in one or more embodiments, the subpanels 302, 303, and 304 are in contact with the upper buccal alveolar soft tissue; whereas, in other embodiments, the subpanels 302, 303, and 304 are not in contact with the upper buccal alveolar soft tissue but are at a particular distance (e.g., from 0.1 cm to 3 cm) of the upper buccal alveolar soft tissue. The alveolar soft tissue can include, for example, the alveolar mucosa. In other embodiments, subpanels 302, 303, and 304 can be configured to be disposed adjacent to the upper lingual alveolar soft tissue. For example, in one or more embodiments, the subpanels 302, 303, and 304 are in contact with the upper lingual alveolar soft tissue; whereas, in other embodiments, the subpanels 302, 303, and 304 are not in contact with the upper lingual alveolar soft tissue but are at a particular distance (e.g., from 0.1 cm to 3 cm) of the upper lingual alveolar soft tissue. Similarly stated, in one or more embodiments, subpanels 302, 303, and/or 304 can be configured to be disposed posterior to the maxillary root area, while in other embodiments, subpanels 302, 303, and/or 304 can be configured to be disposed anterior to the maxillary root area. Similarly, subpanels 306, 307, and/or 308 can be configured to be disposed adjacent to anterior and/or posterior mandibular root area.

In other embodiments, the panels (or other portions of the apparatus) can be disposed at any of the various regions or areas described herein. For example, although in one or more embodiments, the panels are described herein as being in contact with or at a particular distance (e.g., from 0.1 cm to 3 cm) of the upper buccal or lingual alveolar soft tissue, in other embodiments, the panels are configured to be in contact with and/or at a particular distance (e.g., from 0.1 cm to 3 cm) of the lower buccal or lingual alveolar soft tissue. In still other embodiments, an apparatus can comprise a plurality of panels of which at least a first portion are configured to be in contact with or at a particular distance (e.g., from 0.1 cm to 3 cm) of the upper buccal or lingual alveolar soft tissue, and of which at least a second portion is configured to be in contact with or at a particular distance (e.g., from 0.1 cm to 3 cm) from the lower buccal or lingual alveolar soft tissue when the first portion is in contact with or at the particular distance of the upper alveolar soft tissue.

In one or more embodiments, an apparatus is configured to be disposed only adjacent to the maxillary or mandibular root area. For example, in one or more embodiments, the apparatus is in contact with the maxillary or mandibular root area; whereas, in other embodiments, the apparatus is not in contact with the maxillary or mandibular root area but is at a particular distance (e.g., from 0.1 cm to 3 cm) of the maxillary or mandibular root area. Similarly stated, although FIG. 23 depicts the apparatus 300 including an upper portion (panel 301) and a lower portion (panel 305), in other embodiments, the apparatus has only an upper portion or only a lower portion.

Although the apparatus is shown with six panels, in other embodiments, the apparatus can have one or more panels. For example, a single panel can be configured to cover at least a portion of the maxillary and/or mandibular root area or the entirety. In other embodiments, one or more panels can be disposed adjacent to the root area of each tooth. For example, in one or more embodiments, one or more panels are in contact with the root area of each tooth; whereas, in other embodiments, one or more panels are not in contact with the root area of each tooth but are at a particular distance (e.g., from 0.1 cm to 3 cm) of the root area of each tooth.

Although in one or more embodiments the panels described herein cover at least some of the anatomical dimensions (e.g., length) of most tooth roots, variation in soft tissue and boney architecture of individual patients may prevent the panel from covering the apical extent of some tooth roots. In such cases, apical portions of the teeth may receive lower energy density. In one or more embodiments, however, the panels comprise an embedded LED array that is configured to direct light in the direction of such apical portion(s) or is configured to otherwise increase the intensity in the apical portions of the panels.

In one or more embodiments, such as the embodiment depicted in FIG. 24, an apparatus is configured to wrap over the teeth, such that a first portion of the apparatus is disposed adjacent to the anterior root area and a second portion of the apparatus is disposed adjacent to the posterior root area. In such embodiments, the apparatus is relieved over the anatomical crowns in order to provide freedom of tooth movement when the apparatus is in operation. For example, in one or more embodiments, the first portion of the apparatus is in contact with the anterior root area and/or the second portion of the apparatus is in contact with the posterior root area; whereas, in other embodiments, the first portion of the apparatus is not in contact with the anterior root area and/or the second portion of the apparatus is not in contact with the posterior root area but the first portion and/or the second portion of the apparatus is/are at a particular distance (e.g., from 0.1 cm to 3 cm) of the anterior root area or posterior root area, respectively.

Figure 25A:
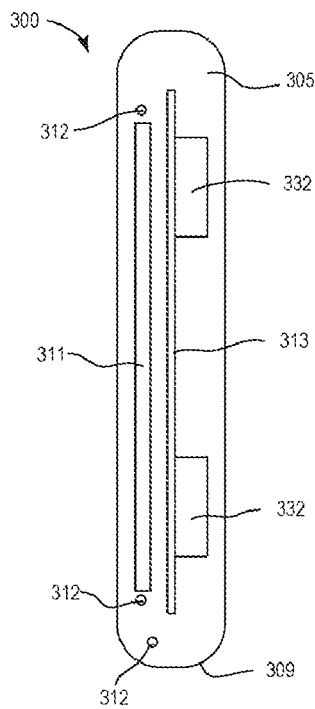
FIG. 25A is a sectional view of the apparatus of FIG. 1, taken along line X-X.

FIG. 25A depicts a cross section of the apparatus of FIG. 23 taken along line X-X. The apparatus 300 can comprise one or more wires 312, a reflective backing 311, a circuit 313, and one or more emitters 332, encased in the panel 305. In one or more embodiments, the one or more emitters 332 can be partially encased within the panel 305 such that at least a portion of the one or more emitters 332 are exposed and can contact, for example, the alveolar soft tissue of the patient when the apparatus is in the patient's mouth. The panel 305 can be constructed of a substantially transparent, flexible, and/or soft polymer, such as a silicone. In other embodiments, the panel 305 can be a rigid plastic, such as an acrylic. The panel 305 can be shaped to cover a specific region of the patient's mouth when the apparatus is worn by the patient. For example, the panel 305 can have a width and a length effective to cover at least four of the patient's tooth roots. A portion of the panel 309 can have a rounded and/or teardrop shape to provide for patient comfort and to allow the apparatus to adapt to the flange area. The portion of the panel 309 can have any shape that does not include sharp or acute edges as such edges would irritate or be uncomfortable in the depth of the vestibule of the patient's mouth.

In one or more embodiments, the panel 305 is at least partially encased in the apparatus, which can have a shape similar to a mouth guard or to a clear dental aligner and can be constructed of any material suitable for use in the mouth. In this manner, the components encased in the panel 305 are also at least partially encased in the apparatus. In one or more embodiments, the panel 305 is fully encased in the apparatus. The panel 305 and components encased therein can be fluidically sealed within the apparatus so that saliva or another fluid cannot contact the panel 305. Sealing the panel 305 in this manner can provide safety benefits, extend the life of the intra-oral apparatus, and/or require less maintenance. For example, if the panel 305 is not fluidically sealed within the apparatus, then the apparatus may require frequent maintenance to clean fluids and other buildup from the panel 305.

The emitters 332 can be any suitable device that is operable to emit light. The emitters 332 can be, for example, light emitting diodes (LEDs). In one or more embodiments, the emitters 332 are optical fibers (or portions thereof) that emit light. In one or more embodiments, the emitters 332 are devices that are connected to and receive light input from one or more optical fibers. The panel 305 can comprise any combination of the LED and optical fiber emitters disclosed herein. In one or more embodiments, the emitters 332 can emit monochromatic light having a wavelength of about 620 nm. In other embodiments, the emitters 332 can emit monochromatic light having a wavelength of about 850 nm. In yet other embodiments, the emitters 332 can be configured to emit a light having a wavelength ranging from about 600 nm to about 1200 nm, emit light at more than one wavelength, progress through a range of wavelengths, and/or emit a broad spectrum light or any suitable wavelength or wavelengths. The emitters 332 can be configured to emit light having any wavelength or characteristic described herein. Such wavelengths and characteristics of light are described in more detail herein.

The emitters 332 can be positioned and arranged within the panel 305 in any suitable manner. The emitters 332 can be arranged, for example, so that they cover and irradiate light to a specific region of the mouth when the apparatus is worn by the patient. In one example, each emitter 332 is positioned over and irradiates light to a different tooth root. In another example, the emitters 332 are grouped together into sets so that one set of emitters is positioned over and irradiates light to a first region of the patient's mouth (e.g., a tooth root) while another set of emitters is positioned over and irradiates light to a second, different region of the patient's mouth (e.g., another tooth root). In this manner, the apparatus and the emitters 332 within each corresponding panel 305 can be customized for a specific patient so that particular needs of the orthodontic treatment are met. As noted herein, the panels, and thus the emitters 332, can be in contact with or at a particular distance from the alveolar soft tissue or tooth root. A light dose emitted by the emitters 332 can be more effective for regulating tooth movement the closer the emitters 332 are to the alveolar soft tissue or tooth root, due to a loss of energy that can occur over a distance between the emitters 332 and the tissue or root. In one or more embodiments, however, the power density of light emitted by emitters 332 can be maximized by positioning the emitters 332 in contact with and/or at the particular distance from the tissue or root, as described herein.

Figure 25B:
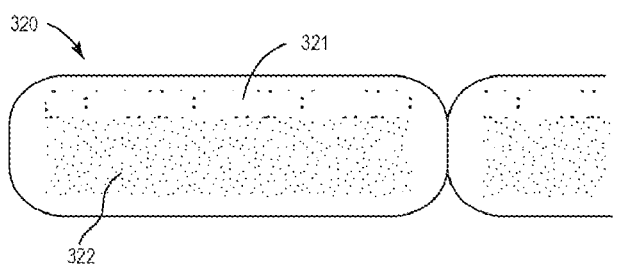
FIG. 25B is a side view of a portion of an intra-oral light-therapy apparatus according to an embodiment of the invention.

In one or more embodiments, as shown in FIG. 25B, a light emitting array 320 has a first portion 321 and a second portion 322. The first portion 321 of the light emitting array 320 is configured to include a greater density of light emitters than a density of light emitters in the second portion 322. In one or more embodiments, the first portion 321 of the light emitting array 320 includes a tighter weave on a portion of a light mat. The first portion 321 of the light emitting array 320 (or light mat) can be disposed at an apical portion of the array. The increased power density at the apex resulting from the tighter weave of the light mat permits a shorter extension to a flange as the increased power at least partially compensates for a shorter extension.

Referring again to FIG. 25A, the circuit 313 can be, for example, a flexible circuit. In one or more embodiments, the circuit 313 comprises a controller (not shown) operable to control the operation of one or more emitters 332. In other embodiments, the circuit 313 can be coupled to a controller, such as an intra-oral or extra-oral controller. In one or more embodiments, the controller can independently control each of the one or more emitters 332. For example, using the circuit 313, the controller can collectively and/or individually control the on/off state, the intensity, the frequency, the pulse, the duty factor, and/or any other suitable parameter of the one or more emitters 332. Any one of these parameters can be changed while the apparatus is in use. By powering on one or more of the emitters 332, the controller enables the one or more emitters 332 to emit light and thereby accelerate bone remodeling and/or tooth movement. By powering off one or more of the emitters 332, the controller minimizes the movement of the teeth in the area, as bone remodeling will not have been accelerated by the light. In one or more embodiments, one or more emitters 332 within panel 305 can be on while one or more other emitters 332 within panel 305 are off In one or more embodiments, when the apparatus is in use, one or more emitters 332 can start in the on state and then, at some later time, switch to the off state. By increasing or decreasing the intensity of the light, the controller can increase or decrease the dosage of light to the patient. A dosage of light is based on intensity and time so, in some instances, increasing the intensity of the light allows a decrease in the amount of time that the light needs to be administered to the patient. As a practical matter, there is a biological threshold of both minimum time and intensity in order to produce a therapeutic result. The controller can operate the emitters 332 at or above this threshold. In one or more embodiments, the intensity of light emitted from one or more emitters 332 within the panel 305 can be increased while the intensity of light emitted from one or more other emitters 332 within the panel 305 is decreased.

This increase and decrease can occur, for example, while the apparatus is in use.

The controller can control the frequency and duty factor so that higher peak intensities can be achieved. High peak intensities can be useful in thicker tissues and/or when dosages of light need to be administered at greater depths. In one or more embodiments, a first emitter within the panel 305 can be disposed adjacent to and targeting a bone region that is deeper beneath the alveolar soft tissue than the bone region that a second emitter within the panel 305 is targeting. In these embodiments, the controller can program or control the first emitter so that it emits light having a higher peak intensity than the second emitter. Controlling the duty factor can also protect the emitters from overheating. For example, the controller can operate one or more emitters 332 at a 25% duty factor and at a frequency of 100 Hz such that the emitters 332 are ON for 11400th of a second and then OFF for 3/400ths of a second. The OFF time would allow the emitters 332 to cool down, thereby avoiding any potential performance degradation associated with higher temperatures.

As disclosed herein, the controller can individually and selectively control the various light emission characteristics of each emitter 332 within the panel 305 and, as a result, each emitter 332 can operate independently of the other emitters 332 within the panel 305. Specifically, each emitter 332 within the panel 305 can emit light having different characteristics, if needed. The panel 305, therefore, can irradiate light at more than one wavelength or otherwise irradiate light having multiple different characteristics. In other embodiments, the controller can collectively control the various light emission characteristics of the emitters 332 within the panel 305. In some instances, all of the emitters 332 within the panel 305 are controlled so that they emit light having the same characteristics. These emitters 332, however, can be operated and controlled independently of emitters within other panels of the apparatus. For example, the emitters 332 can emit light having a wavelength of 850 nm while the emitters within another panel (e.g., subpanel 304 shown in FIG. 23) emit light having a wavelength of 650 nm.

Emitted light characteristics, therefore, can vary from panel to panel within the apparatus. In other instances, the emitters 332 within the panel 305 can form groups and the emitters within each group are collectively controlled. For example, the panel 305 can comprise two groups of emitters 332: the first group of emitters can emit light at a first wavelength and the second group of emitters can emit light at a second, different wavelength. The panel 305, and the emitters 332 therein, can be customized for a specific patient so that an effective amount or dosage of light is administered to the patient and specific regions within the mouth are targeted. This customization can be useful when, for example, one region of the mouth undergoes a different light treatment than another region of the mouth.

In one or more embodiments, the apparatus can comprise an internal power source, such as a battery (not shown). In other embodiments, the apparatus can comprise a port, such that the circuit 313 can be coupled to an external power source.

In one or more embodiments, the circuit 313 can comprise one or more sensors (not shown) to detect the temperature of the apparatus, the patient's alveolar soft tissue and/or the patient's root area. For example, a thermistor or similar temperature measuring device can be placed in the circuitry 313 to monitor the temperature of the emitters 332 (e.g., an LED array) and panel 305 as well as measure the temperature inside the patient's mouth. This information can serve as a method of obtaining temperature-related information as well as monitoring patient compliance. When the circuits are placed in the mouth (i.e., circuit 313 and the circuits from the remaining panels of the apparatus) and when the apparatus emits light, the temperature of the emitters will rise from pre-treatment ambient temperature closer to normal body temperature. By monitoring the change in temperature, the controller can monitor the period of time that the emitters 332 are in the mouth, based on the period of time the temperature is elevated and close to body temperature.

Alternatively, as described in more detail with reference to FIGS. 40A-40C, a photodetector can be placed in the circuit 313 and/or with the emitters 332 to measure the amount of light reflected from the alveolar soft tissue. This configuration can serve as a method of monitoring patient compliance and also serve as a failsafe mechanism to ensure that the emitters 332 do not operate unless the apparatus is within the mouth of the patient.

The reflective backing 311 can be a metallic foil or other suitable reflective material operable to cause the light emitted by the emitters 311 to be directed in a desired direction, in one or more embodiments, substantially one direction, e.g., no more than about 1 to about 10 degrees of a specific direction. For example, the reflective backing 311 can define the back of the apparatus, such that the light is directed towards the alveolar soft tissue or root area of the patient (e.g., the region beneath the alveolar soft tissue that includes bone and roots).

The wires 312 can be super-elastic wires operable to cause the apparatus to conform to the alveolar soft tissue and/or gingiva. In one or more embodiments, the wires 312 can produce a relatively large orthodontic and/or orthopedic force, such as a force operable to urge one or more teeth to move. The force can be, for example, from about 10 to about 1000 grams of force. In one or more embodiments, the force is a heavy force. In other embodiments, the apparatus can be a portion of and/or be coupled to a separate intra-oral apparatus, such as orthodontic braces, retainers and/or any other suitable functional appliance. In some such embodiments, the separate intra-oral apparatus can produce a force in combination with or in lieu of the wires 312 producing a force.

Figure 26:
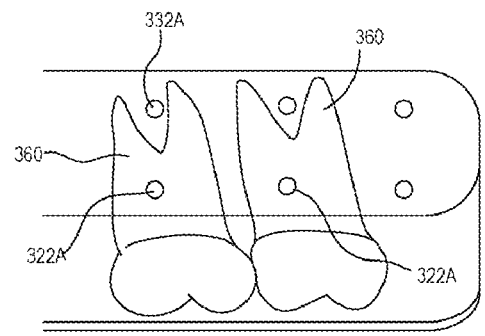
FIGS. 26-30 are schematic diagrams of intra-oral light-therapy apparatuses according to an embodiment of the invention.
Figure 27:
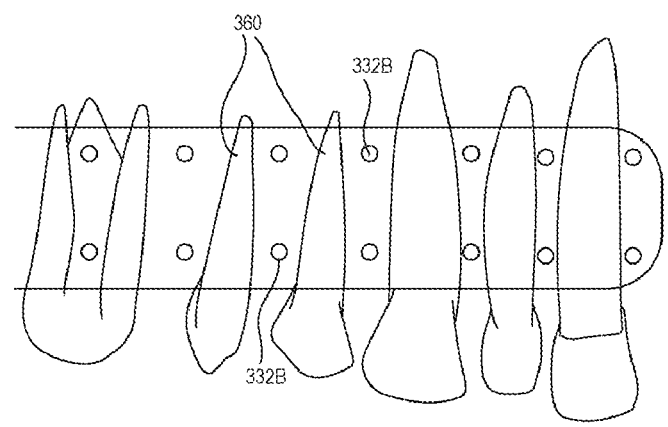
Figure 28:
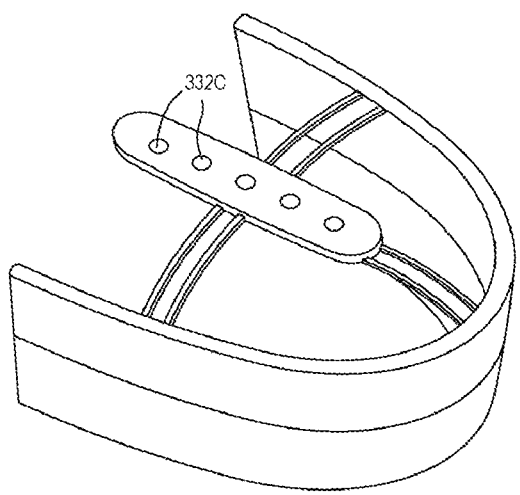

FIGS. 26-28 are schematic diagrams of an apparatus of the invention. As shown in FIG. 26, in one or more embodiments, one or more emitters 332A can be disposed over the roots of one or more teeth 360. In other embodiments, as shown in FIG. 27, one or more emitters 332B can be disposed between the roots of one or more teeth 360. In such embodiments, a mask can be applied to the apparatus and/or the root area of each tooth 360 to prevent the root area of the teeth 360 from being exposed to the light. As is disclosed herein, the mask blocks the light irradiated from the one or more emitters 332A and/or 332B so that little or none of the light reaches the area covered by the mask. The mask can be a tooth mask. The mask can be opaque and/or reflective. In one or more embodiments, the mask comprises an adhesive surface so that the mask can be placed and adhered to an outer surface of the apparatus at a location where light is desired to be blocked. In one or more embodiments, the mask is in the form of a sticker. The adhesive surface of the mask can contact and/or cover one or more panels (or a portion thereof). In one or more embodiments, the opposing outer surface of the mask (or a portion thereof) can contact the alveolar soft tissue (e.g., the alveolar mucosa) when the mask is adhered to the apparatus and the apparatus is in the patient's mouth. In one or more embodiments, more than one mask can be applied to the apparatus and/or the root area of each tooth 360 to prevent the root area of the teeth 360 from being exposed to the light. In some such embodiments, more than one type of mask can be applied. For example, both an opaque mask and a reflective mask can be applied to the apparatus.

In other embodiments, as shown in FIG. 28, one or more emitters 332 can be operable to illuminate the maxillary suture, for example, the midline of the maxillary suture. In one or more embodiments, the one or more emitters 332C emit light directed towards the maxillary suture before, during, and/or after an orthopedic force is exerted on the maxillary suture. The orthopedic force can be exerted by an orthodontic appliance, such as, for example, a Rapid Maxillary Expansion (RME) appliance. A RME appliance can exert orthopedic forces on the patient's molars to open up and expand the maxillary suture for skeletal expansion of the upper jaw (as opposed to an orthodontic expansion where only the teeth move). Light therapy can be useful in these embodiments to accelerate the rate at which the maxillary bone grows and the gaps caused by the skeletal expansion are filled. In one or more embodiments, the present methods are useful for accelerating the fill of bone and/or decreasing the potential for relapse or narrowing of the maxillary arch after orthodontic appliance removal. In one or more embodiments, the one or more emitters 332C emit light directed towards the midline of the palate such that boney regeneration is simulated through light therapy. In one or more embodiments, the apparatus shown in FIG. 28 is customized to fit around the RME appliance or other like fixed orthodontic expander. In one or more embodiments, the apparatus shown in FIG. 28 comprises the one or more emitter 332C that illuminate the maxillary suture as well as one or more other emitters that illuminate the alveolar soft tissue.

The emitters 332A, 332B and/or 332C can operate in a manner similar to the emitters 332 depicted in FIG. 25A.

Figure 29:
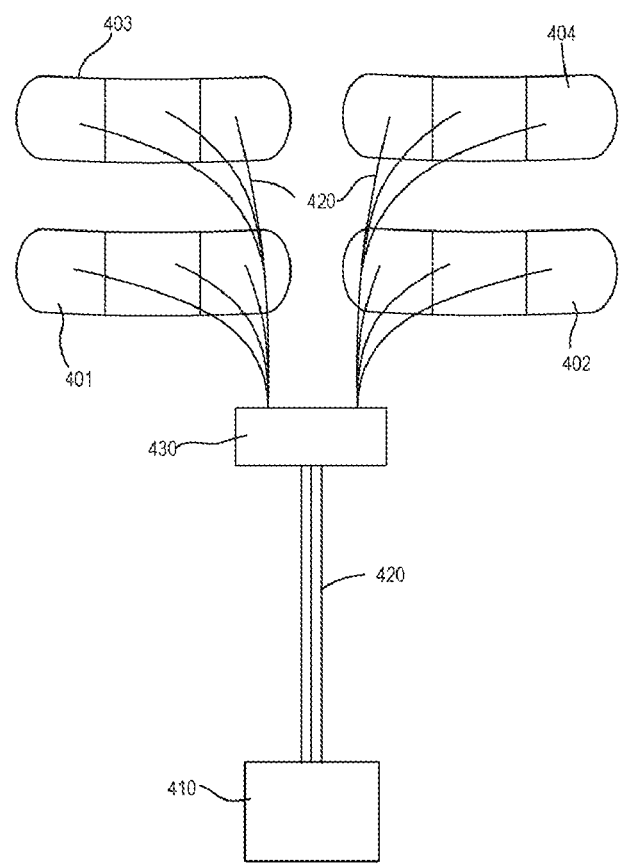

FIG. 29 is a schematic diagram of an apparatus, according to an embodiment. The apparatus comprises four panels 401, 402, 403, 404, a light source 410, one or more optical fiber cables 420, and a controller 430. The panels 401, 402, 403, and/or 404 can be configured to be disposed adjacent to the root area of the upper and/or lower jaw. For example, in one or more embodiments, the panels 401, 402, 403, and/or 404 are in contact with the root area of the upper and/or lower jaw; whereas, in other embodiments, the panels 401, 402, 403, and/or 404 are not in contact with the root area of the upper and/or lower jaw but are at a particular distance (e.g., from 0.1 cm to 3 cm) of the root area of the upper and/or lower jaw. Such configurations can eliminate the need to place electronics in the oral cavity.

The light source 410 can be operable to emit light. For example, in one or more embodiments, the light source 410 can output monochromatic light. For example, the light source 410 can be a laser, an LED, and/or any other suitable light source. The light source 410 can be configured to emit a light having a wavelength ranging from about 600 nm to about 1200 nm, emit light output at more than one wavelength, progress through a range of wavelengths, and/or emit a broad spectrum light output or any suitable wavelength or wavelengths. The light source 410 can output light with any wavelength or characteristic described herein.

The light can be conveyed from the light source 410 to the controller 430 via one or more optical fibers 420. The controller 430 can be, for example, an optical switch.

The controller 430 can be operable to selectively transmit light from the light source 410 to the panels 401, 402, 403, and/or 404 via one or more optical fibers 420. For example, the controller 430 can collectively and/or individually control the on/off state, the intensity, the frequency, the pulse, the duty factor, and/or any other suitable parameters of the light that is delivered to the panels 401, 402, 403, and/or 404. The controller 430 can operate similar to the controller depicted in FIG. 25A.

In one or more embodiments, more than one optical fiber 420 can be directed to each panel. The optical fiber can terminate adjacent to (e.g., from 0.1 cm to 3 cm) or at the root area, similar to the apparatuses shown and described with reference to FIGS. 26 and 27. Thus, each optical fiber can direct light from the light source 410 to the root area. By providing more than one fiber 420, light from the source 410 can be directed and/or controlled to illuminate a specific portion of the root area. In this way, the controller 430 can selectively apply light to the root area of one or more teeth, similar to the emitters 332, 332A, and/or 332B as shown and described herein with reference to FIGS. 25, 26 and 27.

Figure 30:
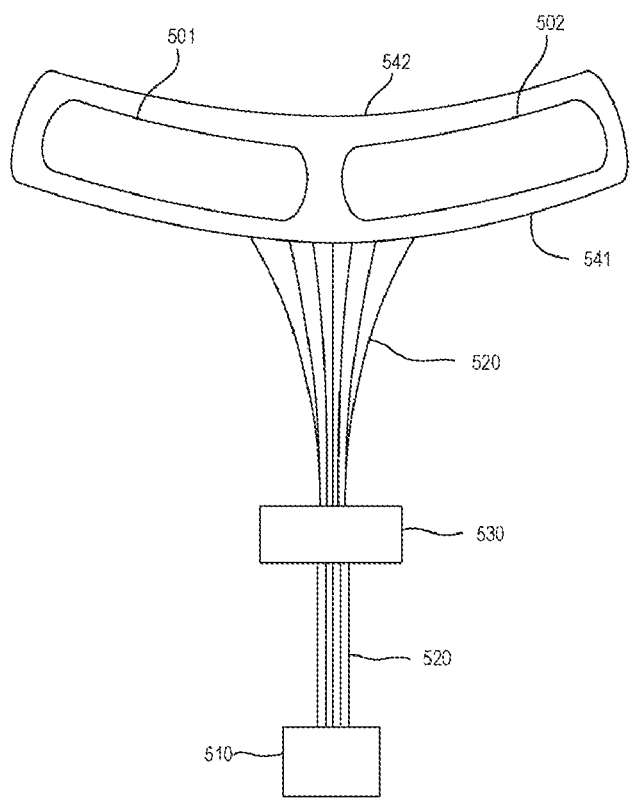

FIG. 30 is a schematic diagram of an apparatus, according to an embodiment. The apparatus comprises two panels 501, 502, a light source 510, an optical fiber ribbon 520, and a controller 530. The panels 501 and 502 can be configured to be disposed adjacent to the root area of the upper jaw as well as the root area of the lower jaw. As is disclosed herein, the panels 501 and 502, for example, can first be disposed adjacent to the root area of the upper jaw; then, after orthodontic treatment of the upper jaw is complete, the panels 501 and 502 can be removed from the upper jaw and placed on the lower jaw such that they are disposed adjacent to the root area of the lower jaw. In one or more embodiments, the panels 501, 502 are in contact with the root area of the upper and/or lower jaw; whereas, in other embodiments, the panels 501, 502 are not in contact with the root area of the upper and/or lower jaw but are at a particular distance (e.g., from 0.1 cm to 3 cm) of the root area of the upper and/or lower jaw. Such configurations can eliminate the need to place electronics in the oral cavity.

The panels 501, 502 can define an upper portion 542. The cross-section of the upper portion 542 can be rounded and/or teardrop shaped (similar to the portion of the panel 309 depicted in FIG. 25A) to provide for patient comfort and to allow the apparatus to adapt to the flange area of the upper and lower jaw. For example, as is disclosed herein, the apparatus can be worn on the upper jaw so that the upper portion 542 of the panels 501, 502 adapt to the upper flange area; then, the apparatus can be removed from the upper jaw, flipped upside down, and then installed on the lower jaw such that the upper portion 542 is now disposed in the lower flange area. In this manner, the upper portion 542 of the panels 501, 502 is configured to fit and adapt to both the upper and lower flange area of the patient's mouth. In one or more embodiments, the panels 501, 502 can also define a lower portion 541 that has a rounded and/or teardrop shaped cross-section so that, for example, the apparatus can be removed from the upper jaw and installed on the lower jaw without having to flip the apparatus. Here, the lower portion 541, as opposed to the upper portion 542, is disposed and configured to fit in the lower flange area.

The portions 541, 542 of the panels 501, 502 can have any shape that does not include sharp or acute edges as such edges would irritate or be uncomfortable in the depth of the vestibule of the patient's mouth. In one or more embodiments, the portions 541 and/or 542 have a shape or cross-sectional shape that disperses forces and minimizes pressure points which would cause discomfort for the patient. In one or more embodiments, the portions 541 and/or 542 have a thicker cross-section than the remaining portions of the panels 501, 502. In this manner, the portions 541 and/or 542 can deflect the delicate mucosal soft tissue and allow full extension of the flanges with little or no discomfort to the patient. More specifically, the portions 541 and/or 542 can deflect buccal tissue away from the alveolus.

The light source 510 can be operable to emit light in the same manner as the light source 410 in reference to FIG. 29. The light can be conveyed from the light source 510 to the controller 530 via the optical fiber ribbon 520. The controller 530 can be operable to selectively transmit light from the light source 510 to the panels 501 and/or 502 via the optical fiber ribbon 520 in the same manner as the controller 430 in reference to FIG. 29. For example, the controller 530 can collectively and/or individually control the on/off state, the intensity, the frequency, the pulse, the duty factor, and/or any other suitable parameters of the light that is delivered to the panels 501 and/or 502.

The optical fiber ribbon 520 can be coupled to the apparatus, as shown in FIG. 30, such that one or more optical fibers of the ribbon 520 are electrically connected and/or directed to each panel 501, 502. For example, one or more of the optical fibers in the ribbon 520 can terminate adjacent to (e.g., from about 0.1 cm to 3 cm) or at the root area, similar to the apparatuses shown and described with reference to FIGS. 26 and 27. Thus, each optical fiber of the ribbon 520 can direct light from the light source 510 to the root area in the same manner as the optical fibers 420 in reference to FIG. 29. The optical fibers of the ribbon 520 can be configured to optically couple the panels 501, 502 together. The optical fiber ribbon 520 can have one or more optical fibers for example, in one or more bundles, therein. For example, the ribbon 520 can have anywhere from 1 fiber to 500 fibers for each panel 501, 502 depending on the specific light emission technology or pattern used for the treatment. The optical fiber ribbon 520 can have any suitable shape and/or size such that the ribbon can comfortably extend from the apparatus to outside the patient's mouth. The ribbon 520 can, for example, have a width of about 0.5 cm to about 1.0 cm. Although the apparatus of FIG. 30 is illustrated and described as having a single ribbon that electrically couples to both panels 501 and 502, in other embodiments, the apparatus comprises more than one ribbon. For example, in one or more embodiments, the apparatus comprises two ribbons. In one or more embodiments, one ribbon can be electrically connected to the panel 501 and the other ribbon can be separately electrically connected to the panel 502. In one or more embodiments, the ribbon 520 is a woven fiber-optic fabric. More specifically, the ribbon 520 in this embodiment can be comprised of one or more optical fibers that are woven into a fabric. In one or more embodiments, light from the woven fiber optic fabric is emitted at about 90 degrees or is emitted perpendicular to the plane of the fabric. An example of a woven fiber optic fabric that is useful with the apparatus of FIG. 30 is LightMat®, which is commercially available from Lumitex, Inc. (http://www.lumitex.com/).

As disclosed herein, the apparatus in FIG. 30 can be installed on either the upper or lower jaw. In one or more embodiments, the apparatus in FIG. 30 is installed during orthodontic treatment. For example, at the outset of the treatment, the apparatus can be installed on the upper jaw such that the upper portion 542 of the apparatus is disposed in the upper flange area. Then, at a later time during the treatment, the patient can remove the apparatus from the upper jaw and install the apparatus on the lower jaw for the remainder of the treatment. In one or more embodiments, the apparatus can be installed on the lower jaw such that the lower portion 541 of the apparatus is disposed within the lower flange area. In this embodiment, the apparatus remains right-side up. In another embodiment, however, the apparatus can be installed on the lower jaw such that the upper portion 542 of the apparatus is disposed within the lower flange area. In other words, after the patient removes the apparatus from his or her upper jaw, he or she rotates the apparatus 180 degrees so that it is upside down and then installs the apparatus on the lower jaw. The upper portion 542, in this embodiment, fits both the upper and lower flange area.

In one or more embodiments, the apparatus comprises an electronic device, such as a position sensor, that can determine the position or orientation of the apparatus relative to the patient's mouth. More specifically, in embodiments where the apparatus is turned upside down (e.g., rotated 180 degrees) for installment on the lower jaw, the apparatus can comprise an electronic device that determines the apparatus's position or orientation in a patient's oral cavity during an orthodontic treatment. For example, the sensor can determine whether the apparatus is being worn on the upper jaw or on the lower jaw. Such an electronic device can be useful in monitoring compliance during orthodontic treatment. In one or more embodiments, the electronic device can be one or more switches, sensors, and/or the like.

Figure 59:
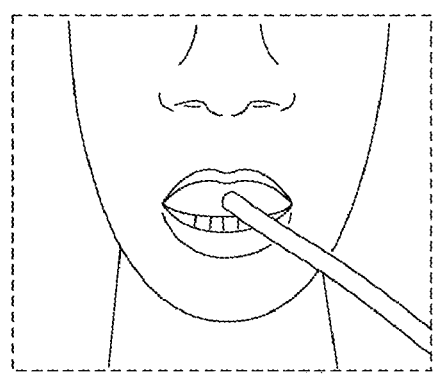
FIG. 59 is an image of the apparatus of FIGS. 52-58 disposed in the oral cavity of and in use by a patient.
Figure 60:
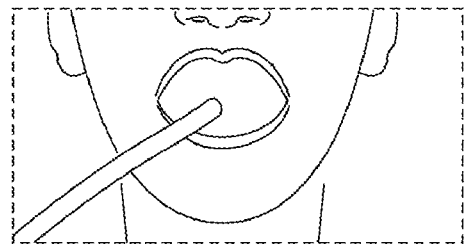
FIG. 60 is an image of an intra-oral light-therapy apparatus according to an embodiment of the invention disposed in the oral cavity of and in use by a patient.
Figure 61:
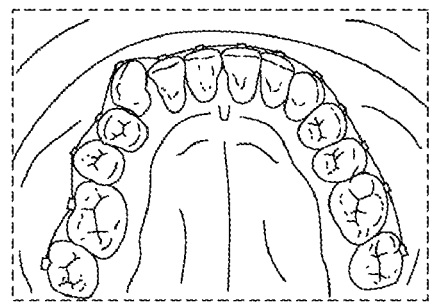
FIG. 61 is an image of an upper arch of a patient prior to light therapy treatment using the intra-oral light-therapy apparatus of FIG. 60.
Figure 62:
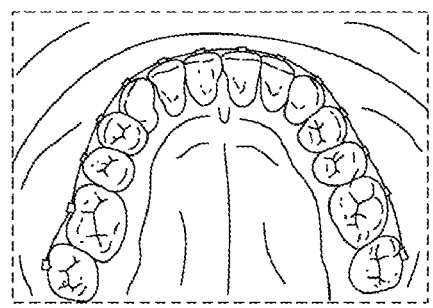
FIG. 62 is an image of the patient's upper arch of FIG. 61 after light therapy treatment using the intra-oral light-therapy apparatus of FIG. 60.
Figure 63:
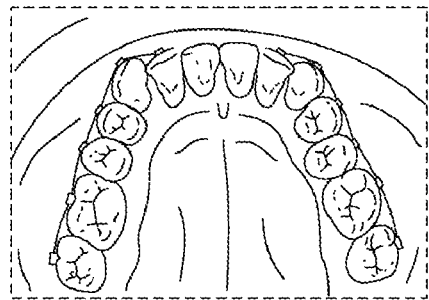
FIG. 63 is an image of the upper arch of a patient prior to light therapy treatment using the intra-oral light-therapy apparatus of FIG. 60.
Figure 64:
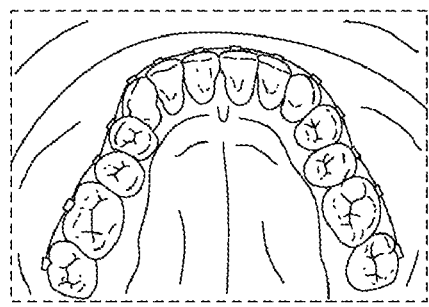
FIG. 64 is an image of the patient's upper arch of FIG. 63 after light therapy treatment using the intra-oral light-therapy apparatus of FIG. 60.

Any of the apparatus illustrated and described herein with reference to FIGS. 23-30 can have any number of panels, which can operate and function in any manner described herein. Although not necessarily illustrated, in one or more embodiments, the panels can be coupled together and/or encapsulated within one or more units. For example, the panels 403 and 404 in FIG. 29 can be coupled together and/or encapsulated in a single unit, similar to a mouth guard that fits the upper teeth. The panels 401 and 402 can likewise be coupled together and/or encapsulated within a single unit, similar to a mouth guard that fits the lower teeth. Example of mouth guards including light emitting panels are shown in FIGS. 52-59 and FIGS. 65-72. It should be noted that although the mouth guard is shown in FIG. 59 positioned with respect to the upper teeth of the patient, the mouth guard is also configured to be positioned with respect to the lower teeth of the patient. In another example, the panels 403 and 404 can be coupled together such at least a portion of the panel 403 overlaps a portion of the panel 404. The panel 403 in this example can emit light at the same wavelength as or at a wavelength different from the panel 404. Furthermore, power output and light treatment intensity can be increased by the layering or overlapping of one or more panels.

In one or more embodiments, any of the intra-oral apparatuses described herein can comprise a handheld controller that houses one or more of a microprocessor, menu-driven software and an LCD screen. The controller can be programmed to calculate and/or monitor one or more light therapy sessions and their duration. A user interface can display session information to the patient so that, for example, the patient is aware of the number of sessions completed and the time remaining in each session. The controller can use any suitable power supply including, for example, a UL-certified power supply. In one or more embodiments, the intra-oral apparatus can comprise four treatment arrays, each of which can comprise a flexible printed circuit board and a set of LEDs mounted to a contoured heat sink and infrared-transmissible lens, in one or more embodiments, a plastic lens, and having conductive cables that attach to the controller.

Figure 31:
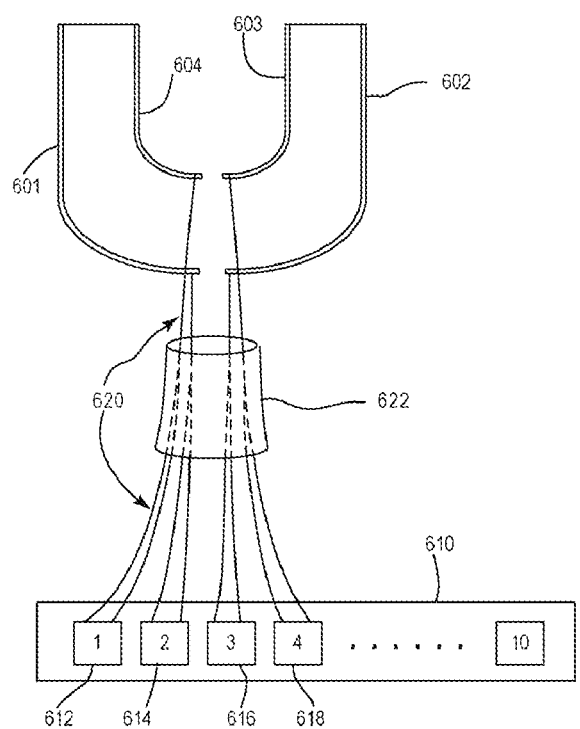
FIG. 31 is a schematic diagram of an intra-oral light-therapy apparatus according to an embodiment of the invention.

FIG. 31 is a schematic diagram of an apparatus, according to an embodiment. The apparatus can be configured for intra-oral light therapy of a patient. The apparatus comprises four panels 601, 602, 603, and 604, a light source 610, and optical fibers 620. The panels 601, 602, 603 and 604 can be configured to be disposed adjacent to the root area of the upper jaw as well as the root area of the lower jaw, for example, in a similar manner as described herein in reference to FIGS. 23-30. More specifically, panels 601 and 602 can be disposed adjacent to the anterior root area of the upper jaw (or lower jaw), and panels 603 and 604 can be disposed adjacent to the posterior root area of the upper jaw (or lower jaw). In other words, the panels 601, 602, 603, 604 can be configured to be disposed anterior (for panels 601, 602) and posterior (for panels 603, 604) to each of the maxillary root area and the mandibular root area. In this manner, in use, the panels 601, 602 can be configured to emit light in a direction towards the panels 603,604, and panels 603, 604 can be configured to emit light in a direction towards the panels 601, 602. The panels 601, 602, 603 and 604, for example, can first be disposed adjacent to the respective anterior or posterior root area of the upper jaw; then, after orthodontic treatment of the upper jaw is complete, the panels 601, 602, 603 and 604 can be removed from the upper jaw and placed on the lower jaw such that they are disposed adjacent to the respective anterior or posterior root area of the lower jaw. In one or more embodiments, the panels 601, 602, 603 and 604 are in contact with the root area of the upper and/or lower jaw; whereas, in other embodiments, the panels 601, 602, 603 and 604 are not in contact with the root area of the upper and/or lower jaw but are at a particular distance (e.g., from 0.1 cm to 3 cm) of the root area of the upper and/or lower jaw. In one or more embodiments, the panels 601, 602 can be configured to be disposed adjacent to (e.g., in contact with or at a particular distance from) the upper and/or lower buccal lingual alveolar soft tissue and panels 603, 604 can be configured to be disposed adjacent to the upper and/or lower lingual alveolar soft tissue. Such configurations can eliminate the need to place electronics in the oral cavity.

The panels can be similar in one or more respects or identical to any panel described herein, including, for example, those described in reference to FIGS. 22-30. Each panel 601, 602, 603, 604 is associated with a bundle of optical fibers 620 that extend to the light source 610. More specifically, each panel 601, 602, 603, 604 is associated with an emitter 632 of the light source 610 via a bundle of optical fibers 620. In this manner, each panel 601, 602, 603, 604, and any housing (not shown in FIG. 31) to which the respective panel is coupled, is optically coupled to the emitter 632 of the light source 610.

The light source 610 can be operable to emit light in the same manner as the light source 410 in reference to FIG. 29 and/or light source 510 in reference to FIG. 30. The light source 610 can comprise, for example, one, two three, four or more (e.g., ten) LEDs (including, for example, the LEDs 612, 614, 616, 618 shown in FIG. 31). At least a portion of the light source 610, for example, including the LEDs 612, 614, 616, 618, can be disposed in an external housing of the apparatus, at least a portion of which is configured to be disposed extra-orally when the panels 601, 602, 603, 604 are disposed in the oral cavity adjacent the root area as described herein. For example, the external housing of the apparatus can be extended through an opening formed by the patient's lips when the panels 601, 602, 603, 604 are disposed in the oral cavity adjacent the root area as described herein.

Figure 32:
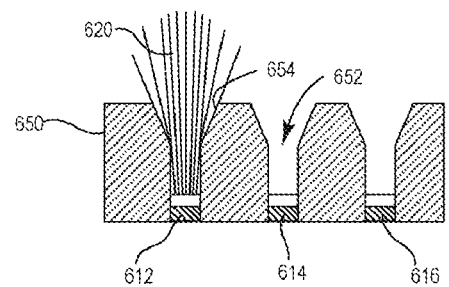
FIG. 32 is a sectional view of a portion of the apparatus of FIG. 31.
Figure 33:
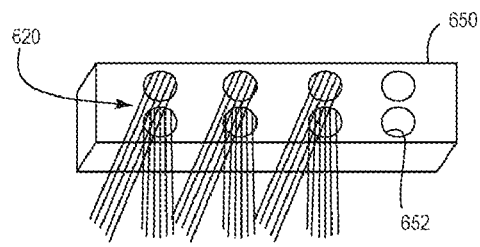
FIG. 33 is a top perspective view of a portion of the apparatus of FIG. 31.
Figure 34:
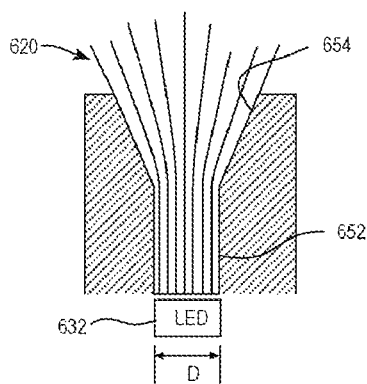
FIG. 34 is a sectional view of a portion of the apparatus of FIG. 31.

The apparatus can comprise a manifold 650 defining one or more openings 652 therethrough. Each opening 652 of the manifold 650 can comprise a tapered surface portion 654 such that at least a portion of the opening 652 is funnel-shaped. A bundle of optical fibers 620 extending between the light source 610 (e.g., one of the LEDs 612, 614, 616, 618) and one of the panels (e.g., panel 601) can be disposed through the opening 652 of the manifold 650. As illustrated in FIG. 32, ends of the optical fibers 620 in the bundle are seated over, or adjacent, the LED 612. For example, in one or more embodiments, ends of the optical fibers 620 in the bundle are seated over an LED package (e.g., LED package 632, shown in FIG. 34, which can comprise, for example, LED 612) or other suitable light source. At least one of the portion of the opening 652 of the manifold 650 proximate to the LED package (or other emitter) 632, or the LED package (or other emitter) 632, can have a diameter equal to or narrower than a diameter of the optical fiber bundle. For example, as shown in FIGS. 33 and 34, each of the optical fiber bundle 620 and the manifold 650 opening 652 proximate to the LED package 632 has a diameter D. The use of the funnel-shaped manifold allows for organization of the optical fibers 620 into groups of smaller bundles, thereby eliminating any need for bulky on-board ferrules. Such organization of the optical fibers 620 via the manifold 650 also provides for addressing of an individual panel 601, 602, 603, 604, as described in more detail herein.

The light can be conveyed from the LEDs (e.g., LED 612, 614, 616, 618) of the light source 610 to the panels 601, 602, 603 and/or 604 via the optical fibers 620. For example, a controller (not shown in FIG. 31) can collectively and/or individually control the on/off state, the intensity, the frequency, the pulse, the duty factor, and/or any other suitable parameters of the light that is delivered to the panels 601, 602, 603 and/or 604.

The optical fibers 620 can be coupled to the apparatus, as shown in FIG. 31, such that bundles of optical fibers 620 are electrically connected and/or directed to each panel 601, 602, 603, 604. For example, the optical fibers 620 can be coupled such that proximal ends of the optical fibers 620 are coupled, or are otherwise adjacent, at least one of the light source 610 and the manifold 650 and such that distal ends of the optical fibers 620 are coupled, or are otherwise adjacent, to one or more panels 601, 602, 603 and/or 604. One or more of the optical fibers 620 (i.e., the distal end of one or more of the optical fibers) can terminate adjacent to (e.g., from about 0.1 cm to 3 cm) or at the root area, similar to the apparatuses shown and described with reference to FIGS. 26 and 27. Thus, each optical fiber 620 can direct light from the light source 610 to the root area in the same manner as the optical fibers 420 in reference to FIG. 29. The optical fibers 620 can be configured to optically couple the panels 601, 602, 603 and/or 604 together. The optical fibers 620 can be bundled in any suitable number of fibers. For example, each panel 601, 602, 603 and/or 604 can be associated with a bundle of anywhere from 1 fiber to 500 fibers depending on the specific light emission technology or pattern used for the treatment. The optical fibers 620 can have any suitable shape and/or size such that the fibers can comfortably extend from the panel to the light source 610 disposed outside the patient's mouth. The optical fibers 620 can, for example, have a collective width of about 0.5 cm to about 1.0 cm. A collar 622 can be disposed about one or more of the bundles of optical fibers 620 to maintain fiber bundles together. The apparatus shown in FIGS. 31-34 can be installed on either the upper or lower jaw, for example, during orthodontic treatment.

Figure 35:
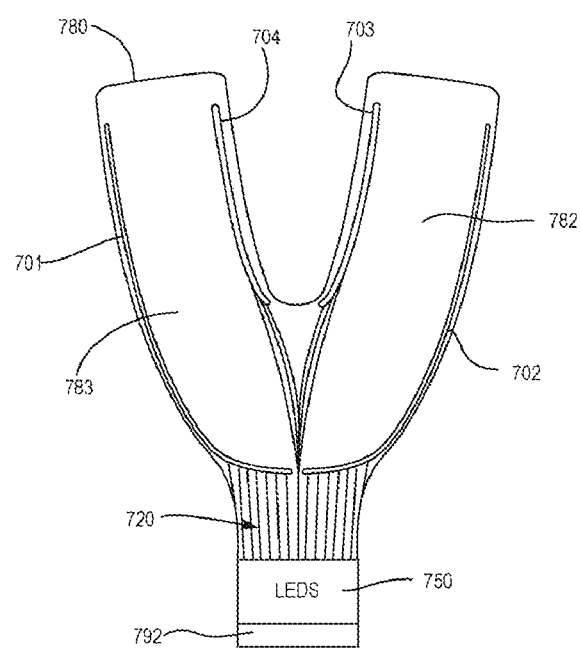
FIG. 35 is a schematic diagram of an intra-oral light-therapy apparatus according to an embodiment of the invention.

FIG. 35 is a schematic diagram of an apparatus, according to an embodiment. The apparatus can be configured for intra-oral light therapy of a patient. The apparatus can be similar in one or more respects or identical to other intra-oral light-therapy apparatuses described herein, including, for example, the apparatus described herein with reference to FIGS. 31-34. The apparatus comprises an intra-oral housing 780 and an external housing 790 that extends from a front portion of the intra-oral housing (e.g., an anterior portion thereof, for example a midpoint or center point of a front/anterior surface of the intra-oral housing) such that at least a portion of the housing is disposed extra-orally when the intra-oral housing is disposed within the oral cavity.

The intra-oral housing 780 comprises one or more panels 701, 702, 703, 704. The panels 701, 702, 703, 704 can comprise light emitting arrays, fiber mats, organic LEDs ("OLEDs"), or any suitable combination of the foregoing. The panels 701, 702, 703, 704 can be configured to be disposed within the patient's oral cavity in any manner described herein with reference to panels 601, 602, 603, 604.

The intra-oral housing 780 can be connected between the panels 701, 702 configured to be positioned adjacent the anterior root area of the jaw (or the buccal alveolar soft tissue) and the panels 703, 704 configured to be positioned adjacent the posterior root area of the jaw (or the lingual alveolar soft tissue). In one or more embodiments, the intra-oral housing 780 comprises a lower portion configured to extend between a lower portion (not shown in FIG. 35) of the panel 701 and a lower portion (not shown in FIG. 35) of the panel 704, and similarly between a lower portion (not shown in FIG. 35) of the panel 702 and a lower portion (not shown in FIG. 35) of the panel 703. In this manner, the intra-oral housing 780 can comprise recessed portions 782, 783 defined by the lower portion of the intra-oral housing and an upper portion of the intra-oral housing including the panels 701, 702, 703, 704. The recessed portions 782, 783 can be configured to receive, or be disposed about, at least a portion of the patient's dentition.

More specifically, the recessed portions 782, 783 are configured to have a depth sufficient to receive at least a portion of the patient's dentition in the lower portion of the intra-oral housing such that the upper portion of the intra-oral housing including the panels 701, 702, 703, 704 is disposed adjacent and/or in contact with the alveolar soft tissue or the root area of the upper and/or lower jaw.

Optical fibers 720 extend between the panels 701, 702, 703, 704 and a light source (not shown in FIG. 35) disposed in the external housing 790 (e.g., at a front portion of the external housing configured to remain outside the oral cavity when the apparatus is in use) such that one or more optical fibers are electrically connected and/or directed to each panel 701, 702, 703, 704. For example, one or more of the optical fibers 720 can terminate adjacent to (e.g., from 0.1 cm to 3 cm) or at the root area, similar to the apparatuses shown and described with reference to FIGS. 26 and 29. Thus, each optical fiber 720 can direct light from the light source to the root area in the same manner as the optical fibers 420 described in reference to FIG. 31. The optical fibers 720 can be configured to optically couple any combination of the panels 701, 702, 703, 704 together. The apparatus can have any suitable number of optical fibers. For example, the apparatus can have anywhere from 1 fiber to 500 fibers for each panel 701, 702, 703, 704 depending on the specific light emission technology or pattern used for the treatment.

The optical fibers 720 can be connected to the light source by a manifold 750. The manifold can be similar in one or more respects or identical to the manifold 650 described with respect to FIGS. 32-34, and thus is not described in detail herein.

The light source can be similar in one or more respects or identical to the light source 610 described herein with reference to FIGS. 31-34, and thus is not described in detail herein. The light source can be operable to emit light. For example, in one or more embodiments, the light source can output monochromatic light. For example, the light source can be or comprise one or more of a laser, an LED, and/or any other suitable light source. The light source can be configured to emit a light having a wavelength ranging from about 600 nm to about 1200 nm, or at any wavelength or wavelength range disclosed herein; emit light output at more than one wavelength; progress through a range of wavelengths; and/or emit a broad spectrum light output or any suitable wavelength or wavelengths. The light source can output light with any wavelength or characteristic described herein.

Figure 36:
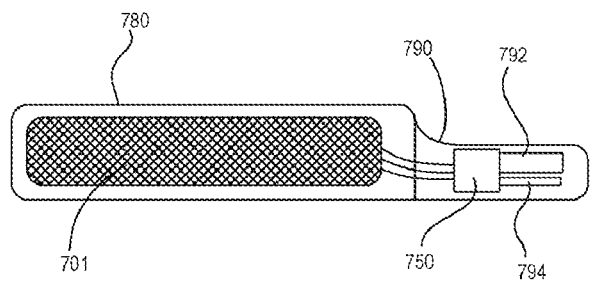
FIG. 36 is a side view of the apparatus of FIG. 35.

The external housing 790 comprises a power source 792 and an electronic circuit 794, as shown in FIG. 36. The power source 792 can be a battery, including, for example, a rechargeable battery. The electronic circuit 794 can comprise a circuit board. The electronic circuit 794 and any associated electronics can be configured to control the apparatus, i.e., during an orthodontic treatment. For example, the electronic circuit is configured to control at least one of an operational state of the light source and/or optical fibers 720, a wavelength, an intensity, a frequency, or a duration of light emission.

Because the apparatus does not require any physical connection to external components during the treatment (e.g., does not require connection to an external light source, external controller, or external power source), the apparatus can be characterized as being self-contained.

The apparatus can be configured to determine whether the apparatus is in an upright or upside down (e.g., rotated 180 degrees) position or orientation (i.e., whether the apparatus is oriented with respect to the upper jaw or the lower jaw). For example, in one or more embodiments, the external housing 790 comprises at least one of a position sensor, a gyroscope and an accelerometer. The gyroscope and/or the accelerometer can be comprise one or more sensors configured to determine the position (or orientation) of the apparatus.

Figure 37:
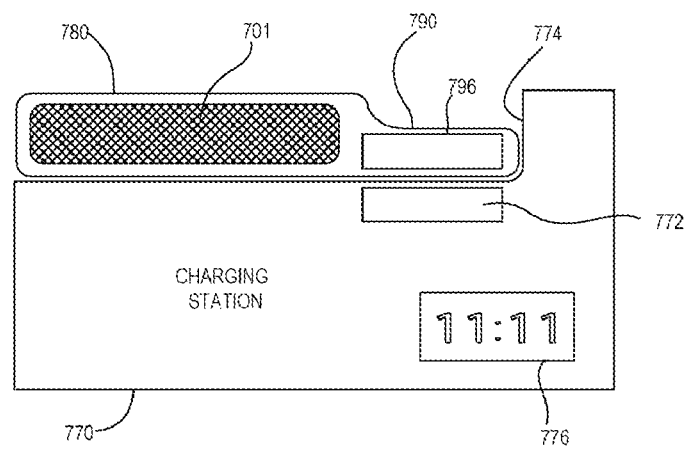
FIG. 37 is a side view of the apparatus of FIG. 35 and a charging station.

In one or more embodiments, the apparatus is a component of a system that also comprises a charging station 770, as shown in FIG. 37. The charging station 770 defines a receiving portion 774 configured to receive at least a portion of the apparatus (e.g., at least a portion of the intra-oral housing 780 and/or the external housing 790), a connection assembly 772, and a display 776. The connection assembly 772 is configured to facilitate charging (or recharging) of the power source 792 disposed in the external housing 790. In one or more embodiments, the connection assembly 772 provides for a physical or wired connection for coupling to a connection assembly 796 of the apparatus to facilitate charging of the power source 792. For example, the connection assembly 772 can comprise a socket disposed on one of the apparatus or the charging station 770 and a corresponding plug disposed on the other of the apparatus or the charging station. In one or more embodiments, the connection assembly 772 is configured for wirelessly charging the power source 792. For example, the connection assembly 772 can be configured to inductively charge the power source 792. The display 776 of the charging station 770 is configured to display information associated with the apparatus and/or the charging station. For example, the display 776 can be configured to display information related to a status or amount of the charge of the power source 792, parameters associated with a treatment protocol, and/or instructions for using one of the charging station 770 or the apparatus. In one or more embodiments, the charging station 770 is configured for uni-directional or bi-directional communication with the apparatus. In this manner, information associated with the treatment protocol and/or treatment history (e.g., patient usage or compliance with the prescribed treatment protocol), including updates including any changes to the treatment protocol and/or treatment history since the most recent information transfer between the apparatus and the charging station.

Figure 38:
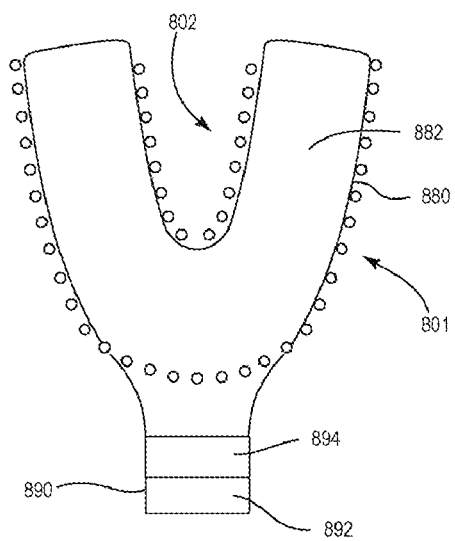
FIGS. 38 and 39 are schematic diagrams of intra-oral light-therapy apparatuses according to an embodiment of the invention.

FIG. 38 is a schematic illustration of an apparatus, according to an embodiment.

The apparatus can be configured for intra-oral light therapy of a patient. The apparatus can be similar in one or more respects, and comprise components similar in one or more respects, or identical, to the apparatus and associated components described herein, including those described herein with reference to FIGS. 35-37. For example, the apparatus comprises an intra-oral housing 880 and an external housing 890. The intra-oral housing 880 is configured to be disposed in an oral cavity. The external housing 890 is extended from a front of the intra-oral housing 880 such that at least a portion of the external housing can extend through an opening formed by the patient's lips and such that at least a portion of the external housing is outside of the oral cavity when the intra-oral housing is disposed in the oral cavity.

The intra-oral housing 880 can be configured to be positioned within the oral cavity in any suitable manner described herein. The intra-oral housing 880 comprises a first light emitting array 801 configured to be disposed adjacent the anterior root area of an upper and/or lower jaw (and/or the buccal alveolar soft tissue) and a second light emitting array 802 configured to be disposed adjacent the lingual root area of an upper and/or lower jaw (and/or the lingual alveolar soft tissue). For example, from a top view, as schematically shown in FIG. 38, the intra-oral housing 880 can have a shape similar to the shape of a U or a horseshoe. Thus, stated another way, the first light emitting array 801 is disposed on an outer portion of the U-shape of the intra-oral housing 880, and the second light emitting array 802 is disposed on an inner portion of the U-shape of the intra-oral housing. In this manner, in use, the light emitting arrays 801, 802 can be configured to emit light in a direction towards the light emitting arrays 803, 804, and light emitting arrays 803, 804 can be configured to emit light in a direction towards the light emitting arrays 801, 802.

The light emitting arrays 801, 802 are at least partially embedded in a material of which the intra-oral housing 880 is constructed. The intra-oral housing 880 can be constructed of any suitable material, including, for example, silicone or another soft, e.g., malleable, material. For example, the light emitting arrays 801, 802 can comprise LEDs, OLEDs, light emitting semiconductors, or any suitable combination thereof, at least partially embedded in the material of which the intra-oral housing 880 is constructed. In one or more embodiments, the light emitting arrays 801, 802 are fully embedded in the intra-oral housing 880 material.

The intra-oral housing 880 can define a recessed portion 882 in a similar manner as that described with respect to recessed portion 782 in reference to FIG. 35, and thus the recessed portion 782 is not described in detail herein.

The external housing 890 comprises a power source 892, electronic circuit 894, and an orientation-sensing mechanism (not shown in FIG. 38). In this manner, the apparatus can be characterized as being self-contained. The power source 892 (e.g., a battery) is configured to provide power to the light emitting arrays 801, 802 via the electronic circuit 894. The electronic circuit 894 can be configured to control the apparatus, e.g., during an orthodontic treatment. The orientation-sensing mechanism is configured to determine a position or orientation of the apparatus, e.g., whether the apparatus is upright for positioning with respect to the upper jaw or upside down for positioning with respect to the lower jaw. The orientation-sensing mechanism can comprise at least one of a position sensor, a gyroscope (e.g., a semi-gyroscope) and an accelerometer.

The apparatus can be configured for use with a charging station, such as charging station 770, in a similar manner as the apparatus described herein with reference to FIGS. 35-37.

Figure 39:
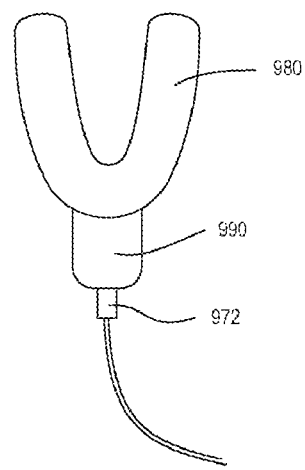

Although the apparatuses described with respect to FIGS. 35-38 have been described as being configured for use with a charging station (e.g., charging station 770), in other embodiments, a self-contained apparatus can be differently configured for charging the power source and/or controlling the emission of light by the apparatus. For example, referring to FIG. 39, an apparatus comprises an intra-oral housing 980 configured to be disposed in an oral cavity and an external housing 990 configured to extend through an opening formed by the patient's lips such that at least a portion of the external housing is outside of the oral cavity when the intra-oral housing is disposed in the oral cavity. The intra-oral housing 980 can be similar in one or more respects, and can comprise components that are similar or identical to those of any intra-oral housing or apparatus for intra-oral light therapy described herein. The external housing 990 can be similar in one or more respects, and can comprise components that are similar or identical to those of external housings 790 and 890 described herein.

A power source (not shown in FIG. 39) in the external housing 990 is configured to be charged via a connector 972 (e.g., a USB mini- or microplug). The apparatus can be electronically linked, or paired, with an external electronic device, such as a mobile phone, including smartphones (e.g., an iPhone® or an Android™ based device). The apparatus can be configured for at least one of wireless uni-directional or wireless bi-directional communication with the external electronic device, such as via a Bluetooth® or other wireless connection. For example, the apparatus can be configured to transmit to the external electronic device information associated with patient usage and/or treatment protocol compliance, and can be configured to receive from the external electronic device information associated with a medical treatment. An application loaded onto the external electronic device can be useful for monitoring and controlling the orthodontic treatment using the apparatus and/or to record and review patient usage history and/or prescribed treatment protocol compliance history.

In one or more embodiments, an apparatus according to an embodiment is configured to detect an amount of light, e.g., its intensity or duration that is irradiated at, absorbed by or reflected by a patient's periodontia (e.g., a portion of the root area of the upper and/or lower jaw and/or the alveolar soft tissue) by the apparatus. In this manner, for example, an apparatus according to an embodiment can be configured to assess patient compliance with a prescribed treatment protocol, as described herein. Referring to FIG. 40A, an apparatus according to an embodiment can comprise a light emitting array 1101, which can be similar or identical to any light emitting array described herein, and one or more photodetectors 1102. In one or more embodiments, the light emitting array 1101 comprises one or more emitters operable to illuminate a region of or associated with a portion of the root area of the upper and/or lower jaw and/or the alveolar soft tissue. At least a portion of the photodetectors 1102, such as one or more sensors of the photodetectors, are configured to be positioned within the oral cavity to detect the transmission or reflection of light (i.e., photons) emitted by the light emitting array 1101 from the alveolar soft tissue (and associated alveolus). For example, the photodetectors 1102, or a sensor thereof, can be positioned on a palatial surface within the oral cavity, and can be in electrical communication with a portion of the photodetector disposed outside of the oral cavity. Detection of the light transmission by the photodetectors 1102 during an orthodontic treatment activates the photodetectors every few seconds. The apparatus can be configured to power off if no reflected light is detected by the photodetectors for a predetermined period of time. The apparatus can be configured to store a record of the history of light detection and of the apparatus being powered off because of a lack of detection. Such usage information can be useful to determine whether the patient is compliant with a prescribed treatment protocol. This configuration can also serve as a failsafe mechanism to ensure that the light emitting array 1101 does not operate unless the apparatus is within the mouth of the patient. This configuration can also be useful for obtaining information about a patient's bone density, where the information can be useful for customizing a dosage of light therapy to be administered to a patient, as described herein. The foregoing compliance assessment mechanism can be included in, or otherwise incorporated into, any apparatus for intra-oral light therapy described herein.

Figure 40A:
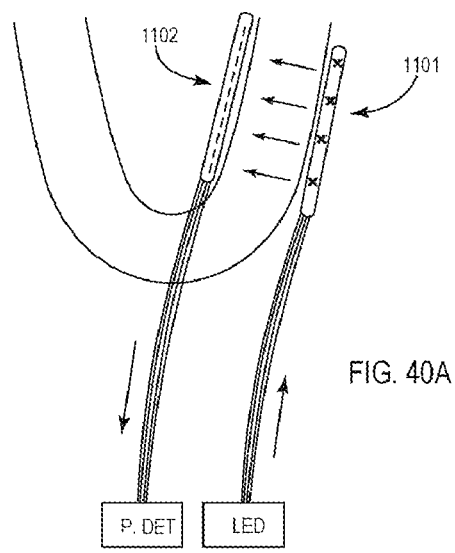
FIG. 40A is a top view of a portion of an intra-oral light-therapy apparatus according to an embodiment of the invention.
Figure 40B:
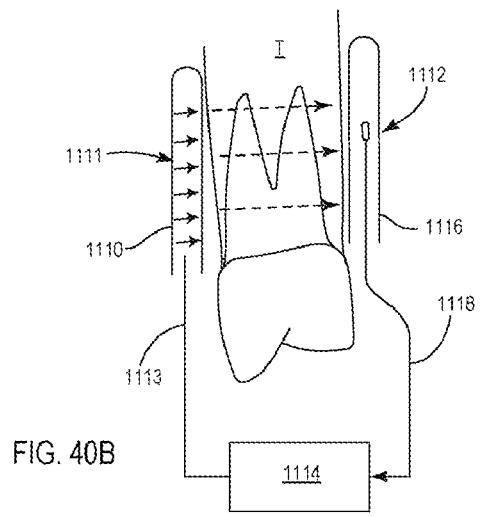
FIG. 40B is a front view of a portion of an intra-oral light-therapy apparatus according to an embodiment of the invention.

In another example, referring to FIG. 40B, an apparatus according to an embodiment is configured to detect an amount of light, e.g., its intensity or duration, that is irradiated at, absorbed by or reflected by a patient's periodontia (e.g., a portion of the root area of the upper and/or lower jaw and/or the alveolar soft tissue) by the apparatus. For example, the apparatus can be configured to determine an energy density that is irradiated at, absorbed by or reflected by the root area from an amount or dosage of light to which the root area was exposed. The apparatus is also configured to determine whether an amount of light being emitted by the apparatus should be adjusted based on the detected amount, intensity and/or duration of light (or energy density) is irradiated at, absorbed by or reflected by the patient's periodontia, as described herein.

In one or more embodiments, the apparatus comprises a mouthpiece having a first flange 1110 and a second flange 1116. The first flange 1110 comprises one or a plurality of light emitters 1111, and is configured to be disposed adjacent the buccal side of a first portion of the root area of the upper and/or lower jaw and/or the alveolar soft tissue (generally designated as tissue T) when the mouthpiece is disposed within the patient's oral cavity. In one or more embodiments, the one or plurality of light emitters 1111 can be at least partially or wholly enclosed in the first flange. In one or more embodiments, the one or plurality of light emitters 1111 is disposed on a surface of the first flange. The one or plurality of light emitters 1111 are positioned such that light emitted therefrom is directed to the first portion of the root area of the upper and/or lower jaw and/or the alveolar soft tissue. The one or plurality of light emitters 1111 is configured to be in electrical communication with a controller 1114, such as via pathway 1113. In this manner, the controller 1114 can control parameters (e.g., duration, intensity, and wavelength) affecting the emission of light by the one or plurality of light emitters 1111.

The second flange 1116 of the mouthpiece comprises one or more photodetectors 1112, and is configured to be disposed adjacent the palatial or lingual side of a second portion, opposite to the first portion, of the root area of the upper and/or lower jaw and/or the alveolar soft tissue when the mouthpiece is disposed within the patient's oral cavity (and the first flange is disposed adjacent the buccal side of the first portion of the root area of the upper and/or lower jaw and/or the alveolar soft tissue). The photodetector 1112 can be at least partially or wholly enclosed within the second flange 1116. The photodetector 1112 is configured to receive light passed through the root area of the upper and/or lower jaw and/or the alveolar soft tissue between the first portion and the second portion. The photodetector 1112 is configured to be in electrical communication with the controller 1114, such as via pathway 1118. The photodetector 1112 is configured to convey information associated with the light received by the photodetector 1112 to the controller 1114. For example, the photodetector 1112 can convey information to the controller 1114 associated with the intensity of light received.

The controller 1114 is configured to execute an algorithm for determining whether a parameter of light emission by the one or plurality of light emitters 1111 should be adjusted, for example, to achieve a target light transmission through the patient's tissue. For example, the controller 1114 can execute the algorithm based on the information associated with the light received by the photodetector 1112 and conveyed to the controller 1114, as well as one or more known parameters (e.g., duration, intensity, and wavelength) associated with the light emission by the one or plurality of light emitters 1111. The controller 1114 can be configured to adjust one or more parameters of light emission by the one or plurality of light emitters 1111 based on the foregoing determination. The parameters of light emission that can be adjusted, or otherwise controlled, by the controller 1114 comprise an intensity of light emitted by the one or plurality of emitters 1111, a duration of emission of light by the one or plurality of light emitters 1111, one or more wavelengths of light, or one or more of the intensity, duration, and wavelength.

In one or more embodiments, the controller 1114 is configured to determine whether the mouthpiece of the apparatus is positioned with respect to (e.g., adjacent) the maxilla or mandible root areas. For example, the controller 1114 can cause the one or plurality of light emitters 1111 to emit light at a known intensity, duration, or wavelength. The controller 1114 can then receive information from the photodetector 1112 associated with the transmission of light through the root area, and then determine whether the light was transmitted through the maxillary root area or the mandibular root area based on the received information. In other words, the controller 1114 can determine whether the mouthpiece was positioned with respect to the maxilla if the light transmission received by the photodetector 1112 is within a first value range, or whether the mouthpiece was positioned with respect to the mandible if the light transmission received by the photodetector 1112 is within a second value range.

In one or more embodiments, the apparatus is configured to be calibrated prior to or at the beginning of a prescribed treatment regime with respect to each of the mandible and maxilla. In this manner, the mouthpiece is positioned with respect to the maxilla, then light is emitted by the one or plurality of light emitters 1111 and an energy density based on the light transmitted through the maxillary root area is detected by the photodetector 1112. With respect to the maxilla, the value of light transmission or reflection (as the case may be), referred to herein as the Iratio, can be calculated as follows, with delivery being the value (e.g., intensity measured in mW/cm$^2$) of light emitted by the emitter and transmission being the value (e.g., intensity measured in mW/cm$^2$) of light received by the photodetector:

$$\frac{I_{delivery}(\max) \; mW/cm^2}{I_{transmission}(\max) \; mW/cm^2} = Y_{1max} \; mW/cm^2$$

Similarly, with respect to the mandible, the Iratio, can be calculated as follows:

$$\frac{I_{delivery}(mnd) \; mW/cm^2}{I_{transmission}(mnd) \; mW/cm^2} = Y_{1mnd} \; mW/cm^2$$

The Iratio can be, for example, based at least in part on photon power density. The controller 1114 can be configured to store an Iratio value (i.e., the YI max and/or Ylmnd). In this manner, the apparatus can reference the stored values to determine whether the mouthpiece is optimally positioned with respect to the maxilla or mandible. In a similar manner as described herein with reference to FIG. 40A, the apparatus can be configured to monitor patient compliance throughout the duration of an orthodontic treatment regime. In use, each Iratio value can be adjusted based on a patient's range of tolerance according to the following calculation: YI±% range of tolerance. In one or more embodiments, the controller 1114 is configured to adjust the delivery to achieve a desired transmission, such as by selectively changing (e.g., increasing or decreasing) the delivery intensity.

Although the Iratio is described herein as being measured in mW/cm$^2$, in one or more embodiments, the Iratio can be measured using a different unit of measurement commensurate with a desired lighting parameter, or characteristic. For example, the Iratio can be measured with respect to light wavelength (in, e.g., nanometers). In this manner, the controller 1114 can be configured to, for example, analyze the cellular photo-absorption state as represented by changes in wavelengths absorbed and/or transmitted by chromophores in the patient's tissue.

Figure 41:
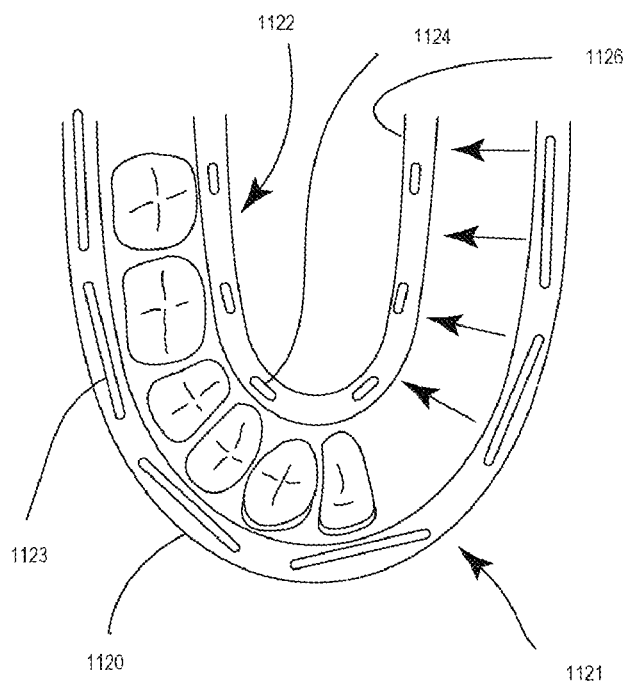
FIG. 41 is a top view of a portion of an intra-oral light-therapy apparatus according to an embodiment of the invention.

Referring to FIG. 41, an apparatus according to an embodiment is configured to control an amount, intensity, wavelength and/or duration of light emitted towards a portion of the root area of the upper and/or lower jaw and/or the alveolar soft tissue and to detect an amount, intensity, wavelength and/or duration of light passed through the root area of the upper and/or lower jaw and/or the alveolar soft tissue. The apparatus can be similar in many respects, or identical to, or comprise components similar in many respects, or identical, to components of, any other apparatus described herein, such as, for example, apparatus described herein with reference to FIGS. 40A and 40B. In one or more embodiments, the apparatus comprises a mouthpiece having a first flange 1120 configured to be disposed on the buccal side of the root area and a second flange 1126 configured to be disposed on the palatial or lingual side of the root area.

One or more light emitters (e.g., a plurality of light emitters) 1121 are disposed in the first flange 1120. The one or more light emitters 1121 comprises individually addressable (or controllable) sections 1123. Parameters affecting the emission of light (e.g., intensity, duration and/or wavelength) by a section of the one or more light emitters 1121 can be controlled separately from and independently of a different section of the one or more light emitters. Stated another way, the intensity, duration, and/or wavelength of light emitted by the one or more light emitters 1121 can vary among the various sections 1123 of the one or more light emitters. The second flange 1126 comprises one or more photodetectors (e.g., a plurality of photodetectors 1122). The plurality of photodetectors 1122 can comprise two or more discrete photodetectors 1124. In one or more embodiments, the one or more photodetectors 1122 comprises a number of photodetectors 1124 equal to the number of sections 1123 in the one or more light emitters 1121. In this manner, each photodetector 1124 can be configured to receive light that was emitted by a corresponding section 1123 of the one or more light emitters 1121 and that passed through the root area between the section 1123 and the photodetector 1124. In this manner, light emission by each section of the one or more light emitters 1121 can be adjusted to accommodate variations in treatment goals for and/or anatomy of different patients, whose alveolar dimensions can vary. These adjustments can be based at least in part on the light received by the corresponding photodetector 1124.

In one or more embodiments, an apparatus including photodetectors for sensing light transmission or reflection, such as the apparatus described herein with reference to FIGS. 40A-41, is configured to perform an initial calibration. For example, in one or more embodiments, to calibrate the apparatus, the patient places the apparatus in the upper arch of the oral cavity. The apparatus registers its orientation (i.e., upright or upside down) using an internal orientation-sensing mechanism (e.g., a gyroscope). A light source, such as one or more LEDs, is activated. One or more optical fibers act as receivers and photodetectors at their distal ends, which are configured to determine photon, or light, transmission or reflection. Activation of the light source and determination of the light transmission or reflection by the receiver/photodetector fibers is repeated, such as for two or three times. An average value of light transmission or reflection is calculated, and the calculated average value can be useful as a threshold orange during the orthodontic treatment. If the amount of light detected becomes inconsistent with the threshold or range, then the apparatus deactivates to stop the treatment.

In one or more embodiments, an apparatus comprises an intra-oral housing that is contoured to complement curvature and/or other physical attributes of a patient's tissue within the patient's oral cavity. For example, referring to FIGS. 42-44, an apparatus according to an embodiment comprises an intra-oral housing 1280 including a front portion 1282 configured to be disposed adjacent buccal alveolar soft tissue of a patient and a rear portion 1284 configured to be disposed adjacent lingual alveolar soft tissue of the patient. A midline M divides left and right sides (also referred to herein as wings or flanges) of the front and rear portions 1282, 1284, respectively, of the intra-oral housing 1280. In one or more embodiments, a height of the left and or right side is configured to correspond to a length including an average incisor root length and a length of the premolars. A portion of the side that is configured to be adjacent the canine teeth can be slightly under-extended compared to, or shorter than, a different (e.g., incisor) portion of the side. A first light emitting array or mat (not shown in FIGS. 42-44) configured to be disposed adjacent the buccal alveolar soft tissue, for example, can have a length substantially equal to a width of two molar teeth. A second, corresponding light emitting array or mat configured to be disposed on the palatial side of the teeth, adjacent the lingual alveolar soft tissue for example, can have a similar length as the first light emitting array. The intra-oral housing 1280 can comprise a palatial portion or wing 1288, which can be configured to move vertically with respect to the first and second sides, e.g., up against the upper hard palate.

The intra-oral housing 1280 comprises one or more distinct segments 1286 that each comprise a first portion extending (e.g., downwardly) from a lower surface of the front portion 1282 of the intra-oral housing, a second portion extending (e.g., downwardly) from a lower surface of the rear portion 1284 of the intra-oral housing, and a third portion extending (e.g., horizontally) between ends of the first portion and the second portion of the segment 1286. In this manner, the segments 1286 (also referred to as bite pads) are configured to be disposed about at least a portion of crowns of one or more teeth adjacent each segment when the intra-oral housing 1280 is disposed in the oral cavity as described herein. The segments 1286 are laterally spaced apart from each other with respect to the front portion 1282 of the intra-oral housing 1280. In this manner, when the intra-oral housing 1280 is disposed in the oral cavity as described herein, the segments 1286, or bite pads, are disposed about the crowns of fewer than all teeth. In one or more embodiments, a first number of the patient's teeth are covered by the segments 1286 and a second number, greater than the first number, are not covered by the segments. For example, each segment 1286 can have a sufficient height, width, and/or depth for being disposed about the crowns of one or two teeth. In use, the patient can bite down on the segments 1286 during the orthodontic treatment, such as to maintain a position of the intra-oral housing 1280 within the oral cavity. Use of the segments, or bite pads, described herein also serves to reduce bulk associated with the surface area of the apparatus, and thus provides enhanced patient comfort.

The segments 1286 can be constructed of a material similar or identical to or different than that of the front and rear portions 1282, 1284 of the intra-oral housing 1280. For example, the front and rear portions 1282, 1284 of the intra-oral housing 1280 can be constructed of a soft, e.g., malleable, material such as silicone, and the segments 1286 can be constructed of a harder, less malleable material, e.g., silicone, that is overmolded with a soft material, such as the soft silicone.

Figure 42:
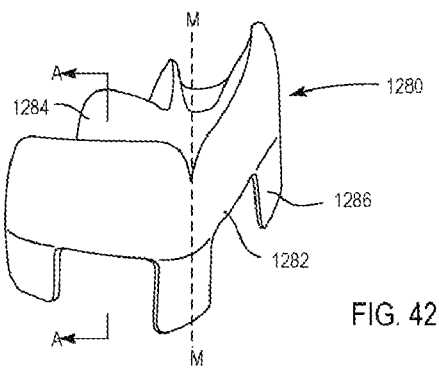
FIG. 42 is a perspective view of an intra-oral light-therapy apparatus according to an embodiment of the invention.
Figure 43:
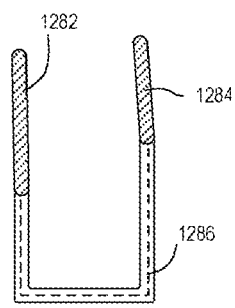
FIG. 43 is a sectional view of the apparatus of FIG. 42 taken along line A-A
Figure 44:
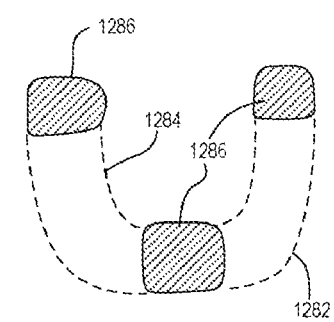
FIG. 44 is a bottom view of the apparatus of FIG. 42.
Figure 45:
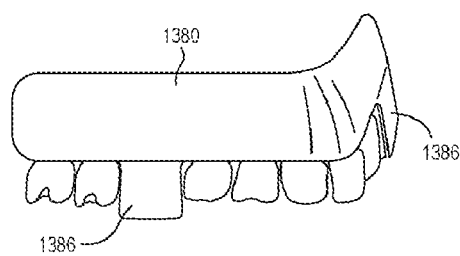
FIG. 45 is a side view of an intra-oral light-therapy apparatus according to an embodiment of the invention in use within an oral cavity.

In the embodiment illustrated in FIGS. 42-44, the intra-oral housing 1280 comprises three bite pad segments. The first segment is extended from the lower surfaces of the front and rear portions 1282, 1284 along the midline M. The second and third segments are extended from the lower surfaces of the front and rear portions 1282, 1284 at ends of the left and right sides of the intra-oral housing 1280 opposite the midline M. In other embodiments, however, the segments can extend from a different location along the lower surfaces of the front and rear portions 1282, 1284. For example, as shown in FIG. 45, an apparatus can comprise an intra-oral housing 1380 including a segment extending from the lower surfaces of front and rear portions of the intra-oral housing at a midline (not shown in FIG. 45) defined by the intra-oral housing, and one or more segments extending from the lower surfaces of the front and rear portions of the intra-oral housing from one or more locations between the midline and left and right ends, respectively, of the intra-oral housing opposite the midline.

Figure 46:
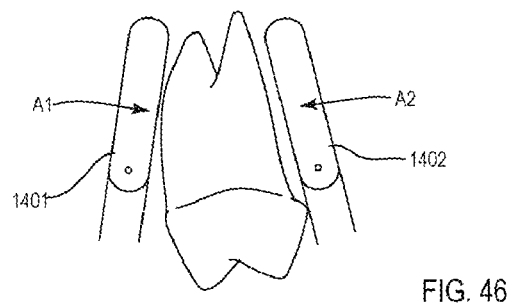
FIGS. 46 and 47 are side and front views, respectively, of portions of intra-oral light-therapy apparatuses according to embodiments of the invention.

In one or more embodiments, at least a portion of an apparatus is biased towards a portion of the patient's body, which can, for example, help maintain the position of the apparatus with respect to a patient's oral cavity. As shown in FIG. 46, an apparatus can comprise a first portion 1401 configured to be disposed adjacent a root area of the jaw between the root area and the buccal mucosa, and a second portion 1402 configured to be disposed adjacent the palatial side of the root area of the jaw. The first portion 140 I is biased in a first direction towards the root area, and the second portion 1402 is biased in a second, opposite direction towards the root area. More specifically, the first portion 1401 is spring-loaded such that a free end of the first portion is moved toward and/or can apply a pressure upon the root area in the first direction, indicated by arrow A1, and the second portion 1402 is spring-loaded such that a free end of the second portion is moved toward and/or can apply a pressure upon the root area in the second direction, indicated by arrow A2. In one or more embodiments, the pressure applied by the first portion 1401 and/or the second portion 1402 is sufficient to displace at least a portion of the patient's tissue. The first and second portions 1401, 1402 can be configured to pivot at a joint disposed adjacent the root area, e.g., immediately above the crown of the tooth.

Figure 47:
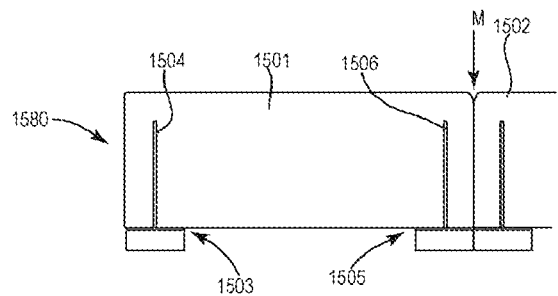

In another example, as shown in FIG. 47, an apparatus can comprise an intra-oral housing 1580 having a right flange 1501 and a left flange 1502 divided by a midline M. The right flange 1501 and left flange 1502 are each configured to be disposed adjacent a root area of the jaw. The right flange 1501 is biased in a first direction towards the root area. The right flange 1501 is coupled to the apparatus by one or more hinges (e.g., two hinges 1503, 1505, as shown in FIG. 47) and comprises one or more wires (e.g., two nitinol or other super-elastic wires, each associated with a respective hinge, as shown in FIG. 47) embedded within the right flange 1501 of the intra-oral housing 1580. For example, the hinges 1503, 1505 can move about a horizontal axis and the nitinol wires 1504, 1506 can be embedded in a silicone of the intra-oral housing 1580 along an axis substantially normal to the horizontal axis of the hinges, e.g., plus or minus 5 degrees of the normal to the horizontal axis. The wires 1504, 1506 are configured to be biased towards the root area. As such, the wires 1504, 1506 push against an apical portion of the right flange and cause the right flange 1501 to push against the tissue of the root area.

The left flange 1502 can be configured similarly to the right flange 1501. In one or more embodiments, the hinges 1503, 1505 and/or wires 1504, 1506 can produce a relatively large orthodontic and/or orthopedic force, such as a force operable to urge one or more teeth to move.

Figure 48:
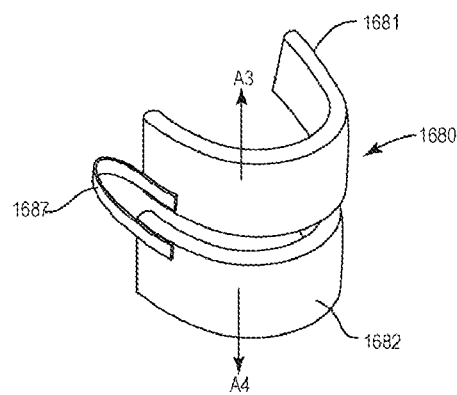
FIG. 48 is perspective view of an intra-oral light-therapy apparatus according to an embodiment of the invention.

In another example, an apparatus according to an embodiment is illustrated in FIG. 48. The apparatus comprises an intra-oral housing 1680 having an upper portion 1681 extended between a first end and a second end, and a lower portion 1682 extended between a first end and a second end. The upper and lower portions 1681, 1682 are each configured to be disposed adjacent a root area within an oral cavity. The upper and lower portions 1681, 1682 have a curvature configured to correspond to a curvature of a patient's dentition (e.g., is U or horseshoe shaped). The first end of the upper portion 1681 is coupled to the first end of the lower portion 1682 by a shape retaining member 1687. The shape retaining member 1687 can comprise, for example, a curved stiff plastic material having shape memory characteristics. The shape retaining member 1687 is biased towards an open configuration in which the first end of the upper portion 1681 is moved in a first direction, indicated by arrow A3, away from the first end of the lower portion 1682 of the intra-oral housing 1680, and the first end of the lower portion 1682 is moved in a second, opposite direction, indicated by arrow A4, away from the first end portion of the upper portion 1681 of the intra-oral housing 1680. The second end of the upper portion 1681 is coupled to the second end of the lower portion 1682 by a similar shape retaining member 1687.

As such, the second end of the upper portion 1681 and second end of the lower portion 1682 are biased away from each other towards the open configuration. In this manner, the upper and lower portions 1681, 1682 of the intra-oral housing 1680 are configured to remain adjacent their respective root portions when the patient jaws are opened. The biasing force exerted by the shape retaining member 1687 is sufficient to move the seating of at least a portion of the upper portion 1681 and/or lower portion 1682 toward a depth of the patient's cheek/alveolus vestibule; such force alone, however, may be insufficient to cause the jaw of the patient to open.

Figure 49:
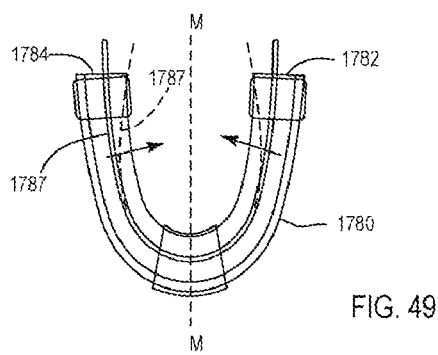
FIGS. 49-51 are top views of intra-oral light-therapy apparatuses according to embodiments of the invention.

A portion of an apparatus according to an embodiment is illustrated in FIG. 49.

The apparatus comprises a substantially U or horseshoe shaped intra-oral housing, e.g., has a curvature approximating the curvature of a U or horseshoe shape. The intra-oral housing can be constructed of a soft silicone. A wire 1787 (e.g., nitinol or other super-elastic wire), or other shape retaining member, is embedded in the intra-oral housing. A first end of the wire is disposed at a first end 1782 of the intra-oral housing 1780, and a second end of the wire is disposed at a second, opposite, end 1784 of the intra-oral housing. The first and second ends of the wire are inwardly biased such that the first end of the intra-oral housing and second end of the intra-oral housing are (or can be) moved in a direction towards each other. In other words, the wire is biased to move from an open position in which the first and second ends 1782, 1784 of the intra-oral housing 1780 are disposed a first distance from a midline M of the intra-oral housing, as shown by the solid line in FIG. 49, to a closed position in which the first and second ends 1782, 1784 are disposed a second distance less than the first distance from the midline M of the intra-oral housing, as shown by the dashed line in FIG. 49. In this manner, the wire causes a portion of the intra-oral housing (e.g., left and right portions and/or light emitting panels) to apply a gentle pressure on the buccal side of the root area towards a lingual or palatial side of the root area. Also in this manner, the intra-oral housing 1780 is configured to cause displacement of a portion of oral soft tissue over the tooth root.

Figure 50:
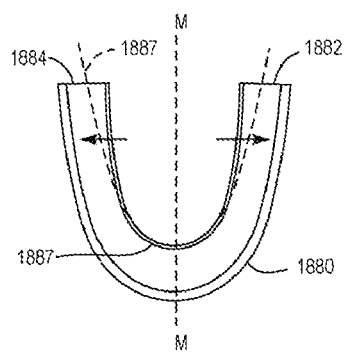

In one or more embodiments, as shown in FIG. 50, an apparatus can comprise an intra-oral housing 1880 having a wire 1887 (e.g., nitinol or other super-elastic wire), or other shape retaining member, configured to bias first and second ends 1882, 1884, respectively, of the intra-oral housing 1880 away from each other, e.g., in a direction opposite to that shown and described with reference to FIG. 49. In other words, the wire 1887 is biased to move from a closed position in which the first and second ends 1882, 1884 are disposed a first distance from a midline M of the intra-oral housing as shown by the solid line in FIG. 50 to an open position in which the first and second ends 1882, 1884 are disposed a second distance greater than the first distance from the midline M of the intra-oral housing as shown by the dashed line in FIG. 50. In this manner, the wire is configured to cause a portion of the intra-oral housing (e.g., left and right portions and/or light emitting panels, not shown in FIG. 50) to apply a gentle pressure on the lingual or palatial side of the root area towards, or in the direction of, the buccal side of the root area. Also in this manner, the intra-oral housing 1880 is configured to cause displacement of a portion of oral soft tissue over the tooth root.

Figure 51:
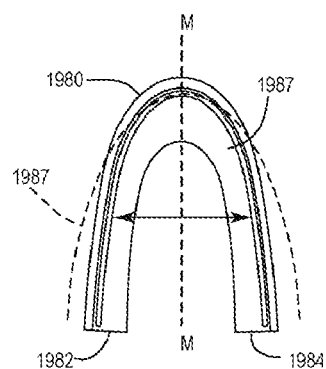
Figure 52:
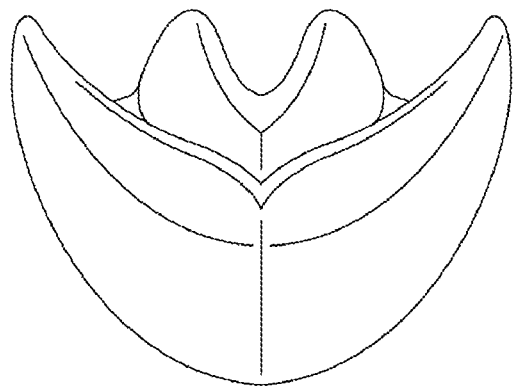
FIGS. 52-55 are perspective views of an intra-oral light-therapy apparatus according to an embodiment of the invention.
Figure 53:
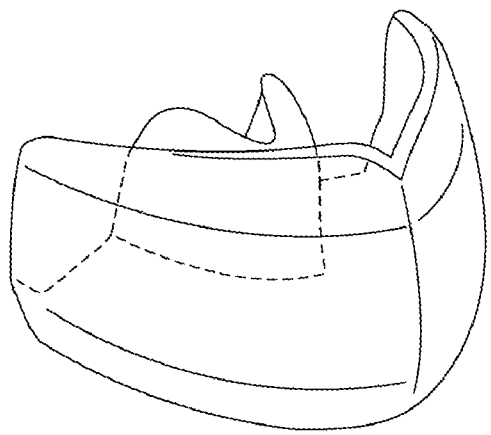
Figure 54:
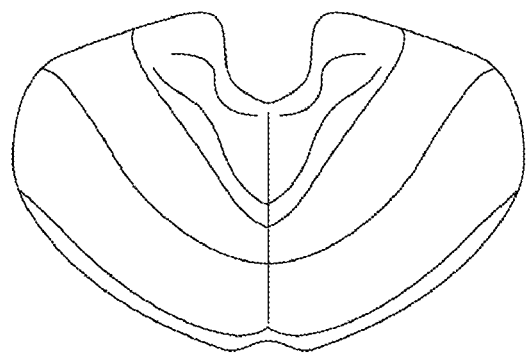
Figure 55:
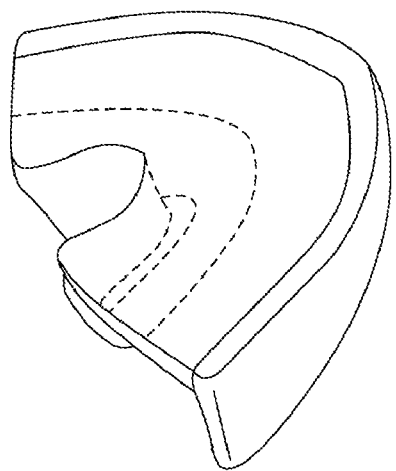
Figure 56:
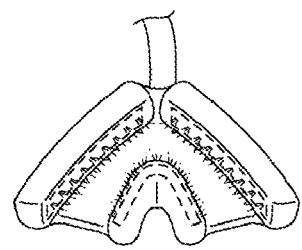
FIGS. 56 and 57 are top and rear views, respectively, of the apparatus of FIGS. 52-55 in a powered (i.e., "on") operational state.
Figure 57:
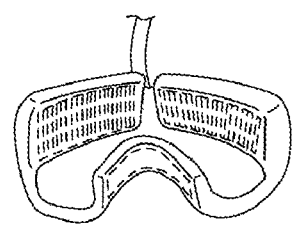
Figure 58:
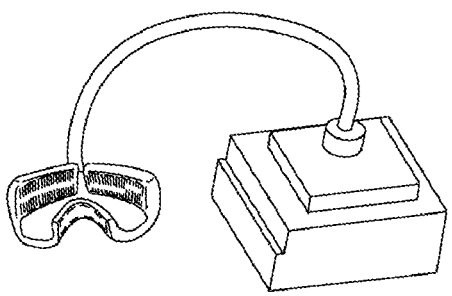
FIG. 58 is a perspective view of the apparatus of FIGS. 56 and 57 coupled to an electronic device.

The wire 1887 can be disposed within the intra-oral housing 1880 in any suitable position. For example, as shown in FIG. 50, the wire 1887 can be positioned adjacent an inner curvature of the intra-oral housing 1880. In other embodiments, however, a wire 1987 can be positioned adjacent an outer curvature of an intra-oral housing 1980, as shown in FIG. 51. The wire 1987 can be similar in many respects to wire 1887, for example, in that the wire 1987 can be configured to bias first and second ends 1982, 1984, respectively, of the intra-oral housing 1980 away from each other, e.g., in a direction opposite to that shown and described with reference to FIG. 49 and similar to that shown and described with reference to FIG. 50. In other words, the wire 1987 is biased to move from a closed position (as shown by the solid line in FIG. 51) to an open position (as shown by the dashed line in FIG. 50) in a similar manner as described herein with reference to FIG. 50. Thus, the wire 1987 is configured to cause a portion of the intra-oral housing 1980 to apply a gentle laterally, and outwardly, directly pressure on the lingual or palatial side of the root area.

Although the apparatuses depicted in FIGS. 49-51 are described as including a wire (e.g., a nitinol wire) as the shape retaining member, in other embodiments, a different shape retaining member (or biasing member) can be included in the apparatus. For example, the shape retaining member can comprise an overmolded plastic insert.

Figure 65:
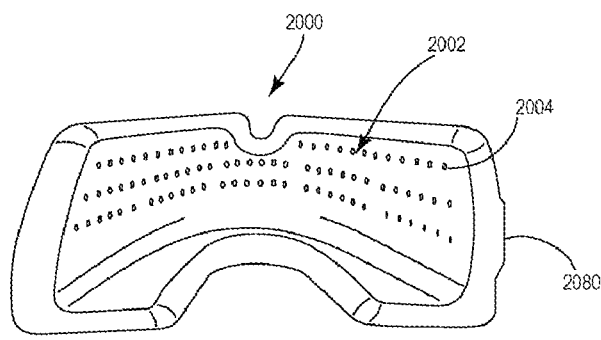
FIG. 65 is a rear view of an intra-oral apparatus according to an embodiment of the invention.
Figure 66:
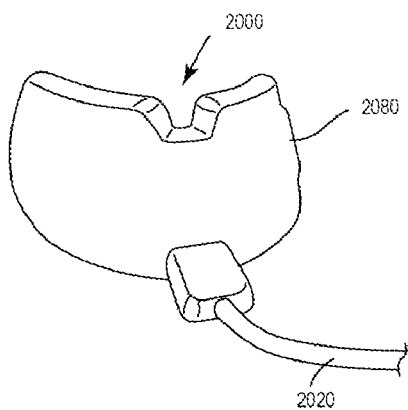
FIG. 66 is a front view of the intra-oral apparatus of FIG. 65.
Figure 67:
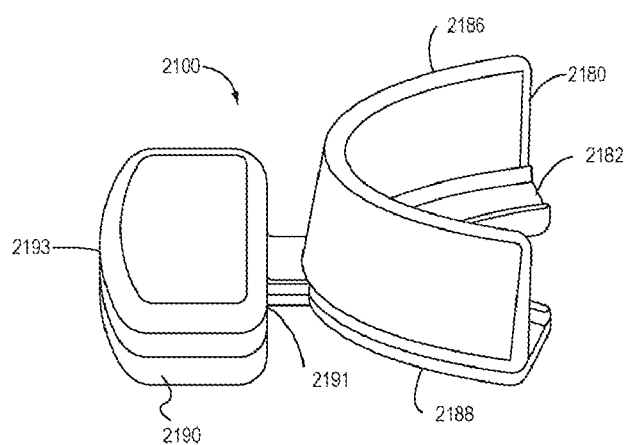
FIGS. 67 and 68 are side and top views of an intra-oral apparatus according to an embodiment of the invention.

An intra-oral apparatus 2000 according to an embodiment of the invention is illustrated in FIGS. 65 and 66. The apparatus 2000 can be the same as or similar in many respects to, or comprise components the same as or similar in many respects to, the intra-oral apparatuses described herein. The intra-oral apparatus 2000 comprises an intra-oral housing 2080 configured to be disposed in an oral cavity of a patient. In one or more embodiments, the intra-oral housing 2080 is configured to be positioned within the oral cavity of the patient with respect to the upper jaw, the lower jaw, or each of the upper and lower jaws. The intra-oral housing 2080 comprises at least one light emitting panel 2002. The light emitting panel 2002 can comprise one or more light emitters 2004, such as LEDs. The intra-oral apparatus 2000 can be configured to irradiate light in any suitable manner described herein. In one or more embodiments, for example, the intra-oral apparatus 2000 can be configured to irradiate light at a density of about 60 mW/cm$^2$.

Although the light emitting panel 2002 is illustrated as including the one or more light emitters 2004 in three parallel rows, in other embodiments, the one or more light emitters can be differently positioned with respect to the light emitting panel and/or the intra-oral housing (e.g., in one or more vertical rows, one or more diagonal rows, a random pattern, or any other suitable configuration). In one or more embodiments, the light emitting panel 2002 is at least partially enclosed within the intra-oral housing 2080. For example, the light emitting panel 2002 can be embedded within the intra-oral housing 2080. The intra-oral housing 2080 can be constructed of any suitable material, including, for example, a soft silicone material. The intra-oral housing 2080 is configured to be electrically coupled to an electronic device, such as a controller (not shown in FIGS. 65-66) as described herein. As shown in FIG. 66, the intra-oral housing 2080 can be coupled to the electronic device by a tether 2020.

The intra-oral apparatus 2000 can be configured for use in an orthodontic treatment, including any such treatment described herein. In one or more embodiments, for example, the intra-oral apparatus 2000 is useful for irradiating at least a portion of the patient's upper jaw for about 3 minutes, the patient's lower jaw for about 3 minutes, or each of the patient's upper and lower jaws for about 3 minutes.

An intra-oral apparatus 2100 according to an embodiment of the invention is illustrated in FIGS. 67-72. The apparatus 2100 can be the same as or similar in many respects to, or comprise components the same as or similar in many respects to, the intra-oral apparatuses described herein. The intra-oral apparatus 2100 comprises an intra-oral housing 2180 configured to be disposed in an oral cavity (e.g., in the mouth) of a patient and an extra-oral housing 2190 (also referred to herein as a "bill") coupled to the intra-oral housing 2180. The extra-oral housing 2190 is coupled to a front portion of the intra-oral housing 2180. For example, the extra-oral housing 2190 can be coupled to the intra-oral housing 2180 by a protrusion 2188. In this manner, the protrusion 2188 is extended through the opening of the patient's mouth, e.g., through the opening between the patient's lips, such that at least a portion of the extra-oral housing 2190 is disposed exterior to the oral cavity of the patient when the intra-oral housing 2180 is disposed within the oral cavity of the patient. Also in this manner, the extra-oral housing 2190, or bill, can be supported with respect to the patient's mouth by the intra-oral housing 2180 and/or the protrusion 2188 when the intra-oral housing 2180 is disposed within the patient's mouth. The extra-oral housing 2190 is configured to at least partially enclose one or more electronic components of the apparatus 2100, as described in more detail herein.

The intra-oral apparatus 2100 is configured to be useful for light therapy with respect to each of the upper jaw and the lower jaw of the patient. In other words, the intra-oral apparatus 2100 can be configured to administer light therapy with respect to the patient's upper jaw when the apparatus is in an upright position, and can be configured to administer light therapy with respect to the patient's lower jaw when the apparatus is in an inverted position. As such, the intra-oral housing 2180 can be configured to be disposed within the patient's oral cavity with respect to each of the upper and lower jaws of the patient. It should be noted that although the intra-oral apparatus 2100 and intra-oral housing 2180 are described as being in the upright position when configured to be oriented with respect to the upper jaw and in the inverted position when configured to be oriented with respect to the lower jaw, in other embodiments, the intra-oral apparatus 2100 and the intra-oral housing 2180 are in the upright position when configured to be oriented with respect to the lower jaw of the patient, and in the inverted position when configured to be oriented with respect to the upper jaw of the patient.

The intra-oral apparatus 2100 can be configured to determine the orientation of the apparatus. Stated another way, the intra-oral apparatus 2100 can be configured to determine if the intra-oral housing 2180 is oriented in the upright or inverted position. For example, the intra-oral apparatus 2100 comprises a gyroscope (not shown in FIG. 69) configured to determine if the intra-oral housing 2180 is oriented in the upright or inverted position. The gyroscope is disposed within, or otherwise coupled to, the extra-oral housing 2190 of the apparatus 2100.

Figure 69:
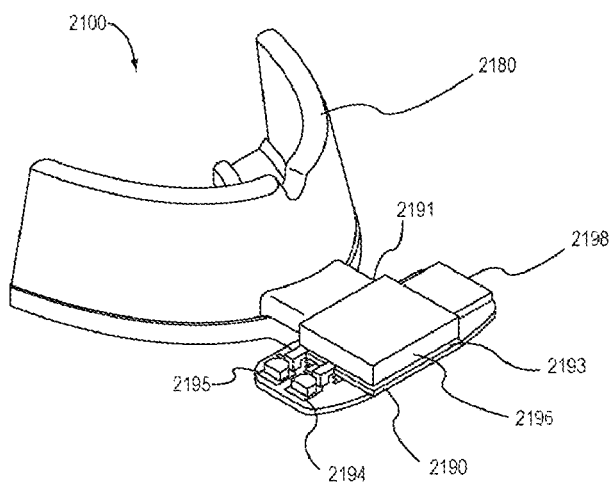
FIG. 69 is a perspective view of a portion of the intra-oral apparatus of FIG. 67.
Figure 70A:
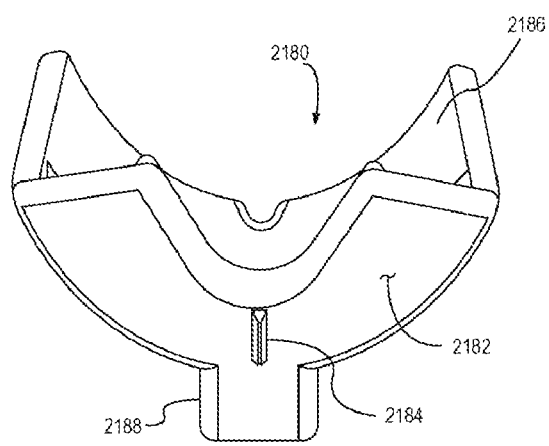
FIGS. 70A and 70B are bottom-rear and top-rear perspective views of a portion of the intra-oral apparatus of FIG. 67.
Figure 70B:
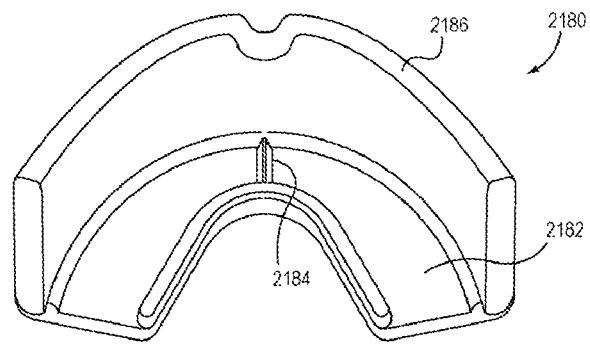

The apparatus 2100 comprises at least one battery, or other suitable power source. For example, as shown in FIG. 69, a first battery 2194 and a second battery 2195 are coupled to the extra-oral housing 2190 of the apparatus 2100. For example, the batteries 2194, 2195 can be disposed in the extra-oral housing 2190. Each battery 2194, 2195 can be configured to provide power to one or more light-emitting panels (schematically illustrated in FIG. 74) disposed within the intra-oral housing 2180, as described in more detail herein. The first battery 2194 can comprise, for example, a rechargeable lithium ion battery. Alternatively or in addition, apparatus 2100 can comprise a charging station that is configured for inductive charging (e.g., to power the apparatus 2100 and/or to charge a battery thereof). For example, apparatus 2100 can comprise a Qi-based charging coil.

A microprocessor 2196 is coupled to the extra-oral housing 2190 of the apparatus 2100. The microprocessor 2196 can be disposed in the extra-oral housing 2190. The microprocessor 2196 is configured to store information related to the patient's use of the intra-oral apparatus 2100. For example, the microprocessor 2196 can be configured to store information associated with the patient's treatment program and use of the apparatus 2100 during the treatment program, including, for example, a schedule of one or more treatment sessions included in the treatment program, an orientation of the apparatus 2100 during a treatment session, a duration of a treatment session, and a duration between a treatment session and one or more previous treatment sessions. The microprocessor 2196 can also be configured to determine whether the patient's usage of the intra-oral apparatus 2100 is in compliance with the patient's treatment program. In other words, the microprocessor 2196 can be configured to determine whether a patient's history of use (including, for example, a number of treatment sessions applied to the upper and/or lower jaw of the patient, duration of the treatment sessions, whether any treatment session was interrupted, and the like) complies with a schedule of treatment sessions specified by the patient's treatment program, including identifying any deviation from the treatment program. The microprocessor's 2196 determination regarding patient compliance can be based, at least in part, on information received from the proximity detector. For example, the proximity detector can be configured to be activated when the apparatus is placed fully into the patient's mouth. The microprocessor 2196 can be configured to transmit information associated with the patient's usage and/or compliance of the apparatus 2100 with an external device. For example, in one or more embodiments, the microprocessor 2196 is configured to transmit the usage and/or compliance information to the external device (e.g., a mobile phone, personal digital assistant, computer, portable electronic device, or the like) via Bluetooth® or another suitable wireless mechanism. For example, as shown in FIG. 69, a Bluetooth® communication module 2198 can be disposed within the extra-oral housing 2190.

The extra-oral housing 2190 comprises a communication mechanism (not shown in FIG. 69) configured to provide indicia of the status of a treatment session. The term "indicia," is used herein as including the singular ("indicium") or the plural ("indicia"), unless the context clearly indicates otherwise. The indicia can comprise one or more of an audible indicia (e.g., a tone, beep, announcement, or the like), a tactile indicia (e.g., a vibration or the like), or a visual indicia (e.g., a light, a displayed message, or the like). More specifically, for example, the extra-oral housing 2190 comprises a light indicia that is configured to indicate a status, or stage, of the treatment session. The light indicia is configured to display no light during a first stage of the treatment session, a blinking or pulsed light during a second stage of the treatment session, and/or a solid light during a third stage of the treatment session. The light indicia can be, for example, configured to display a solid light for a first predetermined duration (e.g., 2 minutes and 30 seconds, 2 minutes and 45 seconds, or 2 minutes and 10 seconds) upon initiation of the treatment session. The light indicia can be configured to display the blinking or pulsed light for a second predetermined duration (e.g., 10, 15 or 30 seconds) following the first predetermined duration as a signal to the patient that the treatment session is nearing its end. The light indicia can be configured to display no light when a treatment session is ended (e.g., after 3 minutes from initiation of the treatment session) and the apparatus 2100 is not irradiating light.

In one or more embodiments, the extra-oral housing 2190 has a sufficient length (e.g., between a first end 2191 of the extra-oral housing engaged with the intra-oral housing 2080 and a second, opposite, end 2193 of the extra-oral housing (i.e., the end of the extra-oral housing farthest from the patient's oral cavity when the intra-oral housing is disposed in the patient's oral cavity)) such that at least a portion of the extra-oral housing is visible to the patient when the intra-oral housing is disposed in the patient's oral cavity. In other words, at least a portion of the extra-oral housing 2190, e.g., including the second end 2193 of the extra-oral housing, is within the patient's line of sight when the intra-oral housing 2180 is disposed with the patient's oral cavity. In this manner, the light indicia can be coupled to the extra-oral housing 2190 in a manner such that the light indicia is within the patient's line of sight during the treatment session.

As noted herein, the intra-oral housing 2180 is configured to be positioned within the oral cavity of the patient with respect to the upper jaw, the lower jaw, or is invertible for positioning with respect to each of the upper and lower jaws. The intra-oral housing 2180 can be similar in one or more respects, and comprise components similar in one or more respects, or identical, to the intra-oral housings described herein, including, for example, the intra-oral housings described herein with reference to FIGS. 35-37 and 65-66. Accordingly, the intra-oral housing 2180 is not described in detail.

The intra-oral housing 2180 comprises a lower portion 2182 and an upper portion 2186. The lower portion 2182 has a first plane, and the upper portion 2186 has a second plane different than the first plane. For example, the upper portion 2186 can be substantially vertical (e.g., plus or minus about 5 degrees from the vertical axis or plane), and the lower portion 2182 can be substantially horizontal (e.g., plus or minus about 5 degrees from the horizontal axis or plane) when the intra-oral housing 2180 is disposed within the patient's oral cavity for a treatment session. In this manner, the upper portion 2186 can be disposed adjacent a portion of a side of the patient's teeth and/or adjacent the alveolar mucosa and the lower portion 2182 can be disposed adjacent an occlusal surface of the patient's teeth. For example, the lower portion 2182 can be configured as a bite pad for the patient to bite down upon during a treatment session.

Figure 68:
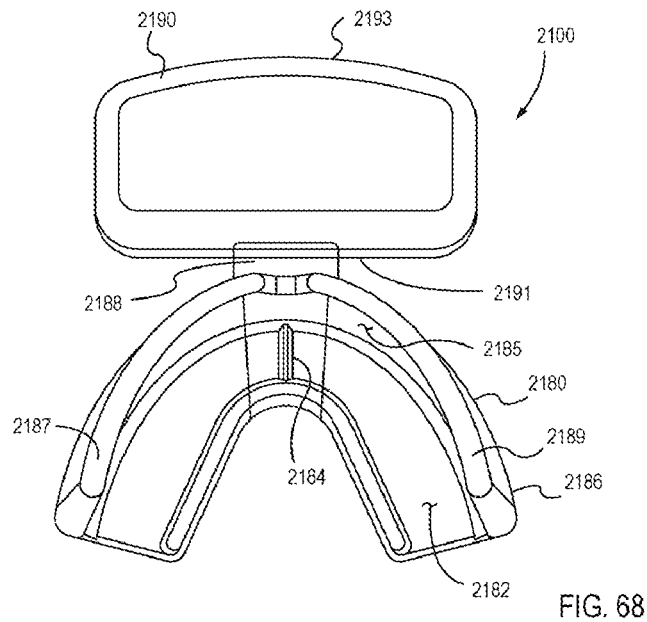

As shown in FIG. 68, the lower portion 2182 of the intra-oral housing 2180 comprises a ridge 2184. The ridge 2184 is disposed along a midline of the intra-oral housing 2180 and is elevated with respect to the first plane of the lower portion 2182. The ridge 2184 facilitates positioning of the intra-oral housing 2180 within the patient's oral cavity by the patient when the intra-oral housing 2180 is disposed within the patient's oral cavity. For example, the intra-oral housing 2180 is configured to be positioned within the patient's oral cavity such that the ridge 2184 is disposed between the patient's front central incisors. Proprioception of the patient related to the teeth and periodontium would permit sensory feedback to the patient regarding the position of the ridge 2184 of the intra-oral housing 2180. In this manner, the ridge 2184 facilitates centering of the intra-oral housing 2180 within the oral cavity, thus promoting symmetry of a light therapy treatment on the alveolus, or other oral tissue, on both sides of the patient's mouth. In other words, in order to promote the symmetrical administration of light therapy to the root area, the intra-oral housing 2180 can be positioned with the midline of the intra-oral housing 2180 seated along the sagittal plane or within (i.e., plus or minus) 5 degrees of the sagittal plane, and the ridge 2184 can facilitate such obtaining such a position.

The upper portion 2186 comprises a first (or left) flange 2187 and a second (or right) flange 2189. The flanges 2187, 2189 are each configured to apically displace oral soft tissue. More specifically, the flanges 2187, 2189 are each configured to displace buccal tissue away from the patient's alveolus. In one or more embodiments, an inner face 2185 of the upper portion 2186 can be spaced apart from the patient's alveolar tissue when the intra-oral housing 2180 is disposed within the patient's mouth and the flanges 2187, 2189 are displacing the buccal tissue. In one or more embodiments, at least a portion of the inner face 2185 of the upper portion 2186 can contact the patient's alveolar tissue when the intra-oral housing 2180 is disposed within the patient's mouth and the flanges 2187, 2189 are displacing the buccal tissue.

The intra-oral housing 2180 can be constructed of any suitable material, including, for example, an elastomeric material (e.g., a soft silicone). More specifically, in one or more embodiments, the intra-oral housing can be fabricated from medical-grade injection molded highly flexible silicone. The ridge 2184 can be constructed of the same material as the intra-oral housing 2180, or at least the same material as the lower portion 2182 of the intra-oral housing 2180. In this manner, when a patient bites together with the upper and lower jaw, the lower portion 2182 of the intra-oral housing 2180, including the ridge 2184, may deform slightly from pressure exerted by an occlusal surface of the patient's teeth. Nonetheless, the ridge 2184 is of sufficient dimensions that the patient should be aware of its position, despite any slight deformation of the lower portion 2182 and/or ridge 2184.

Figure 74:
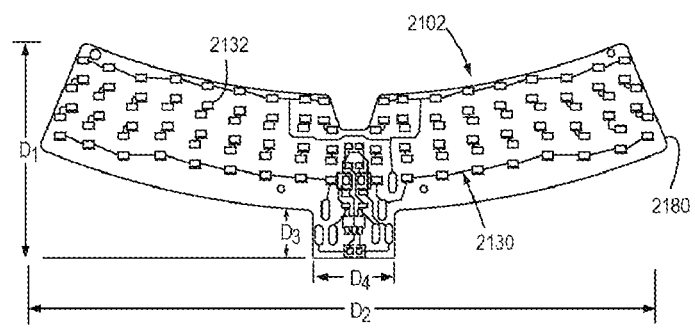
FIG. 74 is a schematic illustration of a portion of the intra-oral apparatus of FIG. 67.

The intra-oral housing 2180 comprises at least one light emitting panel 2102 (the circuitry 2130 of which is schematically illustrated in FIG. 74). The light emitting panel 2102 can comprise one or more light emitters 2132, such as a plurality of LEDs, and a flexible circuit 2130. The intra-oral apparatus 2100 can be configured to irradiate light in any suitable manner described herein to irradiate the alveolus and/or root area of the patient. The LEDs, or other suitable light emitter(s), can be included in the light emitting panel 2102 in any suitable configuration, including in any configuration described herein. In one or more embodiments, the light emitting panel 2102 is at least partially enclosed within the intra-oral housing 2180. For example, the light emitting panel can be embedded within the intra-oral housing 2180 (e.g., in the inner face 2185 of the upper portion 2186 of the intra-oral housing 2180. As noted herein, the intra-oral housing 2180 can be constructed of a soft silicone material. In this manner, the light emitting panel, and thus any LED or light emitter included in the panel, can be embedded in the silicone material such that the light emitting panel is prevented from engaging a portion of the patient's oral tissue when the intra-oral housing 2180 is disposed within the patient's oral cavity. The light emitting panel 2102 can have any suitable dimensions for being coupled to, or embedded in, the upper portion 2186 of the intra-oral housing 2180. For example, as shown in FIG. 74, the light emitting panel 2102 can have a height DI and a width D2 greater than the height D1. In one or more embodiments, for example, the panel 2102 has a height of about 31.9 mm and a width of about 92.5 mm. A portion of the height D1 of the panel 2102 can comprise a lower protrusion that extends downwardly from left and right flanges 2187, 2189 of the intra-oral housing 2180. The protrusion can have a height D3 and a width D4. In one or more embodiments, for example, the protrusion has a height of about 6.9 mm and a width of about 12 mm.

Although specific examples of the dimensions of the panel 2102 are provided, such dimensions are presented by way of example only, and not limitation.

The intra-oral housing 2180 can be configured to be disposed within the patient's oral cavity such that an outer surface of the intra-oral housing 2180 is spaced apart from the alveolar soft tissue of the patient. In this manner, the intra-oral housing 2180 is configured to be spaced apart from (i.e., not touch) the alveolar soft tissue of the patient during the treatment session. In one or more embodiments, for example, at least a portion of the intra-oral housing 2180 can be configured to be disposed over at least a portion of the patient's teeth. A first portion of the intra-oral housing 2180 is disposed about the portion of the patient's teeth and a second portion of the intra-oral housing 2180 is disposed proximate to and spaced apart from the alveolar soft tissue when the intra-oral housing 2180 is disposed in the patient's mouth.

In one or more embodiments, at least a portion (e.g., the first portion) of the intra-oral housing 2180 is configured to snap onto, or otherwise snugly fit, at least a portion of the patient's teeth when the intra-oral housing 2180 is disposed in the patient's mouth for the treatment session. For example, at least a portion of the intra-oral housing 2180 can be biased in a manner similar to that described herein with reference to FIGS. 46 and/or 47. In one or more embodiments, the intra-oral housing 2180 can comprise one or more retractors configured to facilitate opening of the patient's mouth. In one or more embodiments, at least a portion of the intra-oral housing 2180 can be configured to contact at least a portion of the alveolar soft tissue when the intra-oral housing 1280 is disposed within the patient's mouth for the treatment session. In one or more embodiments, at least a portion of the intra-oral housing 2180 is configured to not contact, but be at a particular distance (e.g., from 0.1 cm to 3 cm) from the alveolar soft tissue when the intra-oral housing 2180 is disposed within the patient's mouth for the treatment session.

Figure 71:
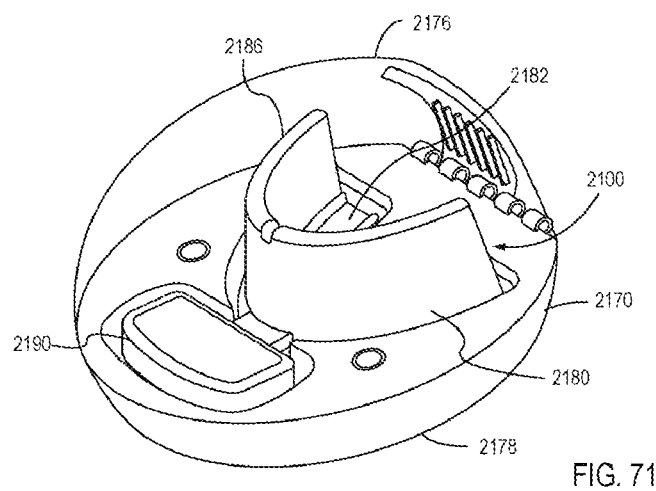
FIGS. 71 and 72 are perspective and front views of the intra-oral apparatus of FIG. 67 and an external station according to an embodiment of the invention.
Figure 72:
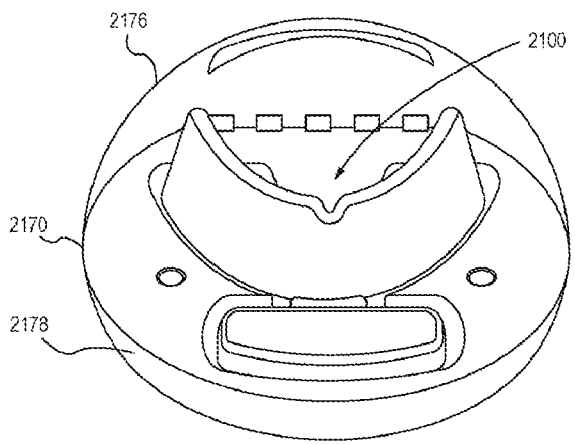
Figure 73:
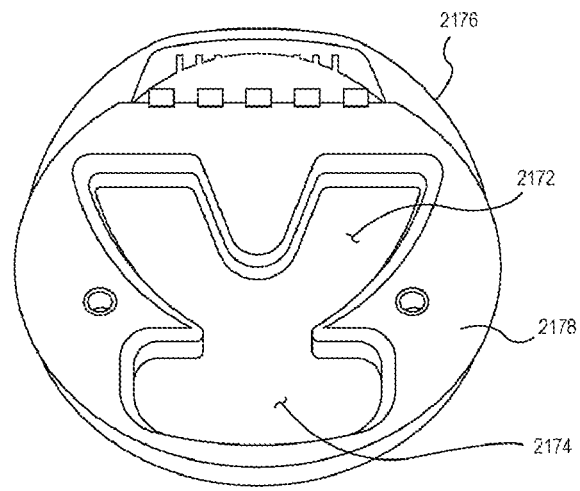
FIG. 73 is a front view of the external station of FIG. 71.

Referring to FIGS. 71-73, the extra-oral housing 2190 can be configured to be disposed on or otherwise coupled to an external station 2170, for example, when the apparatus 2100 is not in use by the patient. The external station 2170 can be, for example a carrying case, charging caddy or station, or the like, or a combination of the foregoing. The station 2170 comprises a base 2178 and a lid 2176 and defines a cavity formed by and between the base 2178 and the lid 2176 when the lid is in a closed position (as shown in FIGS. 71-73). The lid 2176 can be coupled to the base 2178 using any suitable coupling mechanism, for example, using a hinge as shown in FIGS. 71-73. In this manner, the lid 2176 is conveniently moveable between its closed position and an open position (not shown). The base 2178 can define a first recess 2172 configured to receive at least a portion of the intra-oral housing 2180 and a second recess 2174 configured to receive at least a portion of the extra-oral housing 2190. A perimeter of the first recess 2172 can, for example, complement the contour of the intra-oral housing 2180. A perimeter of the second recess 2174 can, for example, complement the contour of the extra-oral housing 2190.

The external station 2170 can be configured to charge the apparatus 2100 when the apparatus 2100 is disposed on or otherwise coupled to the station. In this manner, the battery 2194 can be recharged when the extra-oral housing 2190 is coupled to the charging station. In one or more embodiments, for example, the station 2170 is configured to inductively charge the apparatus 2100. In one or more embodiments, the second end 2193 of the extra-oral housing 2190 comprises a connector (not shown in FIGS. 67-74) configured to be coupled to a complementary or mating connector (not shown in FIGS. 67-74) of the external station 2170.

The intra-oral apparatus 2100 can be configured to determine when the intra-oral housing 2180 is disposed within the patient's mouth (i.e., in a manner suitable for the treatment session). In one or more embodiments, for example, the intra-oral apparatus 2100 comprises a sensor (not shown in FIGS. 67-74) configured to detect reflection of light off of a patient's oral soft tissue. The sensor can be, for example, a proximity detector included, or embedded, in the flexible circuit 2130. Such a proximity detector can, for example, comprise any suitable capacitance detection device. The light emitting panel 2102 can be configured to blink or pulse the LEDs included therein, for example, upon removal of the apparatus 2100 from the external station 2170 based, for example, on feedback from the proximity detector. The LEDs can be configured to blink or pulse at a predetermined rate.

At least a portion of light emitted from the pulsing or blinking LEDs towards the oral soft tissue of the patient's mouth is reflected to the intra-oral housing 2180 and is thereby detected by a sensor or other light detection mechanism (generally referred to as a "light sensor" or "photodetector," not shown in FIGS. 67-74). The light sensor is configured to evaluate the functionality of a portion of the light emitting array 2102 coupled to the left side of the intra-oral housing 2180 and a portion of the light emitting array 2102 coupled to the right side of the intra-oral housing 2180. In this manner, the light sensor facilitates detection of any faulty operation of the apparatus 2100 with respect to each of the left and right sides of the intra-oral housing 2180 before operation of the apparatus 2100 with respect to the patient. Suitable thresholds pertaining to the amount of light detected can be established, and used for example to assess whether the LEDs of the light emitting array 2102 are operating properly. The apparatus 2100 can be configured to initiate irradiation of the oral tissue (i.e., begin a treatment session) when the light sensor detects the light reflected off of the oral soft tissue. In one or more embodiments, the light sensor is configured to transmit a signal to the microprocessor 2196 to initiate the treatment session when the light sensor detects light reflection (e.g., at or above a predetermined threshold) from the oral soft tissue.

The intra-oral apparatus 2100 can be configured for use in an orthodontic treatment, including any treatment described herein. In one or more embodiments, for example, the intra-oral apparatus 2100 is useful to irradiate at least a portion of the patient's upper jaw for about 3 minutes, the patient's lower jaw for about 3 minutes, or each of the patient's upper and lower jaws for about 3 minutes. More specifically, in one treatment program, the intra-oral apparatus 2100 is useful to administer a light-therapy treatment session in which the oral tissue associated with each of the upper arch of the patient's mouth and the lower arch of the patient's mouth (or vice versa) are consecutively irradiated for 3 minutes per day, for a total treatment session of 6 minutes per day.

During the treatment session, for example, the apparatus 2100 is configured to administer the light therapy using 12 Joules/cm$^2$. In one or more embodiments, the 12 Joules/cm$^2$ is administered at an intensity of 150 mW/cm$^2$ for the three minutes duration. As such, the LEDs tend to remain under a thermal threshold of about 41 degrees Celsius in contact with, or within the particular distance of, oral tissue (and thus under a maximum limit of 43 degrees Celsius). In one or more embodiments, the 12 Joules/cm$^2$ can be administered at a higher intensity, such as at an intensity of about 600 mW/cm$^2$ for about 20 seconds or about 1 W/cm$^2$ for about 12 seconds. In other embodiments, the light is administered at an intensity of about 60-12 mW/cm$^2$.

The light is emitted at a wavelength of 850 nm during the treatment session. In one or more embodiments, the light is emitted at a wavelength of 850 nm (±15 nm) during the treatment session. In other words, LEDs can emit light at a blend of wavelengths, and not at a single wavelength like a laser. The peak light emission wavelength ( ),max) by the LEDs is 855 nm. The treatment sessions can be administered for any suitable period, including, but not limited to, a period of four to twelve months. Such a treatment program can, for example, reduce the duration of an average period a patient is expected to need to use an orthodontic appliance (e.g., braces) to achieve a desired orthodontic result from two years to six months. The foregoing treatment program and/or any treatment program described herein can reduce a duration of an orthodontic treatment administered without light therapy, as described herein, by about 50 percent to about 75 percent.

Figure 75:
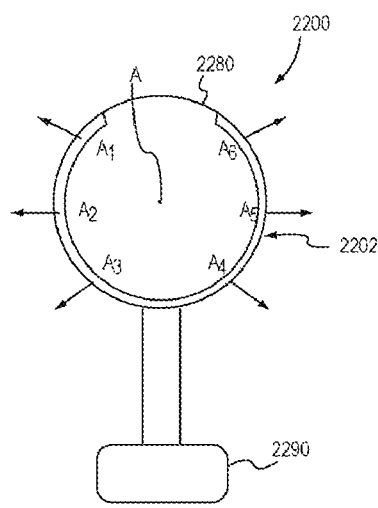
FIG. 75 is a top view of an intra-oral apparatus according to an embodiment of the invention.

Although the intra-oral housing (e.g., intra-oral housing 780, 880, 980, 1280, 1680, 1780, 1880, 1980, 2080, 2180) have been illustrated and described herein as having an arch shape similar to at least one of the upper or lower arch of a patient's teeth, in other embodiments, an light therapy apparatus can comprise an intra-oral housing having another suitable configuration. For example, referring to FIG. 75, an intra-oral apparatus 2200 configured to administer light therapy to a patient's oral tissue (e.g., the oral mucosa and/or root area) comprises an intra-oral housing 2280 and an extra-oral housing 2290 coupled to the intra-oral housing. The extra-oral housing can be similar in many respects, or identical, to the extra-oral housing 2190 described herein with reference to FIGS. 67-69, and is therefore not described in detail herein. Although the intra-oral housing 2280 is shown and described as being coupled to the extra-oral housing 2290, in other embodiments, the intra-oral housing 2280 can be configured to be electrically coupled to a separate electronic device (e.g., via fiber optic cable(s), or other electronic tether as shown and described with respect to FIG. 66) configured to perform the functions of the components of the extra-oral housing 2290.

The intra-oral housing 2280 comprises a light emitting array 2202. The light emitting array 2202 can be the same as or similar in many respects to a light emitting array described herein, and thus is not described in detail with respect to FIG. 65. The intra-oral housing 2280 can be configured to be received in the oral cavity such that a light emitting array 2202 is wholly disposed on the lingual side of the upper and/or lower arches of the patient's teeth. The intra-oral housing 2280 can define a substantially circular perimeter, e.g., having a curvature approximating the curvature of a circle). For example, the intra-oral housing 2280 can be spherical, disc shaped, or the like. For descriptive purposes, the intra-oral housing 2280 can have a shape and can be disposed within a patient's mouth similar to a lollipop. In this manner, the light emitting array 2202 can be disposed adjacent the perimeter of the intra-oral housing 2280 such that the light emitting array 2202 emits light towards the patient's oral tissue (e.g., the oral mucosa and/or the root area) in a direction radiating from a central axis A, as shown by the arrows A1, A2, A3, A4, A5 and A6, in FIG.

75. In one or more embodiments, at least a portion of the intra-oral housing 2280 can be configured to contact at least a portion of the alveolar soft tissue when the intra-oral housing 2280 is disposed within the patient's mouth. In one or more embodiments, at least a portion of the intra-oral housing 2280 is configured to not contact, but be at a particular distance (e.g., from 0.1 cm to 3 cm) from, the alveolar soft tissue when the intra-oral housing 2280 is disposed within the patient's mouth.

Figure 76:
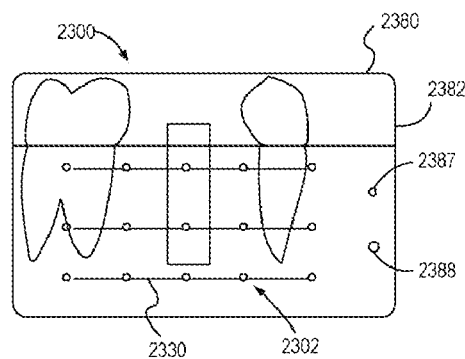
FIG. 76 is a side view of a portion of an intra-oral apparatus according to an embodiment of the invention.
Figure 77:
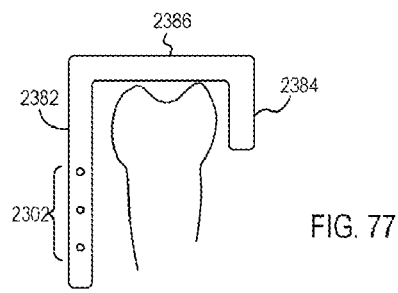
FIGS. 77 and 78 are end and perspective views of the intra-oral apparatus of FIG. 76.
Figure 78:
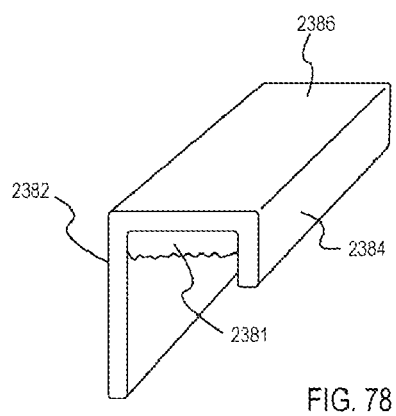

Although the intra-oral apparatus have been illustrated and described herein as being configured to administer light therapy to the upper and/or lower arch of a patient's teeth, in one or more embodiments, an intra-oral apparatus is configured to administer light therapy to a portion or section of the patient's oral mucosa (e.g., the alveolus). For example, referring to FIG. 76, in one or more embodiments, an apparatus 2300 is configured to administer light therapy to three or four teeth of the patient, to a quadrant of the patient's teeth, or to one arch of the patient's teeth. Such an intra-oral apparatus can be beneficial in the case of implantology and/or oral surgery.

The apparatus 2300 comprises an intra-oral housing 2380 configured to be disposed within the oral cavity of the patient. The intra-oral housing 2380 defines a first segment 2382, a second segment 2384 and a third segment 2386 coupling the first segment and the second segment. When the intra-oral housing 2380 is disposed within the patient's oral cavity for a treatment session, the first segment 2382 of the intra-oral housing is configured to be disposed (e.g., vertically) between the patient's teeth and the patient's buccal mucosa, the second segment 2384 is configured to be disposed (e.g., vertically) on the lingual side of the crown of the patient's teeth, and the third segment 2386 is configured to be disposed (e.g., horizontally) adjacent and/or on the occlusal surface of the patient's teeth. The second segment 2384 has a sufficient height (i.e., measured in a direction from the occlusal surface to the root area) to inhibit tipping of the intra-oral housing 2380 towards the patient's cheek. In one or more embodiments, a layer 2381 of moldable material is disposed on an occlusal-facing surface of the third segment 2386 of the intra-oral housing 2380. A moldable impression of the designated teeth can be made using the layer 2381, thus facilitating placement of the intra-oral housing 2380 when the housing is later re-inserted into the oral cavity by the patient (e.g., for a subsequent treatment session).

A flexible circuit 2330 is disposed within the first segment 2382 of the intra-oral housing 2380. The flexible circuit 2330 comprises a light emitting array 2302 configured to administer light therapy, in any manner described herein, to the patient's teeth. For example, the flexible circuit 2330 can comprise a light emitting array 2302 including 15 LEDs, or 15 LEDs per tooth that will be subjected to light therapy. The light emitting array 2302 can comprise LEDs configured to administer, or emit, light ranging from about 600 to about 1200 nm. The flexible circuit 2330 of the intra-oral housing 2380 comprises a sensor 2387. The sensor 2387 can be the same as or similar in many respect to the sensor shown and described herein with reference to FIG. 25A. The sensor 2387 can be configured to detect the temperature of the apparatus 2300, the patient's alveolar soft tissue and/or the patient's root area. For example, a thermistor or similar temperature measuring device can be placed in the circuit 2330 to monitor the temperature of the light emitting array 2302, as well as measure the temperature inside the patient's mouth. This information can serve as a method of obtaining temperature-related information as well as monitoring patient compliance. When the intra-oral housing 2380, and thus the circuit 2330, is placed in the mouth and when the apparatus 2300 emits light, the temperature of the light emitting array 2302 will rise from pre-treatment ambient temperature to closer to normal body temperature. By monitoring the change in temperature, a controller 2314, described in more detail herein, can monitor the period of time that the light emitting array 2302 is in the oral cavity, based on the period of time the temperature is elevated and close to body temperature.

In one or more embodiments, the circuit 2330 comprises a sensor (or proximity detector) that is configured to detect contact of, or a proximity at a particular distance (e.g., from 0.1 cm to 3 cm) from, the first segment and/or light emitted by the light emitting array 2302 with the patient's oral mucosa and/or root area. In this manner, the controller 2314 can detect that the intra-oral housing 2380 is disposed within the patient's oral cavity, and therefore can determine that a treatment session can be initiated.

Figure 79:
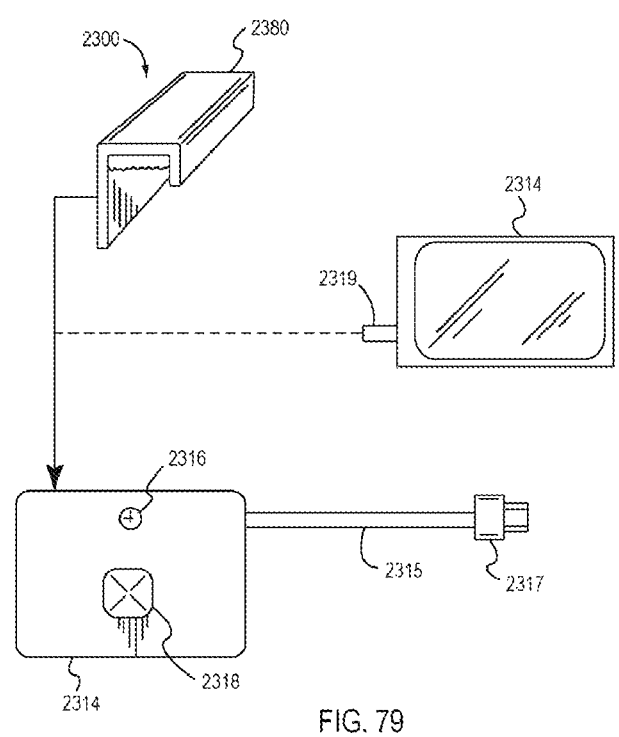
FIG. 79 is a schematic illustration of a system including the intra-oral apparatus of FIG. 76 according to an embodiment of the invention.

Referring to FIG. 79, the intra-oral housing 2380 is configured to be coupled to an external electronic device, e.g., via a wired or wireless connection. The external electronic device can be configured to provide or convey power to the intra-oral housing 2380, for example, for operation of the light emitting array 2302 during a treatment session. The external electronic device can also be configured to control operation of the light-emitting array 2302.

In one or more embodiments, the external electronic device is a controller 2314. The intra-oral housing 2380 can be removably coupleable to the controller 2314. In one or more embodiments, the intra-oral housing 2380 is disposable and the controller 2314 is reusable. In this manner, the intra-oral housing 2380 can be disposed of after a predetermined number of uses and/or after a predetermined period of time, and a second intra-oral housing (not shown) can optionally be used with the controller 2314. The controller 2314 can be electrically coupled to a charger 2317, such as a medical grade USB charger, via a cable 2315, such as a USB cable.

The controller 2314 can be similar in many respects or identical to any controller (e.g., controller 430, 1114) described herein. The controller 2314 can also comprise many components the same as or similar to those disposed within the extra-oral housing 2190 of apparatus 2100. For example, the controller 2314 can comprise a microprocessor. Because the microprocessor can be the same as or similar in many respects to any microprocessor described herein (e.g., microprocessor 2196), it is not described in detail herein. The controller 2314 can be preconfigured with a treatment protocol. The controller 2314 comprises a button 2318 for initiating a treatment session. The button 2318 can also be configured to, for example, pause or stop a treatment session.

The controller 2314 comprises an LED indicator 2316 that can be configured to provide an indicia to the patient of the status of the controller, the intra-oral housing 2380, and/or the treatment program. The LED indicator 2316 can be similar or identical, for example, to the communication mechanism of extra-oral housing 2190, described herein, in that it is configured to indicate a status, or stage, of the treatment session. In one or more embodiments, the LED indicator 2316 is configured to display no light during a first stage of the treatment session, a blinking or pulsed light during a second stage of the treatment session, and/or a solid light during a third stage of the treatment session. The LED indicator 2316 can be, for example, configured to display a solid light for a first predetermined duration (e.g., 2 minutes and 30 seconds, 2 minutes and 45 seconds, or 2 minutes and 10 seconds) upon initiation of the treatment session. The LED indicator 2316 can be configured to display the blinking or pulsed light for a second predetermined duration (e.g., 10, 15 or 30 seconds) following the first predetermined duration as a signal to the patient that the treatment session is nearing its end. The LED indicator 2316 can be configured to display no light when a treatment session is ended (e.g., after 3 minutes from initiation of the treatment session) and the apparatus 2100 is not irradiating light to the patient.

In one or more embodiments, the external electronic device 2314 is a personal electronic device such as a mobile phone (e.g., a smartphone, such as an iPhone®, a tablet, such as an iPad®), a personal digital assistant, or the like. The intra-oral housing 2380 can be coupled to the device 2314 using a connector 2319. In an embodiment in which the device 2390 comprises, for example, a smartphone, the smartphone can be configured to perform any operation or function that the controller is configured to perform. For example, the device 2314 can be configured to provide power to the intra-oral housing 2380. In another example, the device 2314 can comprise an application configured to provide an interface for the patient, control the light-emitting array 2302, and/or record usage information (e.g., compliance information) for subsequent accessing of the information by the patient and/or a physician.

In one or more embodiments, a system comprises a first portion configured to administer light therapy to a patient, as described herein, for a first time period, and a second portion configured to administer light therapy to the patient, as described herein, for a second time period different than the first time period. For example, in one or more embodiments, the system comprises a plurality of apparatus (or intra-oral housings), such that at least a portion of each apparatus is configured to be disposed within the patient's mouth. Each apparatus of the plurality can comprise any apparatus or intra-oral housing described herein. For example, the system comprises a first intra-oral apparatus and a second intra-oral apparatus distinct from the first intra-oral apparatus. The first apparatus is configured to begin administering light therapy to a patient at a first time period beginning at T0. T0 represents the start of a phototherapy session (e.g., corresponding to a date the patient is assigned the first apparatus and/or starts daily usage of the first apparatus). For at least some patients, T0 can also represent the day of maxillary bonding and/or the start of an orthodontic treatment. The start of orthodontic treatment can begin, for example, on the day a conventional fixed orthodontic brackets and wires are installed on the patient's teeth. The first apparatus can be selected based on a position or configuration of the patient's teeth prior to administration of the light therapy. The first apparatus is configured to administer light at a first wavelength, such as, but not limited to, about 850 nm.

The second apparatus is configured to administer light therapy to a patient at a second time period beginning at T>O, subsequent to TO. In one or more embodiments, the second apparatus is optimally configured to administer light therapy to the patient based on a position of the patient's teeth after administration of at least a portion of the light therapy. For example, the second apparatus can comprise a light emitting array differently configured from a light emitting array of the first apparatus. The second apparatus can be configured to administer light at a second wavelength different than the first wavelength, such as, but not limited to, about 620 nm. In this manner, the second apparatus can be selected based, at least in part, on tooth movement that occurred during the light therapy administered in combination with the first apparatus and during a time period between TO and T>O. For example, the first apparatus can be used by the patient at start of the light therapy program and for the first time period, and the second apparatus can be used by the patient beginning about three months after the beginning of the light therapy program and for the second time period. The system can comprise any suitable number of apparatus, such as two, three, four or more apparatus configured to administer the light therapy. For example, the system can comprise the first apparatus configured to administer the light therapy beginning at TO, the second apparatus configured to administer light therapy beginning at T1, and a third apparatus configured to administer light therapy beginning at T2.

In another example, the system can comprise an apparatus having a first light emitting array (e.g., the first portion) and a second light emitting array (e.g., the second portion). The first light emitting array can be configured to administer light at a first wavelength, such as, but not limited to, about 850 nm. The second light emitting array can be configured to administer light at a second wavelength different than the first wavelength, such as, but not limited to, about 620 nm. The first light emitting array and the second light emitting array can be included in a single intra-oral housing. The system, which comprises a first portion configured to emit light at the first wavelength for the first time period and at the second wavelength for the second time period, is beneficial at least because it permits a transition during a light therapy program from a higher light wavelength to a lower light wavelength that can help start to increase bone mineralization in the patient's treated area. Such an increase in bone mineralization can facilitate ensuring a more stable result of the moved teeth following an orthodontic treatment.

Figure 80:
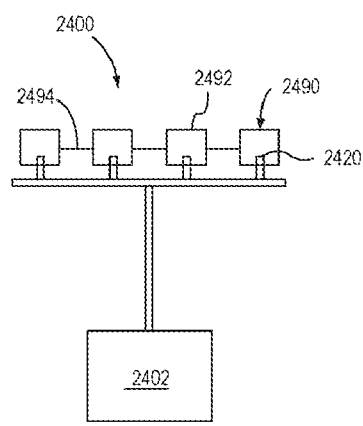
FIG. 80 is a schematic illustration of an intra-oral apparatus according to an embodiment of the invention.
Figure 81:
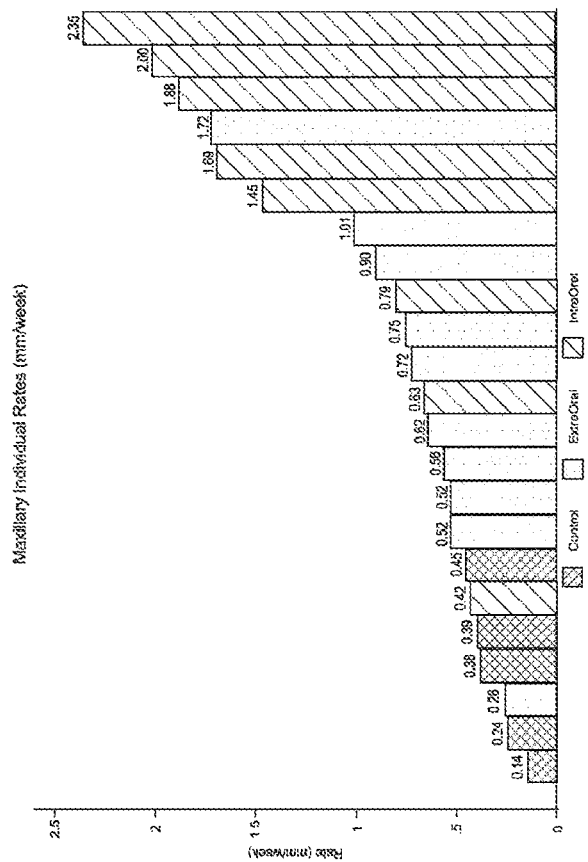
FIG. 81 is a graphical illustration of individual rates of maxillary tooth movement for study group participants.
Figure 82:
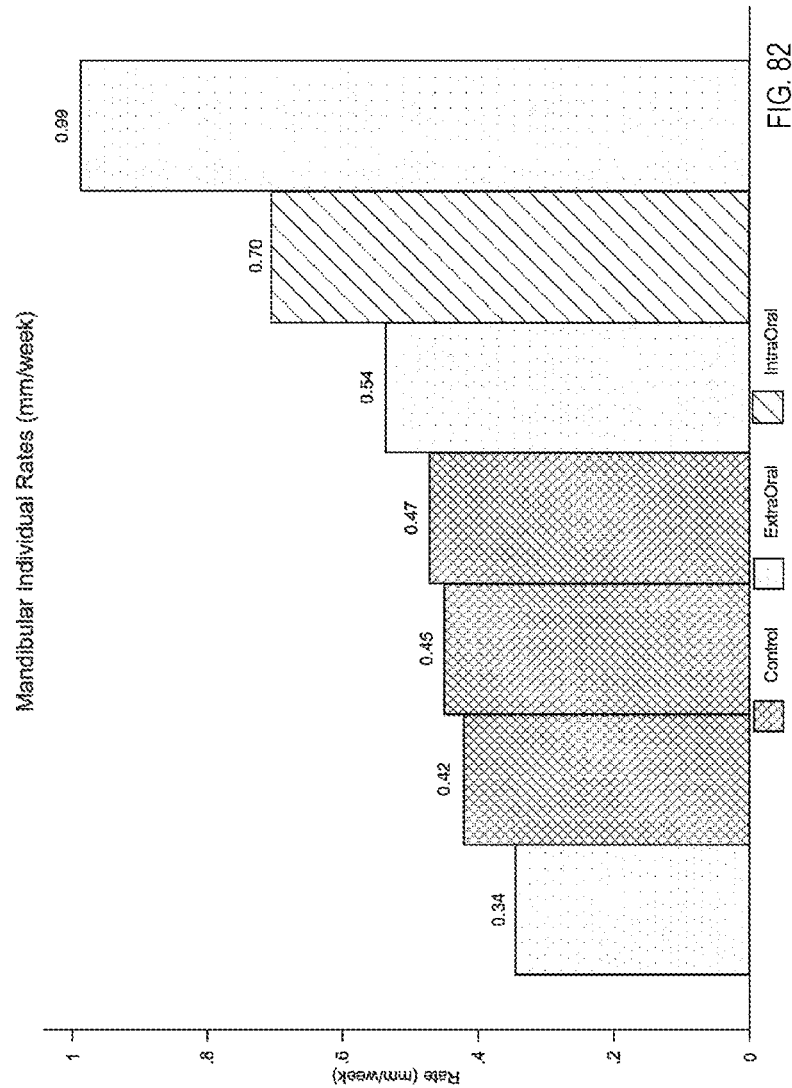
FIG. 82 is a graphical illustration of individual rates of mandibular tooth movement for study group participants.
Figure 83:
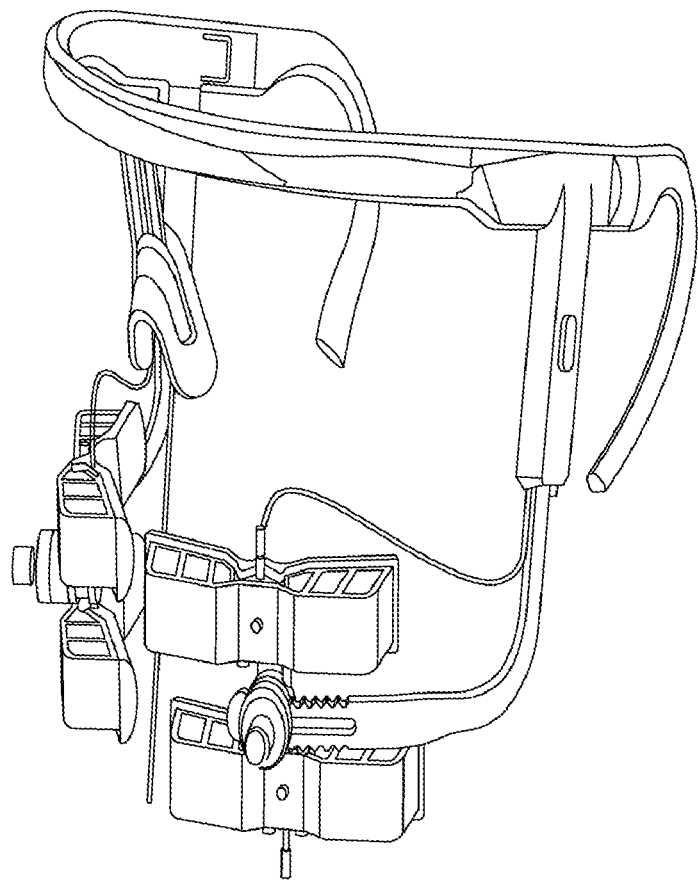
FIG. 83 is a perspective view of a comparative extra-oral light therapy apparatus.

In one or more embodiments, the light therapy apparatus described herein are configured for use in combination with a functional dental appliance, as described in more detail herein. In other embodiments, a light therapy apparatus is integrally formed with a functional appliance configured to exert a force on the teeth of a patient, such as a functional appliance described in more detail herein. For example, referring to FIG. 80, a system 2400 according to an embodiment is configured to regulate tooth movement. The system 2400 comprises one or more light emitters (e.g., fiber optical cable(s)) 2420 and an orthodontic bracket system 2490. The light emitters 2420 can be the same as or similar to any light emitter described herein, including, but not limited to, optical fiber cables 420 depicted in FIG. 29. The light emitters 2420 are coupled to the bracket system 2490. For example, the light emitters 2420 can be coupled to one or more brackets 2492 of the bracket system 2490, to one or more wires 2494 of the bracket system 2490, or any combination of the foregoing. In this manner, a separate intra-oral housing is not needed to maintain a position of the light emitters 2420 with respect to the patient's tooth, root area and/or oral mucosa. The light emitters 2420 are coupleable to a light source 2402.

The light source 2402 can be any suitable light source, including any light source described herein (such as light source 402 depicted in FIG. 29).

A light therapy system according to an embodiment is illustrated in FIGS. 84-113. The system comprises a light therapy apparatus 2500 (see, e.g., FIGS. 84-97) and an external station 2580 (see, e.g., FIGS. 109-113). The light therapy apparatus 2500 is configured to irradiate light in any suitable manner described herein, including, for example, to irradiate the alveolus and/or root area of the patient. Similarly stated, the light therapy apparatus 2500 is configured to administer light therapy to a patient's teeth and/or oral mucosa. More specifically, the light therapy apparatus 2500 is configured to administer light to the patient's teeth and/or oral mucosa sufficient to accelerate orthodontic movement of the patient's teeth and to reduce the overall treatment time for the patient when undergoing orthodontic treatment. In one or more embodiments, the light therapy apparatus 2500 is configured to administer light to the patient's teeth and/or oral mucosa in an amount sufficient to increase alveolar bone volume and/or bone density. The light therapy apparatus 2500 is useful in combination with traditional orthodontic treatment with an orthodontic appliance, such as brackets, wires, and/or aligners. The light therapy apparatus 2500 can be the same as or similar in many respects to, or comprise components the same as or similar in many respects to, the intra-oral apparatuses described herein, including, for example, apparatus 2100. The light therapy apparatus 2500 is configured to be disposed in or on the external station 2580 when the apparatus is not in use for a light therapy treatment session, as described in more detail herein.

The light therapy apparatus 2500 comprises an intra-oral housing 2510 (also referred to herein as a "mouthpiece") configured to be disposed in an oral cavity (e.g., in the mouth, not shown in FIGS. 84 and 85) of a patient and an extra-oral housing 2560 (also referred to herein as a "bill") configured to be coupled to the mouthpiece 2510 and disposed externally to the patient's mouth when the mouthpiece 2510 is disposed within the patient's mouth.

Figure 84:
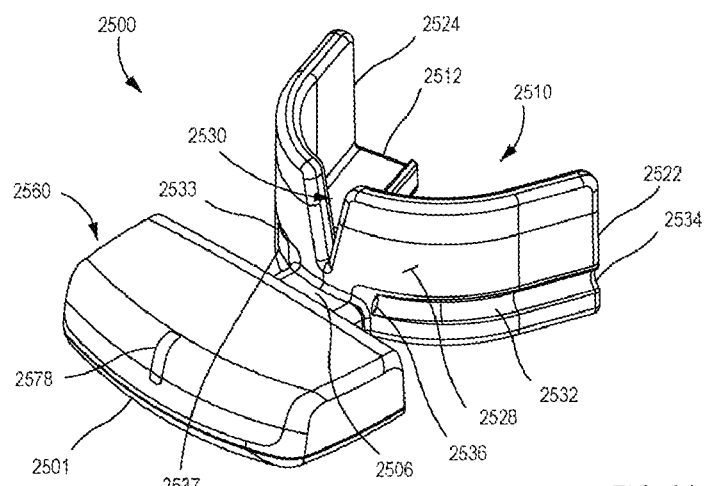
FIGS. 84 and 85 are perspective views of a light therapy apparatus according to an embodiment.
Figure 85:
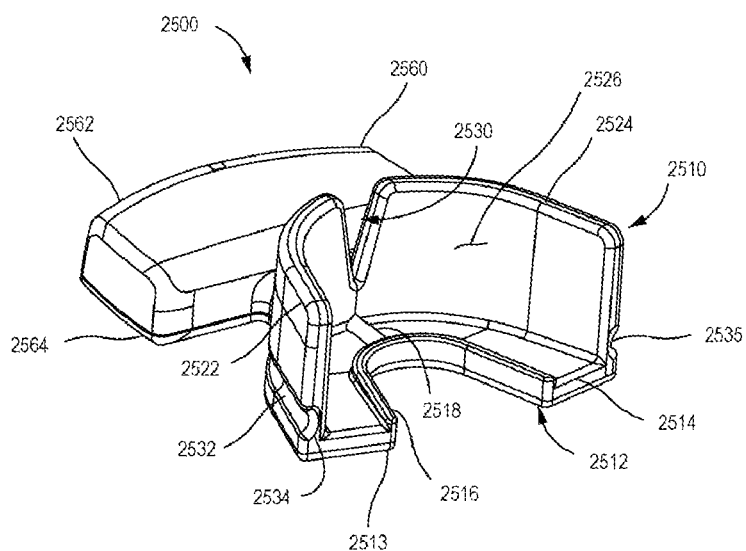
Figure 88:
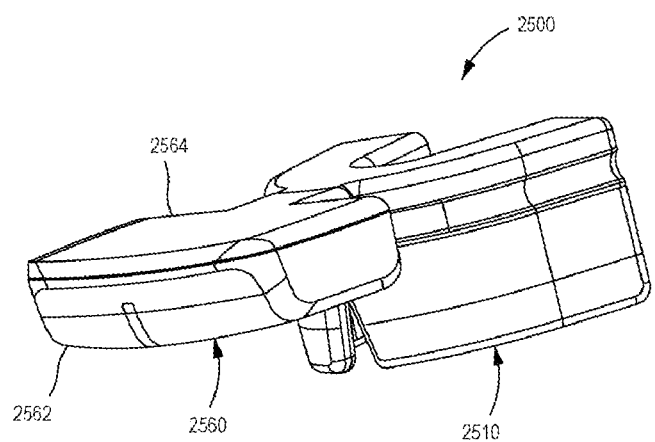
FIG. 88 is a perspective view of the light therapy apparatus of FIG. 84 in an inverted position.
Figure 89:
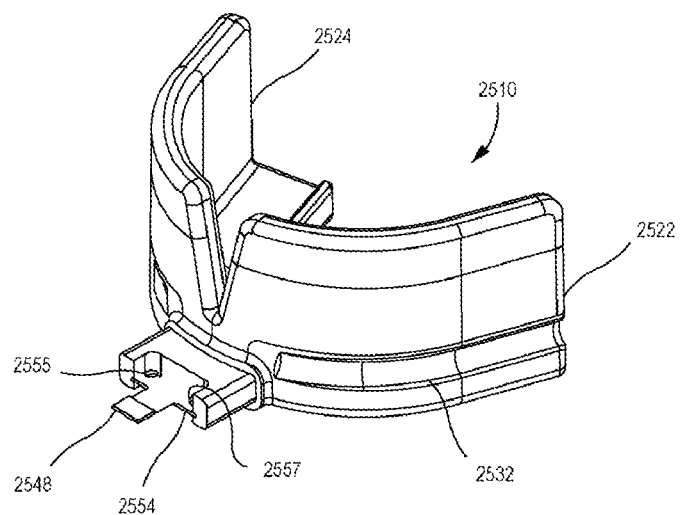
FIG. 89 is a perspective view of a portion of the light therapy apparatus of FIG. 84.

The light therapy apparatus 2500 is configured to be useful for light therapy with the upper jaw and/or the lower jaw of the patient. In other words, the light therapy apparatus 2500 can be configured to administer light therapy with respect to the patient's upper jaw when the apparatus is in an upright position (e.g., as shown in FIG. 84), and can be configured to administer light therapy with respect to the patient's lower jaw when the apparatus is in an inverted position (e.g., as shown in FIG. 88). As such, the mouthpiece 2510 is configured to be disposed within the patient's oral cavity with respect to each of the upper and lower jaws of the patient. Similarly stated, the mouthpiece 2510 is configured matingly adapt to both the upper jaw and the lower jaw, as described herein, thus eliminating the need for a separate mouthpiece for each jaw. It should be noted that although the light therapy apparatus 2500 generally, and the mouthpiece 2510 specifically, may be described as being in the upright position when configured to be oriented with respect to the upper jaw and in the inverted position when configured to be oriented with respect to the lower jaw, in other embodiments, the light therapy apparatus 2500 and the mouthpiece 2510 are in the upright position when configured to be oriented with respect to the lower jaw of the patient, and in the inverted position when configured to be oriented with respect to the upper jaw of the patient.

Figure 86A:
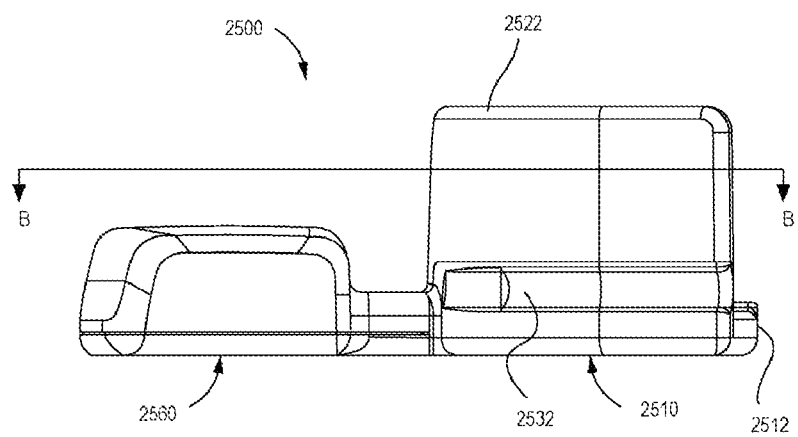
FIG. 86A is a right side view of the light therapy apparatus of FIG. 84. The left side view of the light therapy apparatus of FIG. 84 is a mirror image to the right side view.
Figure 86B:
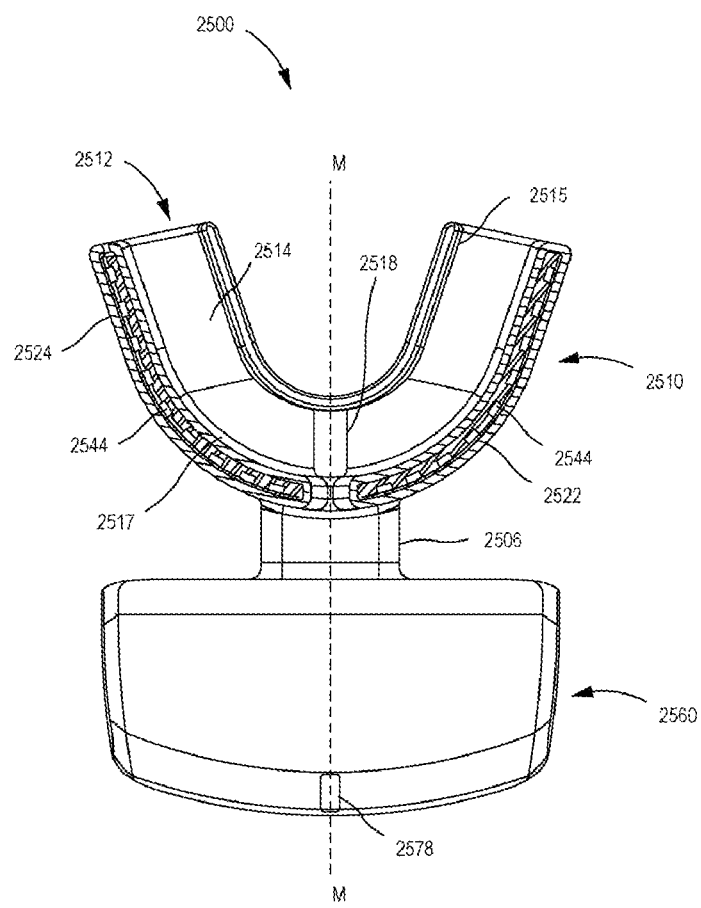
FIG. 86B is a cross-sectional view of the apparatus of FIG. 86A, taken along line B-B in FIG. 86A.

The mouthpiece 2510 can be similar in one or more respects, and comprise components similar in one or more respects, or identical, to the intra-oral housings described herein, including, for example, the intra-oral housings or mouthpieces described herein with reference to FIGS. 35-37, 65-66 and 67-72. The mouthpiece 2510 comprises a bite tray 2512, flanges 2522, 2524, a light array 2542 (see, e.g., FIG. 94), and a support plate 2554 (see, e.g., FIG. 94). The bite tray 2512 is configured to receive at least a portion of the patient's teeth of the upper and/or lower jaw. As such, the bite tray 2512 is generally U-shaped, as shown in FIG. 86B. The bite tray 2512 is configured to facilitate proper positioning of the mouthpiece 2510 within the patient's mouth. The bite tray 2512 generally comprises the lower portion of the mouthpiece 2510. The bite tray 2512 comprises a bite pad 2514 with an inner perimeter (or side wall) 2515 and an outer perimeter (or side wall) 2517. Flanges 2522, 2524, described in more detail herein, generally define an upper portion of the mouthpiece 2510 and are coupled to the outer perimeter 2517 of the bite pad 2514. An inner ridge 2516 is coupled to or otherwise formed on the inner perimeter 2515 of the bite pad 2514. The flanges 2522, 2524 of the mouthpiece 2510 and the inner ridge 2516 each extend and/or protrude from the bite pad 2514 in a first direction. As such, when the mouthpiece 2510 is disposed within the patient's mouth, the bite tray 2512 is positioned within the mouth such that the bite pad 2514 is adjacent the occlusal surface of one or more teeth, the flanges 2522, 2524 are disposed between the one or more teeth and buccal tissue, and the inner ridge 2516 is disposed between the one or more teeth and the tongue. Similarly stated, the bite tray is configured such that when the mouthpiece 2510 is disposed within a mouth, a least a portion of one or more teeth are positioned between the flanges 2522, 2524 and the inner ridge 2516.

The bite tray 2512 can have any thickness suitable for receiving a bite force thereon. In one or more embodiments, the bite pad 2514 can have a constant thickness. In other embodiments, the thickness of the bite pad 2514 can vary spatially. For example, the bite tray 2512, and more specifically, the bite pad 2514, can have a first thickness at an anterior end portion of the bite tray, and a second thickness greater than the first thickness at a posterior end portion of the bite tray. Similarly stated, in one or more embodiments, the thickness of the bite pad 2514 increases along the length of the bite pad 2514 between a first (anterior) portion of the bite pad 2514 and a second (posterior) portion of the bite pad. For example, in one or more embodiments, a thickness of the bite pad 2514 at an anterior portion is between about 5 mm and about 25 mm, and a thickness of the bite pad 2514 at a posterior portion is between about 7 mm and about 27 mm. The increased thickness of the first portion of the bite pad 2514 forces most of the contact between the patient's teeth and the mouthpiece 2510 to be between the posterior teeth (e.g., the molars) and the thicker, second portion of the bite pad 2514. Similarly stated, any pressure exerted by the teeth on the bite tray 2512 will be more concentrated on the thicker portion of the bite pad 2514. Having the greater bite force at the posterior portion of the bite tray 2512 improves patient comfort and helps to avoid damage to the mouthpiece 2510 that may otherwise be caused by the patient's sharper anterior teeth.

Additionally, the increased contact interface between the bite tray 2512 and the posterior teeth also provides for a more universal patient fit, because positional variability of the posterior teeth is often less than that of the anterior teeth. Similarly stated, this arrangement produces a more repeatable (treatment-to-treatment and patient-to-patient) fit because the position of a patient's posterior teeth often varies less amongst different patients' anatomies than the position of the anterior teeth and incisors. In one or more embodiments, the bite pad 2514 is constructed (i.e., is constructed from a material and/or has a sufficient thickness) to withstand a biting force of up to about 340 N. In one or more embodiments, the bite pad 2514 has shear and/or fatigue strength to withstand 50 N of force repeatedly applied to the bite tray 2514.

Figure 87:
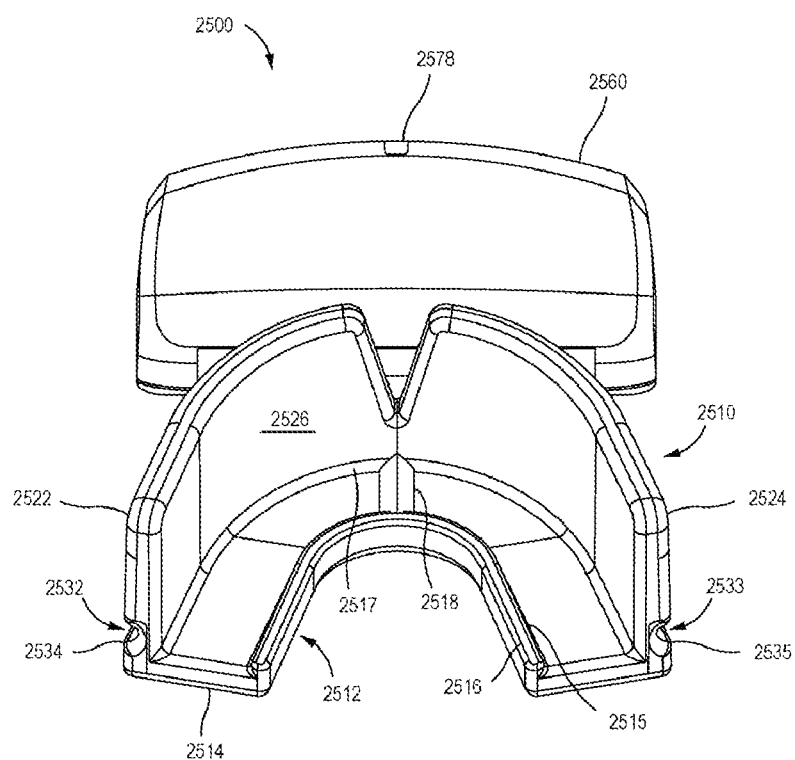
FIG. 87 is a rear perspective view of the light therapy apparatus of FIG. 84.

As shown in FIG. 87, an upper surface of the bite pad 2514 comprises a ridge 2518. The ridge 2518 is disposed along a midline M of the mouthpiece 2510 and is elevated with respect to the upper surface of the bite tray 2512 and/or bite pad 2514. The ridge 2518 can extend between the inner perimeter 2515 of the bite pad 2514 and the outer perimeter 2517 of the bite pad 2514, as best shown in FIG. 86B. The ridge 2518 facilitates positioning of the mouthpiece 2510 within the patient's oral cavity. For example, the mouthpiece 2510 is configured to be positioned within the patient's oral cavity such that the ridge 2518 is disposed between the patient's front central incisors (on either the upper jaw or the lower jaw). Proprioception of the patient related to the teeth and periodontium can produce sensory feedback to the patient regarding the position of the ridge 2518 of the mouthpiece 2510.

In this manner, the ridge 2518 facilitates centering of the mouthpiece 2510 within the oral cavity, thus promoting symmetry of a light therapy treatment on the alveolus, or other oral tissue, on both sides of the patient's mouth. In other words, in order to promote the symmetrical administration of light therapy to the root area, the mouthpiece 2510 can be positioned with the midline M of the mouthpiece 2510 seated along the sagittal plane or within (i.e., plus or minus) 5 degrees of the sagittal plane, and the ridge 2518 can facilitate such positioning in use. The ridge 2518 can have any suitable shape, including, for example, the shape of an inverted V as shown in FIG. 87, such that the point of the V can be disposed between the patient's front central incisors.

As noted above, the upper portion of the mouthpiece 2510 comprises a first (or left) flange 2522 and a second (or right) flange 2524. The upper portion (i.e., the flanges 2522, 2524) of the mouthpiece 2510 is disposed transversely with respect to the bite plate 2514. The flanges 2522, 2524 are configured to be disposed, when the mouthpiece 2510 is disposed within the patient's mouth such that the bite tray is adjacent an occlusal surface of the patient's teeth, adjacent a portion of a side of the patient's teeth and/or adjacent the alveolar mucosa. In this manner, the light array 2542, enclosed in the flanges 2522, 2524, as described in more detail herein, can be useful for administering light to the patient's teeth and/or alveolar mucosa.

The flanges 2522, 2524 collectively contain the light array 2542, and are each configured to be disposed between the buccal tissue and the alveolus. Thus, in use, the flanges 2522 and 2524 displace oral soft tissue to maintain the desired position of the light array 2542 relative to the anatomy of the patient. More specifically, the flanges 2522, 2524 are each configured to displace buccal tissue away from the patient's alveolus. In one or more embodiments, an inner face 2526 of the flanges 2522, 2524 can be spaced apart from the patient's alveolar tissue when the mouthpiece 2510 is disposed within the patient's mouth and the flanges 2522, 2524 are displacing the buccal tissue. In one or more embodiments, at least a portion of the inner face 2526 of the flanges 2522, 2524 can contact the patient's alveolar tissue when the mouthpiece 2510 is disposed within the patient's mouth and the flanges 2522, 2524 are displacing the buccal tissue.

The flanges 2522, 2524 of the mouthpiece 2510 are configured to be flexible and/or deformable. Similarly stated, the flanges 2522, 2524 are constructed from a material and have geometrical dimensions and/or configurations to provide the desired flexibility, as described herein. Moreover, each of the first and second flanges 2522, 2524 are independently deflectable, movable and/or deformable with respect to the mouthpiece 2510 and/or each other. In this manner, the mouthpiece 2510 can be easily disposed within the oral cavity for a variety of different patients having a variety of different anatomical structures, as described herein.

Figure 90:
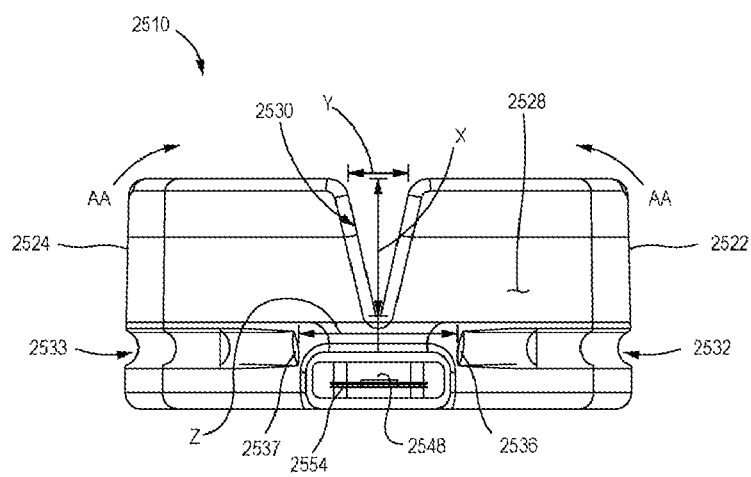
FIG. 90 is a front view of the portion of the light therapy apparatus of FIG. 89.
Figure 91:
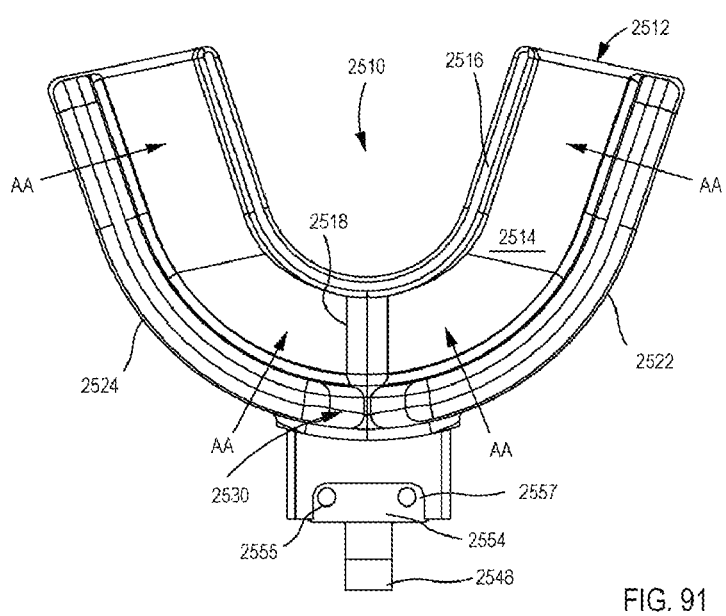
FIG. 91 is a top view of the portion of the light therapy apparatus of FIG. 89.
Figure 92:
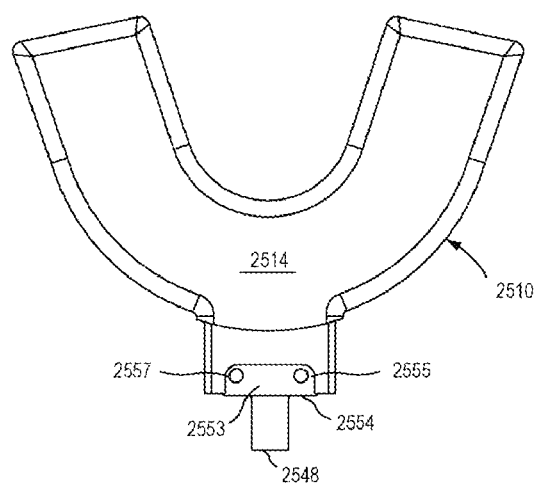
FIG. 92 is a bottom view of the portion of the light therapy apparatus of FIG. 89.

For example, the mouthpiece 2510 comprises particular geometric features (e.g., stress concentration risers, areas having a desired bending moment of inertia, etc.) to produce the desired flexibility, deformability and durability in connection with the material(s) from which the mouthpiece 2510 is constructed. As shown, the mouthpiece 2510 defines a notch 2530 and grooves 2532, 2533 configured to permit, or otherwise increase the ability of, the flanges 2522, 2524 to deflect inwardly towards the teeth, gums, jaw, or the like, as shown by the arrows AA in FIG. 90. As shown in FIG. 90, the mouthpiece 2510 defines the notch 2530 at the midline M (see, e.g., FIG. 86B) of the mouthpiece and between upper portions of the first flange 2522 and the second flange 2524. The notch 2530 is configured to permit the independent and/or inward deflection of each of the first flange 2522 and the second flange 2524, for example, in response to pressure from the patient's lip or inner cheek. In particular, the flanges 2522, 2524 are each configured to deflect inwardly with respect to the bite pad 2514. Similarly stated, when the mouthpiece 2510 is outside of the mouth in an undeformed state (i.e., a first configuration), the first flange 2522 and the second flange 2524 are each approximately perpendicular (i.e., at about 90 degrees) to the bite pad 2514. When the mouthpiece 2510 is disposed inside the mouth, the upper portion of the mouthpiece 2510 and/or the flanges 2522, 2524 are sufficiently flexible such that an angle formed between each flange 2522, 2524 and the bite pad 2514 (a "flange angle") is acute. This "tipping in" allows the flanges 2522, 2524 to conform to the interior surfaces of the mouth, thereby promoting the desired alignment of the light array 2542 relative to the bone and/or teeth. In other embodiments (not shown), the notch 2530 may be absent, and the mouthpiece 2510 can be substantially rigid to prevent deflection of the flanges 2522, 2524.

As shown in FIG. 90, the notch 2530 can be V-shaped, and has a depth X and a width Y at the widest point of the notch. The width Y is at the upper end of the notch adjacent the free end of the flanges 2522, 2524 opposite the bite tray 2512, and is less than the depth X of the notch. The edge of each flange 2522, 2524 that forms a respective side of the notch 2530 tapers towards the point of the V, which point can be aligned with an upper edge of the grooves 2532, 2533. Similarly stated, the portion of the mouthpiece 2510 that defines a lower boundary of the notch 2530 is aligned, in a horizontal plane, with an upper edge of the portion of the mouthpiece 2510 that defines the grooves 2532, 2533. In other embodiments, however, the portion of the mouthpiece 2510 that defines a lower boundary of the notch 2530 can be in any suitable location relative to the grooves 2532, 2533 (e.g., either above or below the grooves).

The mouthpiece 2510 defines at least one groove 2533, 2534 defined by a lower outer (or front) surface of each of the first and second flanges 2522, 2524. For example, as shown in FIG. 90, the mouthpiece 2510 comprises a first groove 2532 and a second groove 2533, each defined by the outer or front surface 2528 of the mouthpiece 2510. In particular, each groove is disposed at a height between the bite pad 2514 and a lower edge of the flexible circuit board 2546 (see, e.g., FIG. 93). Stated another way, the grooves 2532, 2533 can be defined by a base portion of each of the first and second flanges 2522, 2524. The grooves 2532, 2533 each extend about the outer surface 2528 of the mouthpiece 2510 between the posterior end portion of the mouthpiece 2510 and an anterior end portion of the mouthpiece 2510, such that a first end 2534, 2535 of each groove 2532, 2533, respectively, is at or proximate to the posterior end portion of the mouthpiece 2510 and a second end 2536, 2537 of each groove 2532, 2533, respectively, is at or proximate to the anterior end of the mouthpiece 2510.

As shown in FIG. 90, the second ends 2536, 2537 of the grooves 2532, 2533 can be spaced apart. In other words, the second ends 2536, 2537 of the grooves 2532, 2533 do not necessarily meet at the anterior end of the mouthpiece 2510. Similarly stated, the grooves 2532, 2533 are noncontiguous and/or do not share a common boundary. For example, the second ends 2536, 2537 of the grooves 2532, 2533 can be spaced apart by a width of a bridge 2506 extending from the front of the mouthpiece 2510. In another example, as shown in FIG. 90, the second ends 2536, 2537 of the grooves 2532, 2533 can be spaced apart by a distance Z (which can be at least as great as the width Y of the notch 2530). The grooves 2532, 2533 can have any suitable shape, including, for example, that of a semi-circle or U-shape. The grooves 2532, 2533 produce a hinge-like structure (i.e., a "living hinge") about which the flanges 2522, 2524 can rotate, bend and/or deflect. In this manner, the grooves 2532, 2533 and the notch 2530 collectively permit the flanges 2522, 2524 to deflect inwardly, for example, in response to pressure from the patient's lip or inner cheek.

As such, the grooves 2532, 2533 and the notch 2530 collectively facilitate the transition of the mouthpiece 2510 between a first configuration and a second configuration. When the mouthpiece 2510 is in the first configuration, the angle formed between each flange 2522, 2524 and the bite pad 2514 (the "flange angle") has a first value. When the mouthpiece 2510 is in the second configuration, the flange angle has a second value that is different from the first value. In particular, the mouthpiece 2510 can be moved to the second configuration when disposed within the patient's mouth. In one or more embodiments, the second value is less than the first value (i.e., the flanges 2522, 2524 "tip" inward when the mouthpiece 2510 is inserted into the mouth). In one or more embodiments, the flange angle is approximately 90 degrees when the mouthpiece is in the first configuration and is acute when the mouthpiece is in the second configuration. In one or more embodiments, the flange angle is about 80 degrees (e.g., the flanges 2522, 2524 tip inward by about 10 degrees) when the mouthpiece is in the second configuration.

In other embodiments, the flange angle is between about 75 degrees and about 80 degrees (e.g., the flanges 2522, 2524 tip inward by between about 10 degrees and 15 degrees). In yet other embodiments, the flange angle is approximately 85 degrees, 75 degrees, 70 degrees, or 65 degrees (e.g., the flanges 2522, 2524 tip inward by about 5 degrees, 15 degrees, about 20 degrees and about 25 degrees, respectively) when the mouthpiece is in the second configuration.

Without wishing to be bound by theory, it is thought that the flexibility of the mouthpiece 2510, and of the flanges 2522, 2544, provides significant advantages. For example, in contrast to mouthpieces constructed of a hard plastic and/or with a permanent set (or shape), the current arrangement allows for easier insertion and better conformance to the oral tissue of the patient. The flexibility of the mouthpiece 2510 also accommodates variation in patient anatomy (whether between two different patients or for the same patient as that patient's anatomy changes over time). For example, some patients have a pronounced overbite and may need more or less than a 10 degree inward deflection (or "tip-in"). In such instances, the mouthpiece 2510 can conform to the internal structure and/or anatomy within the patient's mouth. As another example, as the orthodontia for a patient works over time, the patient's dental anatomy will change. Accordingly, the mouthpiece 2510 can conform to the internal structure and/or anatomy within the patient's mouth to accommodate such change without requiring new mouthpiece moldings or the like. Finally, the flexible design of the mouthpiece 2510 provides greater comfort for the patient than would be provided by mouthpieces constructed of a hard plastic.

Additionally, the flexible nature of the mouthpiece 2510 and/or the flanges 2522, 2524 may provide manufacturing benefits. In particular, fabrication and/or molding of a mouthpiece having an acute angle between the bite surface and the side surface of the flange (i.e., the internal angle of the flange or the "flange angle") can be difficult. The design of the mouthpiece 2510, however, allows for the molding and/or fabrication to be performed with a flange angle of approximately ninety degrees (or greater), while allowing for an in-use flange angle that is acute (e.g., when the mouthpiece 2510 is in the second configuration, as described herein).

Figure 93:
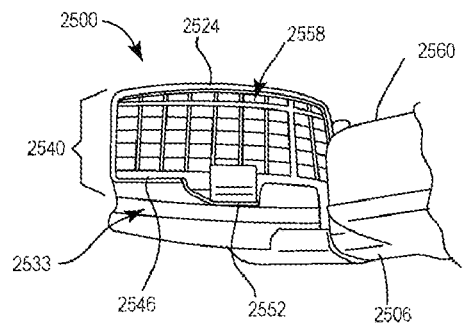
FIG. 93 is a perspective view of a portion of the light therapy apparatus of FIG. 84.
Figure 94:
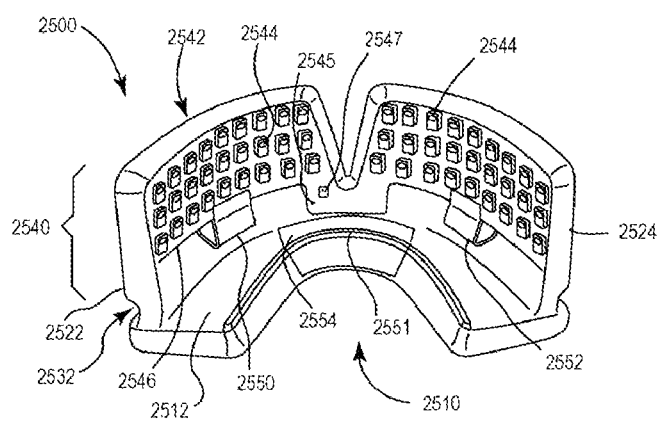
FIG. 94 is a rear view of the light therapy apparatus of FIG. 84.
Figure 95:
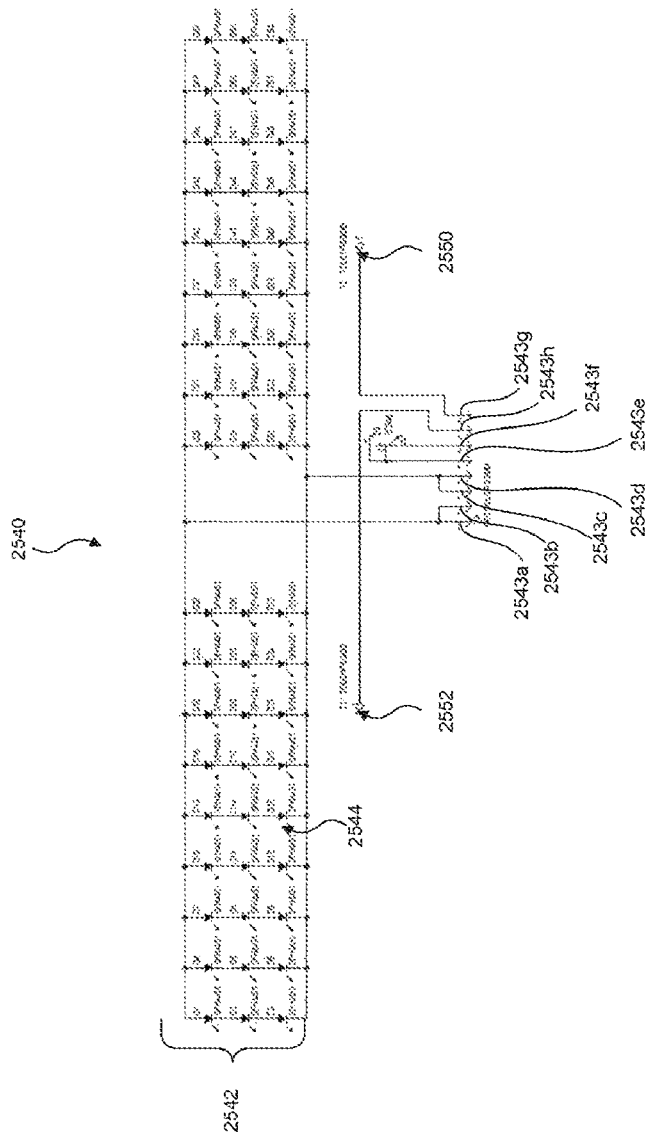
FIG. 95 is a schematic view of a portion of the light therapy apparatus of FIG. 84.

The mouthpiece 2510 of the light therapy apparatus 2500 comprises an electronics assembly 2540, generally shown in FIGS. 93 and 94, and schematically in FIG. 95. In one or more embodiments, at least one or more portions of the mouthpiece 2510 are constructed from a substantially transparent material (e.g., silicone) such that one or more components embedded within the mouthpiece 2510 are visible through the mouthpiece 2510. Thus, for purposes of illustration, portions of the mouthpiece 2510, including portions of the first flange 2522, the second flange 2524 and the bite tray 2512 are shown as being transparent in FIGS. 93 and 94 to show portions of the electronics assembly 2540 and the support plate 2554 disposed therein. The electronics assembly 2540 is configured to cooperatively function with the electronics board 2570 disposed within the bill 2560 to produce the light therapy as described herein. As shown, the electronics assembly 2540 of the mouthpiece 2510 is disposed primarily in the first flange 2522 and the second flange 2524. The electronics assembly 2540 comprises a light array 2542, a flexible circuit board 2546, a pair of capacitance sensors 2549, and one or more conductive components for heat transfer, such as the conductive heat transfer tiles 2558.

FIG. 95 schematically illustrates at least a portion of the electronics assembly 2540 of the mouthpiece 2510, according to one or more embodiments. The light array 2542 comprises one or more light emitters 2544, such as a plurality of LEDs (only one light emitter 2544 in each flange is identified in FIG. 95). The light emitters 2544 are electrically and/or physically coupled to the flexible circuit board 2546 (see also, FIG. 86B). The flexible circuit board 2546 electrically couples the light emitters 2544 to electronic circuitry in the bill 2560, such as via pathways 2543$a$, 2543$b$, 2543$c$, 2543$d$ (see, e.g., FIG. 95). In this manner, the light emitters 2544 can receive power and/or a signal to produce the desired light, as described herein.

Referring to FIG. 94, the light emitters 2544 are disposed on a first, palatial (or lingual) side of the flexible circuit board 2546. In this manner, the light emitters 2544 are configured to emit light toward a patient's teeth and/or adjacent oral tissue when the mouthpiece 2510 is disposed within the patient's mouth. The light emitters 2544 can be configured to emit light at any suitable intensity, wavelength and/or frequency described herein, and can be arranged in two or more rows or a single row on the flexible circuit board 2546. For example, in one or more embodiments, the light emitters 2544 can be configured to emit light in the infrared or near infrared wavelength range. For example, in one or more embodiments, the light emitters 2544 are configured to emit light at a wavelength of about 850 nm. In one or more embodiments, the light emitters 2544 are configured to emit light at a wavelength of 850 nm±5 nm. The light emitters 2544 can be configured to emit light sufficient deliver light energy to the patient's bone to facilitate and/or perform any of the methods described herein. The light emitters 2544 can be configured to emit light at less than 150 mW/cm².

The light emitters 2544 can be disposed on the flexible circuit board 2546 and/or within the flanges 2522, 2524 in any suitable configuration, including any configuration described herein. As described herein, the flange that comprises the light emitters can comprise a notch. In another embodiment, the flange that comprises the light emitters does not comprise a notch. In one or more embodiments, the light emitters 2544 are LEDs coupled to the flexible circuit board 2546 in two or more parallel rows and/or columns. As schematically shown in FIG. 95, the light array 2542 can comprise about 54 light emitters 2544, or LEDs, with about 27 light emitters embedded in the first flange 2522 and about 27 light emitters 2544 embedded in the second flange 2524. The 27 light emitters 2544 can be arranged in any suitable configuration, including for example in nine evenly spaced columns with three spaced apart LEDs per column. In another embodiment, the light emitters are arranged in individual columns with one LED per column. In a further embodiment, the columns are evenly spaced. The flexible circuit board 2546 and light emitters 2544 can have any suitable dimensions for being coupled to, or embedded in, the flanges 2522, 2524 of the mouthpiece 2510. Although the light emitters 2544 are shown as being evenly spaced within the first flange 2522 and the second flange 2524, in other embodiments, the light emitters can be unevenly spaced within the first flange 2522 and/or the second flange 2524. For example, in one or more embodiments, a mouthpiece can comprise a series of light emitters that are spaced apart by a first amount near the anterior portion of the mouthpiece and a second, different amount near the posterior portion of the mouthpiece.

As shown in FIG. 93, the one or more conductive heat transfer tiles 2558 are disposed on a second, or buccal, side of the flexible circuit board 2546 of the mouthpiece 2510. The tiles can be constructed of any suitable conductive material (e.g., copper, aluminum or the like) and are configured to promote heat transfer away from the light therapy apparatus 2500 and/or the light emitters 2544 and to the patient's buccal tissue. Similarly stated, in use, the copper tiles 2558 can transfer heat from the apparatus 2500 to the patient's cheek, where the patient's naturally occurring circulatory system will draw the heat away from the cheek area. In this manner, the tiles 2558 can facilitate the compliance with applicable temperature regulations and industry standards (e.g., IEC 60601, IEC 60601-2-57, IEC 60601-1-11, EN 62471, etc., described herein) during light therapy administration.

The tiles 2558 can be operatively coupled to the light emitters 2544 in any suitable manner. In one or more embodiments, the flexible circuit board 2546 has a layer on its second side that comprises the one or more heat transfer tiles 2558. The tiles 2558 are spaced apart from each other, and thus may be characterized as being discrete. The discrete nature of the tiles 2558 enhances, or at least does not lessen, the flexibility of the flanges 2522, 2524 of the mouthpiece 2510. In other embodiments, however, the tiles 2558 need not be discrete elements.

In one or more embodiments, at least a portion of the flexible circuit board 2546 is disposed within the bridge 2506 of the light therapy apparatus 2500. For example, the flexible circuit board 2546 can comprise a tab portion 2548 disposed in the bridge 2506. The tab portion 2548 of the flexible circuit board 2546 is configured to electrically couple the electronics assembly 2540 of the mouthpiece 2510 with electronic components, described in more detail herein, disposed in the bill 2560. In this manner, the electronic components disposed in the bill 2560 can control operation of the apparatus 2500, and emission of light using the light array 2542, as described in more detail herein.

The mouthpiece 2510 can be constructed of any suitable material, including, for example, an elastomeric material (e.g., a soft silicone). The terms hardness (or softness, as applicable), strength and/or resistance to deformation are used herein to denote a one or more properties associated with the mouthpiece 2510. The properties include, for example, material properties, such as the yield strength, the modulus of elasticity, the modulus of rigidity, the hardness and/or the elongation percentage. The hardness of a material or the mouthpiece 2510 may be characterized as its "durometer," in reference to the apparatus used to measure the hardness of the types of material used to form mouthpieces.

In one or more embodiments, the mouthpiece 2510 can be fabricated from medical-grade injection-molded, highly flexible and very low durometer silicone. For example, during manufacture of the mouthpiece 2510, the silicone can be overmolded onto at least a portion of the electronics assembly 2540 of the mouthpiece 2510, including one or more of the flexible circuit board 2546, light emitters 2544, and the copper tiles 2558. In this manner, the portion of the electronics assembly 2540, such as one or more of the flexible circuit board 2546, light emitters 2544, and the copper tiles 2558, are fully encapsulated or embedded within the molded silicone. In this manner, the electronics can be protected for repeated applications within the mouth. In one or more embodiments, the silicone can be have a hardness (or softness) of about 22 Shore A In one or more embodiments, the silicone can be have a hardness (or softness) of about 30 Shore A Although soft, the silicone is tear resistant, a desirable characteristic because of the sharpness of a patient's teeth (and the anterior teeth in particular). Moreover, the silicone is hydrophobic, and therefore will not absorb water. Suitable silicones include those offered by Bluestar Silicones, East Brunswick, NJ under the name Silbione®, including Silbione® LSR 4305, Silbione® LSR 4310, Silbione® LSR 4325, and Silbione® LSR 4325 PEX (www.bluestarsilicones.com).

In one or more embodiments, the silicone and/or portions of the mouthpiece 2510 are substantially transparent, such that one or more components embedded within the silicone are visible through the silicone. Moreover, in this manner, the mouthpiece 2510 can provide suitable optical properties for allowing the light produced and/or conveyed by the light emitters 2544 to pass through the mouthpiece 2510 to the desired target tissue. In one or more embodiments, the mouthpiece 2510 and/or the flanges 2522, 2524 can comprise one or more components configured to filter, focus and/or otherwise act upon the light produced by the light emitters 2544. In other embodiments, the mouthpiece 2510 can comprise air gaps between the light emitters 2544 and the surface of the flanges 2522, 2524 to facilitate focusing of the light. As shown in FIG. 86B, however, the mouthpiece 2510 is constructed such that the light emitters 2544 are fully encapsulated or embedded within the molded silicone such that no space or air gap exists between the silicone material and the portion of the electronics assembly 2540. Similarly stated, the mouthpiece 2510 is devoid of an air gap between the light emitters 2544 and the material of the mouthpiece 2510, thus no air gap lensing is needed to produce the desired optical properties of the light produced by the light emitters 2544.

The ridge 2518 can be constructed of the same material as the mouthpiece 2510, or at least the same material as the bite tray 2512 of the mouthpiece 2510. In this manner, when a patient bites together with the upper and lower jaw, the bite tray 2512 of the mouthpiece 2510, including the ridge 2518, may deform slightly from pressure exerted by an occlusal surface of the patient's teeth. Nonetheless, the ridge 2518 is of sufficient dimensions that the patient should be aware of its position, despite any slight deformation of the bite tray 2512 and/or ridge 2518.

The extra-oral housing, or bill, 2560 is coupled to a front portion of the mouthpiece 2510 by the bridge 2506. In this manner, the bill 2560 is disposed exterior to the oral cavity of the patient when the mouthpiece 2510 is disposed within the oral cavity of the patient. Also in this manner, the bill 2560 can be supported with respect to the patient's mouth by the mouthpiece 2510 and/or the bridge 2506 when the mouthpiece 2510 is disposed within the patient's mouth.

The apparatus 2500 can comprise a support plate 2554. The support plate 2554 is configured to provide structural support to the silicone material of the mouthpiece 2510. The support plate 2554 is configured to help support the bill 2560 with respect to the mouthpiece 2510, for example, when the mouthpiece 2510 is disposed within the patient's mouth. The support plate 2554 has a proximal portion 2551 (see, e.g., FIG. 94) and a distal portion 2553 (see, e.g., FIG. 92). The proximal portion 2551 of the support plate 2554 is coupled to and/or within the mouthpiece 2510. For example, the proximal portion 2551 of the support plate 2554 can be embedded in the silicone material of the bite pad 2514. The support plate 2554 can be substantially planar (e.g., with crests or troughs in the plane having a height no more than 5% of a thickness of the support plate 2554), and the proximal portion 2551 of the support plate 2554 can be disposed within the mouthpiece 2510 such that the support plate is substantially parallel (e.g., plus or minus about 5 degrees) to the upper surface of the bite pad 2514. At least a portion of the support plate 2554 is disposed in the bridge 2506. The distal portion 2553 of the support plate 2554 is configured to couple the mouthpiece 2510 and the bill 2560. For example, the distal portion 2553 of the support plate 2554 can define two apertures 2555, 2557 each configured to receive a protrusion, or guide pin, (not shown in FIGS. 92 and 94) of the bill 2560. In one or more embodiments, at least the distal portion 2553 of the support plate 2554 defining the apertures 2555, 2557 is exposed with respect to (or is not disposed within) the material of the mouthpiece 2510.

The bill 2560 of the light therapy apparatus 2500 comprises a first, or top, portion 2562 and a second, or bottom, portion 2564 and forms a cavity (not shown) therebetween. Although the bill 2560, in combination with the bridge 2506, is shown in FIGS. 84-88 as generally having a T-shape, in other embodiments, the bill 2560 can have any suitable shape. The bill 2560 is configured to at least partially enclose one or more electronic components of the apparatus 2500, as described in more detail herein, which components can be disposed in the cavity of the bill 2560.

The apparatus 2500 comprises at least one battery, or other suitable power source. For example, a battery 2568 is disposed in the cavity of the bill 2560. The battery 2568 can be electrically coupled to and to provide power to one or more electronic components of the bill 2560, including, for example, one or more of an electronics board 2570, a microcontroller 2572, a system clock, a wireless transmitter 2576, and other electronic components of the bill 2560. The battery 2568 is configured to provide power to the electronics assembly 2540 of the mouthpiece 2510. More specifically, the battery 2568 is configured to provide power to the light array 2542 to enable the light emitters 2544 to irradiate light during a treatment session. The battery 2568 can comprise, for example, a rechargeable lithium ion battery. In one or more embodiments, the battery is a lithium-ion polymer battery, also referred to as a lithium polymer or LIPO battery. In one or more embodiments, the battery 2568 is disposed within the cavity of the bill 2560 between an accelerometer 2567 and the electronics board 2570.

In one or more embodiments, the apparatus 2500 is configured to wirelessly charge, or recharge, the battery 2568. For example, an induction receiver coil 2569 can be disposed in the cavity of the bill 2560. The induction receiver coil 2569 is configured for inductively charging the battery 2568, as described in more detail herein. The induction receiver coil 2569 can comprise, for example, a Qi-based charging coil.

The electronics board 2570 is disposed in the bill 2560 of the apparatus 2500.

The electronics board 2570 is electrically coupled to the flexible circuit board 2546 of the mouthpiece 2510 (e.g., via the tab portion 2548 of the flexible circuit board 2546), thereby electrically coupling electronic components of the bill 2560 with the electronic assembly 2540 of the mouthpiece 2510. Electronic circuitry within the bill 2560 electrically couples the electronics board 2570, the microcontroller 2572, the system clock, the wireless transmitter 2576, one or more switches, and other electronic components of the bill 2560.

The light therapy apparatus 2500 is configured to detect movement of the apparatus. More specifically, the apparatus 2500 is configured to detect when the apparatus is moved in any one of three axes or dimensions (also referred to herein as three-dimensional movement). Referring to FIGS. 96A-96F, in one or more embodiments, the apparatus 2500 comprises an accelerometer 2567 disposed within the cavity of the bill 2560. The accelerometer 2567 can be, for example, a piezoelectric sensor. The accelerometer 2567 can be coupled to the bill 2560 (e.g., to the first portion 2562 of the bill) by any suitable coupling mechanism, including, but not limited to, an adhesive, such as double-sided tape. The accelerometer 2567 is electrically coupled to the electronics board 2570. In one or more embodiments, two electronic leads or wires (not shown in FIG. 96A-96F or 97) couple the accelerometer 2567 and the electronics board 2570. The accelerometer 2567 is configured to detect three-dimensional, or three-axis, movement of the light therapy apparatus 2500.

The accelerometer 2567 can be configured to send an electrical signal to a microcontroller 2572 of the apparatus 2500 when the three-dimensional movement is detected. The microcontroller 2572 is disposed in the cavity of the bill 2560. The microcontroller 2572 is in electrical communication with the accelerometer 2567, and is configured to receive the electrical signal from the accelerometer 2567. The detected movement of the apparatus 2500 can be useful for controlling the light emissions and/or other aspects of the performance of the apparatus. For example, in one or more embodiments, when the microcontroller 2572 detects movement of the apparatus 2500, the microcontroller 2572 can move the apparatus 2500 from a "sleep" state (in which the light emitters 2544 are prevented from being actuated) to a "wake" state (in which the light emitters 2544 are enabled).

In one or more embodiments, the light therapy apparatus 2500 can be configured to determine the orientation of the apparatus. Stated another way, the light therapy apparatus 2500 can be configured to determine if the mouthpiece 2510 is oriented in the upright or inverted position. For example, in one or more embodiments, the accelerometer 2567 is configured to determine if the apparatus 2500 is oriented in the upright or inverted position. The accelerometer 2567 is configured to send a signal associated with the orientation of the apparatus 2500 to the microcontroller 2572 (see FIG. 96B). In this manner, the electronics board 2570 and/or the microcontroller 2572 can adjust and/or control the operation of the apparatus 2500 as a function of the orientation of the mouthpiece 2510, as described herein.

Figure 96A:
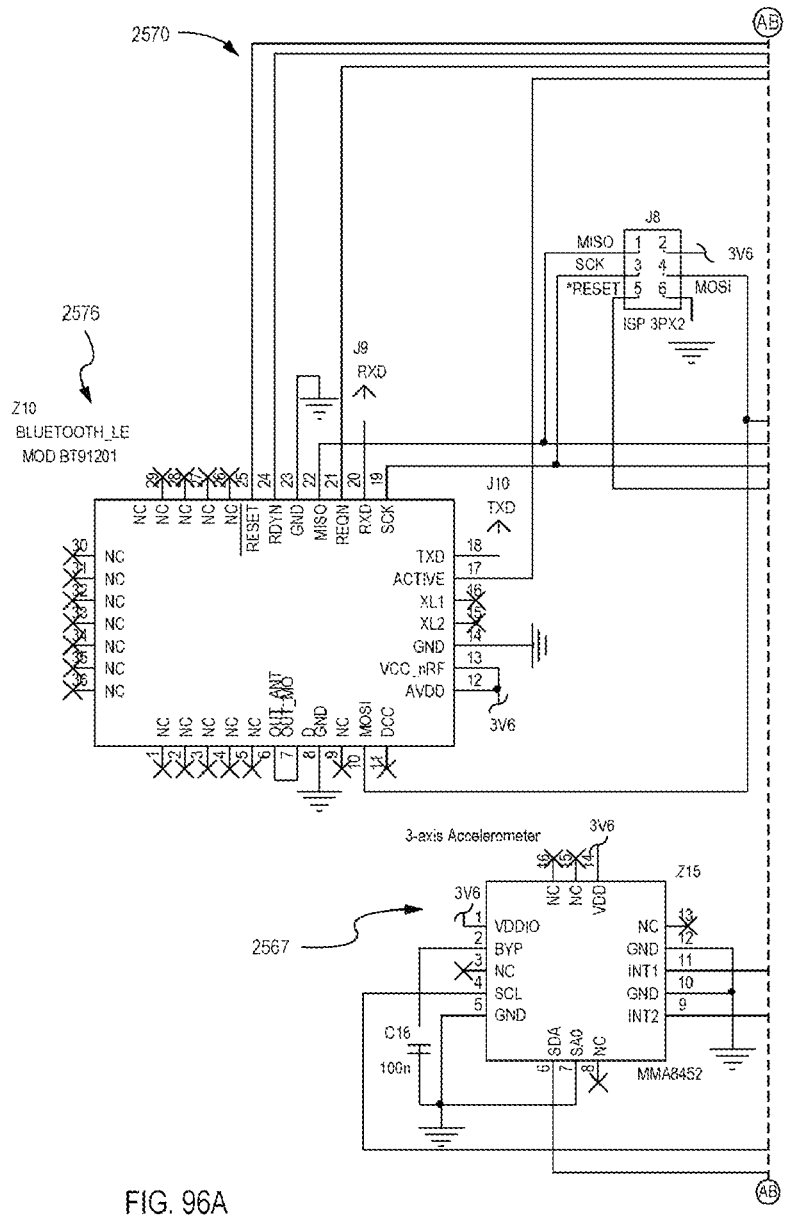
FIGS. 96A-96F are electrical schematics of portions of the light therapy apparatus of FIG. 84.
Figure 96B:
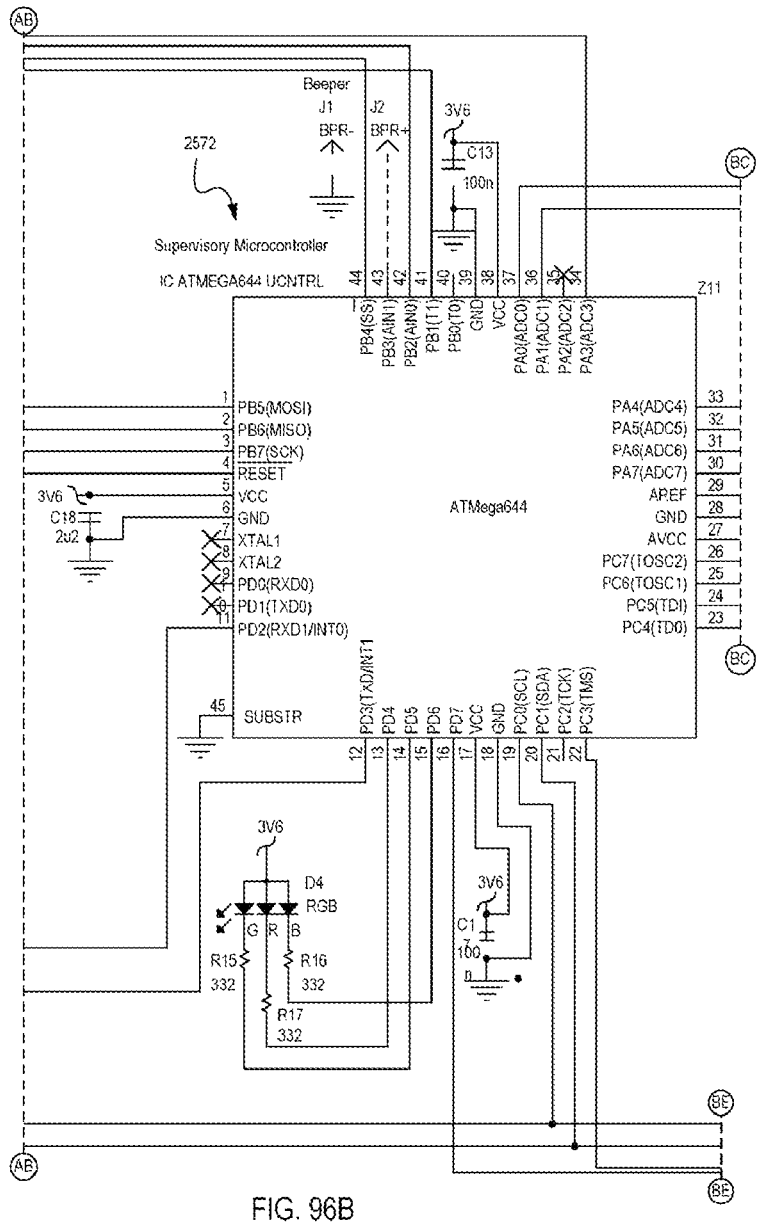
Figure 96C:
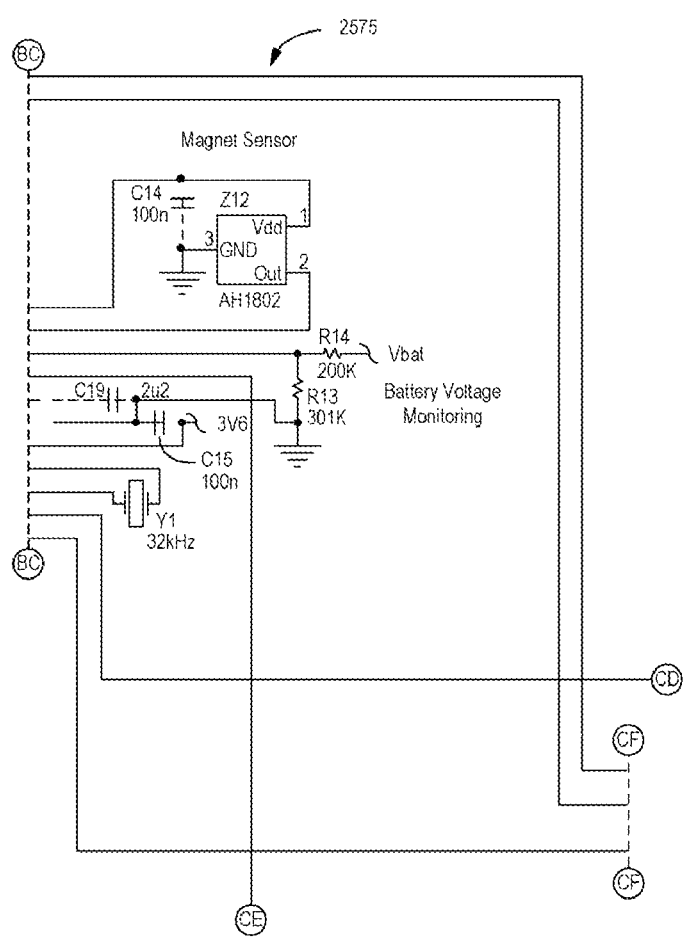
Figure 96D:
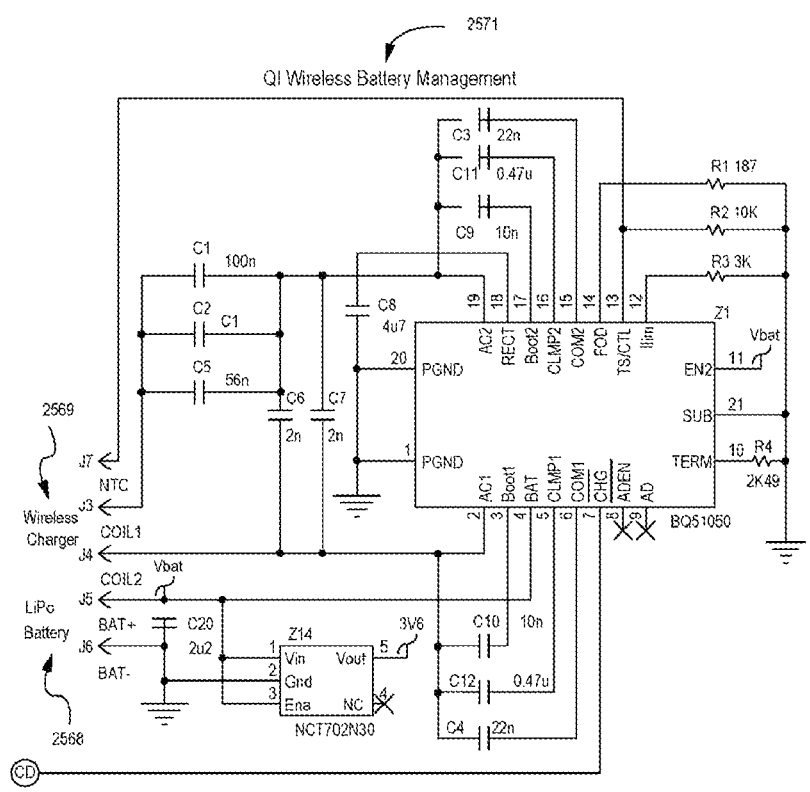

Electronic circuitry disposed in the bill 2560 of the apparatus 2500 comprises a switch 2575 (also referred to herein as a magnet switch or sensor, schematically illustrated in FIG. 96C) that is moveable from a first position (or configuration) to a second position (or configuration). More specifically, the switch 2575 is configured to move from its first position to its second position when the switch is activated by a magnet located in close proximity to the switch. When the switch 2575 is in its second position, the apparatus 2500 is maintained in its sleep state, even if movement is detected by the accelerometer 2567. In one or more embodiments, the external station 2580 comprises the magnet 2596 (see e.g., FIG. 112) configured to activate the switch 2575.

In this manner, when the apparatus 2500 is disposed on the external station 2580, the magnet 2596 of the external station 2580 causes the switch to move from its first position to its second position, thereby preventing the apparatus 2500 from moving to its wake state from its sleep state, regardless of whether the accelerometer 2567 detects movement of the apparatus. This helps to prevent inadvertent waking and/or activation of the apparatus 2500, as may otherwise occur if the external station 2580 is moved with the apparatus 2500 disposed therein (e.g., for transport). The microcontroller 2572 is configured to determine whether the switch 2575 is in its first position or its second position. In this manner, the microcontroller 2572 is configured to determine whether the apparatus 2500 is disposed on the external station 2580.

The light therapy apparatus 2500 can also be configured to determine whether the mouthpiece 2510 is disposed within the patient's mouth (i.e., in a manner suitable for the treatment session). In this manner, the apparatus 2500 can be configured to only irradiate light for the treatment session when the apparatus 2500 has determined that the mouthpiece 2510 is disposed in the patient's mouth. In one or more embodiments, for example, the light therapy apparatus 2500 comprises a capacitance detection system configured to detect a capacitance change when the mouthpiece 2580 is disposed within the patient's mouth. Referring to FIGS. 93-96F, the capacitance detection system can comprise a capacitance sensor 2549 (see, e.g., FIG. 96F) disposed in the bill 2560 and configured to be in electrical communication with a first capacitance electrode 2550 and a second capacitance electrode 2552, each coupled to the flexible circuit board 2546 of the mouthpiece 2510. The flexible circuit board 2546 is configured to electrically couple the electrodes 2550, 2552 to the capacitance sensor 2549 in the bill 2560, such as via pathways 2543a-b and 2543c-d, respectively.

At least a portion of the sensors 2550, 2552 can be embedded in the flanges 2522, 2524 of the mouthpiece 2510, for example, in a similar manner as disclosed herein with respect to the light array 2542. The electrodes 2550, 2552 are spaced apart on the flexible circuit board 2546. In one or more embodiments, the electrodes 2550, 2552 are disposed at opposing locations with respect to the flexible circuit board 2546, as shown in FIG. 94, such that the first electrode 2550 is beneath the portion of the light array 2542 embedded in the first flange 2522 and the second electrode 2552 is beneath the portion of the light array 2542 embedded in the second flange 2524. In this manner, the apparatus 2500 is configured to detect a capacitance change bilaterally. In one or more embodiments, each electrode 2550, 2552 is extended posteriorly within the patient's mouth, thus providing for more "horizontal" contact with the patient's oral tissue for more robust sensing of the capacitance change.

The electrodes 2550, 2552 are configured to be disposed in close proximity to the patient's buccal tissue, which has a high capacitance, when the mouthpiece 2510 is disposed within the patient's mouth in preparation for treatment. The patient's saliva or wet buccal tissue can activate the capacitance of each electrode 2550, 2552. The apparatus 2500 is configured to irradiate light only after a predetermined capacitance change has been registered. Stated another way, the apparatus 2500, and the microcontroller 2572 more specifically, is configured to turn on the light emitters 2544 only after the predetermined capacitance change has been registered. The capacitance change is registered by the microcontroller 2572, which is configured to execute an algorithm to register the change in capacitance, when (1) the capacitance change threshold is detected by the capacitance sensor 2549 with respect to each electrode 2550, 2552 (i.e., bilaterally), and/or (2) the capacitance change is detected for a predetermined duration (e.g., for at least 2 seconds). When the microcontroller 2572 registers the capacitance change, a switch (also referred to herein as the "capacitance switch," not shown in FIG. 96F, but generally included in the capacitance sensor 2549 components) in the bill 2560 and in electrical communication with the microcontroller 2572 is moved from a first position in which the light emitters 2544 are off, to a second position, in which the light emitters 2544 are on, thereby moving the apparatus 2500 to an active state in which the light emitters 2544 are irradiating light.

Because bilateral capacitance change is required to move the switch to its second position, the incidence of false positives that may result from the use of only one electrode is limited. In other embodiments, however, a light therapy apparatus can comprise only a single capacitance electrode. In yet other embodiments, a light therapy apparatus can comprise any other suitable detection mechanism for determining when the mouthpiece 2510 is positioned with the mouth.

Also, the capacitance detection system of the light therapy apparatus 2500 improves patient safety and/or compliance. For example, the light emitters 2544 can be configured to emit infrared light, so it is desirable to prevent emission of the light until the mouthpiece 2510 is properly disposed within the patient's mouth (e.g., to avoid the possibility of emitting radiation that could be harmful to the eyes). The arrangement of the capacitance sensor also eliminates the need for a manual "on/off" switch on the bill 2560. Such manual switches are prone to user error. For example, the patient may accidentally turn the light emitters off when the patient intended to begin a light therapy treatment session, as the patient may not readily discern whether the light emitters are off or on.

In one or more embodiments, the apparatus 2500 is configured to detect reflection of light off of a patient's oral soft tissue. The light emitters 2544 can be configured to emit light, such as in a blinking or pulsing manner. The light emitters 2544 can be configured to blink or pulse at a predetermined rate. At least a portion of light emitted from the pulsing or blinking light emitters 2544 towards the oral soft tissue of the patient's mouth is reflected to the mouthpiece 2510 and is thereby detected by a sensor or other light detection mechanism (generally referred to as a "light sensor" or "photodetector," not shown in FIGS. 84-97). The light sensor is configured to evaluate the functionality of a portion of the light array 2542 coupled to the first flange 2522 of the mouthpiece 2510 and a portion of the light array 2542 coupled to the second flange 2524 of the mouthpiece 2510. In this manner, the light sensor facilitates detection of any faulty operation of the apparatus 2500 with respect to each of the flanges 2522, 2544 of the mouthpiece 2510 before operation of the apparatus 2500 with respect to the patient.

Suitable thresholds pertaining to the amount of light detected can be established, and used for example to assess whether the light emitters 2544 of the light array 2542 are operating properly. The apparatus 2500 can be configured to initiate irradiation of the oral tissue (i.e., begin a treatment session) when the light sensor detects the light reflection off of the oral soft tissue and/or when the capacitance detection system detects a threshold capacitance change. In one or more embodiments, at least one of the light sensor or the capacitance detection system is configured to transmit a signal to the microcontroller 2572 in the bill 2560 to initiate the treatment session when the light sensor detects light reflection (e.g., at or above a predetermined threshold) from the oral soft tissue or when the capacitance sensor 2549 detects the threshold capacitance change.

The light sensor can also be configured to track the patient's compliance with a treatment program. For example, the light sensor can be configured to transmit a signal to the microcontroller 2572 each time the light sensor detects the light reflection at a suitable threshold, to indicate that the mouthpiece 2510 is disposed in the patient's mouth. In this manner, the microcontroller 2572 can track the occurrences of when the patient placed the mouthpiece into the patient's mouth based on the signal transmitted by the light sensor.

Figure 96E:
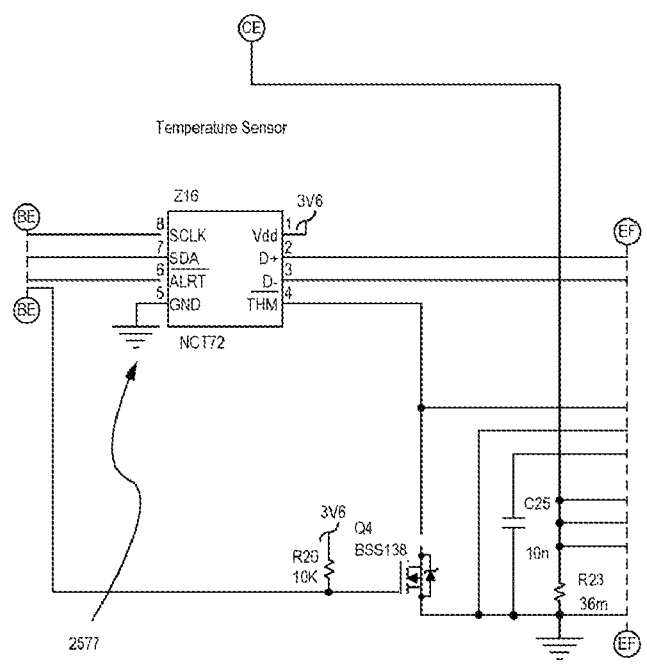
Figure 96F:
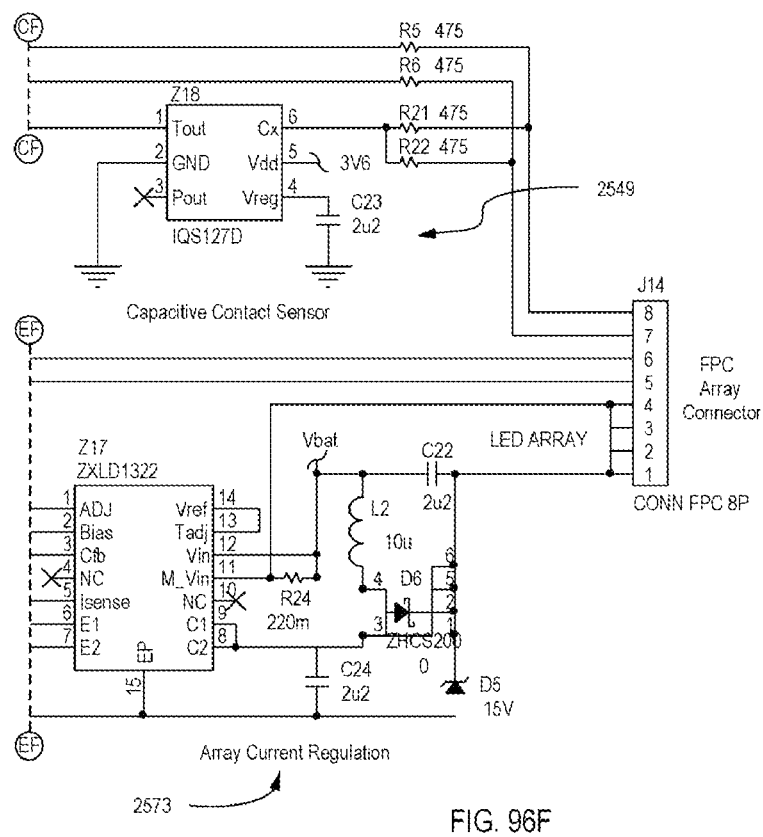

In addition to controlling the operation of the apparatus 2500 based on movement and/or positioning within the mouth, the microcontroller 2572 can also control the operation of the apparatus 2500 and/or the light emitters 2544 based on the temperature of various regions of the apparatus and/or the anatomy of the patient. In particular, as disclosed herein, regulatory requirements and/or industry standards may set limits on the temperature of a medical apparatus in the mouth of a patient. The light therapy apparatus 2500 is configured to ensure the apparatus complies with an applicable regulatory requirement and/or industry standard. A temperature sensor 2577 (schematically shown in FIG. 96E), such as a thermocouple, is disposed in the bill 2560 and is configured to be in communication with the microcontroller 2572. The temperature sensor 2577 is coupled to one or more contacts 2545, 2547, disposed on the flexible circuit board 2546 of the mouthpiece 2510. As schematically shown in FIGS. 95 and 96E, the contacts 2545, 2547 can be coupled to the temperature sensor 2577 via pathways 2543e, 2543f. The temperature sensor 2577 is configured to measure the temperature of the mouthpiece 2510 (e.g., via the contacts 2545, 2547) during a light therapy treatment session. The temperature sensor is configured to transmit an electrical signal associated with the measured temperature to the microcontroller 2572, or the like). In one or more embodiments, the position of the temperature sensor, or its contacts 2545, 2547, with respect to the flexible circuit board 2546 may vary from a position set forth in a regulation or industry standard. As such, the apparatus 2500 can be configured to execute a temperature algorithm (e.g., via the microcontroller 2572) that is configured to correct and/or adjust the temperature as measured by the temperature sensor based on the difference between the sensor's actual position and the position set forth in the regulation or standard, thereby calculating an adjusted temperature used to control the operation of the light therapy apparatus 2500.

In one or more embodiments, the light therapy apparatus 2500 is configured to temporarily cease light irradiation when a first predetermined temperature threshold is met or exceeded by at least one of the measured temperature or the adjusted temperature. The first predetermined temperature threshold can be a temperature sufficiently high to cause discomfort to the patient, but less than the regulatory (or industry standard) limit. In use, when the first predetermined temperature is met or exceeded, the light emitters 2544 are turned off, and the treatment session is paused. For example, the treatment session can be paused for a cooling period to permit the apparatus' 2500 temperature to drop to at least a predetermined temperature, or to a temperature lower than the first predetermined temperature threshold. For example, during a three-minute treatment session, the cooling period can be about 20 seconds or about 30 seconds. If the temperature of the apparatus 2500 is sufficiently reduced, the light emitters 2544 are turned on (e.g., via the microcontroller 2572) and the treatment session is resumed.

In one or more embodiments, the light therapy apparatus 2500 is configured to cease light irradiation when a second predetermined temperature threshold, greater than the first predetermined temperature threshold, is met or exceeded by at least one of the measured temperature or the adjusted temperature. The second predetermined temperature threshold can be a temperature equivalent to the regulatory (or industry standard) limit. In one or more embodiments, the second predetermined temperature threshold ranges from about 45 degrees Celsius to about 55 degrees Celsius. In one or more embodiments, the second predetermined temperature threshold is about 48 degrees Celsius. If the second predetermined temperature threshold is met or exceeded, the light emitters 2544 are turned off, and the treatment session is ended. In such embodiments, the apparatus 2500 does not automatically resume the treatment program when the second predetermined temperature threshold is met or exceeded by at least one of the measured of adjusted temperature of the apparatus 2500.

The light therapy apparatus 2500 is configured to track a patient's compliance with a prescribed treatment program of light therapy treatment sessions. As such the apparatus 2500 is configured to store data associate with the patient's history of usage of the apparatus 2500. The apparatus 2500 can be configured to store data including one or more of (1) a total number of light therapy treatment sessions initiated and/or completed using the apparatus, (2) a total number of days the apparatus was used for administering light therapy treatment sessions, (3) whether the apparatus was used for administering light therapy to the upper or lower jaw (e.g., per treatment session), (4) a duration that light was administered by the apparatus for a particular date and time (e.g., if the patient completed less than a full treatment session, the apparatus can store the duration that light was administered), and (5) the date and time that light was administered using the apparatus 2500, or any combination of the foregoing.

In one or more embodiments, the light therapy apparatus 2500 is useful for treating a patient in combination with an orthodontic appliance, such as an aligner. In one or more embodiments, an aligner typically has a prespecified (e.g., by the manufacturer) duration of disposition that specifies the amount of time a user/patient should wear each aligner, usually for the purpose of effecting a predetermined and estimated amount of treatment (e.g., a prespecified amount of tooth movement affected by the aligner). In one or more embodiments, the use of the light therapy apparatus 2500 in combination with the aligner results in the use of the aligner for a first predetermined duration. During such use (i.e., during the first predetermined duration), the light therapy apparatus 2500 is useful for treating the patient for a second predetermined duration. In one or more embodiments, the same predetermined and estimated amount of orthodontic treatment is applied to the patient by this approach in the first predetermined duration as would have otherwise been applied using aligners alone in the disposition duration. In one or more embodiments, the disposition duration is about 18 hours, about 19 hours, about 20 hours, about 21 hours, about 22 hours, about 23 hours, including all values and subranges in between. In one or more embodiments, the first predetermined duration is about 7 hours, about 8 hours, about 9 hours, about 10 hours, about 11 hours, about 12 hours, about 13 hours, about 14 hours, about 15 hours, about 16 hours, about 17 hours, including all values and subranges in between. In one or more embodiments, the second predetermined duration is at least about 4 hours, at least about 5 hours, at least about 6 hours, at least about 7 hours, at least about 8 hours, at least about 9 about or at least about IO hours, including all values, ranges and subranges in between. In one or more embodiments, the first predetermined duration is about 25% or less than the disposition duration, about 30% or less, about 35% or less, about 40% or less, about 45% or less, about 50% or less, about 55% or less, about 60% or less, about 65% or less, about 70% or less, about 70% or less, including all values and subranges in between.

The microcontroller 2572 is configured to transmit the stored data (i.e., the patient compliance information) to an external device. For example, the light therapy apparatus 2500 can be configured to transmit the patient compliance information to a mobile phone, personal digital assistant, computer, portable electronic device, the external station 2580, or the like. The apparatus 2500 can comprise a transmitter 2576 disposed in the bill 2560. In one or more embodiments, the transmitter 2576 is a wireless transmitter 2576 configured to wirelessly transmit data to the external device. The wireless transmitter 2576 can be configured to transmit the data via Bluetooth® or another suitable wireless mechanism and/or protocol. In one or more embodiments, the apparatus 2500 is configured for one-way transmission of data to the external device, e.g., via the transmitter 2576. In other embodiments, however, the transmitter is a transceiver, and therefore is configured for bi-directional communication of data with the external device. Bi-directional communication is useful for example for communication between the patient and his or her prescribing orthodontist.

As disclosed herein, the light therapy apparatus 2500 can have any suitable number of operational states or statuses. For example, in one or more embodiments, the light therapy apparatus 2500 can have a sleep state and a wake state. In the sleep state, the apparatus 2500 is prevented from irradiating light for a light therapy treatment session. The apparatus 2500 can be in a low power state during its sleep state, such that there is minimal electrical activity. Even in the sleep state, however, particular electronic components may continue to operate, such as a system clock (not shown). Additionally, in the sleep state, the apparatus 2500 can have a charge status or a communication status. In the charge status, the battery 2568 of the apparatus 2500 is being charged (or recharged), but the apparatus 2500 remains asleep. In the charge status, the wireless transmitter 2576, or other radio mechanism, of the apparatus 2500 is configured to wirelessly transmit information (e.g., patient compliance data) to the external device, however the apparatus remains in its sleep state.

In the wake state, the apparatus 2500 can be configured to have a ready status, an error status, a waiting status, an advertise status, an active status, a cooling status, a paused status, and a done status, or any combination thereof. In one or more embodiments, the apparatus 2500 is configured to be in its communication status when in the wake state instead of, or in addition to, when the apparatus is in the sleep state.

In the ready status, the apparatus 2500 is ready to begin irradiating light for the treatment session, but has not begun irradiating light. For example, in the ready status, the apparatus may be configured to begin the light therapy treatment session upon confirmation that the mouthpiece 2510 is properly disposed within the patient's mouth. In the error status, the apparatus 2500 has detected an error and is prevented from irradiating light for the treatment session. Like in the ready status, the apparatus 2500 in the waiting status is ready to begin irradiating light for the treatment session, but has not begun irradiating light. The apparatus 2500 is configured to enter the waiting status subsequent to the ready status, as described in more detail herein. In the advertise status, the apparatus 2500 is configured to produce an alert to the patient that the apparatus is ready for use in the treatment session. In the active status, the apparatus 2500 is irradiating light for the treatment session. In the cooling status, light irradiation from the apparatus 2500 is interrupted, or paused, for a predetermined period to permit the apparatus to cool down. In the paused status, light administration is temporarily ceased for a non-temperature related reason. In the done status, the apparatus 2500 has completed irradiating light for the treatment session, and therefore ceases light administration. In the communication status, the apparatus 2500 is configured to communicate with an external device.

Figure 98:
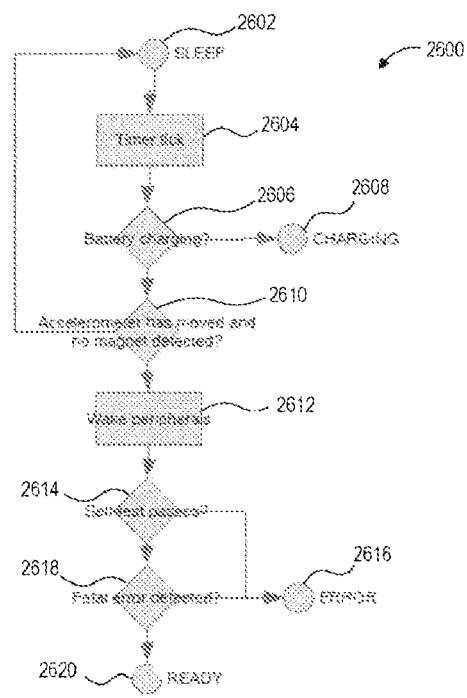
FIGS. 98-108 are logic flow charts representing code configured to be executed by the light therapy apparatus of FIG. 84, according to various embodiments.

The apparatus 2500 (e.g., via the microcontroller 2572) is configured to execute various algorithms, including executing various logic sequences, to control the state or status of the apparatus. For example, as schematically illustrated in FIG. 98, the apparatus 2500 is configured to execute an algorithm 2600 for determining whether the apparatus can move from the sleep state to the wake state. Although the following descriptions refer to particular portions of the light therapy apparatus 2500, any of the methods described herein can be performed by any of the apparatuses described herein. Referring to FIG. 98, in the sleep state 2602, the system clock operates to keep time 2604. At 2606, the algorithm 2600 queries whether the battery 2568 is charging. If the battery 2568 is being charged, the apparatus 2500 enters the charge status 2608. If the battery 2568 is not charging, the algorithm 2600 queries, at 2610, (1) whether the accelerometer has moved (or detected three-dimensional movement of the apparatus 2500), and (2) whether no magnet (e.g., in the external station 2580) is detected. If the answer to either of query (1) or (2) is negative, i.e., that either the accelerometer has not moved (or detected three-dimensional movement) or that the magnet is detected, the apparatus 2500 remains in the sleep state. If the answer to both query (1) and (2) is affirmative, i.e., that the accelerometer has moved (or detected three-dimensional movement) and that no magnet is detected, peripheral electronics of the apparatus 2500 are awoken, at 2612. When the peripheral electronics are awake, the apparatus 2500 is generally referred to as being in its wake state (not shown in FIG. 98). The apparatus 2500 is then configured to perform a self-test to confirm the functionality of the peripheral electronics. The algorithm 2600 queries, at 2614, whether the apparatus 2500 passes the self-test. If the apparatus 2500 fails the self-test, the apparatus 2500 moves to the error status 2616. If the apparatus 2500 passes the self-test, the algorithm 2600 queries, at 2618, whether a fatal error is detected. If the fatal error is detected, the apparatus 2500 moves to the error status 2616. If the fatal error is not detected, the apparatus 2500 moves to the ready status 2620.

Figure 99:
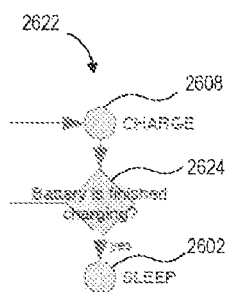

Referring to FIG. 99, in the charge status 2608, the apparatus 2500 (i.e., via the microcontroller 2572) is configured to execute an algorithm 2622 to query, at 2624, whether the battery 2568 has completed charging (e.g., is fully charged or is charged to at least a predetermined charge level). If charging the battery is incomplete, the apparatus 2500 remains in the charge status 2608. If the battery has completed charging, the apparatus 2500 returns to the (non-charging) sleep state 2602.

Figure 100:
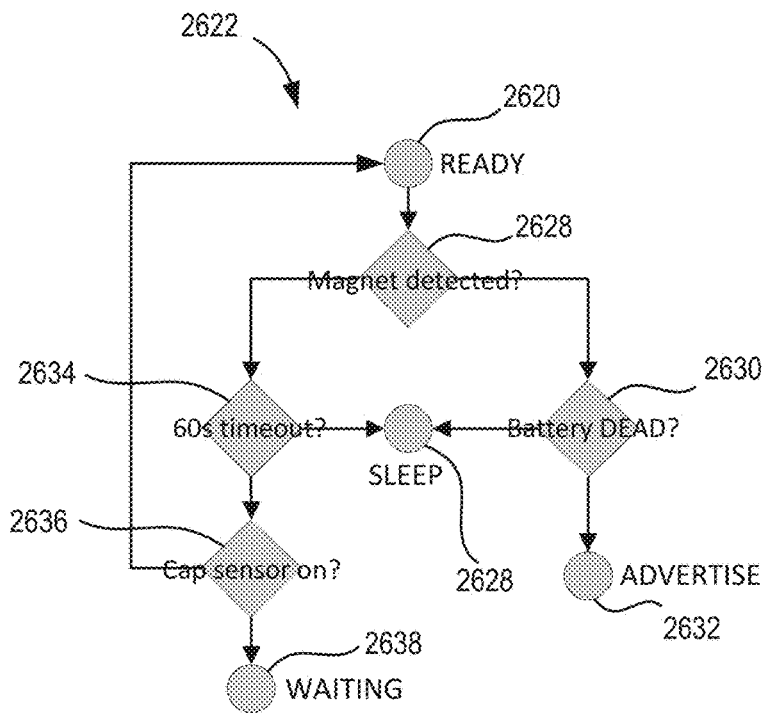

Referring to FIG. 100, in the ready status 2620, the apparatus 2500 is configured to execute an algorithm 2626 to query, at 2628, whether a magnet (e.g., in the external station 2580) is detected. The apparatus 2500 can determine if the magnet is detected based on whether the magnet switch in the bill 2560 is in its first position or its second position, as disclosed herein. If the magnet switch is in its second position, the microcontroller 2572 can determine that the electronic circuitry within which the magnet switch is disposed is complete, and thereby determining that the magnet is detected. If the magnet is detected, the algorithm queries, at 2630 whether the battery 2568 is low or depleted, and in need of charging. If the battery 2568 is low or depleted, the apparatus 2500 enters the advertise status 2632. The apparatus 2500 can be configured to alert the patient or other user that the battery 2568 is low or depleted, and in need of charging, when the apparatus is in the advertise status 2632. For example, in the advertise status, the apparatus 2500 can be configured to provide one or more of an audible indicia or a visual indicia (e.g., via a light color and/or pattern emitted by the light indicator 2578), as described herein. If the battery 2568 is not low or depleted, and therefore not in need of charging, the apparatus 2500 enters the sleep state 2602.

Returning to operation 2628, if the apparatus 2500 determines that the magnet is not detected, the algorithm 2626 then queries, at 2634, whether a predetermined period of time has elapsed. The predetermined period of time is intended to be a sufficient duration during which a patient can remove the apparatus 2500 from the external station 2580 and dispose the apparatus in the patient's mouth to begin a light therapy treatment session.

Generally, the predetermined period of time is on the order of seconds or minutes. For example, the predetermined period can be 20 seconds, 30 seconds, 40 seconds, 50 seconds, 60 seconds, 70 seconds, or more. In one or more embodiments, the predetermined period of time is 60 seconds. If the predetermined period of time has elapsed, the apparatus 2500 enters the sleep state 2602. In this manner, the apparatus 2500 is configured to help prevent depletion of the battery 2568 due to the apparatus maintaining itself the ready status 2620 beyond the predetermined period of time. If the predetermined period of time has not elapsed, the algorithm 2626 queries, at 2636, whether the capacitance sensor 2549 is on. Stated another way, the algorithm 2626 queries whether the capacitance sensor 2549 indicates that the electrodes 2550, 2552 are, at the time of the query, detecting a capacitance change. If the capacitance sensor 2549 is on, the apparatus 2500 enters the waiting status 2638. If the capacitance sensor 2549 is not on (stated another way, if at least one of the capacitance electrodes 2550, 2552 does not, at the time of the query, detect a capacitance change, i.e., the sensor 2549 is "off"), the apparatus 2500 remains in the ready status 2620. If the apparatus 2500 remains in the ready status 2620, the algorithm 2626 can be reexecuted until the apparatus enters a different status, such as one of the advertise 2632, sleep 2602, or waiting 2638 statuses.

Figure 101:
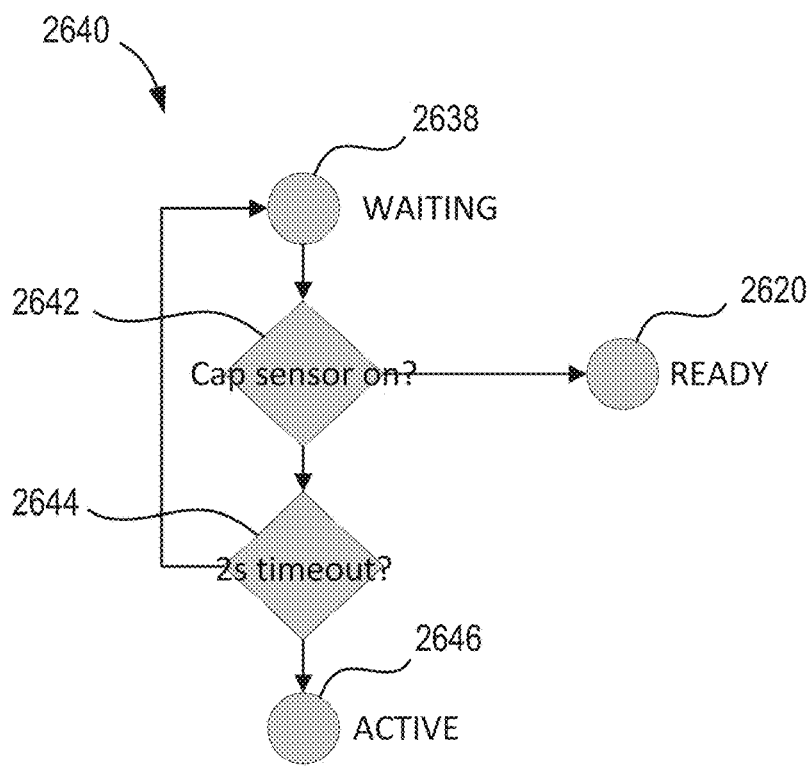

Referring to FIG. 101, in one or more embodiments, the apparatus 2500 is configured to execute an algorithm 2640 to determine whether the apparatus 2500 has been properly disposed within the patient's mouth. Such information can be conveyed to for example, the patient's prescribing physician via the transmitter 2576. More specifically, when the apparatus 2500 is in the waiting status 2638, the apparatus is configured to execute an algorithm 2640 to query, at 2642, whether the capacitance sensor 2549 is on (e.g., whether the sensor 2549 has detected a capacitance change). In one or more embodiments, the capacitance sensor 2549 is configured to turn on when a capacitance change detected by each capacitance electrode 2550, 2552 is at or exceeds a predetermined threshold. The query, at 2642, is intended to determine whether the apparatus 2500 has been disposed within the patient's mouth in preparation for administration of the light therapy treatment session. If at least one of the capacitance electrodes 2550, 2552 has not detected a capacitance change at or exceeding the predetermined threshold, the capacitance sensor 2549 is off and the apparatus 2500 returns to the ready status 2620.

If it is determined that the capacitance sensor 2549 is on, the algorithm 2640 queries, at 2644, whether a predetermined period of time has elapsed subsequent to the determination that the capacitance sensor 2549 is on. The query, at 2642, is intended to determine whether the apparatus 2500 is properly positioned within the patient's mouth, thereby ensuring substantially balanced light administration to each side of the patient's mouth (e.g., with the light energy difference between the sides being no more than plus or minus about 5%). Generally, the predetermined period of time is a duration on the order of seconds. For example, the predetermined period of time can be a duration ranging from about 1 second to about 5 seconds. In one or more embodiments, the predetermined period of time is a duration of 2 seconds. If the algorithm 2640 determines that the capacitance sensor 2549 was not on for the predetermined period of time, the apparatus 2500 remains in the waiting status 2638. If the capacitance sensor 2549 remained on for the predetermined period of time, the apparatus 2500 enters the active status 2646. In one or more embodiments, the microcontroller 2572 registers the bilateral detection of the capacitance change at or exceeding the predetermined threshold for the predetermined period of time.

Figure 102:
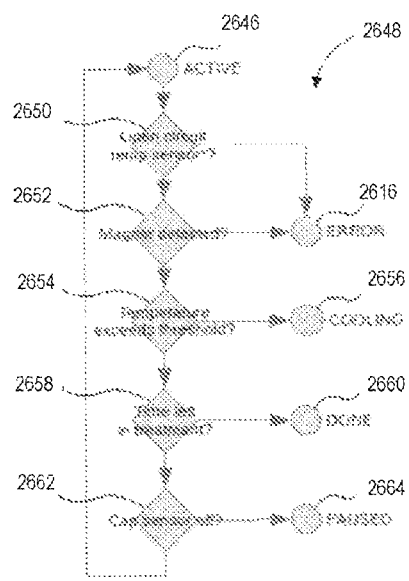

Referring to FIG. 102, when in the active status 2646, the apparatus 2500 is configured to execute an algorithm 2648 to query, at 2650, whether the temperature sensor 2577 (e.g., the thermocouple) is detected or functional. For example, the temperature sensor 2577 can indicate to the microcontroller 2572 that it is functional if the temperature sensor confirms it is able to determine a temperature based on information received from the one or more contacts 2545, 2547 on the flexible circuit board 2546. If the temperature sensor 2577 is not detected or is not functional, the apparatus 2500 enters the error status 2616. If it is determined that the temperature sensor 2577 is detected, or is functional, the algorithm 2648 is configured to query, at 2652, whether the magnet is detected. If it is determined that the magnet is detected, the apparatus 2500 enters the error status 2616. As can be understood in view of the description regarding apparatus 2500 herein, the apparatus 2500 is not intended to be in the active status (in which light can be emitted) and concurrently disposed on the external station 2580 such that the magnet can be detected.

If, at 2652, it is determined that the magnet is not detected, the algorithm 2648 is configured to query, at 2654, whether a temperature of the apparatus 2500 exceeds a predetermined temperature threshold. As disclosed herein, in one or more embodiments, the temperature of the apparatus 2500 is the temperature measured by the temperature sensor 2577. In other embodiments, the temperature of the apparatus 2500 is the adjusted temperature calculated by the microcontroller 2572 based on the measured temperature.

If it is determined that the temperature exceeds the predetermined temperature threshold, the apparatus 2500 enters the cooling status 2656.

If it is determined that the temperature does not exceed (i.e., is at or below) the first predetermined temperature threshold, the algorithm 2648 is configured to query, at 2658, whether any time remains for administering the treatment session. As disclosed herein, for example, a treatment session can be about 3 minutes in duration. As such, the algorithm 2648 is configured to determine whether any of the 3 minutes for the treatment session remains, i.e., has not yet been completed. If it is determined that no time remains in the treatment session, the apparatus enters the done status 2660.

If it is determined that time remains in the treatment session, the algorithm 2648 is configured to query, at 2662, whether the capacitance sensor 2549 is off If the capacitance sensor 2549 is off, the apparatus 2500 enters the paused status 2664. The capacitance sensor 2549 may have turned off, for example, because the patient removed the mouthpiece 2510 from the patient's mouth, or inadvertently shifted the mouthpiece 2510 within the patient's mouth such that at least one electrode 2550, 2552 does not have the threshold capacitance charge. If the capacitance sensor 2549 is on, the apparatus 2500 remains in the active status 2646, and the algorithm 2648 is reexecuted. The algorithm 2648 can be configured to be automatically reexecuted until the apparatus 2500 enters a status other than the active status 2646, such as one of the error status 2616, cooling status 2656, done status 2660, or paused status 2664.

Figures 103, 104:
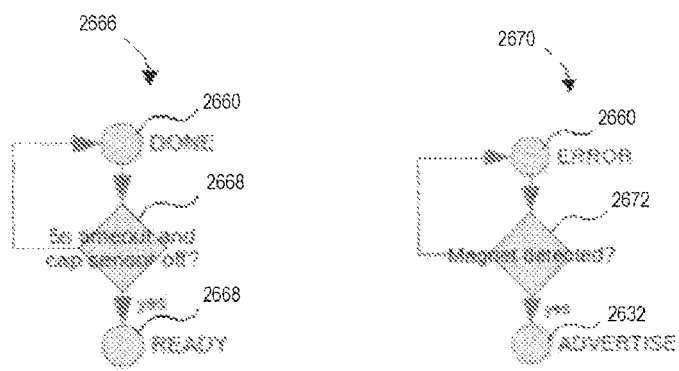

Referring to FIG. 103, when the apparatus 2500 is in the done status 2660, the apparatus 2500 is configured to execute an algorithm 2666 configured to determine if the apparatus should enter the ready status. Specifically, the algorithm 2666 is configured to query, at 2668, whether a predetermined period of time has elapsed since the apparatus 2500 entered the done status 2660. The predetermined period of time can be on the order of seconds, such as, for example, two seconds, three second, four seconds, five seconds, six seconds, or more. In one or more embodiments, the algorithm 2666 is configured to query whether 5 seconds have elapsed since the apparatus 2500 entered the done status. The algorithm 2666 is also configured to query whether the capacitance sensor 2549 is off The algorithm can be configured to execute both queries, i.e., whether the predetermined period of time has elapsed and whether the capacitance sensor 2549 is off, concurrently. If it is determined that (1) the predetermined period of time has elapsed, and (2) the capacitance sensor 2549 is off, the apparatus 2500 enters the ready status 2620. If either the predetermined time period has not elapsed or the capacitance sensor 2549 is on, the apparatus 2500 remains in the done status 2660, and the apparatus 2500 can be configured to reexecute the algorithm 2666 until the apparatus enters a different status (e.g., the ready status 2620).

Referring to FIG. 104, when the apparatus 2500 is in the error status 2616, the apparatus 2500 is configured to execute an algorithm 2670 to determine if the apparatus should enter a different status, such as the advertise status 2632. The algorithm 2670 is configured to query, at 2672, whether the magnet is detected. If it is determined that the magnet is detected (e.g., if the apparatus 2500 is disposed on the external station 2580), the apparatus 2500 enters the advertise status 2632. If it is determined that the magnet is not detected, the apparatus 2500 remains in the error status 2616. The apparatus 2500 can be configured to reexecute the algorithm 2670 until the apparatus enters a different status (e.g., the advertise status 2632).

Figure 105:
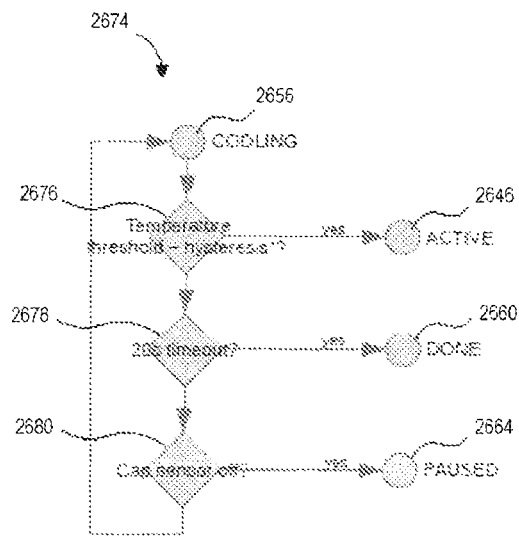

As disclosed herein, when the apparatus 2500 is in the cooling status, light emission from the light array 2542 during a treatment session is, at least temporarily, ceased to permit the apparatus to cool down. The apparatus 2500 can be configured to execute an algorithm to determine if the apparatus should move from the cooling status 2656 to a different status, such as the active status 2646, done status 2660, or paused status 2664. Referring to FIG. 105, the apparatus 2500 is configured to execute an algorithm 2674 to query, at 2676, whether the temperature of the apparatus is less than the predetermined temperature threshold. More specifically, in one or more embodiments, the algorithm 2674 is configured to query, at 2676, whether the temperature of the apparatus 2500 is less than the predetermined temperature threshold value minus a hysteresis value. In the cooling status 2656, temperature of the apparatus 2500 should continue lowering until the apparatus 2500 reaches an ambient temperature of its environment. As such, a real-time temperature of the apparatus 2500 at the moment the apparatus determines an answer to the query, at 2676, may be less than the measured (or adjusted) temperature used to determine the answer to the query. The hysteresis value is a value used to adjust for the time lag between the temperature being measured (or adjusted) and the execution of the algorithm. If it is determined that the temperature of the apparatus 2500 is less than the predetermined temperature threshold, and in one or more embodiments less than the predetermined temperature threshold minus the hysteresis value, the apparatus enters (or returns) to the active status 2646.

If it is determined that the temperature of the apparatus 2500 is not less than the predetermined temperature threshold, and, in one or more embodiments is not less than the predetermined temperature threshold minus the hysteresis value, the algorithm 2674 is configured to query, at 2678, whether a predetermined time period has elapsed since the apparatus 2500 entered the cooling status 2656. The predetermined time period can be on the order of seconds, for example ranging from about 5 seconds to about 30 seconds. In one or more embodiments, the predetermined time period is 20 seconds. If it is determined that the predetermined time period has elapsed, the apparatus 2500 enters the done status 2660.

If it is determined that the predetermined time period has not elapsed, the algorithm 2674 is configured to query, at 2680, whether the capacitance sensor 2549 is off If it is determined that the capacitance sensor 2549 is off, the apparatus 2500 enters the paused status. If it is determined that the capacitance sensor 2549 is on, the apparatus 2500 remains in the cooling status 2656. The apparatus 2500 can be configured to reexecute the algorithm 2674 until the apparatus enters a different status, such as the active status 2646, the done status 2660, or the paused status 2664.

Figure 106:
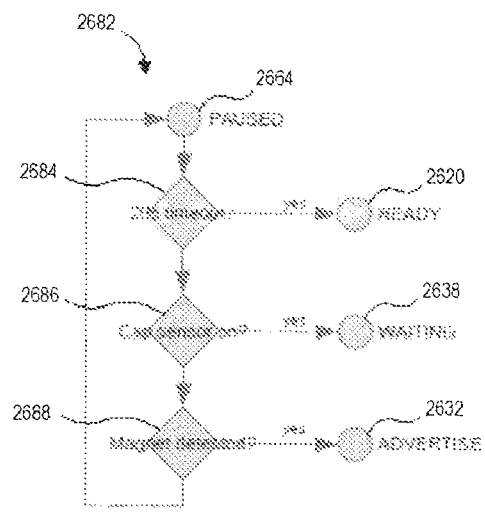

The apparatus 2500 can be configured to determine whether the apparatus, when in the paused status 2664, should enter a different status, such as one of the ready status 2620, the waiting status 2638, or the advertise status 2632. Referring to FIG. 106, the apparatus 2500 can be configured to execute an algorithm 2682, when the apparatus is in the paused status 2664, configured to query, at 2684, whether a predetermined period of time has elapsed since the apparatus 2500 entered the paused status. The predetermined time period can be on the order of seconds, for example ranging from about 5 seconds to about 30 seconds. In one or more embodiments, the predetermined time period is 20 seconds. If it is determined that the predetermined time period has elapsed, the apparatus 2500 enters the ready status 2620. If it is determined that the predetermined time period has not elapsed, the algorithm 2682 is configured to query, at 2686, whether the capacitance sensor 2549 is on. If it is determined that the capacitance sensor 2549 is on, the apparatus 2500 enters the waiting status 2638. If it is determined that the capacitance sensor 2549 is not on, the algorithm is configured to query, at 2688, whether the magnet is detected. If it is determined that the magnet is detected, the apparatus 2500 enters the advertise status 262. If it is determined that the magnet is not detected, the apparatus 2500 remains in the paused state 2664. The apparatus 2500 can be configured to reexecute the algorithm 2682 until the apparatus enters a different status, such as the ready status 2620, the waiting status 2638, or the advertise status 2632.

Figure 107:
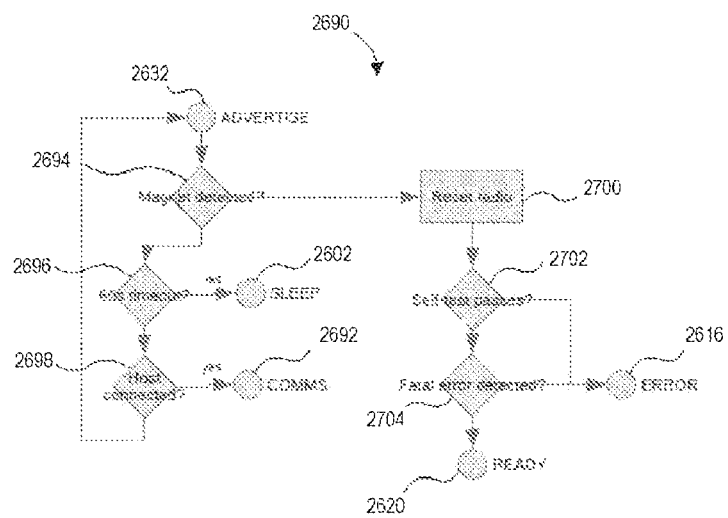

The apparatus 2500 can be configured to determine whether the apparatus, when in the advertise status 2632, should enter a different status, such as one of the sleep status 2602, communication status 2692, error status 2616, or ready status 2620. Referring to FIG. 107, the apparatus 2500 can be configured to execute an algorithm 2690, when the apparatus is in the advertise status 2632, configured to query, at 2694, whether the magnet is detected. As disclosed herein, the magnet may be detected, for example, if the apparatus 2500 is disposed on the external station 2580. If it is determined that the magnet is detected, the algorithm 2690 is configured to query, at 2696 whether a predetermined period of time has elapsed since the apparatus 2500 entered the advertise status 2632. The predetermined time period can be on the order of seconds or minutes, for example ranging from about 20 seconds to about 2 minutes. In one or more embodiments, the predetermined time period ranges from about 45 seconds to about 75 seconds. In one or more embodiments, the predetermined time period is 60 seconds. If it is determined that the predetermined time period has elapsed, the apparatus 2500 enters the sleep status 2602. If it is determined that the predetermined time period has not elapsed, the algorithm 2690 queries, at 2698, whether the external device (also referred to as a host device, e.g., a mobile phone, personal digital assistant, computer, portable electronic device, or the like) is connected to, or is in communication with, the apparatus 2500. If it is determined that the external device is connected to, or is in communication with, the apparatus 2500, the apparatus enters the communication status 2692. If it is determined that the external device is not connected to, or is not in communication with, the apparatus 2500, the apparatus remains in the advertise status 2632. The apparatus 2500 can then reexecute the algorithm 2690.

Returning to the algorithm's query, at 2694, of whether the magnet is detected, if the magnet is not detected, the apparatus 2500 is configured to reset its wireless transmitter, or other radio mechanism, as indicated at 2700. The algorithm 2690 is configured to query, at 2702, whether the apparatus 2500 passes a self-test. In one or more embodiments, as part of the query, the algorithm 2690 can be configured to execute the self-test. In other embodiments, the algorithm 2690 can be configured to cause the apparatus 2500 to execute a different algorithm (not shown) for performing the self-test. The self-test can be configured to determine whether the wireless transmitter 2576, or other radio mechanism, of the apparatus 2500 is functional. If it is determined that the apparatus 2500 did not pass the self-test, the apparatus enters the error status 2616. If it is determined that the apparatus 2500 passes the self-test, the algorithm 2690 is configured to query, at 2704, whether a fatal error is detected. If it is determined that a fatal error is detected, the apparatus 2500 enters the error status 2616. If it is determined that a fatal error is not detected, the apparatus 2500 enters the ready status 2620. The apparatus 2500 can be configured to reexecute at least a portion of the algorithm 2690 until the apparatus enters a different status, such as the sleep status 2602, communication status 2692, error status 2616, or ready status 2620.

Figure 108:
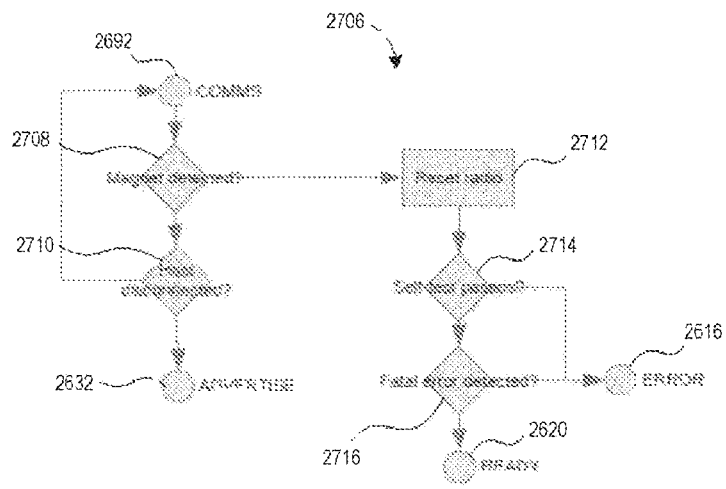

The apparatus 2500 can be configured to determine whether the apparatus, when in the communication status 2692, should enter a different status, such as one of the advertise status 2632, error status 2616, or ready status 2620. Referring to FIG. 108, the apparatus 2500 can be configured to execute an algorithm 2706, when the apparatus is in the communication status 2692, configured to query, at 2708, whether the magnet is detected. As disclosed herein, the magnet may be detected, for example, if the apparatus 2500 is disposed on the external station 2580. If it is determined that the magnet is detected, the algorithm 2706 is configured to query, at 2710, whether the external device (also referred to as a host device, e.g., a mobile phone, personal digital assistant, computer, portable electronic device, or the like) is disconnected from, or is not in communication with, the apparatus 2500. If it is determined that the external device is disconnected from, or is not in communication with, the apparatus 2500, the apparatus enters the advertise status 2632. If it is determined that the external device is not disconnected from, or is in communication with, the apparatus 2500, the apparatus remains in the communication status 2692. The apparatus 2500 can then reexecute the algorithm 2706.

Returning to the algorithm's query, at 2708, of whether the magnet is detected, if the magnet is not detected, the apparatus 2500 is configured to reset its wireless transmitter, or other radio mechanism, as indicated at 2712. The algorithm 2706 is configured to query, at 2714, whether the apparatus 2500 passes the self-test. In one or more embodiments, the algorithm 2706 can be configured to execute the self-test. In other embodiments, the algorithm 2706 can be configured to cause the apparatus to execute a different algorithm (not shown) for performing the self-test. As described herein, the self-test can be configured to determine whether the wireless transmitter 2576, or other radio mechanism, of the apparatus 2500 is functional. If it is determined that the apparatus 2500 did not pass the self-test, the apparatus enters the error status 2616. If it is determined that the apparatus passes the self-test, the algorithm 2706 is configured to query, at 2716, whether a fatal error is detected. If it is determined that a fatal error is detected, the apparatus 2500 enters the error status 2616. If it is determined that a fatal error is not detected, the apparatus 2500 enters the ready status 2620. The apparatus 2500 can be configured to reexecute the algorithm 2706 until the apparatus enters a different status, such as the advertise status 2632, error status 2616, or ready status 2620.

Although the algorithms (e.g., algorithms 2600, 2622, 2626, 2640, 2648, 2666, 2670, 2674, 2682, 2690, 2706) have been illustrated and described herein as executing particular queries or steps in a particular order, in one or more embodiments, particular queries or steps can be differently ordered and/or particular queries or steps can be omitted. For example, in one or more embodiments, the algorithm query regarding whether the apparatus 2500 passes a self-test can be omitted. In another example, in one or more embodiments, the algorithm can query whether the capacitance sensor 2549 is on (or off, as applicable for a particular query), after (e.g., with respect to the waiting status algorithm) or before (e.g., with respect to the ready status algorithm) the query regarding whether a predetermined period of time has elapsed.

Furthermore, although the algorithms (e.g., algorithms 2600, 2622, 2626, 2640, 2648, 2666, 2670, 2674, 2682, 2690, 2706) have been illustrated and described herein as being distinct algorithms, in one or more embodiments, the executable code represented by the algorithms described herein can be included in a single algorithm. In other embodiments, the executable code represented by the algorithms described herein can be included in two or more algorithms. Moreover, the apparatus 2500 can be configured to execute algorithms in addition to those illustrated and described herein. For example, the apparatus 2500 can be configured to execute an algorithm configured to permit a maximum of two treatment sessions to be administered by the apparatus 2500 per day.

In another embodiment, the apparatus 2500 can be configured to permit a maximum of four treatments sessions per day (e.g., two treatment sessions per upper and lower arch, per day).

In one or more embodiments, the light therapy apparatus 2500 is configured to provide indicia of a state or status of the apparatus. The term "indicia," is used herein as including the singular ("indicium") or the plural ("indicia"), unless the context clearly indicates otherwise. The indicia can comprise one or more of an audible indicia (e.g., a tone, beep, announcement, or the like), a tactile indicia (e.g., a vibration or the like), or a visual indicia (e.g., a light, a displayed message, or the like). The bill 2560 comprises an indicator light 2578 configured to emit at least one of a pattern of light or a color of light, or both, indicative of the status of the light therapy apparatus 2500 or a treatment session being administered by the apparatus. More specifically, for example, the indicator light 2578 is configured to indicate, based on a combination of (1) the color of the light being emitted and (2) whether the light is being emitted in a solid pattern, a slow blink pattern or a fast blink pattern, a status of the apparatus. The indicator light 2578 can be or comprise a light pipe.

For example, the indicator light 2578 can be configured to emit no light when the apparatus 2500 is turned off In one or more embodiments, a patient may be instructed to return the apparatus 2500 to the external station 2580 when no light is emitted by the indicator light 2578. The indicator light 2578 can be configured to emit a green, solid light when the apparatus 2500 is ready to begin a treatment session. The indicator light 2578 can be configured to emit a green, fast blink light when the apparatus 2500 is ready to begin a treatment session and should be recharged after the treatment session. The indicator light 2578 can be configured to emit a green, slow blink light when the apparatus 2500 is being charged and/or when the apparatus 2500 is in wireless communication with an application of the external device.

The indicator light 2578 can be configured to emit a blue, solid light when the apparatus 2500 is activated and providing a treatment session. The indicator light 2578 can be configured to emit a blue, fast blink light when the treatment session is paused, but the treatment session may be continued. The indicator light 2578 can be configured to emit a blue, slow blink light when the treatment session is complete and the apparatus 2500 should be removed from the patient's mouth. The indicator light 2578 can be configured to emit a red, blinking light when the battery 2568 is low, indicating that the apparatus 2500 should be returned to the external station 2580 for recharging. The indicator light 2578 can be configured to emit a red, solid light when the apparatus 2500 is has detected an error, indicating that the reset protocol for the apparatus 2500 should be followed by the patient, which may including placing the apparatus 2500 on the external station 2580 and/or contacting customer support.

In one or more embodiments, the apparatus 2500 is configured to provide the audible indicia to the patient. For example, in one or more embodiments, the apparatus 2500 is configured to beep to alter the patient that at least one of (1) a treatment session has begun, (2) a treatment session has been paused, (3) the treatment session has ended.

Although the indicator light 2578 has been described as being configured to emit a specific color and pattern (e.g., green, solid) for a specific status (e.g., ready to begin treatment), in other embodiments, the apparatus 2500 can be programmed to cause the indicator light 2578 to emit light in any suitable combination of color and pattern for a variety of statuses.

The light therapy apparatus 2500 can be configured for use in an orthodontic treatment, including any treatment described herein.

In use, upon removal from its case, the light therapy apparatus 2500 is configured to automatically wake up from the sleep state, and go into a ready state (or pre-treatment mode), as described herein. In the ready state, the apparatus 2500 will periodically check for tissue contact. The patient places the mouthpiece 2510 into their mouth and positions the apparatus 2500 comfortably to begin treatment. Correct positioning is achieved by centering the mouthpiece 2510 in the mouth and setting the ridge 2518 in between the patient's central incisors. Once the apparatus 2500 is positioned correctly, the patient will bite down on the bite pad 2514. The light therapy apparatus 2500 detects when tissue contact has been achieved, and will automatically begin treatment, as described in more detail herein.

In one or more embodiments, for example, the light therapy apparatus 2500 is useful to irradiate at least a portion of the patient's upper jaw for about 3 minutes, the patient's lower jaw for about 3 minutes, or each of the patient's upper and lower jaws for about 3 minutes. More specifically, in one treatment program, the light therapy apparatus 2500 is useful to administer a light-therapy treatment session in which the oral tissue associated with each of the upper arch of the patient's mouth and the lower arch of the patient's mouth (or vice versa) are consecutively irradiated for 3 minutes per day, for a total treatment session of 6 minutes per day. During the treatment session, the light can be irradiated concurrently from all light emitters 2544 in the light array 2542. Also during treatment, the light emitters 2544 can comprise embedded LEDs configured to activate and directly illuminate the alveolar mucosa and alveolar bone. Administration of a first light therapy session of the treatment program can begin on the same date that the patient's orthodontic treatment begins (e.g., the day that brackets and wires are installed on the patient's teeth, e.g., T0).

As used herein, "alveolar mucosa" refers to oral mucosa that is immediately apical to mucogingival junction. Alveolar soft tissue (such as alveolar mucosa) is distinguished from gum tissue (or "gingiva"), for example, by the patient's mucogingival junction. The mucogingival junction is a line of demarcation between gum tissue and the alveolar mucosa, and gum tissue is therefore distinct from alveolar mucosa.

The light can be emitted at any suitable wavelength or combinations of wavelengths in accordance with the methods described herein. In one or more embodiments, the light is emitted at a wavelength of about 850 nm during the treatment session. In other embodiments, the light is emitted at a wavelength of 850 nm (±5 nm) during the treatment session. In one or more embodiments, the light emitters 2544 and/or LEDs can emit light at a blend of wavelengths, and not at a single wavelength like a laser. The peak light emission wavelength ( ),max) by the LEDs, can be, for example, 855 nm.

The treatment sessions can be administered for any suitable period, including, but not limited to, a period of four to twelve months. In one or more embodiments, use of the light therapy apparatus 2500 to administer light therapy treatment sessions according to a treatment program is continued until the patient's Little's Irregularity Index ("LIi") score, described in more detail herein, is determined to be less than 1 (i.e., T1). The patient's treatment program can continue until the patient's dental malocclusion is completely resolved (e.g. the patient's LIi is about zero) and/or an acceptable clinical outcome has been achieved, which, in one or more embodiments, is determined at the patient's final orthodontic appointment during which the orthodontic appliance (e.g., brackets and wires) are uninstalled. In one or more embodiments, use of the light therapy apparatus 2500 to administer light therapy treatment sessions according to a treatment program is continued until the patient's orthodontic appliance is uninstalled from the patient's teeth (i.e., T2). The light therapy apparatus 2500 can be configured to administer the treatment sessions in a clinical setting or in a home environment.

Such a treatment program can, for example, reduce the duration of an average period a patient is expected to need to use an orthodontic appliance (e.g., braces) to achieve a desired orthodontic result. For example, the apparatus 2500 can be useful during the treatment program to reduce the duration of the treatment program from two years to six months. The foregoing treatment program and/or any treatment program described herein can reduce a duration of an orthodontic treatment administered without light therapy, as described herein, by about 50 percent to about 75 percent.

Referring to FIGS. 109-113, the light therapy apparatus 2500 can be configured to be disposed on, in or otherwise coupled to the external station 2580, for example, when the apparatus 2500 is not in use by the patient. The external station 2580 can be, for example a carrying case, charging caddy or station, or the like, or a combination of the foregoing.

Figure 109:
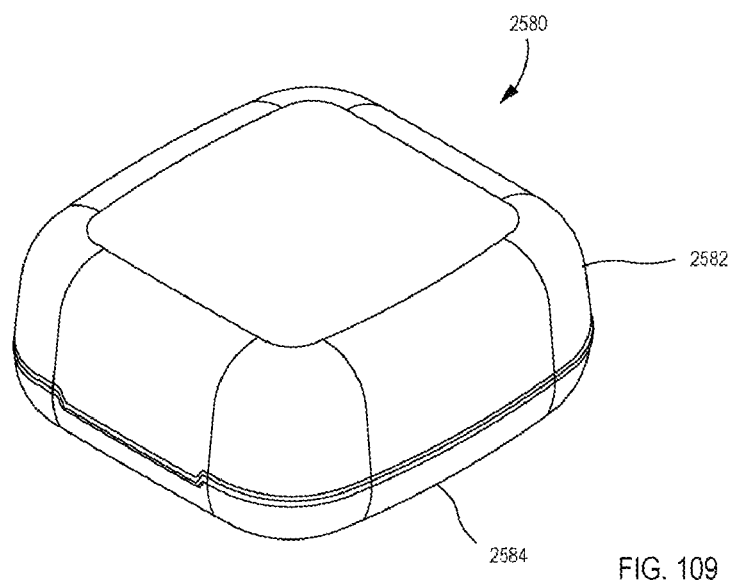
FIG. 109 is a perspective view of an external station according to an embodiment, within which the light therapy apparatus of FIG. 84 can be disposed.
Figure 110:
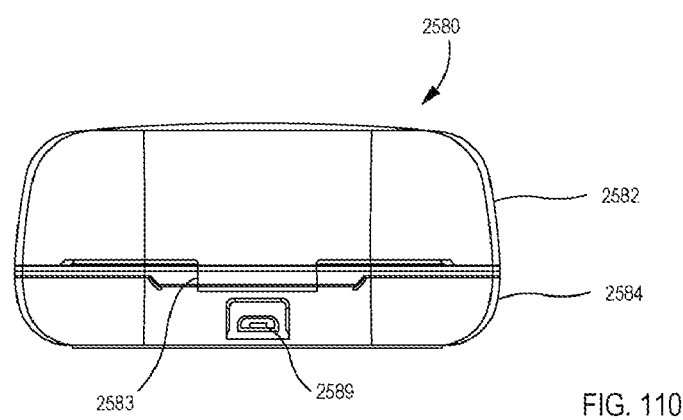
FIG. 110 is a rear view of the external station of FIG. 109.
Figure 111:
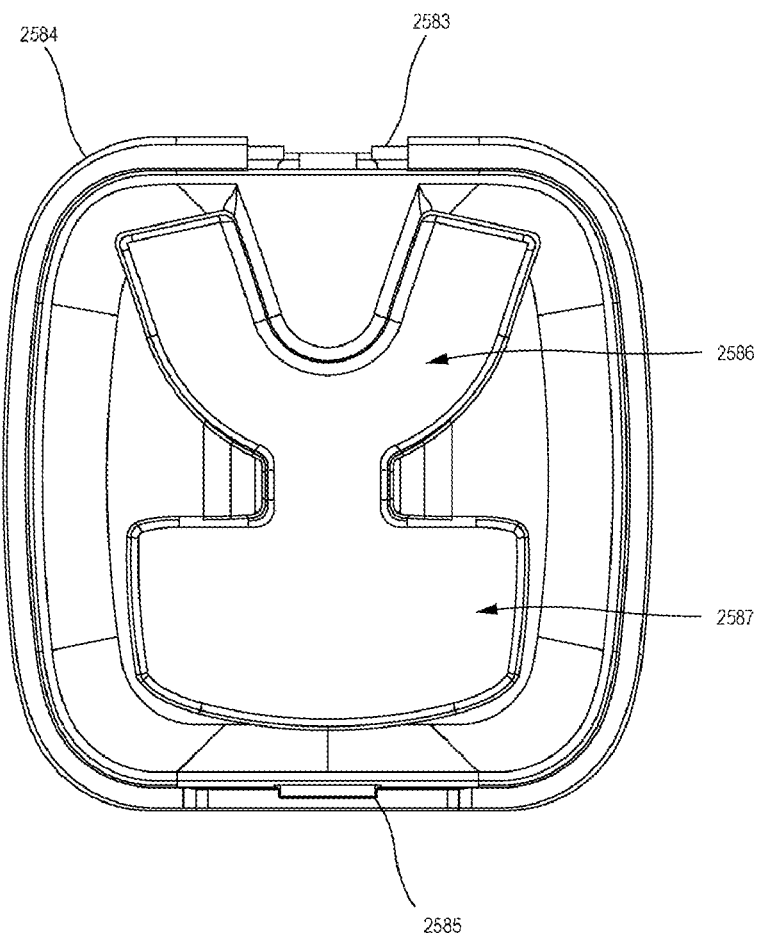
FIG. 111 is a top view of a bottom portion of the external station of FIG. 109.

The station 2580 comprises a base 2584 and a lid 2582 and defines a cavity (not shown in FIGS. 109-113) formed by and between the base 2584 and the lid 2582 when the lid is in a closed position (as shown in FIG. 109). The lid 2582 can be coupled to the base 2584 using any suitable coupling mechanism, for example, using a hinge 2583 as shown in FIGS. 110 and 111. In this manner, the lid 2582 is conveniently moveable between its closed position and an open position (not shown).

The base 2584 can comprise a locking mechanism configured to secure the lid 2582 to the base 2584. For example, the base can comprise a latch 2585 configured to matingly engage a recess (not shown) in the lid 2582 to secure the lid in the closed position. The base 2584 and lid 2582 can be constructed of any suitable material, including, for example a plastic such as Bisphenol A-free polypropylene. In one or more embodiments, at least one of the base 2584 and lid 2582 is constructed of a material that is resistance to impact and/or scratches.

Figure 112:
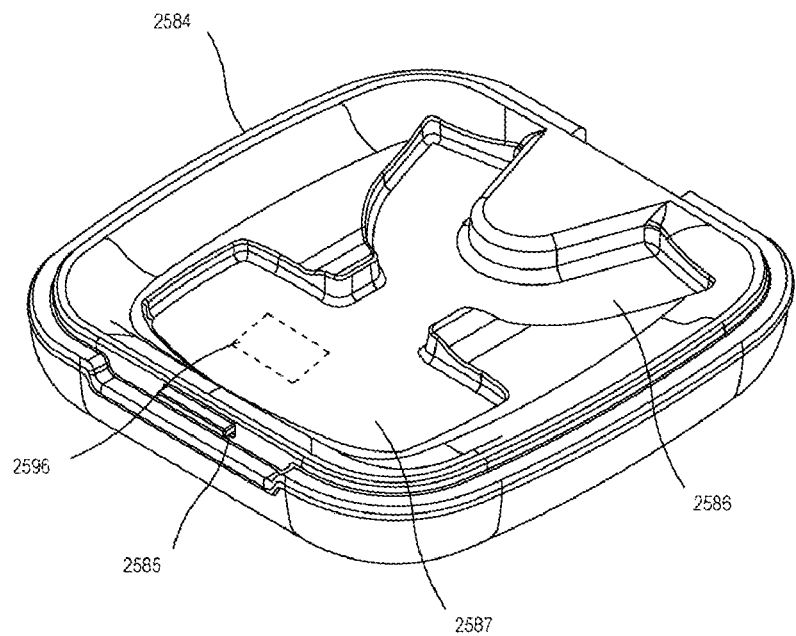
FIG. 112 is a perspective view of the bottom portion of the external station of FIG. 109.
Figure 113:
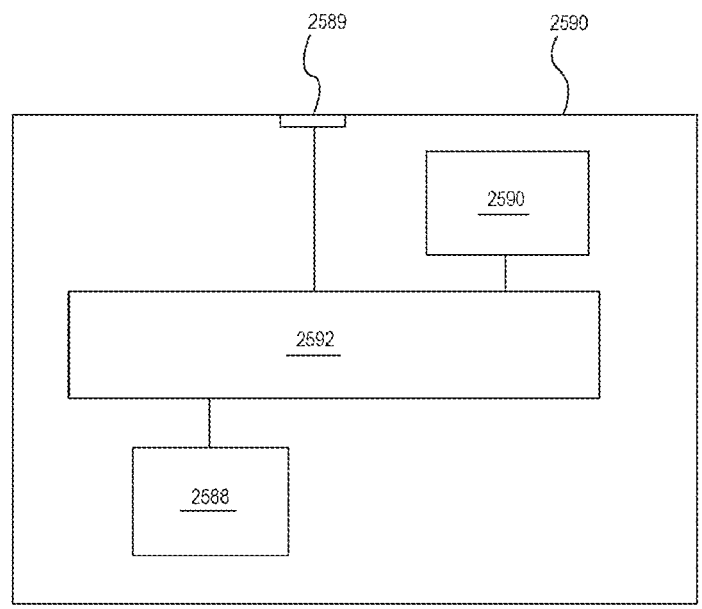
FIG. 113 is a schematic illustration of electronic components of the external station of FIG. 109.
Figure 114:
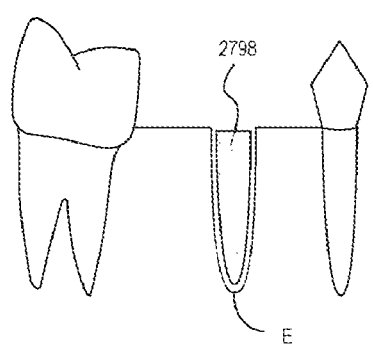
FIG. 114 is a side view of a barrier implant implanted at an extraction site according to an embodiment.

The base 2584 can define a first recess 2586 configured to receive at least a portion of the mouthpiece 2510 and a second recess 2587 configured to receive at least a portion of the bill 2560. In one or more embodiments, as shown in FIGS. 111 and 112, the first recess 2586 is in continuous with the second recess 2587. A perimeter of the first recess 2586 can, for example, complement the contour of the mouthpiece 2510. A perimeter of the second recess 2587 can, for example, complement the contour of the bill 2560.

The external station 2580 can be configured to charge the apparatus 2500 when the apparatus 2500 is disposed on or otherwise coupled to the station. In this manner, the battery 2568 can be recharged when the bill 2560 is coupled to the charging station. In one or more embodiments, for example, the station 2580 is configured to inductively charge the apparatus 2500, e.g., by inductively charging the battery 2568 via the induction receiver coil 2569 of the mouthpiece 2510. More specifically, an electronics assembly 2590 (schematically illustrated in FIG. 113) comprises a wireless charger (e.g., an induction transmitter coil) 2588 configured to induce an electromagnetic field in the induction receiver coil 2569, and the induction receiver coil is configured to convert the received energy into an electrical current for charging the battery 2568.

In one or more embodiments, the external station 2580 is configured to be coupled to a computer or other electronic device, such as via a USB, micro-USB or other suitable cable (not shown) received in a port 2589 of the external station 2580. For example, the USB cable can be configured for charging the external station 2580. In other embodiments, the external station 2580 can be configured to be charged by any conventional power supply. In one or more embodiments, external station 2580 is configured to be coupled to a medical grade power supply, such as a medical grade 6 W power supply manufactured by TRUMPower. The power supply can be configured to comply with applicable regulatory standards and/or regulations. For example, the power supply can be configured to comply with IEC 60601-1 and/or other applicable standards. Electronic circuitry 2592 is configured to couple the port 2589 to the induction transmitter coil 2588, thus facilitating the inductive charging of the apparatus 2500 with no electrical connections between the apparatus 2500 and the external station 2580.

In one or more embodiments, the external station 2580 is configured to sanitize or otherwise disinfect at least a portion of the light therapy apparatus 2500. For example, the external station 2580 can comprise a light emitter 2594 configured to emit an ultraviolet light, or other suitable wavelength light, such as a blue light, to disinfect the mouthpiece 2510 when the apparatus 2500 is disposed in the external station 2580. In one or more embodiments, the lid 2582 of the external station 2580 must be in the closed position for the station to emit the disinfecting light. For example, in one or more embodiments, when the lid 2582 is in its closed position, a switch (not shown) is moved to a closed position, thereby completing an electrical circuit including the light emitter 2594 such that the light emitter 2594 can irradiate the light. In one or more embodiments, emission of the disinfecting light can be controlled via the electronics assembly 2590 of the external station 2580.

The external station 2580 comprises a magnet 2596 (schematically illustrated with phantom lines in FIG. 112). As described above, the magnet 2596 is configured to cause the magnet switch 2575 of the bill 2560 to move from its first position to its second position when the apparatus 2500 is disposed on the base 2584 of the external station 2580.

Although the light therapy apparatus 2500 and external station 2580 have been described herein as being configured to comply with various industry standards, the apparatus 2500 and/or external station 2580 can be configured to comply with additional or alternative industry standards. For example, the apparatus 2500 and external station 2580 can be configured to be compliant with one or more of the following standards, or any combination thereof: IEC/EN 60601-1 Ed. 3.1: 2012—Medical Electrical Equipment Part 1: General requirements for basic safety and essential performance; IEC/EN 60601—1-2 Ed. 3: 2007—Collateral standard: Electromagnetic compatibility—Requirements and tests; EN 62471: 2009—Photobiological safety of lamps and lamp systems; IEC 60601-2-57: Ed. 1.0: 2011—Medical Electrical Equipment Part 2-57: Particular requirements for the basic safety and essential performance of non-laser light source equipment intended for therapeutic, diagnostic, monitoring and cosmetic/aesthetic use; EN 60529 Ed. 2.1: 2001—Degrees of protection provided by enclosures; IEC 60601-1-11—Collateral Standard: Requirements for medical electrical equipment and medical electrical systems used in the home healthcare environment; ISO 10993-1: 2009—Biological evaluation of medical devices—Part 1: Evaluation and testing within risk management process; ISO/BS/EN 14971: 2012—Medical Devices—Application of risk management to medical devices.

Figure 126:
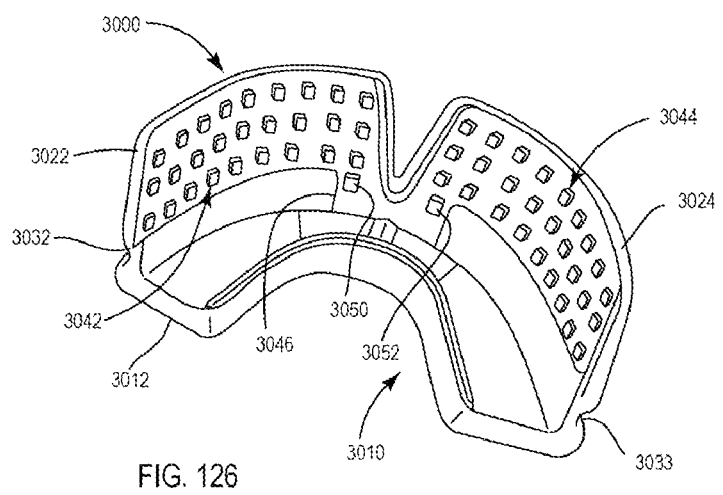
FIGS. 126-127 are rear perspective and rear views of a light therapy apparatus according to an embodiment.
Figure 127:
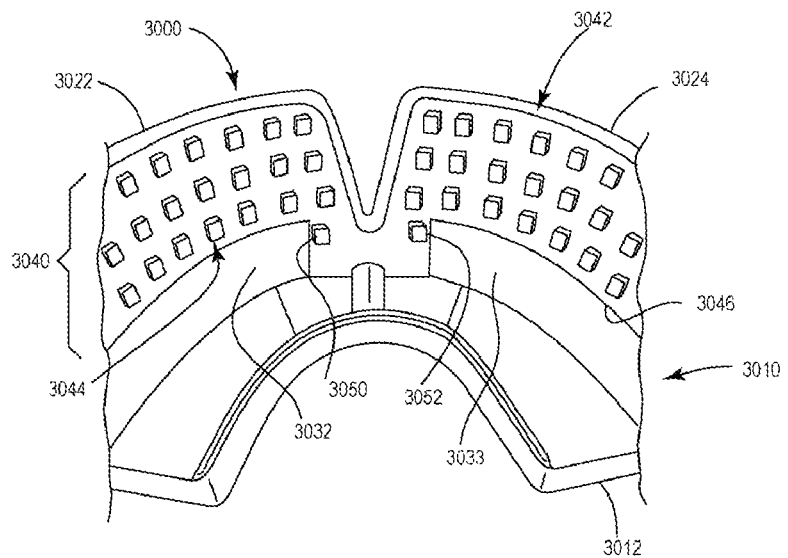

Although light therapy apparatus have been shown and described herein (e.g., light therapy apparatus 2500) as including a capacitance detection system to determine whether a mouthpiece (e.g., mouthpiece 2510) is disposed within the patient's mouth (i.e., in a manner suitable for the treatment session), in other embodiments, a light therapy apparatus can comprise a different mechanism to determine whether the mouthpiece is disposed within the patient's mouth. As shown in FIGS. 126-127, in one or more embodiments a light therapy apparatus 3000 comprises a mouthpiece 3010 configured to be disposed within a mouth of a patient. The light therapy apparatus 3000 can be similar, or identical, to light therapy apparatus 2500, and mouthpiece 3010 can be similar to mouthpiece 2510, except as described herein. For example, mouthpiece 3010 comprises a bite tray 3012, flanges 3022, 3024 transversely coupled to the bite tray, an electronics assembly 3040 including a light array 3042 and a flexible circuit board 3046, each of which is similar to a corresponding component of mouthpiece 2510, and thus is not described in detail with respect to mouthpiece 3010. In one or more embodiments, at least one or more portions of the mouthpiece 3010 are constructed from a substantially transparent material (e.g., silicone) such that one or more components embedded within the mouthpiece 3010 are visible through the mouthpiece 3010. Thus, for purposes of illustration, portions of the mouthpiece 3010, including portions of the first flange 3022, the second flange 3024 and the bite tray 3012 are shown as being transparent in FIGS. 126 and 127 to show portions of the electronics assembly 3040 and the structure disposed therein.

The light therapy apparatus 3000 is configured to determine whether the mouthpiece 3010 is disposed within the patient's mouth (i.e., in a manner suitable for a treatment session, as described herein). In this manner, the light therapy apparatus 3000 can be configured to only irradiate light for the treatment session when the apparatus 3000 has determined that the mouthpiece 3010 is disposed in the patient's mouth. The mouthpiece 3010 comprises a first light emitter 3050 and a second light emitter 3052, each of which is configured and positioned to detect or measure an amount of light reflected by a portion of the patient's oral tissue. For example, the first and second light emitters 3050, 3052 can be configured to detect light emitted from the light emitters 3044 of the light array 3042 and reflected by the patient's oral soft tissue. In one or more embodiments, the light emitters 3044 can be configured to emit light, such as in a blinking or pulsing manner. The light emitters 3044 can be configured to blink or pulse at a predetermined rate. At least a portion of light emitted from the pulsing or blinking light emitters 3044 towards the oral soft tissue of the patient's mouth is reflected to the mouthpiece 3010 and is thereby detected by the first and second light emitters 3050, 3052. Suitable optical proximity thresholds (e.g., related to an amount of detected optical power reflected from skin of the patient) can be established and used in assessing whether the light emitters 3044 of the light array 3042 (and, by proxy, the mouthpiece 3010) are is properly disposed in the patient's mouth for administering a treatment session. The apparatus 3000 can be configured to initiate irradiation of the oral tissue (i.e., begin the treatment session) when the first and second light emitters 3050, 3052 detect the light reflection from the oral soft tissue.

Each of the first and second light emitters 3050, 3052, can be coupled to the flexible circuit board 3046 in any suitable location. In one or more embodiments, the first and second light emitters 3050, 3052 are disposed on the flexible circuit board 3046 such that each of the first and second light emitters 3050, 3052 is positioned close to the patient's gum when the mouthpiece 3010 is disposed within the patient's mouth. As shown in FIGS. 126-127, the first and second light emitters 3050, 3052 are each disposed offset from parallel rows and/or columns of light emitters 3044 of the light array 3042.

Each of the first and second light emitters 3050, 3052 can be disposed between a bottom row (in the orientation of the apparatus 3000 shown in FIG. 127) of light emitters 3044 and the bite tray 3012 of the mouthpiece 3010. In one or more embodiments, the first and second light emitters 3050, 3052 are substantially level (e.g., protruding or regressed by no more than 2-3 mm) with grooves 3032, 3033 defined by an outer face of the mouthpiece 3010. In use, when light is emitted from the light emitters 3044 of the light array 3042, the first and second light emitters 3050, 3052 each measure and/or produce a signal associated with an amount of light reflected by the patient's oral tissue (e.g., the gum). As such, the first and second light emitters 3050, 3052 act as a sensor configured to detect light. Each of the first and second light emitters 3050, 3052 comprises a diode (not shown in FIGS.

126-127) configured to produce an electrical current associated with the amount of light detected or received. The first and second light emitters 3050, 3052, and their diodes, can be configured to send a signal associated with the measured light to a controller (e.g., in an extra-oral housing or bill) of the light therapy apparatus 3000. In one or more embodiments, the diodes of the first and second light emitters 3050, 3052 is configured to measure reflected light at about 855 nm.

At least a portion of the first and second light emitters 3050, 3052 can be embedded in the flanges 3022, 3024 of the mouthpiece 3010, for example, in a similar manner as disclosed herein with respect to the light array 2542. The first and second light emitters 3050, 3052 are spaced apart on the flexible circuit board 3046. In one or more embodiments, the first and second light emitters 3050, 3052 are disposed at opposing locations with respect to the flexible circuit board 3046, as shown in FIG. 127, such that the first light emitter 3050 is beneath the portion of the light array 3042
embedded in the first flange 3022 and the second light emitter 3052 is beneath the portion of the light array 3042 embedded in the second flange 3024. In this manner, the apparatus 3000 is configured to detect reflected light bilaterally.

As disclosed herein, the first and second light emitters 3050, 3052 are configured to be disposed in close proximity to the patient's oral (e.g., gum) tissue when the mouthpiece 3010 is disposed within the patient's mouth in preparation for treatment.

The apparatus 3000 is configured to irradiate light only after a predetermined amount of reflected light has been measured. Stated another way, the apparatus 3000, and the controller more specifically, is configured to turn on the light emitters 3044 for a treatment session only after the predetermined amount of reflected light has been measured. The measured amount of reflected light is registered by the controller, which is configured to execute an algorithm to register the amount of reflected light, when (1) the predetermined amount of reflected light is detected by each of the first and second light emitters 3050, 3052 (i.e., bilaterally), and/or (2) the predetermined amount of reflected light is detected for a predetermined duration (e.g., for at least 2 seconds).

An intra-oral housing 3110 (also referred to herein as a "mouthpiece" of a light therapy apparatus 3100 according to an embodiment is illustrated in FIGS. 128-132. In one or more embodiments, at least one or more portions of the mouthpiece 3110 are constructed from a substantially transparent material (e.g., silicone) such that one or more components embedded within the mouthpiece 3110 are visible through the mouthpiece 3110. Thus, for purposes of illustration, portions of the mouthpiece 3110, including portions of the first flange 3122 and the second flange 3124 are shown as being transparent in FIGS. 128-132 to show portions of the electronics assembly 3140 and the structure disposed therein. The light therapy apparatus 3100 can be included in a light therapy system that is similar in many respects to the light therapy system described herein with respect to FIGS. 84-113. The light therapy apparatus 3100 is configured to irradiate light in any suitable manner described herein, including, for example, to irradiate the alveolus and/or tooth root area of the patient. Similarly stated, the light therapy apparatus 3100 is configured to administer light therapy to a patient's teeth and/or oral mucosa. More specifically, the light therapy apparatus 3100 is configured to administer light to the patient's teeth and/or oral mucosa sufficient to accelerate orthodontic movement of the patient's teeth and to reduce the overall treatment time for the patient when undergoing orthodontic treatment. The light therapy apparatus 3100 can be the same as or similar in many respects to, or comprise components the same as or similar in many respects to, the intra-oral apparatuses described herein, including, for example, apparatus 2100, apparatus 2500, and apparatus 3000.

The light therapy apparatus 3100 (and any light therapy apparatus described herein) is configured to be useful in combination with traditional orthodontic treatment with an orthodontic appliance, such as brackets and wires, or aligners. Furthermore, in one or more embodiments, any light therapy apparatus shown and described herein can be useful with any suitable orthodontic appliance, including, but not limited to, substantially transparent aligners. Such aligners are orthodontic appliances configured to move a patient's teeth and generally comprise one or more substantially transparent, removable trays that fit over one or more of the patient's teeth. Each tray of the set of trays is worn by the patient in a predetermined sequence or order, and sometimes for a specified amount or period of time. In particular instances, such aligners or trays generally conform to a patient's teeth but is slightly out of alignment with the starting (e.g., initial) tooth configuration. In this manner, the aligners or trays can exert a force on the teeth. In one or more embodiments, the orthodontic appliance (e.g., brackets and wires or an aligner) is configured to exert a force on one or more of the patient's teeth in an amount (or magnitude) effective to move the patient's teeth towards alignment. In one or more embodiments, the orthodontic appliance is configured to exert a force on one or more of the patient's teeth in an amount (or magnitude) effective to move the patient's teeth, for example, in one or more embodiments, for alignment. Similarly stated, the orthodontic appliance is configured to exert a force to minimize or close a gap or space between the patient's teeth. For example, the orthodontic appliance can be configured to exert an orthodontic force, a less-than-orthodontic force, or a heavy force, as described in detail herein, or a combination thereof, on one or more of the patient's teeth in an amount (or magnitude) effective for tooth movement (e.g., towards alignment or to minimize or close a gap between the patient's teeth).

The intra-oral housing 3110 of the light therapy apparatus 3100 is configured to be disposed in an oral cavity (e.g., in the mouth, not shown in FIGS. 128-132) of a patient. The intra-oral housing 3110 can be configured to be electronically and/or physically coupled to an external controller. In one or more embodiments, for example, the intra-oral housing 3110 is configured to be coupled to an extra-oral housing (or "bill," not shown in FIGS. 128-132) that is disposed externally to the patient's mouth when the intra-oral housing (or mouthpiece) 3110 is disposed within the patient's mouth. The
extra-oral housing can be similar in many respects, or identical, to the extra-oral housing 2560 described herein with respect to FIGS. 84-113, and thus is not described in detail with respect to light therapy apparatus 3100. In other embodiments, the intra-oral housing 3110 is configured to be coupled to the controller via one or more wire or cable connectors (not shown in FIGS. 128-132).

Figure 130:
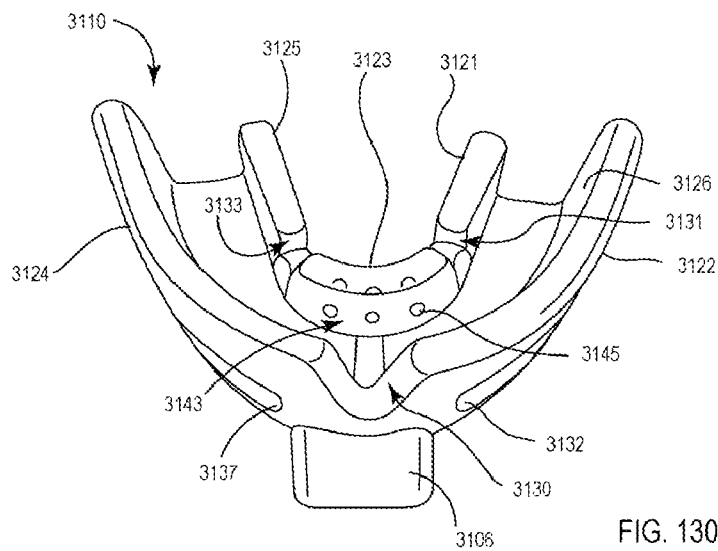
FIG. 130 is a top perspective view of the light therapy apparatus of FIG. 128.
Figure 131:
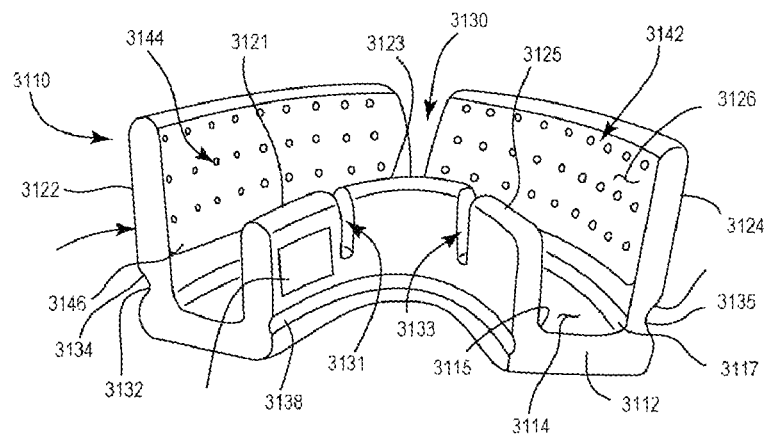
FIG. 131 is a rear view of the light therapy apparatus of FIG. 128.

The light therapy apparatus 3100 is configured to be useful for light therapy with the upper jaw and/or the lower jaw of the patient. In other words, the light therapy apparatus 3100 can be configured to administer light therapy with respect to the patient's upper jaw when the apparatus is in an upright position (e.g., as shown in FIG. 131), and can be configured to administer light therapy with respect to the patient's lower jaw when the apparatus is in an inverted position (e.g., not shown in FIGS. 128-132). As such, the mouthpiece 3110 is configured to be disposed within the patient's oral cavity with respect to each of the upper and lower jaws of the patient. Similarly stated, the mouthpiece 3110 is configured to matingly adapt to both the upper jaw and the lower jaw, as described herein, thus eliminating the need for a separate mouthpiece for each jaw. It should be noted that although the light therapy apparatus 3100 generally, and the mouthpiece 3110 specifically, may be described as being in the upright position when configured to be oriented with respect to the upper jaw and in the inverted position when configured to be oriented with respect to the lower jaw, in other embodiments, the light therapy apparatus 3100 and the mouthpiece 3110 are in the upright position when configured to be oriented with respect to the lower jaw of the patient, and in the inverted position when configured to be oriented with respect to the upper jaw of the patient.

The mouthpiece 3110 can be similar in one or more respects, and comprise components similar in one or more respects to the intra-oral housings described herein, including, for example, the intra-oral housings or mouthpieces described herein with reference to FIGS. 35-37, 52-59, 65-72, 84-113 and 126-127. The mouthpiece 3110 comprises a bite tray 3112, flanges 3122, 3124, 3121, 3123, 3125, light arrays 3142, 3143 (see, e.g., FIG. 131). The mouthpiece 3110 can optionally comprise a support plate (not shown in FIGS. 128-132) similar or identical to the support plate 2554 of mouthpiece 2510. The bite tray 3112 is configured to receive at least a portion of the patient's teeth of the upper and/or lower jaw. As such, the bite tray 3112 is generally U-shaped, as shown in FIG. 131. The bite tray 3112 is configured to facilitate proper positioning of the mouthpiece 3110 within the patient's mouth. The bite tray 3112 generally comprises the lower portion of the mouthpiece 3110. The bite tray 3112 comprises a bite pad 3114 with an inner perimeter (or side wall) 3115 and an outer perimeter (or side wall) 3117 (see FIG. 131).

Flanges 3122, 3124, 3121, 3123, 3125, described in more detail herein, generally define an upper portion of the mouthpiece 3110. Outer flanges 3122, 3124 are coupled to the outer perimeter 3117 of the bite pad 3114. Inner flanges 3121, 3123, 3125 are coupled to the inner perimeter 3115 of the bite pad 3114. The flanges 3122, 3124, 3121, 3123, 3125 of the mouthpiece 3110 each extend and/or protrude from the bite pad 3114 in a first direction. As such, when the mouthpiece 3110 is disposed within the patient's mouth, the bite tray 3112 is positioned within the mouth such that the bite pad 3114 is adjacent the occlusal surface of one or more teeth, the outer flanges 3122, 3124 are disposed between the one or more teeth and buccal tissue, and the inner flanges 3121, 3123, 3125 are disposed between the one or more teeth and the tongue and/or palate.

Similarly stated, the bite tray 3112 is configured such that when the mouthpiece 3110 is disposed within a mouth, a least a portion of one or more teeth are positioned between the outer flanges 3122, 3124 and the inner flanges 3121, 3123, 3125.

The bite tray 3112 can be similar in many respects, or identical, to the bite tray 2512 described with respect to FIGS. 84-113, and thus is not described in detail with respect to mouthpiece 3110. For example, the bite pad 3114 the bite tray 3112 can have any thickness suitable for receiving a bite force thereon, including a constant or spatially varied thickness as described with respect to bite pad 2514. In another example, the bite tray 3112 (and/or bite pad 3114) can be of any suitable dimensions, including those described herein with respect to bite tray 2512 (and/or bite pad 2514, respectively), and can be constructed of any suitable material, including those described herein with respect to bite tray 2512 (and/or bite pad 2514).

Figure 128:
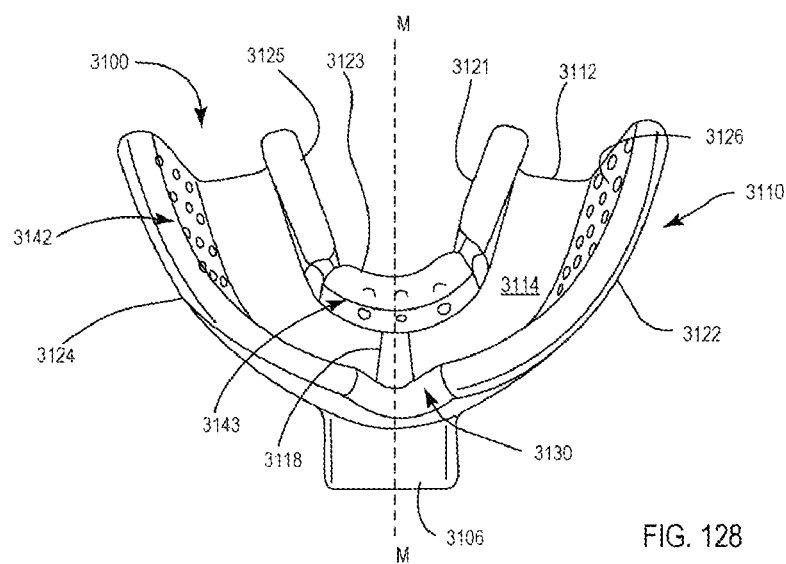
FIG. 128 is a top view of a light therapy apparatus according to an embodiment.

As shown in FIG. 128, an upper surface of the bite pad 3114 comprises a ridge 3118. The ridge 3118 is disposed along a midline M of the mouthpiece 3110 and is elevated with respect to the upper surface of the bite tray 3112 and/or bite pad 3114. The ridge 3118 can extend between the inner perimeter 3115 of the bite pad 3114 and the outer perimeter 3117 of the bite pad 3114. The ridge 3118 facilitates positioning of the mouthpiece 3110 within the patient's oral cavity. For example, the mouthpiece 3110 is configured to be positioned within the patient's oral cavity such that the ridge 3118 is disposed between the patient's front central incisors (on either the upper jaw or the lower jaw). Proprioception of the patient related to the teeth and periodontium can produce sensory feedback to the patient regarding the position of the ridge 3118 of the mouthpiece 3110.

In this manner, the ridge 3118 facilitates centering of the mouthpiece 3110 within the oral cavity, thus promoting symmetry of a light therapy treatment on the alveolus, or other oral tissue, on both sides of the patient's mouth. In other words, in order to promote the symmetrical administration of light therapy to the root area, the mouthpiece 3110 can be positioned with the midline M of the mouthpiece 3110 seated along the sagittal plane or within (i.e., plus or minus) 5 degrees of the sagittal plane, and the ridge 3118 can facilitate such positioning in use. The ridge 3118 can have any suitable shape, including, for example, the shape of an inverted V, such that the point of the V can be disposed between the patient's front central incisors.

As noted above, the upper portion of the mouthpiece 3110 comprises outer and inner flanges. The outer flanges comprise an outer first (or left) flange 3122 and an outer second (or right) flange 3124. The inner flanges comprise an inner first (or left) flange 3121, an inner second (or middle) flange 3123, and an inner third (or right) flange 3125. Although the outer and inner flanges are shown and described herein as including two and three flanges, respectively, in other embodiments, a mouthpiece can comprise a different number of outer and/or inner flanges.

The upper portion (i.e., the flanges 3122, 3124, 3121, 3123, 3125) of the mouthpiece 3110 is disposed transversely with respect to the bite plate 3114. The flanges 3122, 3124, 3121, 3123, 3125 are configured to be disposed, when the mouthpiece 3110 is disposed within the patient's mouth, such that the bite tray 3112 is adjacent an occlusal surface of the patient's teeth, adjacent a portion of a side of the patient's teeth and/or adjacent the alveolar mucosa. For example, the outer flanges 3122, 3124 can be disposed adjacent a portion of a buccal side of the patient's teeth and/or adjacent a buccal side of the alveolar mucosa. In this manner, a light array 3142 enclosed in the outer flanges 3122, 3124 (also referred to herein as "first light array"), as described in more detail herein, is useful for administering light to the patient's teeth and/or alveolar mucosa (e.g., towards the buccal side of the patient's teeth and/or alveolar mucosa). In another example, the inner flanges 3121, 3123, 3125 can be disposed adjacent a portion of a lingual or palatial side of the patient's teeth and/or adjacent a lingual or palatial side of the alveolar mucosa. In this manner, a light array 3143 enclosed in the inner flanges 3121, 3123, 3125 (also referred to herein as "second light array"), as described in more detail herein, is useful for administering light to the patient's teeth and/or alveolar mucosa (e.g., towards the lingual or palatial side of the patient's teeth and/or alveolar mucosa).

The outer flanges 3122, 3124 collectively contain the first light array 3142, and are each configured to be disposed between the buccal tissue and the alveolus. Thus, in use, the outer flanges 3122 and 3124 displace oral soft tissue to maintain the desired position of the light array 3142 relative to the anatomy of the patient. More specifically, the outer flanges 3122, 3124 are each configured to displace buccal tissue away from the patient's alveolus. In one or more embodiments, an inner face 3126 of the outer flanges 3122, 3124 can be spaced apart from the patient's alveolar tissue when the mouthpiece 3110 is disposed within the patient's mouth and the outer flanges 3122, 3124 are displacing the buccal tissue. In one or more embodiments, at least a portion of the inner face 3126 of the outer flanges 3122, 3124 can contact the patient's alveolar tissue when the mouthpiece 3110 is disposed within the patient's mouth and the outer flanges 3122, 3124 are displacing the buccal tissue.

The inner flanges 3121, 3123, 3125 collectively contain the second light array 3143, and are each configured to be disposed between the patient's tongue and/or palate and the alveolus. Thus, in use, the inner flanges 3121, 3123, 3125 can displace oral soft tissue to maintain the desired position of the second light array 3143 relative to the anatomy of the patient. More specifically, the inner flanges 3121, 3123, 3125 are each configured to displace lingual tissue away from, or otherwise prevent the lingual tissue from contacting, the patient's alveolus. In one or more embodiments, an inner face 3127 of the inner flanges 3121, 3123, 3125 (see FIG. 129) can be spaced apart from the patient's alveolar tissue when the mouthpiece 3110 is disposed within the patient's mouth and the inner flanges 3121, 3123, 3125 are displacing the lingual tissue. In one or more embodiments, at least a portion of the inner face 3127 of the inner flanges 3121, 3123, 3125 can contact the patient's alveolar tissue when the mouthpiece 3110 is disposed within the patient's mouth and the inner flanges 3121, 3123, 3125 are displacing the lingual tissue.

The flanges 3122, 3124, 3121, 3123, 3125 of the mouthpiece 3110 are configured to be flexible and/or deformable. Similarly stated, the flanges 3122, 3124, 3121, 3123, 3125 are constructed from a material and have geometrical dimensions and/or configurations to provide the desired flexibility, as described herein. Moreover, each of the outer first and second flanges 3122, 3124 and the inner first, second and third flanges 3121, 3123, 3125 is independently deflectable, movable and/or deformable with respect to the mouthpiece 3110 and/or each other. In this manner, the mouthpiece 3110 can be easily disposed within the oral cavity for a variety of different patients having a variety of different anatomical structures, as described herein.

For example, the mouthpiece 3110 comprises particular geometric features (e.g., stress concentration risers, areas having a desired bending moment of inertia, etc.) to produce the desired flexibility, deformability and durability in connection with the material(s) from which the mouthpiece 3110 is constructed. As shown, the mouthpiece 3110 defines a notch 3130 and grooves 3132, 3133 configured to permit, or otherwise increase the ability of, the outer flanges 3122, 3124 to deflect inwardly towards the teeth, gums, jaw, or the like (as described above with respect to mouthpiece 312510 and FIG. 90). As shown in FIGS. 128-131, the mouthpiece 3110 defines the notch 3130 aligned with the midline M of the mouthpiece and between upper portions of the outer first flange 3122 and the outer second flange 3124. The notch 3130 is configured to permit the independent and/or inward deflection of each of the outer first flange 3122 and the outer second flange 3124, for example, in response to pressure from the patient's lip or inner cheek. In particular, the outer flanges 3122, 3124 are each configured to deflect inwardly with respect to the bite pad 3114. Similarly stated, when the mouthpiece 3110 is outside of the mouth in an undeformed state (i.e., a first configuration), the outer first flange 3122 and the outer second flange 3124 are each approximately perpendicular (e.g., at about 90 degrees) to the bite pad 3114. When the mouthpiece 3110 is disposed inside the mouth, the upper portion of the mouthpiece 3110 and/or the outer flanges 3122, 3124 are sufficiently flexible such that an angle formed between each outer flange 3122, 3124 and the bite pad 3114 (an "outer flange angle") is acute. This "tipping in" allows the outer flanges 3122, 3124 to conform to the interior surfaces of the mouth, thereby promoting the desired alignment of the light array 3142 relative to the bone and/or teeth.

The configuration of the notch 3130, including its shape and dimensions, can be similar in many respects, or identical, to notch 2530 described herein (e.g., with respect to FIG. 90), and thus is not described in detail with respect to mouthpiece 3110. For example, in one or more embodiments, an edge of each outer flange 3122, 3124 that forms a respective side of the notch 3130 tapers towards the point of a V-shape of the notch, which point can be substantially aligned (e.g., plus or minus about 5 degrees) with an upper edge of the grooves 3132, 3133. In another example, in other embodiments, the portion of the mouthpiece 3110 that defines a lower boundary of the notch 3130 can be in any suitable location relative to the grooves 3132, 3133 (e.g., either above or below the grooves).

The mouthpiece 3110 defines at least one groove 3132, 3133 defined by a lower outer (or front) surface of each of the outer first and second flanges 3122, 3124. For example, the mouthpiece 3110 comprises the first groove 3132 and the second groove 3133, each defined by the outer or front surface 3128 of the mouthpiece 3110. The grooves 3132, 3133 can each be similar in many respects, or identical, to grooves 2532, 2533 described with respect to mouthpiece 2510 and FIGS. 84-113. The grooves 3132, 3133 are each disposed at a height between the bite pad 3114 and a lower edge of a flexible circuit board 3146 (see, e.g., FIGS. 129 and 131) of the mouthpiece 3110. Stated another way, the grooves 3132, 3133 can be defined by a base portion of each of the outer first and second flanges 3122, 3124. The grooves 3132, 3133 each extend about the outer surface 3128 of the mouthpiece 3110 between the posterior end portion of the mouthpiece 3110 and an anterior end portion of the mouthpiece 3110, such that a first end 3134, 3135 of each groove 3132, 3133, respectively, is at or proximate to the posterior end portion of the mouthpiece 3110 and a second end 3136, 3137 of each groove 3132, 3133, respectively, is at or proximate to the anterior end of the mouthpiece 3110.

Figure 129:
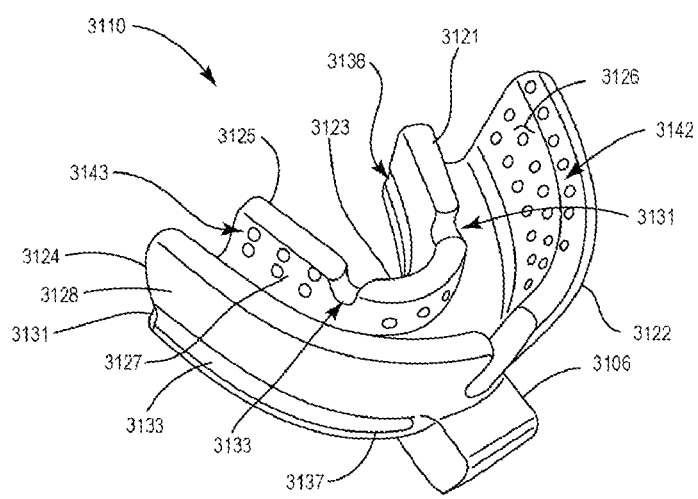
FIG. 129 is a perspective view of the light therapy apparatus of FIG. 128.
Figure 132:
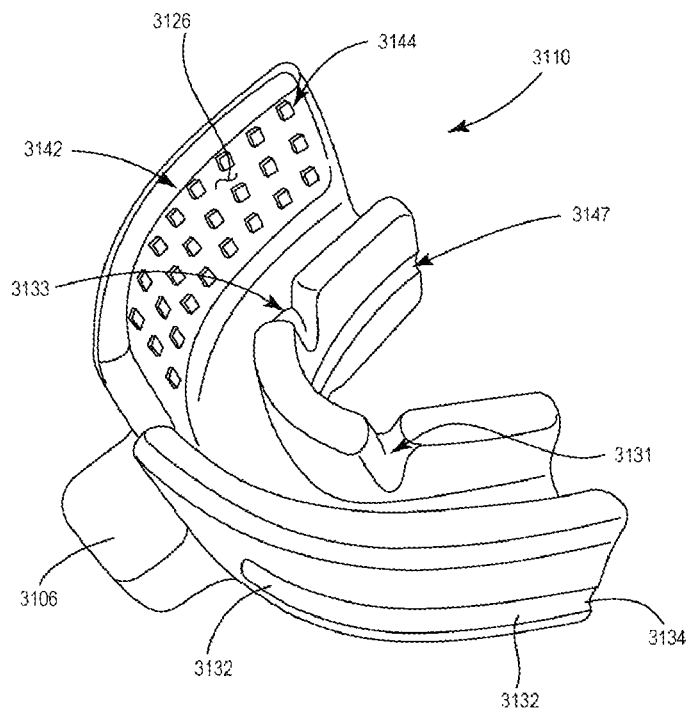
FIG. 132 is a perspective view of the light therapy apparatus of FIG. 128.

As shown in FIGS. 129 and 132, the second ends 3136, 3137 of the grooves 3132, 3133 can be spaced apart. In other words, the second ends 3136, 3137 of the grooves 3132, 3133 do not necessarily meet at the anterior end of the mouthpiece 3110. Similarly stated, the grooves 3132, 3133 are noncontiguous and/or do not share a common boundary. For example, the second ends 3136, 3137 of the grooves 3132, 3133 can be spaced apart by a width of a bridge 3106 extending from the front of the mouthpiece 3110. In another example, the second ends 3136, 3137 of the grooves 3132, 3133 can be spaced apart by a distance at least as great as a width of the notch 3130. The grooves 3132, 3133 can have any suitable shape, including, for example, that of a semi-circle or U-shape. The grooves 3132, 3133 produce a hinge-like structure (i.e., a "living hinge") about which the flanges 3122, 3124 can rotate, bend and/or deflect. In this manner, the grooves 3132, 3123 and the notch 3130 collectively permit the flanges 3122, 3124 to deflect inwardly, for example, in response to pressure from the patient's lip or inner cheek.

As such, the grooves 3132, 3133 and the notch 3130 collectively facilitate the transition of the mouthpiece 3110 between a first configuration and a second configuration. When the mouthpiece 3110 is in the first configuration, the angle formed between each flange 3122, 3124 and the bite pad 3114 (the "outer flange angle") has a first value. When the mouthpiece 3110 is in the second configuration, the outer flange angle has a second value that is different from the first value. In particular, the mouthpiece 3110 can be moved to the second configuration when disposed within the patient's mouth. In one or more embodiments, the second value is less than the first value (i.e., the outer flanges 3122, 3124 "tip" inwardly toward the bite plate 3112 when the mouthpiece 2510 is inserted into the mouth). In one or more embodiments, the outer flange angle is approximately 90 degrees when the mouthpiece is in the first configuration and is acute when the mouthpiece is in the second configuration. In one or more embodiments, the outer flange angle is about 80 degrees (e.g., the outer flanges 3122, 3124 tip inward toward the bite plate 3112 by about 10 degrees) when the mouthpiece is in the second configuration. In other embodiments, the outer flange angle is between about 75 degrees and about 80 degrees (e.g., the outer flanges 3122, 3124 tip inward toward the bite plate 3112 by between about 10 degrees and 15 degrees). In yet other embodiments, the outer flange angle is approximately 85 degrees, 75 degrees, 70 degrees, or 65 degrees (e.g., the outer flanges 3122, 3124 tip inward toward the bite plate by about 5 degrees, 15 degrees, about 20 degrees and about 25 degrees, respectively) when the mouthpiece is in the second configuration.

As shown, the mouthpiece 3110 also defines notches 3131, 3131' configured to permit, or otherwise increase the ability of, the inner flanges 3121, 3123, 3125 to deflect inwardly towards the bite plate 3112 (or outwardly towards the teeth, gums, jaw, or the like in a direction opposite to the inward deflection described above with respect to outer flanges 3122, 3124). As shown in FIGS. 129-131, the mouthpiece 3110 defines a first notch 3131 between upper portions of the first and second inner flanges 3121, 3123 of the mouthpiece, and a second notch 3131' between upper portions of the second and third inner flanges 3123, 3125 of the mouthpiece. Each notch 3131, 3131' of the inner flanges 3121, 3123, 3125 can be positioned on the mouthpiece 3110 equidistant from the midline M. An edge of the first and second inner flanges 3121, 3123 forms a respective side of the first notch 3131. An edge of the second inner flange 3123 (different from the edge forming a side of the first notch 3131) and an edge of the third inner flange 3123 form respective sides of the second notch 3131'.

The first and second notches 3131, 3131' are configured to permit the independent and/or inward deflection of each of the inner first, second and third flanges 3121, 3123, 3125, for example, in response to pressure from the patient's tongue. In particular, the inner flanges 3121, 3123, 3125 are each configured to deflect inwardly with respect to the bite pad 3114. Similarly stated, when the mouthpiece 3110 is outside of the mouth in its first configuration, in an undeformed state, the inner first, second and third flanges 3121, 3123, 3125 are each approximately perpendicular to the bite pad 3114. When the mouthpiece 3110 is disposed inside the mouth, the upper portion of the mouthpiece 3110 and/or the inner flanges 3121, 3123, 3125 are sufficiently flexible such that an angle formed between each inner flange 3121, 3123, 3125 and the bite pad 3114 (an "inner flange angle") is acute. This "tipping in" allows the inner flanges 3122, 3124 to conform to the interior surfaces of the mouth, thereby promoting the desired alignment of the second light array 3143 relative to the bone and/or teeth.

The first and second notches 3131, 3131' of the inner flanges 3121, 3123, 3125 can have any suitable shape and/or dimension. As shown in FIGS. 129 and 132, an upper portion of the notches 3131, 3131' can be U-shaped. In one or more embodiments, a lower portion of the notches 3131, 3131' can be a vertically elongate opening or slit extended from the U-shaped upper portion of each notch 3131, 3131'. In one or more embodiments, the lower portion of each notch 3131, 3131' can comprise an unbroken portion of material disposed adjacent a lower end of the U-shaped portion. The lower portion of each notch 3131, 3131' has a thickness less than a thickness of an adjacent inner flange (e.g., flange 3121, 3123, 3125) and is configured to separate, break, and/or otherwise tear, when a deflection force is applied to one or more of the inner flanges 3121, 3123, 3125. In this manner, the lower portion of each notch 3131, 3131' can be configured, to separate, break, and/or otherwise tear, when the mouthpiece is in its second configuration within the patient's mouth to form a vertically elongate opening or slit extended from the lower end of the U-shaped portion of the notch.

The mouthpiece 3110 can define a groove 3138 defined by a lower outer (or rear) surface of the inner flanges 3121, 3123, 3125. For example, as shown in FIG. 131, the mouthpiece 3110 comprises the groove 3138 defined by an outer or rear surface of the mouthpiece 3110. The groove 3138 can be similar in many respects, or identical, to grooves 3132, 3133. The groove 3138 is disposed at a height between the bite pad 3114 and a lower edge of a flexible circuit board 3147 (see, e.g., FIG. 131) of the mouthpiece 3110. Stated another way, the groove 3138 can be collectively defined by a base portion of each of the first, second and third inner flanges 3121, 3123, 3125, such that such that ends of the groove 3138 are each at or proximate to the posterior end portion of the mouthpiece 3110.

The groove 3138 can have any suitable shape, including, for example, that of a semi-circle or U-shape. The groove 3138 produces a hinge-like structure (i.e., a "living hinge") about which the inner flanges 3121, 3123, 3125 can rotate, bend and/or deflect. In this manner, the groove 3128 and the first and second notches 3131, 3131' collectively permit the inner flanges 3121, 3123, 3125 to deflect inwardly with respect to the bite plate (or outwardly with respect to the tongue and/or palate), for example, in response to pressure from the patient's tongue.

As such, the groove 3138 and the first and second notches 3131, 3131' collectively facilitate the transition of the mouthpiece 3110 between its first configuration and its second configuration. When the mouthpiece 3110 is in the first configuration, the angle formed between each inner flange 3121, 3123, 3125 and the bite pad 3114 (the "inner flange angle") has a first value. When the mouthpiece 3110 is in the second configuration, the inner flange angle has a second value that is different from the first value. In particular, the mouthpiece 3110 can be moved to the second configuration when disposed within the patient's mouth. In one or more embodiments, the second value is less than the first value (i.e., the inner flanges 3121, 3123, 3125 3124 "tip" inwardly towards the bite plate when the mouthpiece 2510 is inserted into the mouth). In one or more embodiments, the inner flange angle is approximately 90 degrees when the mouthpiece is in the first configuration and is acute when the mouthpiece is in the second configuration. In one or more embodiments, the inner flange angle is about 80 degrees (e.g., the inner flanges 3121, 3123, 3125 tip inward towards the bite plate by about 10 degrees) when the mouthpiece is in the second configuration. In other embodiments, the inner flange angle is between about 75 degrees and about 80 degrees (e.g., the inner flanges 3121, 3123, 3125 tip inward toward the bite plate by between about 10 degrees and 15 degrees). In yet other embodiments, the inner flange angle is approximately 85 degrees, 75 degrees, 70 degrees, or 65 degrees (e.g., the inner flanges 3121, 3123, 3125 tip inward towards the bite plate by about 5 degrees, 15 degrees, about 20 degrees and about 25 degrees, respectively) when the mouthpiece is in the second configuration.

The flexibility of the mouthpiece 3110, and of the flanges 3122, 3124, 3121, 3123, 3125 in particular, provides significant advantages. For example, in contrast to mouthpieces constructed of a hard plastic and/or with a permanent set (or shape), the current arrangement allows for easier insertion and better conformance to the oral tissue of the patient. The flexibility of the mouthpiece 3110 also accommodates variation in patient anatomy (whether between two different patients or for the same patient as that patient's anatomy changes over time). For example, some patients have a pronounced overbite and may need more or less than a 10 degree inward deflection (or "tip-in"). In such instances, the mouthpiece 3110 can conform to the internal structure and/or anatomy within the patient's mouth. As another example, as the orthodontia for a patient works over time, the patient's dental anatomy will change. Accordingly, the mouthpiece 3110 can conform to the internal structure and/or anatomy within the patient's mouth to accommodate such change without requiring new mouthpiece moldings or the like.

Finally, the flexible design of the mouthpiece 3110 provides greater comfort for the patient than would be provided by mouthpieces constructed of a hard plastic.

Additionally, the flexible nature of the mouthpiece 3110 and/or the flanges 3122, 3124, 3121, 3123, 3125 provides manufacturing benefits. In particular, fabrication and/or molding of a mouthpiece having an acute angle between the bite surface and the side surface of the flange (i.e., the internal angle of the flange or the "flange angle") can be difficult. The design of the mouthpiece 3110, however, allows for the molding and/or fabrication to be performed with a flange angle of approximately ninety degrees (or greater), while allowing for an in-use flange angle that is acute (e.g., when the mouthpiece 3110 is in the second configuration, as described above). The mouthpiece 3110 of the light therapy apparatus 3100 comprises an electronics assembly 3140, generally shown in FIG. 131. The electronics assembly 3140 can be similar in many respects, or identical to, the electronics assembly 2540 of mouthpiece 2510 described herein (e.g., with respect to FIGS. 93-95). As shown, a first portion of the electronics assembly 3140 of the mouthpiece 3110 is disposed primarily in the flanges 3122, 3124. The first portion of the electronics assembly 3140 comprises a light array 3142 and a flexible circuit board 3146. A second portion of the electronics assembly 3140 is disposed primarily in the inner flanges 3121, 3123, 3125. The second portion of the electronics assembly 3140 comprises a light array 3143 and a flexible circuit board 3147. The light arrays 3142, 3143 each comprise one or more light emitters 3144, 3145, such as a plurality of LEDs. The light emitters 3144, 3145 are electrically and/or physically coupled to the flexible circuit boards 3146, 3147, respectively (only a portion of the flexible circuit board 3147 is shown in FIG. 109). The flexible circuit boards 3146, 3147, respectively, electrically couple the light emitters 3144, 3145, respectively, to electronic circuitry outside of the mouthpiece 3110 (e.g., in an extra-oral housing or via electrical connectors to an external controller, not shown). In this manner, the light emitters 3144, 3145, respectively, can receive power and/or a signal to produce the desired light, as described herein.

Referring to FIG. 131, the light emitters 3144 of the first portion of the electronics assembly 3140 are disposed on a first, palatial (or lingual) side of the flexible circuit board 3146 of the first portion of the electronics assembly. The light emitters 3145 of the second portion of the electronics assembly 3140 are disposed on a buccal side of the flexible circuit board 3147 of the second portion of the electronics assembly. In this manner, the light emitters 3144, 3145 are configured to emit light toward a patient's teeth and/or adjacent oral tissue when the mouthpiece 3110 is disposed within the patient's mouth. Stated another way, the light emitters 3144 are configured to emit light towards the anterior root area of an upper and/or lower jaw and/or the buccal alveolar soft tissue and the light emitters 3145 are configured to emit light towards a posterior root area of an upper and/or lower jaw and/or the lingual alveolar soft tissue.

The light emitters 3144, 3145 can be configured to emit light at any suitable intensity, wavelength and/or frequency described herein. For example, in one or more embodiments, the light emitters 3144, 3145 can be configured to emit light in the infrared or near infrared wavelength range. For example, in one or more embodiments, the light emitters 3144, 3145 are configured to emit light at a wavelength of about 850 nm. In one or more embodiments, the light emitters 3144, 3145 are configured to emit light at a wavelength of 850 nm±5 nm. The light emitters 3144, 3145 can be configured to emit light sufficient deliver light energy to the patient's bone to facilitate and/or perform any of the methods described herein. The light emitters 3144, 3145 can be configured to emit light at less than 150 mW/cm 2.

The light emitters 3144, 3145 can be disposed on the flexible circuit boards 3146, 3147, respectively, and/or within the flanges 3122, 3124 and the inner flanges 3121, 3123, 3125, respectively, in any suitable configuration, including any configuration described herein. For example, in one or more embodiments, the light emitters 3144, 3145 are LEDs coupled to the flexible circuit boards 3146, 3147 in two or more parallel rows and/or columns. In one or more embodiments, the light emitters 3144 are coupled to the flexible circuit board 3146 of the first portion of the electronics assembly 3140 in three parallel rows, and the light emitters 3145 are coupled to the flexible circuit board of the second portion of the electronics assembly in two parallel rows.

The light array 3142 of the first portion of the electronics assembly 3140 can comprise about 54 light emitters 3144, or LEDs, with about 27 light emitters embedded in the first flange 3122 and about 27 light emitters 3144 embedded in the second flange 3124. The 27 light emitters 3144 can be arranged in any suitable configuration, including for example in nine evenly spaced columns with three spaced apart light emitters, or LEDs, per column. The light array 3143 of the second portion of the electronics assembly 3140 can comprise about 18 or 20 light emitters 3145, or LEDS, with about 6 light emitters embedded in each of the first and third inner flanges 3121, 3125, and 6 light emitters embedded in the second (or middle) panel 3123. The 6 light emitters 3145 can be arranged in any suitable configuration, including, for example, in three evenly spaced columns with two spaced apart light emitters, or LEDs, per column. The flexible circuit boards 3146, 3147 and light emitters 3144, 3145 can have any suitable dimensions for being coupled to, or embedded in, the outer flanges 3122, 3124 and the inner flanges 3121, 3123, 3125, respectively, of the mouthpiece 3110.

Figure 133:
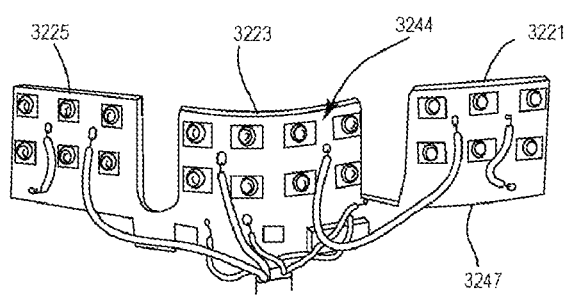
FIG. 133 is a front view of a portion of a light therapy apparatus according to an embodiment.

Although the mouthpiece 3110 has been shown as including 6 light emitters 3145 embedded in the inner flanges 3121, 3123, 3125, in other embodiments, the mouthpiece can comprise a different number of light emitters in the inner flanges, and each inner flange can comprise a different number of light emitters than another inner flange. For example, as shown in FIG. 133, a flexible circuit board 3247 comprises first and third portions 3221, 3225, each having six (6) light emitters in two evenly spaced rows configured to be disposed in each of a first and third inner flange (not shown in FIG. 133) and a middle portion 3223 having eight (8) light emitters 3244 in two evenly spaced rows and configured to be disposed in a second (or middle) inner flange (not shown in FIG.

133). As also shown in FIG. 133, the flexible circuit board 3247 is configured such that its first portion 3221 is spaced apart from its second portion 3223, and its second portion is spaced apart from its third portion 3225, which facilitates the deflection (or "tipping in") of the inner flanges.

Returning to FIGS. 128-132, although the light emitters 3144 are shown as being evenly spaced within their respective flanges 3122, 3124 or inner flanges 3121, 3123, 3125, in other embodiments, the light emitters can be unevenly spaced within their respective flanges 3122, 3124 and/or inner flanges 3121, 3123, 3125. For example, in one or more embodiments, a mouthpiece can comprise a series of light emitters that are spaced apart by a first amount near the anterior portion of the mouthpiece and a second, different amount near the posterior portion of the mouthpiece. Light emitters of the series of light emitters can be disposed on or in the mouthpiece.

The mouthpiece 3110 can be constructed of any suitable material, including, for example, any material described herein with respect to mouthpiece 2510, and thus such material is not described in detail with respect to mouthpiece 3110. For example, the mouthpiece 3110 can be constructed of an elastomeric material (e.g., a soft silicone). In another example, the mouthpiece 3110 can be fabricated from medical-grade injection-molded, highly flexible and very low durometer silicone. In another example, the silicone and/or portions of the mouthpiece 3110 are substantially transparent, such that one or more components embedded within the silicone are visible through the silicone. Moreover, in this manner, the mouthpiece 3110 can provide suitable optical properties for allowing the light produced and/or conveyed by the light emitters 3144, 3145 to pass through the mouthpiece 3110 to the desired target tissue. In one or more embodiments, the mouthpiece 3110, the flanges 3122, 3124, and/or the inner flanges 3121, 3123, 3125 can comprise one or more components configured to filter, focus and/or otherwise act upon the light produced by the light emitters 3144, 3145. In other embodiments, the mouthpiece 3110 can comprise air gaps between the light emitters 3144, 3145 and the surface of the flanges 3122, 3124 and inner flanges 3121, 3123, 3125, respectively, to facilitate focusing of the light. As shown in FIGS. 128-132, however, the mouthpiece 3110 is constructed such that the light emitters 3144, 3145 are fully encapsulated or embedded within the molded silicone such that no space or air gap exists between the silicone material and the first and second portions of the electronics assembly 3140.

Similarly stated, the mouthpiece 3110 is devoid of an air gap between the light emitters 3144, 3145 and the material of the mouthpiece 3110, thus no air gap lensing is needed to produce the desired optical properties of the light produced by the light emitters 3144, 3145.

Figure 134:
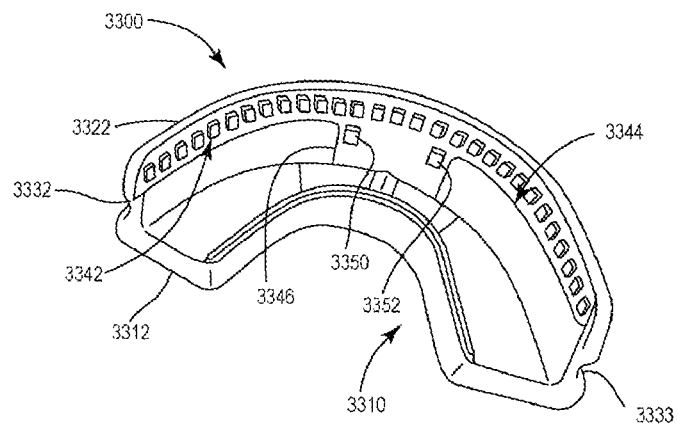
FIGS. 134-135 are rear perspective and rear views of a light therapy apparatus according to one or more embodiments.
Figure 135:
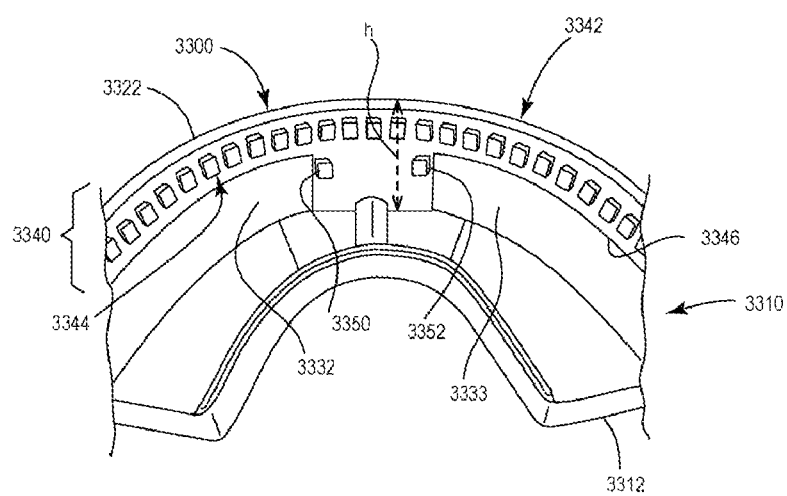

As shown in FIGS. 134-135, in one or more embodiments, the intraoral light therapy apparatus 3300 provided herein comprises a single row of light emitters such as LEDs 3342. The single row of LEDs, in one or more embodiments provides about 50 milliwatt (mW) to about 200 mW of light power per cm2, for example about 50 mW to about 150 mW per cm2. In a further embodiment, the light emitters of one of the therapy apparatuses provided herein that comprises a single row of light emitters provides about 100 mW per cm2 of light power.

As shown in FIGS. 134-135, in one or more embodiments the light therapy apparatus having a single row of light emitters 3300 (i.e., columns of light emitters with a single light emitter, e.g., LED per column) comprises an intra-oral housing or mouthpiece 3310 configured to be disposed within a mouth of a patient. The mouthpiece 3310 comprises a bite tray 3312, a flange 3322 transversely coupled to the bite tray, an electronics assembly 3340 including a light array 3342 and a flexible circuit board 3346. In one or more embodiments, the light therapy apparatus 3300 comprises an extra-oral housing (not shown) configured to be disposed outside the mouth of the patient.

The light emitters are coupled to the electronics assembly such that zones of the light emitters are individually addressable. One or more light emitters (e.g., one or more LEDs) can constitute a zone of light emitters. In one or more embodiments, from about 1 to about 20, from about 1 to about 15, from about 1 to about 10, or from about 1 to about 9, or from about 1 to about 8, or from about 1 to about 7, or from about 1 to about 6, or from about 1 to about 5, or from about 1 to about 4 light emitters are included in a zone of light emitters. It will be understood by one of skill in the art that the number of light emitters harnessed during light therapy will vary depending on patient presentation and ultimate treatment protocol.

The outer flange (also referred to as "buccal flange") of a single row light emitter light therapy apparatus provided herein can be characterized by a height "h". In one or more embodiments, the height "h" is about 1 cm, about 1.2 cm, about 1.5 cm, about 1.8 cm, about 2.1 cm, about 2.4 cm, about 2.7 cm or about 3 cm, including all values, ranges and subranges in between. As illustrated in FIGS. 134-135, in one or more embodiments, the outer flange 3322 can be relatively shorter, or have a lower profile, than the flange 3022 of the mouthpiece 3010.

In one or more embodiments, the outer flange 3322 can be relatively more rigid than the flange 3022 and/or 3024, while still providing a comfortable feel and fit to a user/patient. In one or more embodiments, the rigidity of the flange is achieved by not including a notch in the flange. Specifically, in one or more embodiments, the mouthpiece 3310 can comprise a single outer flange 3322 formed between the ends of the mouthpiece 3010 with a continuous top edge, such that there is no notch present, unlike the gap depicted in other embodiments, e.g., in the mouthpiece 3010 between the outer flange 3022 and the outer flange 3024.

As also illustrated in FIGS. 134-135, and as disclosed herein, in one or more embodiments, the light array 3342 includes a single row of light emitters such as LEDs. The reduced number of light emitters in the mouthpiece 3310 provides for reduced power consumption when compared to the mouthpiece 3010. In one or more embodiments, the number of light emitters in the light array 3342 is about 15, about 18, about 21, about 24, about 27, about 30, about 33, about 36, about 39, about 42, about 45, including all values and subranges in between. In one or more embodiments, the number of light emitters in the light array 3342 is greater than the number of light emitters in a single row of the light array 3042. In this manner, in one or more embodiments, the mouthpiece 3310 has relatively fewer light emitters than the mouthpiece 3010, but has a relatively greater density of light emitters, such that the optical power density during use can be similar, or even greater, with the mouthpiece 3310 than with the mouthpiece 3010. Generally, the power density of any of the light emitters disclosed herein can be about 30 $mW/cm^2$ about 40 $mW/cm^2$, about 50 $mW/cm^2$, about 60 $mW/cm^2$, about 80 $mW/cm^2$, about 100 $mW/cm^2$, about 120 $mW/cm^2$, about 140 $mW/cm^2$ about 150 $mW/cm^2$, including all values and sub ranges in between.

In one or more embodiments, the outer flange 3312 is sized such that the row of light emitters of the light array 3342 is positioned above the upper gum line of the patient during use. In some embodiments, the outer flange 3312 is sized such that the row of light emitters of the light array 3342 is positioned at the gum line of the patient during use, between the gum line and the most apical portion of the tooth root during use, or at the most apical portion of the tooth root during use.

In one or more embodiments, at least one or more portions of the mouthpiece 3310 are constructed from one or more substantially transparent materials (e.g., silicone) such that one or more components embedded within the mouthpiece 3310 are visible through the mouthpiece 3310. Thus, for purposes of illustration, portions of the mouthpiece 3310, including portions of the outer flange 3322, the bite tray 3312 is shown as being transparent in FIGS. 112 and 113 to show portions of the electronics assembly 3340 and the structure disposed therein. In one or more embodiments, multiple layers of material are used to increase the rigidity of the outer flange 3322.

The light therapy apparatus 3300 is configured to determine whether the mouthpiece 3310 is disposed within the patient's mouth (i.e., in a manner suitable for a treatment session, as described herein). In this manner, the light therapy apparatus 3300 can be configured to only irradiate light for the treatment session when the apparatus 3300 has determined that the mouthpiece 3310 is disposed in the patient's mouth. The mouthpiece 3310 comprises a first light emitter 3350 and a second light emitter 3352, each of which is configured and positioned to detect or measure an amount of light reflected by a portion of the patient's oral tissue. For example, the first and second light emitters 3350, 3352 can be configured to detect light emitted from the light emitters 3344 of the light array 3342 and reflected by the patient's oral soft tissue. In one or more embodiments, the light emitters 3344 can be configured to emit light, such as in a blinking or pulsing manner, and can be addressable individually, or in groups. The light emitters 3344 can be configured to blink or pulse at a predetermined rate. At least a portion of light emitted from the pulsing or blinking light emitters 3344 towards the oral soft tissue of the patient's mouth is reflected to the mouthpiece 3310 and is thereby detected by the first and second light emitters 3350, 3352. Suitable optical proximity thresholds (e.g., related to an amount of detected optical power reflected from skin of the patient) can be established and used in assessing whether the light emitters 3344 of the light array 3342 (and, by proxy, the mouthpiece 3310) are is properly disposed in the patient's mouth for administering a treatment session. The apparatus 3300 can be configured to initiate irradiation of the oral tissue (i.e., begin the treatment session) when the first and second light emitters 3350, 3352 detect the light reflection from the oral soft tissue.

Each of the first and second light emitters 3350, 3352, can be coupled to the flexible circuit board 3346 in any suitable location. In one or more embodiments, the first and second light emitters 3350, 3352 are disposed on the flexible circuit board 3346 such that each of the first and second light detectors 3350, 3352 is positioned close to the patient's gum when the mouthpiece 3310 is disposed within the patient's mouth. As shown in FIGS. 134-135, the first and second light emitters 3350, 3352 are each disposed offset from a single parallel row of light emitters 3344 of the light array 3342. Each of the first and second light detectors 3350, 3352 can be disposed between the single row (in the orientation of the apparatus 3300 shown in FIG. 135) of light emitters 3344 and the bite tray 3012 of the mouthpiece 3010. In one or more embodiments, the first and second light emitters 3350, 3352 are substantially level with grooves 3332, 3333 (e.g., protruding or regressed by no more than 2-3 mm) defined by an outer face of the mouthpiece 3310. In use, when light is emitted from the light emitters 3344 of the light array 3342, the first and second light emitters 3350, 3352 each measure and/or produce a signal associated with an amount of light reflected by the patient's oral tissue (e.g., the gum). As such, the first and second light emitters 3350, 3352 act as a sensor configured to detect reflected light. Each of the first and second light emitters 3350, 3352 in one or more embodiments, comprises a diode (not shown in FIGS. 134-135) configured to produce an electrical current associated with the amount of light detected or received. The first and second light emitters 3350, 3352, and their one or more diodes, can be configured to send a signal associated with the measured reflected light to a controller (e.g., in an extra-oral housing or bill) of the light therapy apparatus 3300. In one or more embodiments, the one or more diodes of the first and second light emitters 3350, 3352 are configured to measure reflected light at about 815 nm, about 820 nm, about 825 nm, about 830 nm, about 835 nm, about 840 nm, about 845 nm, about 850 nm, about 855 nm, about 860 nm, about 865 nm, about 870 nm, about 875 nm, about 880 nm, about 885 nm, about 890 nm, about 895 nm, about 900 nm, including all values and subranges in between.

At least a portion of the first and second light emitters 3350, 3352 can be fully or at least partially embedded in the outer flange 3322 of the mouthpiece 3310, for example, in a similar manner as disclosed herein with respect to the light array 2542. The first and second light emitters 3350, 3352 are spaced apart on the flexible circuit board 3346. In one or more embodiments, the first and second light emitters 3350, 3352 are disposed at opposing locations with respect to the flexible circuit board 3346, as shown in FIG. 135. In this manner, the apparatus 3300 is configured to detect reflected light bilaterally.

As disclosed herein, the first and second light emitters 3350, 3352 are configured to be disposed in close proximity (e.g., based on measurement of reflected light in response to irradiance) to the patient's oral (e.g., gum) tissue when the mouthpiece 3310 is disposed within the patient's mouth in preparation for treatment. The apparatus 3300 is configured to irradiate light only after a predetermined amount of reflected light has been measured. Stated another way, the apparatus 3300, and the controller more specifically, can be configured to turn on the light emitters 3344 for a treatment session only after the predetermined amount of reflected light has been measured. The measured amount of reflected light is registered by the controller, which is configured to execute an algorithm to register the amount of reflected light, when (1) the predetermined amount of reflected light is detected by each of the first and second light emitters 3350, 3352 (i.e., bilaterally), and/or (2) the predetermined amount of reflected light is detected for a predetermined duration (e.g., for at least 2 seconds).

An intra-oral housing 3610 (also referred to herein as a "mouthpiece") of a light therapy apparatus 3600 according to an embodiment is illustrated in FIGS. 136-140. In one or more embodiments, at least one or more portions of the mouthpiece 3610 are constructed from a substantially transparent material (e.g., silicone) such that one or more components embedded within the mouthpiece 3610 are visible through the mouthpiece 3610. Thus, for purposes of illustration, portions of the mouthpiece 3610, including portions of the outer flange 3622, are shown as being transparent in FIGS. 136-140 to show portions of the electronics assembly 3640 and the structure disposed therein. The light therapy apparatus 3600 can be included in a light therapy system that is similar in many respects to the light therapy system described herein with respect to FIGS. 84-113. The light therapy apparatus 3600 is configured to irradiate light in any suitable manner described herein, including, for example, to irradiate the alveolus and/or tooth root area of the patient. Similarly stated, the light therapy apparatus 3600 is configured to administer light therapy to a patient's teeth and/or oral mucosa. More specifically, the light therapy apparatus 3600 is configured to administer light to the patient's teeth and/or oral mucosa sufficient to accelerate orthodontic movement of the patient's teeth and to reduce the overall treatment time for the patient when undergoing orthodontic treatment. In this manner, aspects of bone health can be improved by usage of the light therapy apparatus 3600, alone or in combination with use of an orthodontic appliance, when compared with use of an orthodontic appliance in the absence of light therapy.

The light therapy apparatus 3600 can be the same as or similar in many respects to, or comprise components the same as or similar in many respects to, the intra-oral apparatuses described herein, including, for example, apparatus 2100, apparatus 2500, apparatus 3000, and apparatus 3100. However, as described above, the light therapy apparatus 3600 comprises a single row of light emitters in contrast to previously described embodiments. In addition, the light therapy apparatus 3600 has an increased rigidity in one or more embodiments, due to a flange with a continuous top edge, i.e., a notch is not present.

The light therapy apparatus 3600 (and any light therapy apparatus described herein) is configured to be useful in combination with traditional orthodontic treatment with an orthodontic appliance, such as brackets and wires, or aligners. Furthermore, in one or more embodiments, any light therapy shown and described herein can be used with any suitable orthodontic appliance, including, but not limited to, substantially transparent aligners. Such aligners are orthodontic appliances and are described above.

The intra-oral housing 3610 of the light therapy apparatus 3600 is configured to be disposed in an oral cavity (e.g., in the mouth, not shown in FIGS. 128-132) of a patient. The intra-oral housing 3610 can be configured to be electronically and/or physically coupled to an external controller. In one or more embodiments, for example, the intra-oral housing 3610 is configured to be coupled to an extra-oral housing (or "bill," not shown in FIGS. 136-140) that is disposed externally to the patient's mouth when the intra-oral housing (or mouthpiece) 3610 is disposed within the patient's mouth. The extra-oral housing can be similar in many respects, or identical, to the extra-oral housing 2560 described herein with respect to FIGS. 84-113, and thus is not described in detail with respect to light therapy apparatus 3600. In other embodiments, the intra-oral housing 3610 is configured to be coupled to the controller via one or more wire or cable connectors (not shown in FIGS. 136-140).

Figure 138:
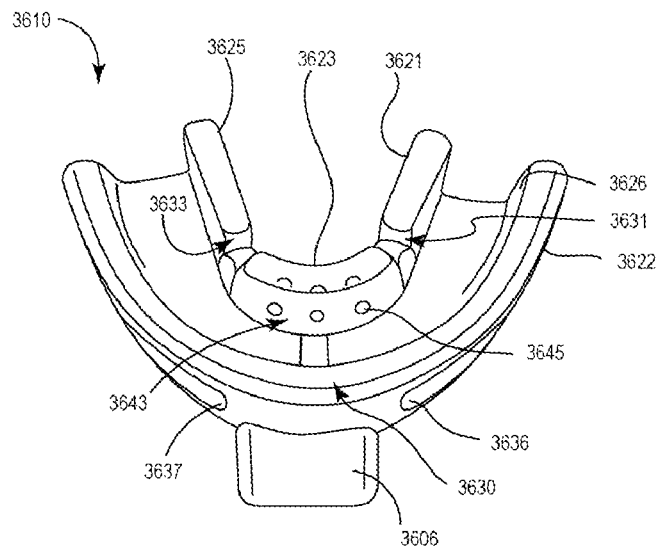
FIG. 138 is a top perspective view of the light therapy apparatus of FIG. 136.
Figure 139:
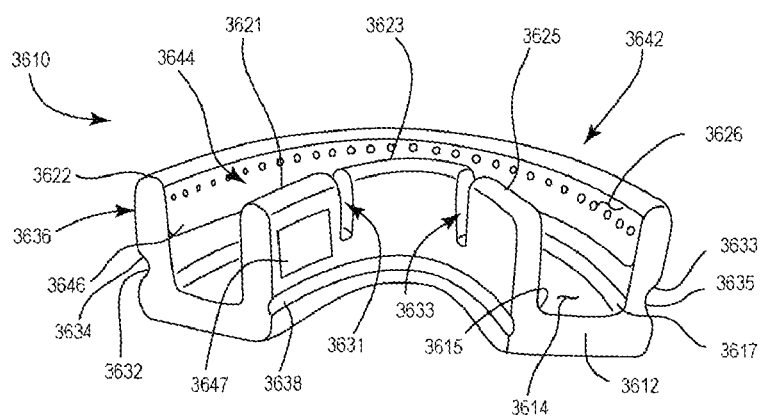
FIG. 139 is a rear view of the light therapy apparatus of FIG. 136.

The light therapy apparatus 3600 is configured to be useful for light therapy with the upper jaw and/or the lower jaw of the patient. In other words, the light therapy apparatus 3600 can be configured to administer light therapy with respect to the patient's upper jaw when the apparatus is in an upright position (e.g., as shown in FIG. 139), and can be configured to administer light therapy with respect to the patient's lower jaw when the apparatus is in an inverted position (not shown in FIGS. 136-140). As such, the mouthpiece 3610 is configured to be disposed within the patient's oral cavity with respect to each of the upper and lower jaws of the patient. Similarly stated, in one or more embodiments, the mouthpiece 3610 is configured to matingly adapt to both the upper jaw and the lower jaw, as described herein, thus eliminating the need for a separate mouthpiece for each jaw. It should be noted that although the light therapy apparatus 3600 generally, and the mouthpiece 3610 specifically, may be described as being in the upright position when configured to be oriented with respect to the upper jaw and in the inverted position when configured to be oriented with respect to the lower jaw, in other embodiments, the light therapy apparatus 3600 and the mouthpiece 3610 are in the upright position when configured to be oriented with respect to the lower jaw of the patient, and in the inverted position when configured to be oriented with respect to the upper jaw of the patient.

The mouthpiece 3610 can be similar in one or more respects, and comprise components similar in one or more respects to the intra-oral housings described herein, including, for example, the intra-oral housings or mouthpieces described herein with reference to FIGS. 35-37, 52-59, 65-72, 84-113, 126-127, and 134-135. The mouthpiece 3610 comprises a bite tray 3612, flanges 3622, 3621, 3623, 3625, light arrays 3642, 3643 (see, e.g., FIG. 139). The mouthpiece 3610 can optionally comprise a support plate (not shown in FIGS. 136-140) similar or identical to the support plate 2554 of mouthpiece 2510. The bite tray 3612 is configured to receive at least a portion of the patient's teeth of the upper and/or lower jaw. As such, the bite tray 3612 is generally U-shaped, as shown in FIG. 139. The bite tray 3612 is configured to facilitate proper positioning of the mouthpiece 3610 within the patient's mouth. The bite tray 3612 generally comprises the lower portion of the mouthpiece 3610. The bite tray 3612 comprises a bite pad 3614 with an inner perimeter (or side wall) 3615 and an outer perimeter (or side wall) 3617 (see FIG. 139).

Flanges 3622, 3621, 3623, 3625, described in more detail herein, generally define an upper portion of the mouthpiece 3610. The outer flange 3622 is coupled to the outer perimeter 3617 of the bite pad 3614. Inner flanges 3621, 3623, 3625 are coupled to the inner perimeter 3615 of the bite pad 3614. The flanges 3622, 3621, 3623, 3625 of the mouthpiece 3610 each extend and/or protrude from the bite pad 3614 in a first direction. As such, when the mouthpiece 3610 is disposed within the patient's mouth, the bite tray 3612 is positioned within the mouth such that the bite pad 3614 is adjacent the occlusal surface of one or more teeth, the outer flange 3622 is disposed between the one or more teeth and buccal tissue, and the inner flanges 3621, 3623, 3625 are disposed between the one or more teeth and the tongue and/or palate. Similarly stated, the bite tray 3612 is configured such that when the mouthpiece 3610 is disposed within a mouth, a least a portion of one or more teeth are positioned between the outer flange 3622 and the inner flanges 3621, 3623, 3625.

The bite tray 3612 can be similar in many respects, or identical, to the bite tray 2512 described with respect to FIGS. 84-113, and thus is not described in detail with respect to mouthpiece 3610. For example, the bite pad 3614 the bite tray 3612 can have any thickness suitable for receiving a bite force thereon, including a constant or spatially varied thickness as described with respect to bite pad 2514. In another example, the bite tray 3612 (and/or bite pad 3614) can be of any suitable dimensions, including those described herein with respect to bite tray 2512 (and/or bite pad 2514, respectively), and can be constructed of any suitable material, including those described herein with respect to bite tray 2512 (and/or bite pad 2514).

Figure 136:
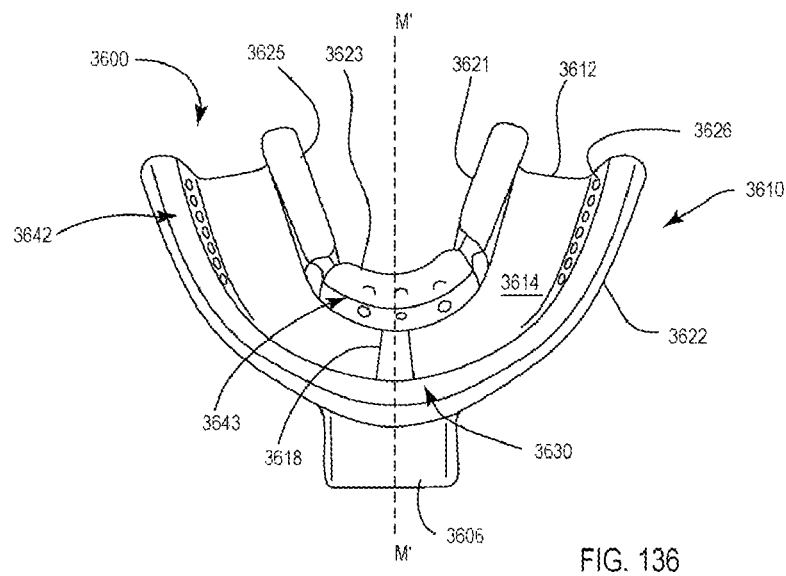
FIG. 136 is a top view of a light therapy apparatus according to one or more embodiments.

As shown in FIG. 136, in one or more embodiments, an upper surface of the bite pad 3614 comprises a ridge 3618. The ridge 3618 is disposed along a midline M' of the mouthpiece 3610 and is elevated with respect to the upper surface of the bite tray 3612 and/or bite pad 3614. The ridge 3618 can extend between the inner perimeter 3615 of the bite pad 3614 and the outer perimeter 3617 of the bite pad 3614. The ridge 3618 facilitates positioning of the mouthpiece 3610 within the patient's oral cavity. For example, the mouthpiece 3610 is configured to be positioned within the patient's oral cavity such that the ridge 3618 is disposed between the patient's front central incisors (on either the upper jaw or the lower jaw). Proprioception of the patient related to the teeth and periodontium can produce sensory feedback to the patient regarding the position of the ridge 3618 of the mouthpiece 3610.

In this manner, the ridge 3618 facilitates centering of the mouthpiece 3610 within the oral cavity, thus promoting symmetry of a light therapy treatment on the alveolus, or other oral tissue, on both sides of the patient's mouth. In other words, in order to promote the symmetrical administration of light therapy to the root area, the mouthpiece 3610 can be positioned with the midline M' of the mouthpiece 3610 seated along the sagittal plane or within (i.e., plus or minus) 5 degrees of the sagittal plane, and the ridge 3618 can facilitate such positioning in use. The ridge 3618 can have any suitable shape, including, for example, the shape of an inverted V, such that the point of the V can be disposed between the patient's front central incisors.

As noted above, the upper portion of the mouthpiece 3610 comprises an outer flange 3622 and inner flanges. The inner flanges comprise an inner first (or left) flange 3621, an inner second (or middle) flange 3623, and an inner third (or right) flange 3625. Although the outer flange and the inner flanges are shown and described herein as including one and three flanges, respectively, in other embodiments, a mouthpiece can comprise a different number of outer and/or inner flanges.

As illustrated in FIGS. 136-140, in one or more embodiments, the flange 3622 can be relatively shorter, or have a lower profile, than the flange 3122 of the mouthpiece 3110. In one or more embodiments, the flange 3622 can be relatively more rigid than the flange 3122 and/or 3124, while still providing a comfortable feel and fit to a user/patient. As also illustrated in FIGS. 136-140, in one or more embodiments, the mouthpiece 3610 can comprise a single outer flange 3622 formed between the ends of the mouthpiece 3610, such that there is no notch present, unlike the notch 3130 in the mouthpiece 3110 between the flange 3122 and the flange 3124.

As also illustrated in FIGS. 136-140, in one or more embodiments, the light array 3642 can comprise a single row of light emitters such as LEDs, and is differentiated in this manner from the light array 3142, which can comprise multiple rows and columns of light emitters. The reduced number of light emitters in the mouthpiece 3610 provides for reduced power consumption when compared to the mouthpiece 3110. In one or more embodiments, the number of light emitters in the light array 3642 is about 15, about 18, about 21, about 24, about 27, about 30, about 33, about 36, about 39, about 42, about 45, including all values and subranges in between. In one or more embodiments, the number of light emitters in the light array 3642 is greater than the number of light emitters in a single row of the light array 3142. In this manner, in one or more embodiments, the mouthpiece 3610 has relatively fewer light emitters than the mouthpiece 3110, but has a relatively greater density of light emitters, such that the optical power density during use can be similar, or even greater, with the mouthpiece 3610 than with the mouthpiece 3110. In one or more embodiments, the flange 3612 is sized such that the row of light emitters of the light array 3642 is positioned above the upper gum line of the patient during use.

The upper portion (i.e., the flanges 3622, 3622, 3623, 3625) of the mouthpiece 3610 is disposed transversely with respect to the bite plate 3614. The flanges 3622, 3621, 3623, 3625 are configured to be disposed, when the mouthpiece 3610 is disposed within the patient's mouth, such that the bite tray 3612 is adjacent an occlusal surface of the patient's teeth, adjacent a portion of a side of the patient's teeth and/or adjacent the alveolar mucosa. For example, the outer flange 3622 can be disposed adjacent a portion of a buccal side of the patient's teeth and/or adjacent a buccal side of the alveolar mucosa. In this manner, a light array 3642 enclosed in the outer flange 3622 (also referred to herein as "first light array"), as described in more detail herein, can be useful for administering light to the patient's teeth and/or alveolar mucosa (e.g., towards the buccal side of the patient's teeth and/or alveolar mucosa). In another example, the inner flanges 3621, 3623, 3625 can be disposed adjacent a portion of a lingual or palatial side of the patient's teeth and/or adjacent a lingual or palatial side of the alveolar mucosa. In this manner, a light array 3643 enclosed in the inner flanges 3621, 3623, 3625 (also referred to herein as "second light array"), as described in more detail herein, can be useful for administering light to the patient's teeth and/or alveolar mucosa (e.g., towards the lingual or palatial side of the patient's teeth and/or alveolar mucosa).

The outer flange 3622 contains the first light array (single row) 3642, and is configured to be disposed between the buccal tissue and the alveolus. Thus, in use, the outer flange 3622 displaces oral soft tissue to maintain the desired position of the light array 3642 relative to the anatomy of the patient. More specifically, the outer flange 3622 is configured to displace buccal tissue away from the patient's alveolus. In one or more embodiments, an inner face 3626 of the outer flange 3622 can be spaced apart from the patient's alveolar tissue when the mouthpiece 3610 is disposed within the patient's mouth and the outer flange 3622 is displacing the buccal tissue. In one or more embodiments, at least a portion of the inner face 3626 of the outer flange 3622 can contact the patient's alveolar tissue when the mouthpiece 3610 is disposed within the patient's mouth and the outer flange 3622 is displacing the buccal tissue.

Figure 137:
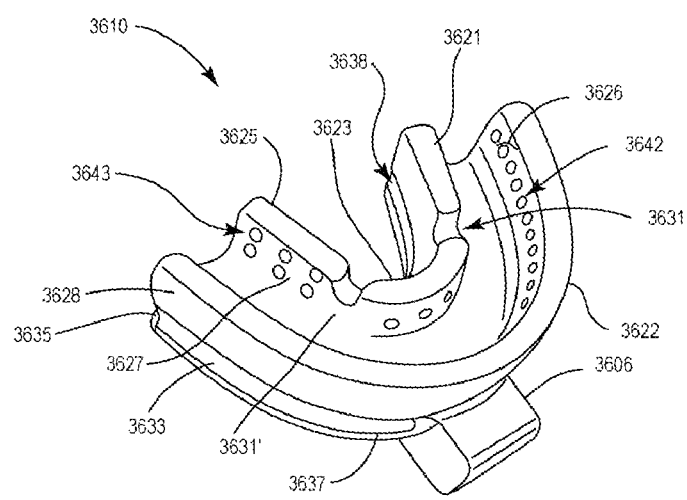
FIG. 137 is a perspective view of the light therapy apparatus of FIG. 136.

In some embodiment, the inner flange or inner flanges contain a second light array. For example, as shown in FIG. 137, the inner flanges 3621, 3623, 3625 collectively contain the second light array 3643, and are each configured to be disposed between the patient's tongue and/or palate and the alveolus. Thus, in use, the inner flanges 3621, 3623, 3625 can displace oral soft tissue to maintain the desired position of the second light array 3643 relative to the anatomy of the patient. More specifically, the inner flanges 3621, 3623, 3625 are each configured to displace lingual tissue away from, or otherwise prevent the lingual tissue from contacting, the patient's alveolus. In one or more embodiments, an inner face 3627 of the inner flanges 3621, 3623, 3625 (see FIG. 137) can be spaced apart from the patient's alveolar tissue when the mouthpiece 3610 is disposed within the patient's mouth and the inner flanges 3621, 3623, 3625 are displacing the lingual tissue. In one or more embodiments, at least a portion of the inner face 3627 of the inner flanges 3621, 3623, 3625 can contact the patient's alveolar tissue when the mouthpiece 3610 is disposed within the patient's mouth and the inner flanges 3621, 3623, 3625 are displacing the lingual tissue.

The outer flange 3622 and inner flanges 3621, 3623, 3625 of the mouthpiece 3610 are configured in one or more embodiments to be flexible and/or deformable. Similarly stated, the outer flange 3622 and the inner flanges 3621, 3623, 3625 are constructed from a material and have geometrical dimensions and/or configurations to provide the desired flexibility, as described herein. Moreover, each of the inner first, second and third flanges 3621, 3623, 3625 is independently deflectable, movable and/or deformable with respect to the mouthpiece 3610 and/or each other. In this manner, the mouthpiece 3610 can be easily disposed within the oral cavity for a variety of different patients having a variety of different anatomical structures, as described herein.

For example, the mouthpiece 3610 comprises particular geometric features (e.g., stress concentration risers, areas having a desired bending moment of inertia, etc.) to produce the desired flexibility, deformability and durability in connection with the material(s) from which the mouthpiece 3610 is constructed. As shown, the mouthpiece 3610 defines grooves 3632, 3633 configured to permit, or otherwise increase the ability of, the outer flange 3622 to deflect inwardly towards the teeth, gums, jaw, or the like (as described above with respect to mouthpiece 2510 and FIG. 90). In particular, the outer flange 3622 is configured to deflect inwardly with respect to the bite pad 3614. Similarly stated, when the mouthpiece 3610 is outside of the mouth in an undeformed state (i.e., a first configuration), the outer flange 3622 is approximately perpendicular (e.g., about 90 degrees) to the bite pad 3614. When the mouthpiece 3610 is disposed inside the mouth, the upper portion of the mouthpiece 3610 and/or the outer flange 3622 are sufficiently flexible such that an angle formed between the outer flange 3622 and the bite pad 3614 (an "outer flange angle") is acute. This "tipping in" allows the outer flange 3622 to conform to the interior surfaces of the mouth, thereby promoting the desired alignment of the light array 3642 relative to the bone and/or teeth.

The mouthpiece 3610 defines at least one groove 3632, 3633 defined by a lower outer (or front) surface of the outer flange 3622. For example, the mouthpiece 3610 comprises the first groove 3632 and the second groove 3633, each defined by the outer or front surface 3628 of the mouthpiece 3610. The grooves 3632, 3633 can each be similar in many respects, or identical, to grooves 2532, 2533 described with respect to mouthpiece 2510 and FIGS. 84-113, and to grooves 3132, 3133 described with respect to mouthpiece 3110 and FIGS. 128-132. The grooves 3632, 3633 are each disposed at a height between the bite pad 3614 and a lower edge of a flexible circuit board 3646 (see, e.g., FIGS. 137 and 139) of the mouthpiece 3610. Stated another way, the grooves 3632, 3633 can be defined by a base portion of the outer flange 3622. The grooves 3632, 3633 each extend about the outer surface 3628 of the mouthpiece 3610 between the posterior end portion of the mouthpiece 3610 and an anterior end portion of the mouthpiece 3610, such that a first end 3634, 3635 of each groove 3632, 3633, respectively, is at or proximate to the posterior end portion of the mouthpiece 3610 and a second end 3636, 3637 of each groove 3632, 3633, respectively, is at or proximate to the anterior end of the mouthpiece 3610.

Figure 140:
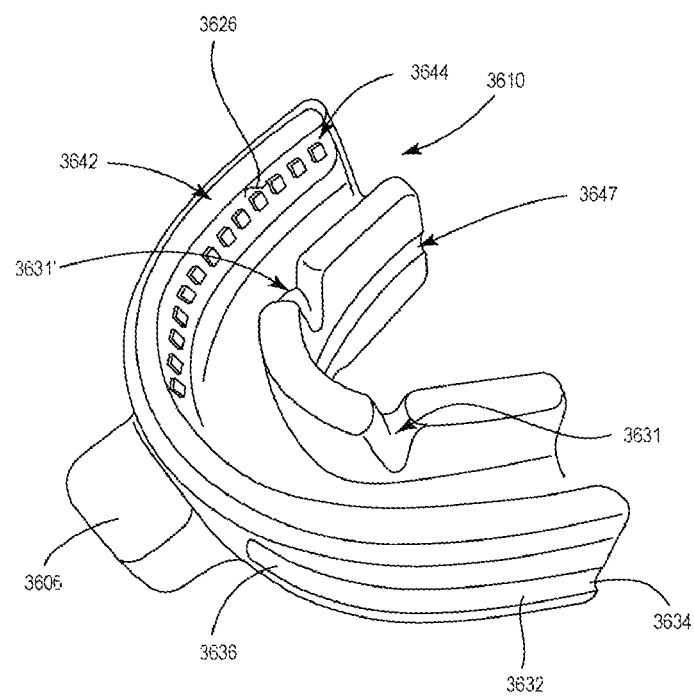
FIG. 140 is a perspective view of the light therapy apparatus of FIG. 136.

As shown in FIGS. 137 and 140, the second ends 3636, 3637 of the grooves 3632, 3633 can be spaced apart. In other words, the second ends 3636, 3637 of the grooves 3632, 3633 do not necessarily meet at the anterior end of the mouthpiece 3610. Similarly stated, the grooves 3632, 3633 are noncontiguous and/or do not share a common boundary. For example, the second ends 3636, 3637 of the grooves 3632, 3633 can be spaced apart by a width of a bridge 3606 extending from the front of the mouthpiece 3610. The grooves 3632, 3633 can have any suitable shape, including, for example, that of a semi-circle or U-shape. The grooves 3632, 3633 produce a hinge-like structure (i.e., a "living hinge") about which the outer flange 3622 can bend and/or deflect inwardly, for example, in response to pressure from the patient's lip or inner cheek.

As such, the grooves 3632, 3633 collectively facilitate the transition of the mouthpiece 3610 between a first configuration and a second configuration. When the mouthpiece 3610 is in the first configuration, the angle formed between the outer flange 3622 and the bite pad 3614 (the "outer flange angle") has a first value. When the mouthpiece 3610 is in the second configuration, the outer flange angle has a second value that is different from the first value. In particular, the mouthpiece 3610 can be moved to the second configuration when disposed within the patient's mouth. In one or more embodiments, the second value is less than the first value (i.e., the outer flange 3622 "tips" inwardly toward the bite plate 3612 when the mouthpiece 3610 is inserted into the mouth). In one or more embodiments, the outer flange angle is approximately 90 degrees when the mouthpiece is in the first configuration and is acute when the mouthpiece is in the second configuration. In one or more embodiments, the outer flange angle is about 80 degrees (e.g., the outer flange 3622 tips inward toward the bite plate 3612 by about 10 degrees) when the mouthpiece is in the second configuration. In other embodiments, the outer flange angle is between about 75 degrees and about 80 degrees (e.g., the outer flange 3622 tips inward toward the bite plate 3612 by between about 10 degrees and 15 degrees). In yet other embodiments, the outer flange angle is approximately 85 degrees, 75 degrees, 70 degrees, or 65 degrees (e.g., the outer flange 3622 tips inward toward the bite plate by about 5 degrees, 15 degrees, about 20 degrees and about 25 degrees, respectively) when the mouthpiece is in the second configuration.

As shown, the mouthpiece 3610 also defines notches 3631, 3631' configured to permit, or otherwise increase the ability of, the inner flanges 3621, 3623, 3625 to deflect inwardly towards the bite plate 3612 (or outwardly towards the teeth, gums, jaw, or the like in a direction opposite to the inward deflection described above with respect to outer flange 3622). As shown in FIGS. 137-139, the mouthpiece 3610 defines a first notch 3631 between upper portions of the first and second inner flanges 3621, 3623 of the mouthpiece, and a second notch 3631' between upper portions of the second and third inner flanges 3623, 3625 of the mouthpiece. Each notch 3631, 3631 of the inner flanges 3621, 3623, 3625 can be positioned on the mouthpiece 3610 equidistant from the midline M'. An edge of the first and second inner flanges 3621, 3623 forms a respective side of the first notch 3631. An edge of the second inner flange 3623 (different from the edge forming a side of the first notch 3631) and an edge of the third inner flange 3623 form respective sides of the second notch 3631'.

The first and second notches 3631, 3631' are configured to allow the independent and/or inward deflection of each of the inner first, second and third flanges 3621, 3623, 3625, for example, in response to pressure from the patient's tongue. In particular, the inner flanges 3621, 3623, 3625 are each configured to deflect inwardly with respect to the bite pad 3614. Similarly stated, when the mouthpiece 3610 is outside of the mouth in its first configuration, in an undeformed state, the inner first, second and third flanges 3621, 3623, 3625 are each approximately perpendicular (e.g., about 90 degrees) to the bite pad 3614. When the mouthpiece 3610 is disposed inside the mouth, the upper portion of the mouthpiece 3610 and/or the inner flanges 3621, 3623, 3625 are sufficiently flexible such that an angle formed between each inner flange 3621, 3623, 3625 and the bite pad 3614 (an "inner flange angle") is acute. This "tipping in" allows the inner flanges 3621, 3623, 3625 to conform to the interior surfaces of the mouth, thereby promoting the desired alignment of the second light array 3643 relative to the bone and/or teeth.

The first and second notches 3631, 3631' of the inner flanges 3621, 3623, 3625 can have any suitable shape and/or dimension. As shown in FIGS. 137 and 140, an upper portion of the notches 3631, 3631' can be U-shaped. In one or more embodiments, a lower portion of the notches 3631, 3631' can be a vertically elongate opening or slit extended from the U-shaped upper portion of each notch 3631, 3631'. In one or more embodiments, the lower portion of each notch 3631, 3631' can comprise an unbroken portion of material disposed adjacent a lower end of the U-shaped portion. The lower portion of each notch 3631, 3631' has a thickness less than a thickness of an adjacent inner flange (e.g., flange 3621, 3623, 3625) and is configured to separate, break, and/or otherwise tear, when a deflection force is applied to one or more of the inner flanges 3621, 3623, 3625. In this manner, the lower portion of each notch 3631, 3631' can be configured, to separate, break, and/or otherwise tear, when the mouthpiece is in its second configuration within the patient's mouth to form a vertically elongate opening or slit extended from the lower end of the U-shaped portion of the notch.

The mouthpiece 3610 can define a groove 3638 defined by a lower outer (or rear) surface of the inner flanges 3621, 3623, 3625. For example, as shown in FIG. 139, the mouthpiece 3610 comprises the groove 3638 defined by an outer or rear surface of the mouthpiece 3610. The groove 3638 can be similar in many respects, or identical, to grooves 3632, 3631'. The groove 3638 is disposed at a height between the bite pad 3614 and a lower edge of a flexible circuit board 3647 (see, e.g., FIG. 139) of the mouthpiece 3610. Stated another way, the groove 3638 can be collectively defined by a base portion of each of the first, second and third inner flanges 3621, 3623, 3625, such that such that ends of the groove 3638 are each at or proximate to the posterior end portion of the mouthpiece 3610.

The groove 3638 can have any suitable shape, including, for example, that of a semi-circle or U-shape. The groove 3638 produces a hinge-like structure (i.e., a "living hinge") about which the inner flanges 3621, 3623, 3625 can rotate, bend and/or deflect. In this manner, the groove 3628 and the first and second notches 3631, 3631' collectively permit the inner flanges 3621, 3623, 3625 to deflect inwardly with respect to the bite plate (or outwardly with respect to the tongue and/or palate), for example, in response to pressure from the patient's tongue.

As such, the groove 3638 and the first and second notches 3631, 3631' collectively facilitate the transition of the mouthpiece 3610 between its first configuration and its second configuration. When the mouthpiece 3610 is in the first configuration, the angle formed between each inner flange 3621, 3623, 3625 and the bite pad 3614 (the "inner flange angle") has a first value. When the mouthpiece 3610 is in the second configuration, the inner flange angle has a second value that is different from the first value. In particular, the mouthpiece 3610 can be moved to the second configuration when disposed within the patient's mouth. In one or more embodiments, the second value is less than the first value (i.e., the inner flanges 3621, 3623, 3625 "tip" inwardly towards the bite plate when the mouthpiece 3110 is inserted into the mouth). In one or more embodiments, the inner flange angle is approximately 90 degrees when the mouthpiece is in the first configuration and is acute when the mouthpiece is in the second configuration. In one or more embodiments, the inner flange angle is about 80 degrees (e.g., the inner flanges 3621, 3623, 3625 tip inward towards the bite plate by about 10 degrees) when the mouthpiece is in the second configuration. In other embodiments, the inner flange angle is between about 75 degrees and about 80 degrees (e.g., the inner flanges 3621, 3623, 3625 tip inward toward the bite plate by between about 10 degrees and 15 degrees). In yet other embodiments, the inner flange angle is approximately 85 degrees, 75 degrees, 70 degrees, or 65 degrees (e.g., the inner flanges 3621, 3623, 3625 tip inward towards the bite plate by about 5 degrees, 15 degrees, about 20 degrees and about 25 degrees, respectively) when the mouthpiece is in the second configuration.

For example, some patients have a pronounced overbite and may need more or less than a 10 degree inward deflection (or "tip-in"). In such instances, the mouthpiece 3610 can conform to the internal structure and/or anatomy within the patient's mouth. As another example, as the orthodontia for a patient works over time, the patient's dental anatomy will change. Accordingly, the mouthpiece 3610 can conform to the internal structure and/or anatomy within the patient's mouth to accommodate such change without requiring new mouthpiece moldings or the like.

In one or more embodiments, the design of the mouthpiece 3610 allows for the molding and/or fabrication to be performed with a flange angle of approximately ninety degrees (or greater), while allowing for an in-use flange angle that is acute (e.g., when the mouthpiece 3610 is in the second configuration, as described above).

The mouthpiece 3610 of the light therapy apparatus 3600 comprises an electronics assembly 3640, generally shown in FIG. 139. The electronics assembly 3640 can be similar in many respects, or identical to, the electronics assembly 2540 of mouthpiece 2510 described herein (e.g., with respect to FIGS. 93-95). As shown, a first portion of the electronics assembly 3640 of the mouthpiece 3610 is disposed primarily in the flange 3622. The first portion of the electronics assembly 3640 comprises a light array 3642 and a flexible circuit board 3646. A second portion of the electronics assembly 3640 is disposed primarily in the inner flanges 3621, 3623, 3625. The second portion of the electronics assembly 3640 comprises a light array 3643 and a flexible circuit board 3647. The light arrays 3642, 3643 each comprise one or more light emitters 3644, 3645, such as a plurality of LEDs. The light emitters 3644, 3645 are electrically and/or physically coupled to the flexible circuit boards 3646, 3647, respectively (only a portion of the flexible circuit board 3647 is shown in FIG. 139). The flexible circuit boards 3646, 3647, respectively, electrically couple the light emitters 3644, 3645, respectively, to electronic circuitry outside of the mouthpiece 3610 (e.g., in an extra-oral housing or via electrical connectors to an external controller, not shown). In this manner, the light emitters 3644, 3645, respectively, can receive power and/or a signal to produce the desired light, as described herein.

Referring to FIG. 139, the light emitters 3644 of the first portion of the electronics assembly 3640 are disposed on a first, palatial (or lingual) side of the flexible circuit board 3646 of the first portion of the electronics assembly. The light emitters 3645 of the second portion of the electronics assembly 3640 are disposed on a buccal side of the flexible circuit board 3647 of the second portion of the electronics assembly. In this manner, the light emitters 3644, 3645 are configured to emit light toward a patient's teeth and/or adjacent oral tissue when the mouthpiece 3610 is disposed within the patient's mouth. Stated another way, the light emitters 3644 are configured to emit light towards the anterior root area of an upper and/or lower jaw and/or the buccal alveolar soft tissue and the light emitters 3645 are configured to emit light towards a posterior root area of an upper and/or lower jaw and/or the lingual alveolar soft tissue.

The light emitters 3644, 3645 can be configured to emit light at any suitable intensity, wavelength and/or frequency described herein. For example, in one or more embodiments, the light emitters 3644, 3645 can be configured to emit light in the infrared or near infrared wavelength range. For example, in one or more embodiments, the light emitters 3644, 3645 are configured to emit light at a wavelength of about 850 nm. In one or more embodiments, the light emitters 3644, 3645 are configured to emit light at a wavelength from about 585 nm to about 665 nm, from about 605 nm to about 645 nm, at about 625 nm, from about 815 nm to about 895 nm, from about 835 nm to about 855 nm, including all values and subranges in between. The light emitters 3644, 3645 can be configured to emit light sufficient deliver light energy to the patient's bone to facilitate and/or perform any of the methods described herein. The light emitters 3644, 3645 can be configured to emit light at less than 150 mW/cm 2.

The light emitters 3644, 3645 can be disposed on the flexible circuit boards 3646, 3647, respectively, and/or within the flange 3622 and the inner flanges 3621, 3623, 3625, respectively, in any suitable configuration, including any configuration described herein. For example, in one or more embodiments, the light emitters 3644, 3645 are LEDs coupled to the flexible circuit boards 3646, 3647 in two or more parallel rows and/or columns. In one or more embodiments, the light emitters 3644 are coupled to the flexible circuit board 3646 of the first portion of the electronics assembly 3640 in a single row, and the light emitters 3645 are coupled to the flexible circuit board of the second portion of the electronics assembly in two parallel rows.

The light array 3643 of the second portion of the electronics assembly 3640 can comprise about 18 or 20 light emitters 3645, or LEDS, with about 6 light emitters embedded in each of the first and third inner flanges 3621, 3625, and 6 light emitters embedded in the second (or middle) panel 3623. The 6 light emitters 3645 can be arranged in any suitable configuration, including, for example, in three evenly spaced columns with two spaced apart light emitters, or LEDs, per column. The flexible circuit boards 3646, 3647 and light emitters 3644, 3645 can have any suitable dimensions for being coupled to, or embedded in, the outer flange 3622 and the inner flanges 3621, 3623, 3625, respectively, of the mouthpiece 3610.

Although the mouthpiece 3610 has been shown as including 6 light emitters 3645 embedded in the inner flanges 3621, 3623, 3625, in other embodiments, the mouthpiece can comprise a different number of light emitters in the inner flanges, and each inner flange can comprise a different number of light emitters than another inner flange, as best illustrated in FIG. 133, described above.

Returning to FIGS. 136-140, although the light emitters 3644, 3645 are shown as being evenly spaced within the outer flange 3622 or inner flanges 3621, 3623, 3625, in other embodiments, the light emitters can be unevenly spaced within the outer flange 3622 and/or inner flanges 3621, 3623, 3625. For example, in one or more embodiments, a mouthpiece can comprise a series of light emitters that are spaced apart by a first amount near the anterior portion of the mouthpiece and a second, different amount near the posterior portion of the mouthpiece.

The mouthpiece 3610 can be constructed of any suitable material, including, for example, any material described herein with respect to mouthpiece 2510 and/or mouthpiece 3110, and thus such material is not described in detail with respect to mouthpiece 3610. For example, the mouthpiece 3610 can be constructed of an elastomeric material (e.g., a soft silicone). In another example, the mouthpiece 3610 can be fabricated from medical-grade injection-molded, highly flexible and very low durometer silicone. In another example, the silicone and/or portions of the mouthpiece 3610 are substantially transparent, such that one or more components embedded within the silicone are visible through the silicone. Moreover, in this manner, the mouthpiece 3110' can provide suitable optical properties for allowing the light produced and/or conveyed by the light emitters 3644, 3645 to pass through the mouthpiece 3610 to the desired target tissue. In one or more embodiments, the mouthpiece 3610, the outer flange 3622 and/or the inner flanges 3621, 3623, 3625 can comprise one or more components configured to filter, focus and/or otherwise act upon the light produced by the light emitters 3644, 3645. In other embodiments, the mouthpiece 3610 can comprise air gaps between the light emitters 3644, 3645 and the surface of the outer flange 3622 and inner flanges 3621, 3623, 3625, respectively, to facilitate focusing of the light. As shown in FIGS. 136-140, however, the mouthpiece 3610 is constructed such that the light emitters 3644, 3645 are fully encapsulated or embedded within the molded silicone such that no detectable space or air gap exists between the silicone material and the first and second portions of the electronics assembly 3640. Similarly stated, the mouthpiece 3610 is devoid of an air gap between the light emitters 3644, 3645 and the material of the mouthpiece 3610, thus no air gap lensing is needed to produce the desired optical properties of the light produced by the light emitters 3644, 3645.

In one or more embodiments, any light therapy apparatus disclosed herein (e.g., the light therapy apparatus 3100 and/or the light therapy apparatus 3600) is useful for treating patients with a history of periodontal disease, and/or with reduced periodontal support. In one or more embodiments, the light therapy apparatuses disclosed herein are useful with orthodontic treatment with an orthodontic appliance. In one or more embodiments, the light therapy apparatuses disclosed herein are useful with orthodontic treatment with an orthodontic appliance to retain teeth in their final, desired position, i.e., after treatment. In one or more embodiments, orthodontic treatment with the light therapy apparatuses disclosed herein result in initiating and/or accelerating, relative to no treatment, one or more of orthodontic tooth movement, osteoblast proliferation, collagen deposition, osteoblast activity (e.g., as measured by osteoblast activity markers), osteoclast activity (e.g., as measured by osteoclast activity markers), combinations thereof, and/or the like. In one or more embodiments, orthodontic treatment with the light therapy apparatuses disclosed herein result in initiating and/or accelerating, relative to orthodontic treatment alone, one or more of orthodontic tooth movement, osteoblast proliferation, collagen deposition, osteoblast activity, osteoclast activity, combinations thereof, and/or the like. In one or more embodiments, orthodontic treatment with the light therapy apparatuses disclosed herein in combination with orthodontic treatment result in initiating and/or accelerating, relative to no treatment, one or more of orthodontic tooth movement, osteoblast proliferation, collagen deposition, osteoblast activity, osteoclast activity, combinations thereof, and/or the like. In one or more embodiments, orthodontic treatment with the light therapy apparatuses disclosed herein in combination with orthodontic treatment result in initiating and/or accelerating, relative to orthodontic treatment alone, one or more of orthodontic tooth movement, osteoblast proliferation, collagen deposition, osteoblast activity, osteoclast activity, combinations thereof, and/or the like.

FIGS. 141A-141F illustrate an intra-oral apparatus 3700, according to an embodiment of the invention. The apparatus 3700 can comprise components of other intra-oral apparatuses described herein. The intra-oral apparatus 3700 comprises an intra-oral housing/mouthpiece 3780 configured to be disposed in an oral cavity (e.g., in the mouth) of a patient and an extra-oral housing 3790 (also referred to herein as a "bill") coupled to the intra-oral housing 3780.

In one or more embodiments, the intra-oral housing 3780 can be the same as or similar in many respects to, or comprise components the same as or similar in many respects to, the intra-oral apparatuses described herein. For example, and as illustrated in FIGS. 141A-141F, the intra-oral housing 3780 can be structurally and/or functionally similar to the mouthpiece 3310. For example, the intra-oral housing 3780 can comprise, similar to the mouthpiece 3310, a bite tray (similar to the bite tray 3312, a single outer flange without a notch (similar to the flange 3322), an electronics assembly (similar to the electronics assembly 3340) including a light array (similar to the light array 3342) and a flexible circuit board (similar to the flexible circuit board 3346). In one or more embodiments, the intra-oral housing 3780 can be structurally and/or functionally similar to the mouthpiece 3610. For example, the intra-oral housing 3780 can comprise, similar to the mouthpiece 3610, a bite tray (similar to the bite tray 3612), an outer flange without a notch (similar to the outer flange 3622), inner flanges (similar to the inner flanges 3621, 3623, 3625), and light arrays (similar to the light arrays 3642, 3643).

FIGS. 141A-141F depict the extra-oral housings 3780 and 3790. In one or more embodiments, the extra-oral housing 3790 can comprise a microprocessor (not shown) (e.g., similar to the microprocessor 2196) configured to store and execute a treatment protocol specific to the nature/capabilities of the intra-oral housing 3780. In some embodiments, the microprocessor of the extra-oral housing 3790 can be configured to execute a treatment protocol that accounts for the single row of light emitters on the intra-oral housing 3780.

Figure 141A:
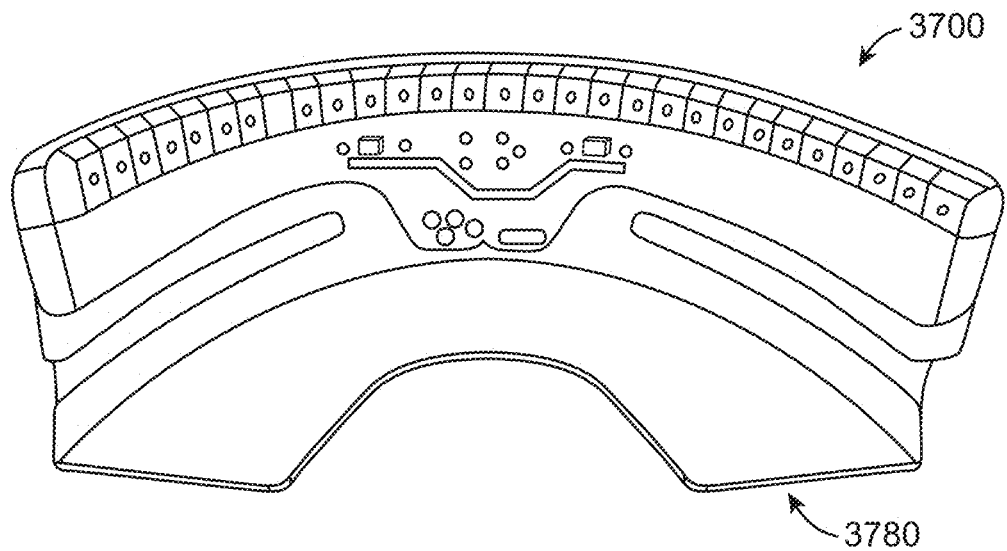
FIGS. 141A-141F are illustrative embodiments of a light therapy apparatus.
Figure 141B:
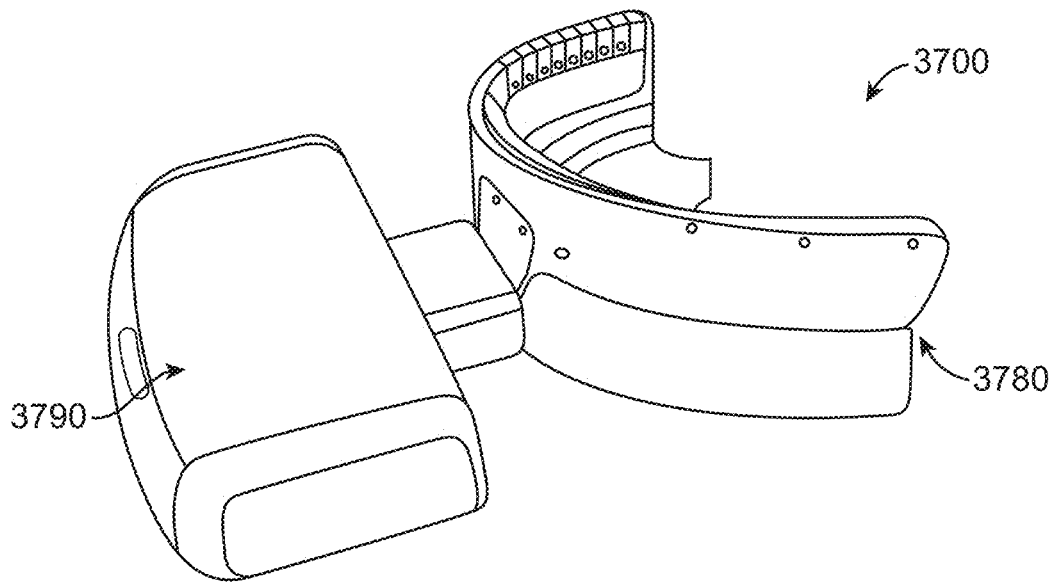
Figure 141C:
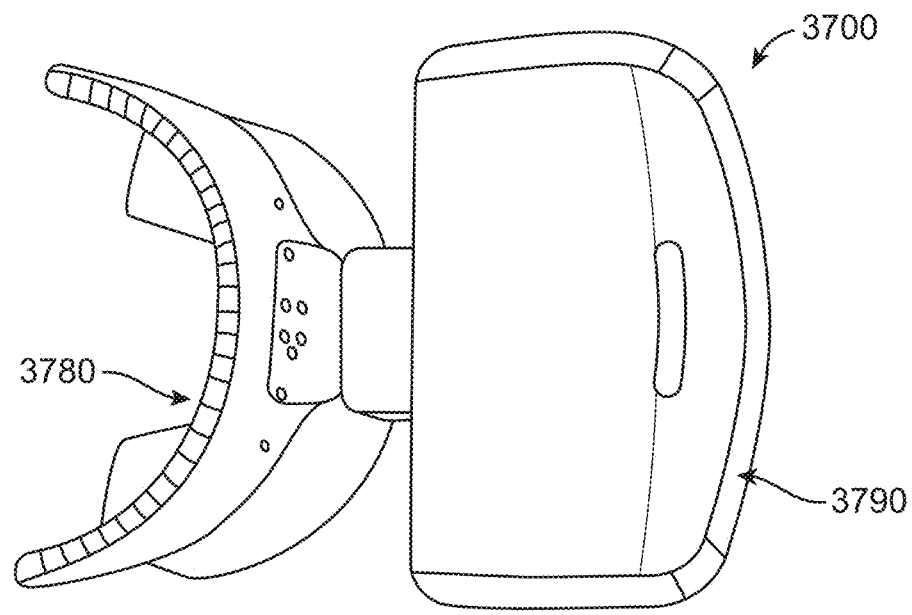
Figure 141D:
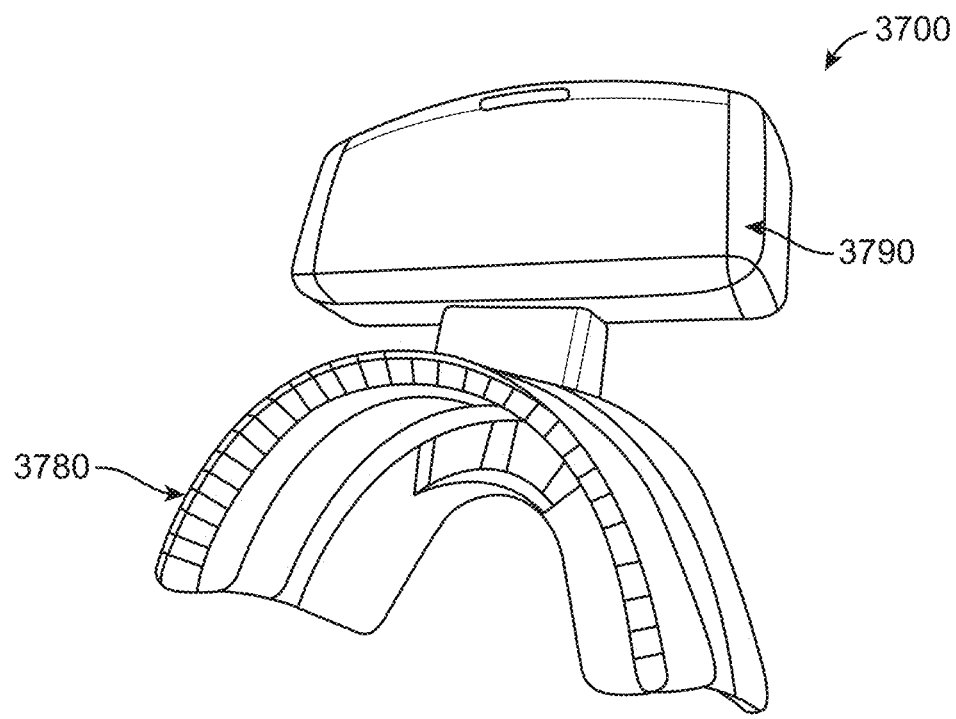
Figure 141E:
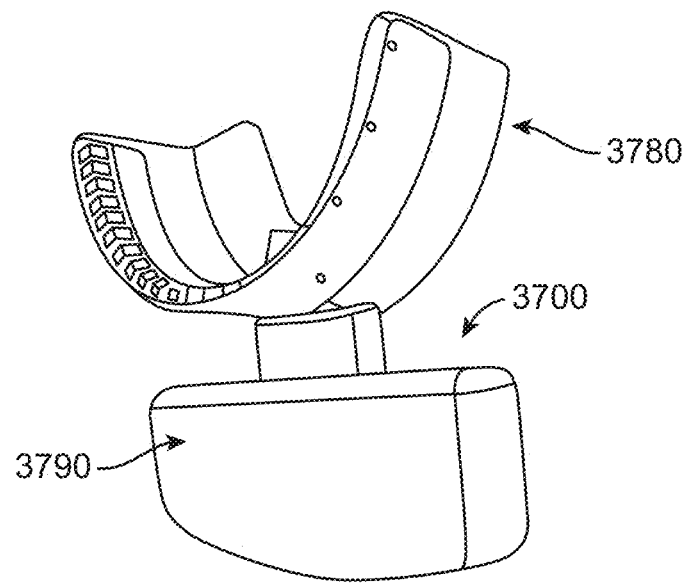
Figure 141F:
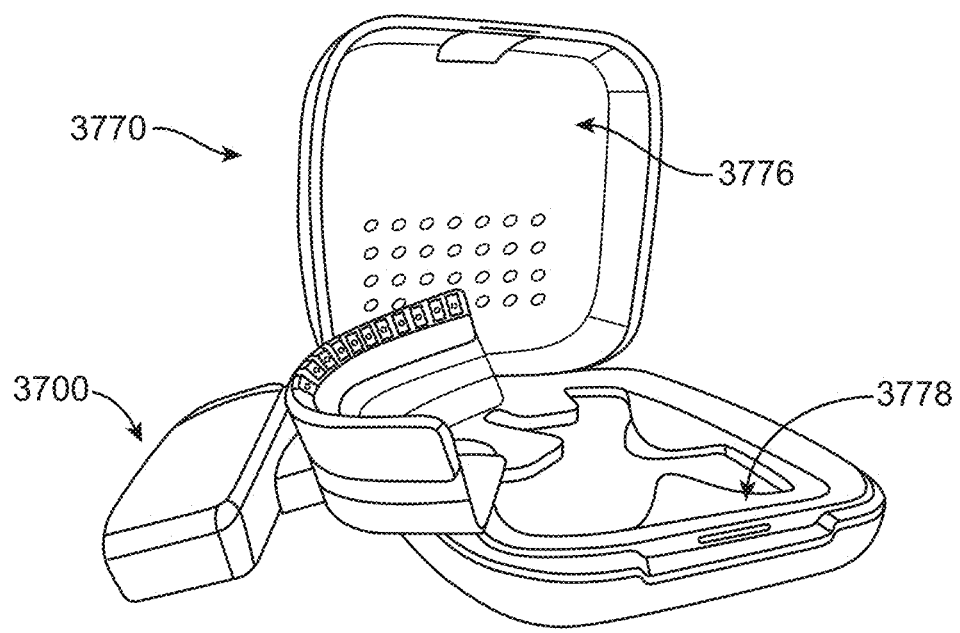
Figure 142:
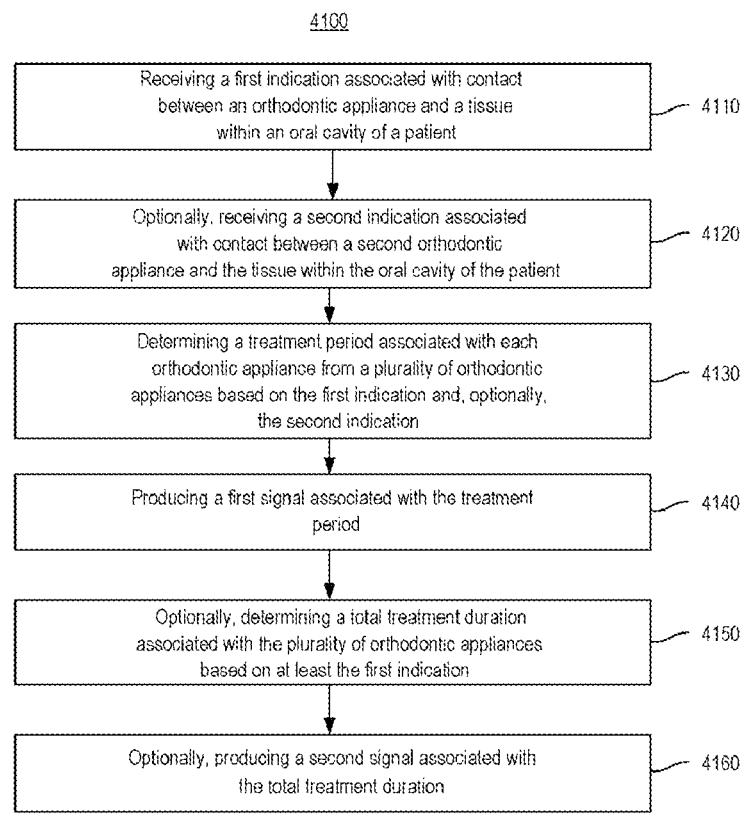
FIG. 142 is a flow chart of a method according to an embodiment.
Figure 146:
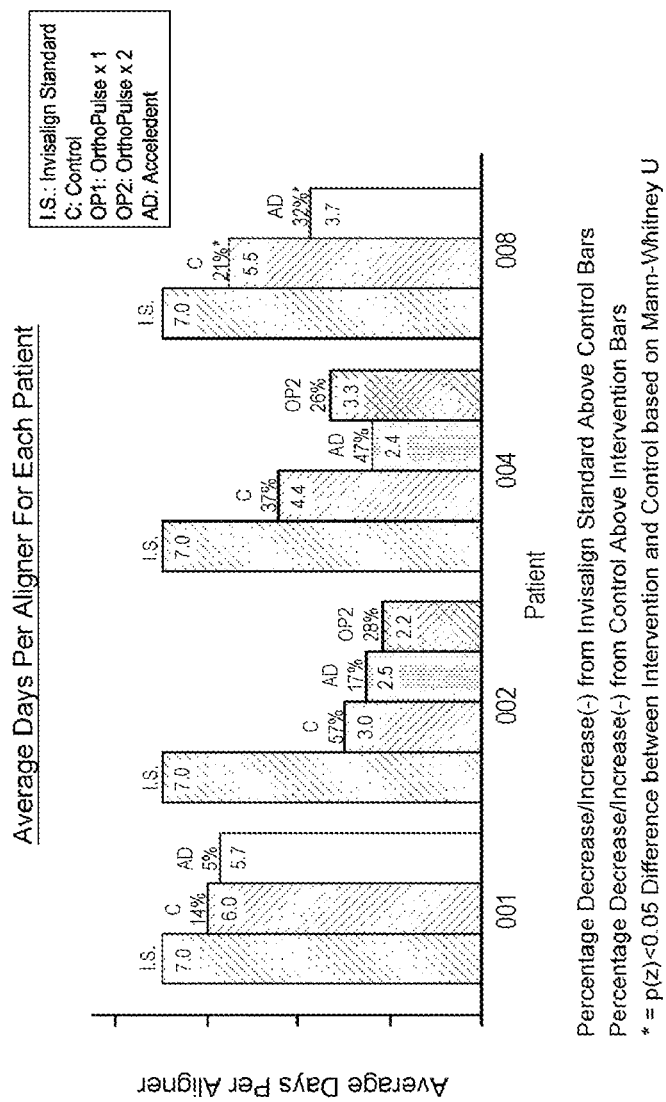
FIGS. 146-148 are bar graphs showing an average number of days per aligner for individual patients in the study described in Example 12.
Figure 147:
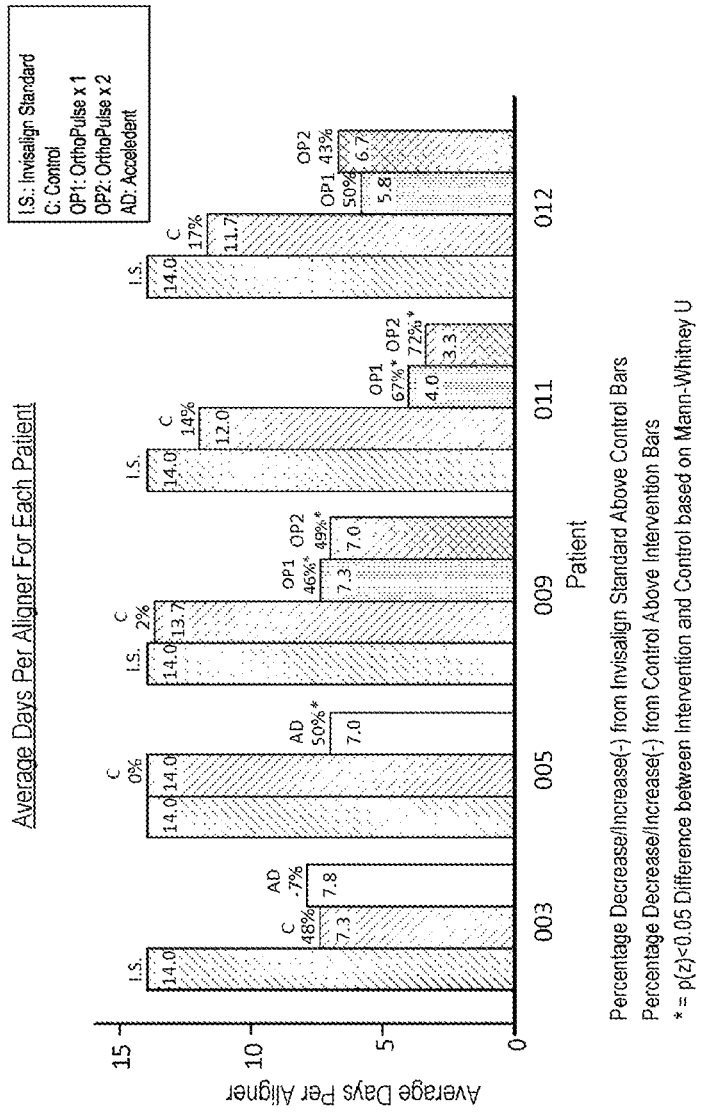
Figure 148:
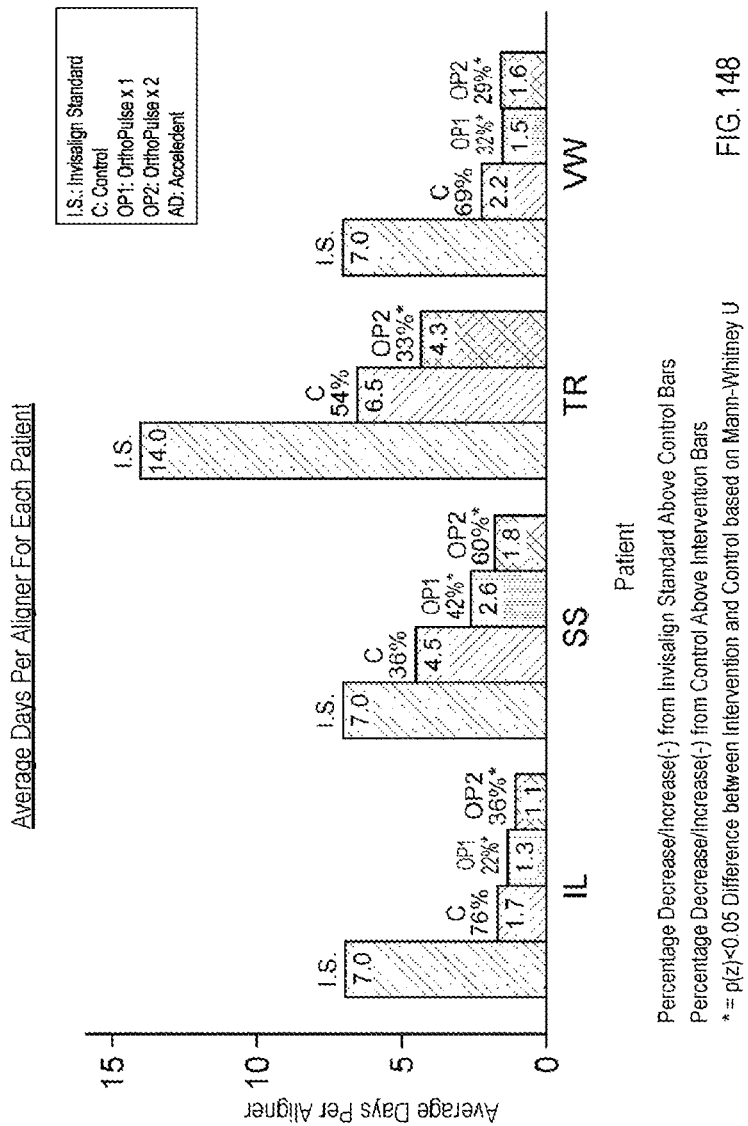
Figure 149:
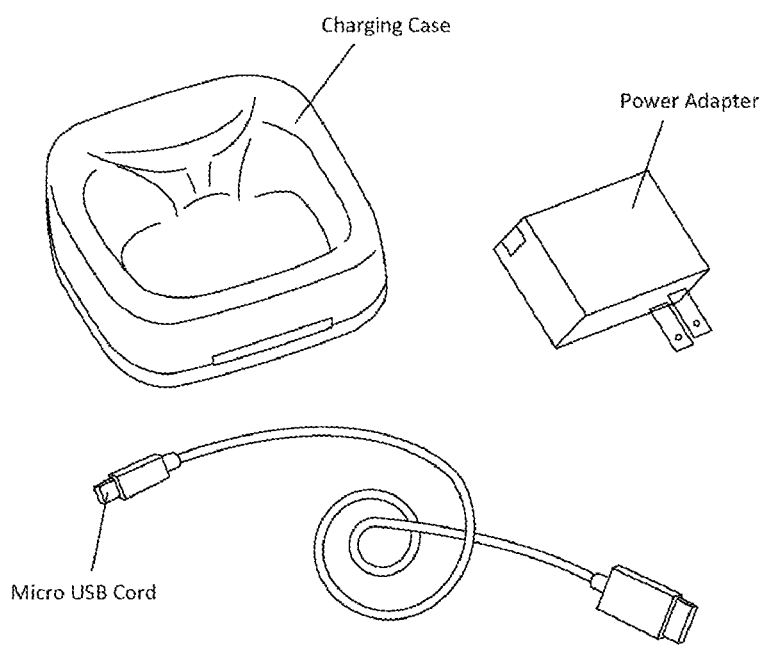
FIG. 149 is a schematic of one or more embodiments of the light therapy apparatus disclosed herein.
Figure 150:
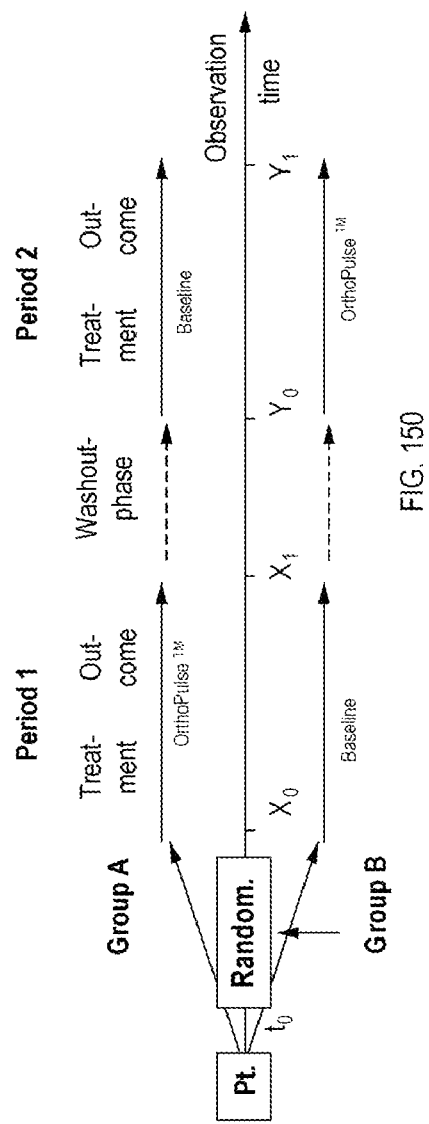
FIG. 150 is a schematic of the crossover trial design and orthodontic procedures described in Example 13.
Figure 151:
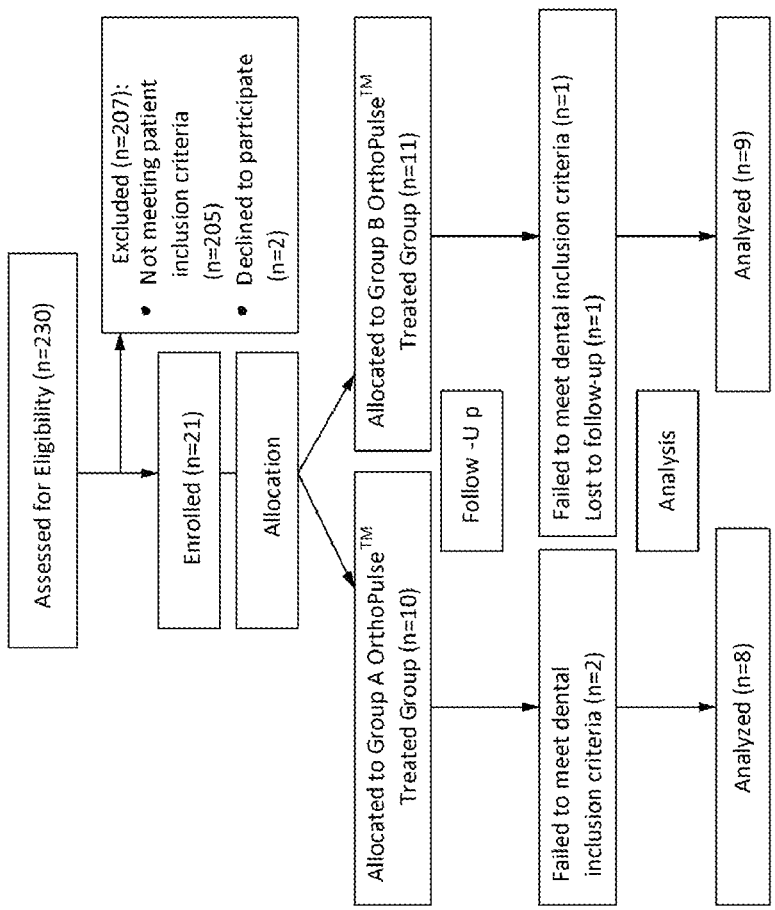
FIG. 151 is a consort chart of the patients screened for the study set forth in Example 13.
Figure 152A:
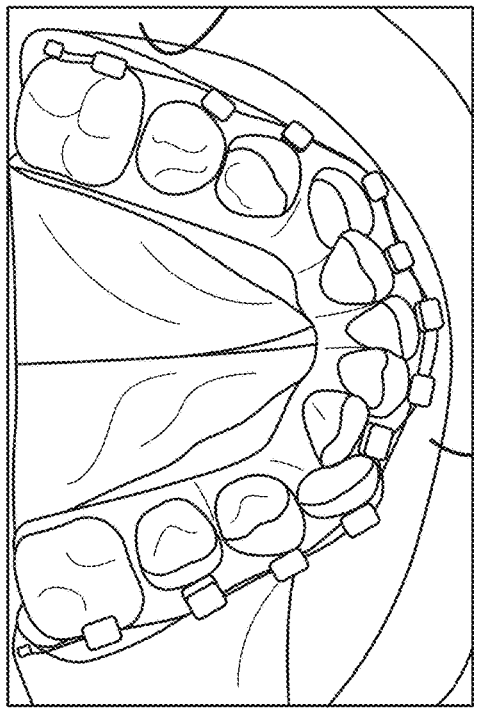
FIGS. 152A and 152B show two cases treated with conventional orthodontic brackets and wires.
Figure 152B:
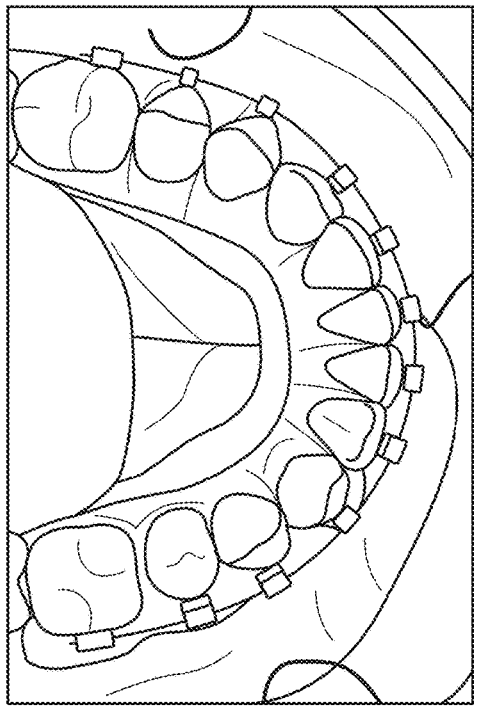
Figure 152C:
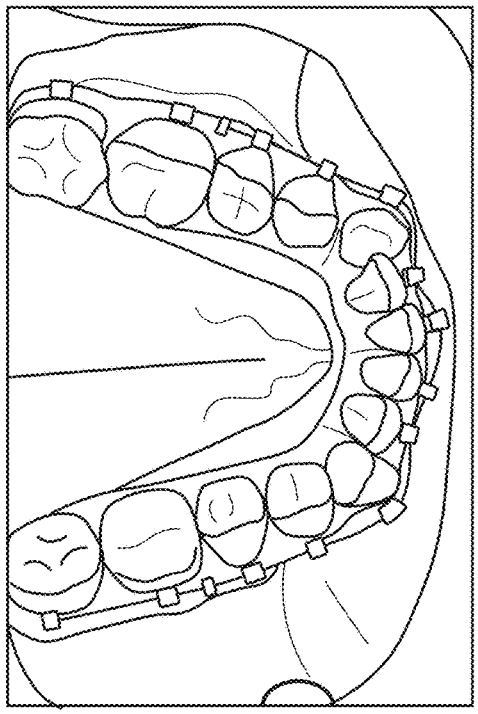
FIGS. 152C and 152D show two cases treated with intra-oral light therapy.
Figure 152D:
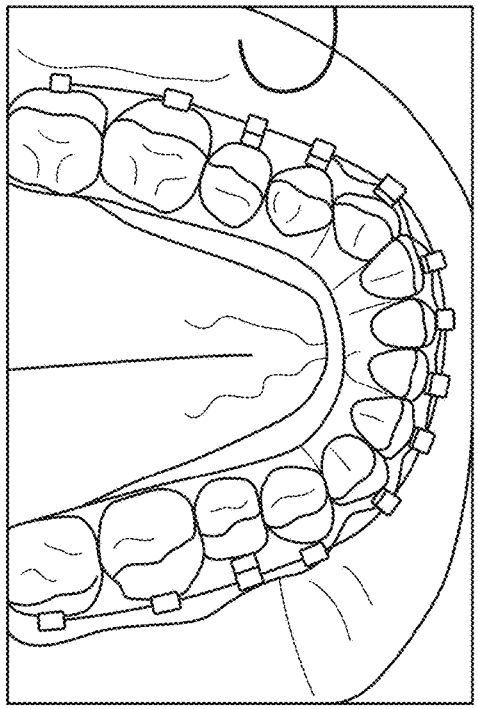
Figure 153:
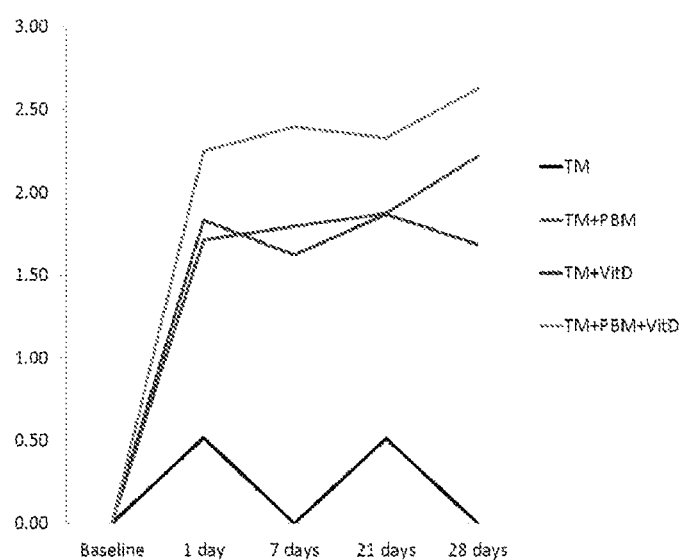
FIG. 153 illustrates magnitude of tooth movement in response to Vitamin D supplementation and intra-oral light therapy in rats.
Figure 154:
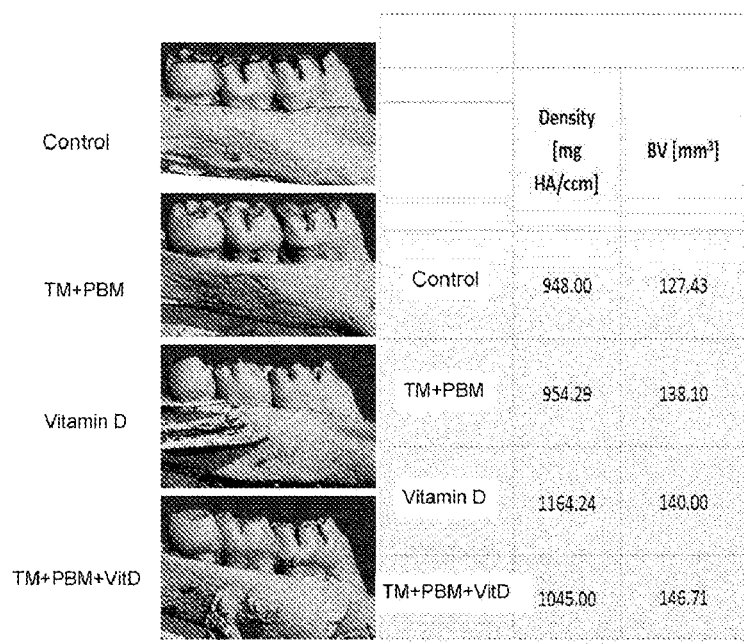
FIG. 154 illustrates MicroCT analyses of bone specimens in response to TM with or without Vitamin D supplementation and intra-oral light therapy in rats.
Figure 155:
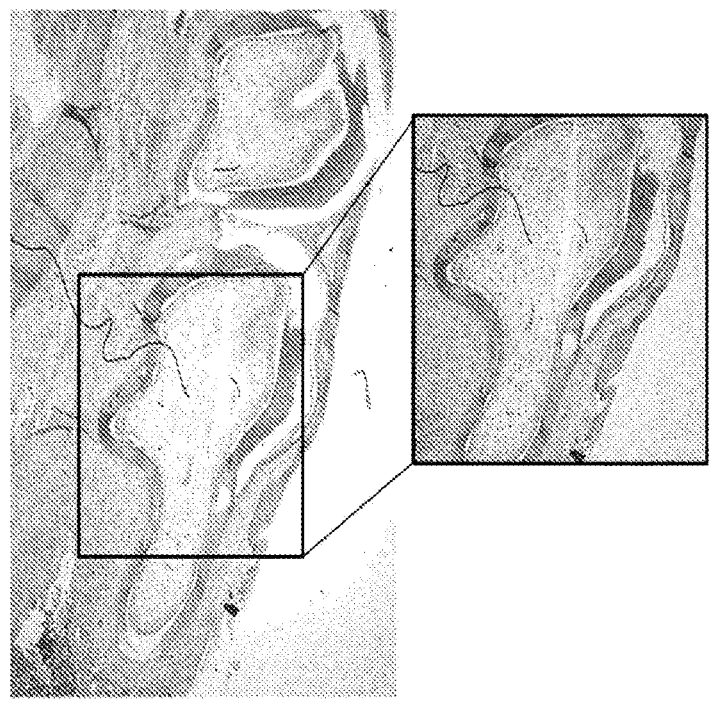

Referring to FIG. 141F in particular, the extra-oral housing 3790 can be configured to be disposed on or otherwise coupled to an external station 3770, for example, when the apparatus 3700 is not in use by the patient. The external station 2170 can be, for example a carrying case, charging caddy or station, or the like, or a combination of the foregoing. In one or more embodiments, the external station 3770 can comprise a base 3778 and a lid 3776 (e.g., similar to the base 2178 and the lid 2176, respectively) and defines a cavity configured to hold the intra-oral apparatus 3700.

A light therapy apparatus 3800 according to an embodiment is illustrated in FIGS. 156A-156D. The light therapy apparatus 3800 can be included in a light therapy system that is similar in many respects to the light therapy systems described herein, such as with respect to FIGS. 84-113 and 126-141. The light therapy apparatus 3800 is configured to irradiate light in any suitable manner described herein, including, for example, to irradiate the alveolus and/or tooth root area of the patient, such as via the oral mucosa, for example. Similarly stated, the light therapy apparatus 3800 is configured to administer light therapy to the root of a patient's teeth and/or oral mucosa. More specifically, the light therapy apparatus 3800 is configured to administer light to the patient's teeth and/or oral mucosa sufficient to reduce the overall treatment time for the patient when using one or more appliances that exert a force on one or more of the patient's teeth.

The light therapy apparatus 3800 (and any light therapy apparatus described herein) is useful in combination with traditional orthodontic treatment with an orthodontic appliance, such as brackets and wires, an aligner, or the like. In some embodiments, the light therapy apparatus 3800 is useful prior to treatment with an orthodontic appliance. In some embodiments, the light therapy apparatus 3800 is useful simultaneously with treatment with an orthodontic appliance. For example, the light therapy apparatus 3800 can be disposed within the patient's mouth concurrently with the orthodontic appliance being disposed within the patient's mouth. In some embodiments, the light therapy apparatus 3800 can be disposed within the patient's mouth such that the light therapy apparatus generally is disposed around or over at least a portion of the orthodontic appliance. In some embodiments, the light therapy apparatus 3800 is useful after treatment with an orthodontic appliance. For example, the light therapy apparatus 3800 can be disposed within the patient's mouth for a period of time during which the orthodontic appliance is removed from or otherwise not present within the patient's mouth. In some embodiments, for example, the light therapy apparatus 3800 is useful during a period of time when a patient has removed a removable appliance (such as an aligner) from the patient's mouth. Furthermore, in one or more embodiments, any light therapy apparatus shown and described herein can be useful (e.g., used in combination) with any suitable orthodontic appliance, including, but not limited to, one or more substantially transparent aligners. Such aligners are orthodontic appliances useful for moving a patient's teeth and can adhere, be disposed over, and/or generally conform to one or more of the patient's teeth. In some embodiments, the aligners comprise one or more substantially transparent, removable trays that fit over one or more of the patient's teeth. Each aligner from the set of aligners can be worn by the patient in a predetermined sequence or order, and sometimes for a specified amount or period of time. In particular instances, the aligner (or tray) generally conforms to a patient's teeth but is slightly out of alignment with the starting (e.g., initial) tooth configuration. The aligner can exert a force on one or more teeth (e.g., due to the slight misalignment of the aligner with respect to the one or more teeth).

The orthodontic appliance (e.g., an aligner or brackets and wires) can be configured to exert a force on one or more of the patient's teeth in an amount (or magnitude) effective to move at least one tooth of the patient towards alignment. In some embodiments, the orthodontic appliance is configured to exert a force to move a patient's teeth laterally, e.g., to minimize or close a gap or space between the patient's teeth. In some embodiments, the orthodontic appliance is configured to exert a force to move a patient's teeth rotationally, e.g., to align the patient's teeth. For example, the orthodontic appliance can be configured to exert an orthodontic force, a less-than-orthodontic force, or a heavy force, as described in detail herein, or a combination thereof, on one or more of the patient's teeth in an amount (or magnitude) effective for tooth movement (e.g., towards alignment or to minimize or close a gap between the patient's teeth).

The light therapy apparatus 3800 comprises an intra-oral housing 3810 (also referred to herein as a "mouthpiece"). The intra-oral housing 3810 of the light therapy apparatus 3800 is configured to be disposed in an oral cavity (e.g., in the mouth, not shown in FIGS. 156A-156D) of a patient. The intra-oral housing 3810 can be configured to be electronically and/or physically coupled to an external controller. In one or more embodiments, for example, the intra-oral housing 3810 is configured to be coupled to an extra-oral housing 3880 (also referred to as an "external housing") that is disposed externally to the patient's mouth when the intra-oral housing (or mouthpiece) 3810 is disposed within the patient's mouth. The extra-oral housing 3880 can be similar in many respects, or identical, to any extra-oral housing described herein (e.g., the extra-oral housing 2560 described herein with respect to FIGS. 84-113), and thus is not described in detail with respect to light therapy apparatus 3800. In other embodiments, the intra-oral housing 3810 is configured to be coupled to the controller in a different manner, such as via a wire, cable connector, or the like (not shown in FIGS. 156A-156D).

The light therapy apparatus 3800 is configured to administer light therapy to the upper jaw and/or the lower jaw of the patient. In other words, the light therapy apparatus 3800 can be configured to administer light therapy with respect to the patient's upper jaw when the apparatus is in a first (e.g., an upright position) in which the light therapy apparatus is disposed within the patient's mouth with respect to the upper jaw (e.g., as shown in FIG. 156C), and can be configured to administer light therapy with to the patient's lower jaw when the apparatus is in a second (e.g., an inverted) position in which the light therapy apparatus is disposed within the patient's mouth with respect to the lower jaw (not shown in FIGS. 156A-156D). As such, the mouthpiece 3810 can be selectively disposed within the patient's oral cavity with respect to each of the upper jaw and the lower jaw of the patient. Similarly stated, the mouthpiece 3810 is configured to be positioned within the mouth such that light therapy can be administered via the mouthpiece 3810 to the upper jaw and the lower jaw, respectively, as described herein, thus eliminating the need for a separate mouthpiece dedicated to the upper jaw or the lower jaw, respectively. It should be noted that although the light therapy apparatus 3800 generally, and the mouthpiece 3810 specifically, may be described as being in the upright position when configured to be oriented with respect to the upper jaw and in the inverted position when configured to be oriented with respect to the lower jaw, in other embodiments, the light therapy apparatus 3800 and the mouthpiece 3810 are in the upright position when configured to be oriented with respect to the lower jaw of the patient, and in the inverted position when configured to be oriented with respect to the upper jaw of the patient.

Generally described with respect to FIGS. 156A-156D, the mouthpiece 3810 comprises a bite tray 3812, a flange 3822, and one or more light emitters 3844. The mouthpiece 3810 can optionally comprise a support plate (not shown in FIGS. 156A-156D) similar or identical to the support plate 2554 of mouthpiece 2510.

The bite tray 3812 is configured to facilitate proper positioning of the mouthpiece 3810 within the patient's mouth. The bite tray 3812 generally defines a lower portion of the mouthpiece 3810. The bite tray 3812 is substantially U-shaped, as seen in FIG. 156B. The bite tray 3812 comprises a bite pad 3814, posterior ends 3812A, 3812B (e.g., the "free" ends of the U shape) and an anterior end 3812C. In some embodiments, the posterior ends 3812A, 3812B each extend from about 1 cm to about 3 cm (including all values and subranges in between) beyond the bite pad 3814, and are useful for latching, hooking, and/or generally securing the tray to the patient's posterior teeth (e.g., each end 3812A, 3812B can hook onto a terminal posterior tooth). The extent/degree of flexibility and/or the nature of flexibility (e.g., inward, towards the patient's mouth) of the posterior ends 3812A, 3812B can be the same as or different than the rest of the bite tray 3812.

The bite pad 3814 of the bite tray 3812 is configured to be disposed adjacent to and/or contact an occlusal surface of at least one tooth of the patient when the mouthpiece 3810 is disposed within the patient's mouth. In some embodiments, the bite tray 3812 is configured to receive at least a portion of one or more of the patient's teeth. Stated another way, in some embodiments, the bite tray 3812 defines a recess within which at least a portion of one or more teeth can be disposed or received when the mouthpiece is disposed within the patient's mouth. The posterior ends 3812A, 3812B generally delineate posterior edges of the bite tray 3812 in a posterior portion of the mouthpiece 3810.

The bite tray 3812 can be similar in many respects to the bite tray 2512 described with respect to FIGS. 84-113, and thus is not described in detail with respect to the mouthpiece 3810. For example, the bite pad 3814 of the bite tray 3812 can have any thickness suitable for receiving a bite force thereon, including a constant or spatially varied thickness as described with respect to bite pad 2514. In another example, the bite tray 3812 (and/or bite pad 3814) can be of any suitable dimensions, including those described herein with respect to bite tray 2512 (and/or bite pad 2514, respectively), and can be constructed of any suitable material, including those described herein with respect to bite tray 2512 (and/or bite pad 2514).

Figure 156A:
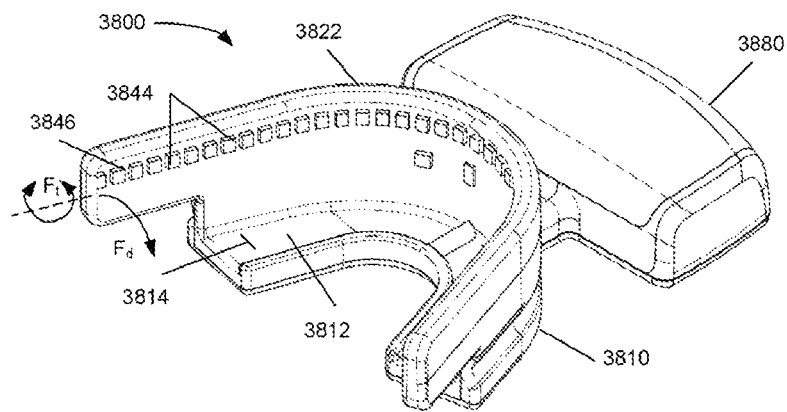
Figure 156B:
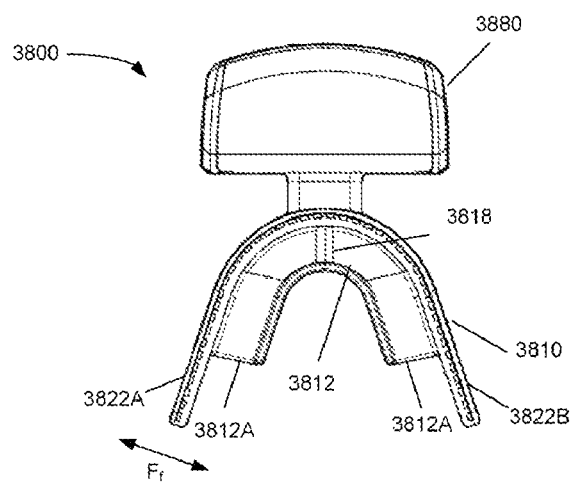
Figure 156C:
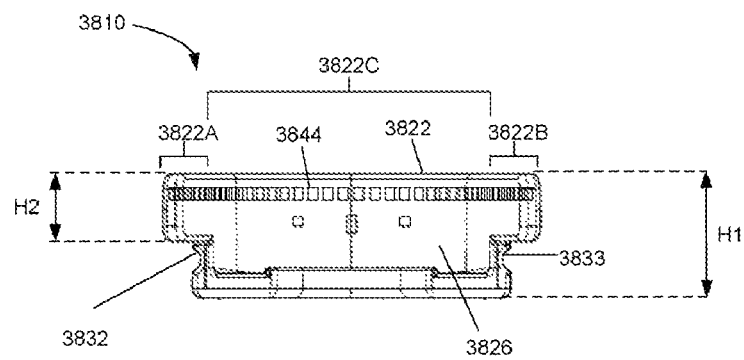

As shown in FIGS. 156A-156B, a surface (e.g., an upper) surface of the bite pad 3814 comprises a ridge 3818. The ridge 3818 is disposed along a midline of the mouthpiece 3810 and is elevated with respect to the surface of the bite tray 3812 and/or bite pad 3814. The ridge 3818 can be extended or disposed across a width (or a portion thereof) of the bite pad 3814 (e.g., from an outer perimeter portion of the bite tray 3812 to an inner perimeter portion of the bite tray 3812). The ridge 3818 facilitates positioning of the mouthpiece 3810 within the patient's oral cavity. For example, the mouthpiece 3810 can be configured to be positioned within the patient's oral cavity such that the ridge 3818 is disposed between the patient's front central incisors (on either the upper jaw or the lower jaw). Proprioception of the patient related to the teeth and periodontium can produce sensory feedback to the patient regarding the position of the ridge 3818 of the mouthpiece 3810.

In this manner, the ridge 3818 facilitates centering of the mouthpiece 3810 within the oral cavity, thus promoting symmetry of a light therapy treatment on the alveolus, or other oral tissue, on both sides of the patient's mouth. In other words, in order to promote the symmetrical administration of light therapy to the root area, the mouthpiece 3810 can be positioned in the patient's mouth with the midline of the mouthpiece 3810 seated along the sagittal plane or within (i.e., plus or minus) 5 degrees of the sagittal plane, and the ridge 3818 can facilitate such positioning in use. The ridge 3818 can have any suitable shape, including, for example, the shape of an inverted V (when seen in the view of FIG. 156B), such that the point or center of the V can be disposed between the patient's front central incisors.

The flange 3822, described in more detail herein, generally defines an upper portion of the mouthpiece 3810. The flange 3822 is coupled to the bite tray 3812. In some embodiments, at least a portion of the flange 3822 is coupled to the outer perimeter portion of the bite pad 3814. The flange 3822 is extended or protruded from the bite tray 3812, as illustrated in FIGS. 156A-156D and described in more detail herein. The upper portion (e.g., the flange 3822) of the mouthpiece 3810 is disposed transversely with respect to the bite pad 3814. As such, when the mouthpiece 3810 is disposed within the patient's mouth, the bite tray 3812 is positioned within the mouth such that the bite pad 3814 of the bite tray 3812 is adjacent the occlusal surface of one or more teeth, and the flange 3822 is disposed between the one or more teeth and buccal tissue. Stated another way, the flange 3822 is configured to be disposed adjacent a portion of a side of the patient's teeth and/or adjacent the alveolar mucosa, when the mouthpiece 3810 is disposed within the patient's mouth, such that the bite tray 3812 is adjacent an occlusal surface of the patient's teeth. For example, the flange 3822 can be disposed adjacent a portion of a buccal side of the patient's teeth and/or adjacent a buccal side of the alveolar mucosa. In this manner, one or more light emitters 3844 enclosed in the flange 3822, as described in more detail herein, are configured to administer light to the patient's teeth and/or alveolar mucosa (e.g., towards the buccal side of the patient's teeth and/or alveolar mucosa). Although the flange 3822 is shown and described herein as a single flange, in other embodiments, the mouthpiece 3810 can comprise two or more flanges.

The flange 3822 is generally U-shaped, e.g., in a manner similar to the bite tray 3812. The flange 3822 comprises two posterior portions 3822A, 3822B and an anterior portion 3822C. The posterior portions 3822A, 3822B of the flange 3822 can be characterized as the portions of the flange 3822 that extend, protrude, project, and/or jut out beyond the posterior ends 3812A, 3812B, respectively, of the bite tray 3812.

Generally, the anterior portion 3822C of the flange 3822 can be characterized as the portion of the flange that is coupled to the bite tray 3812. Stated another way, the bite tray 3812 has a U-shaped outer perimeter portion and a U-shaped inner perimeter portion.

The outer perimeter portion of the bite tray 3812 is coupled to the flange 3822. The length of the outer perimeter portion of the bite tray 3812 is less than the length of the flange 3822 from each opposing end of the posterior portions 3822A and 3822B of the flange 3822.

During use, in some embodiments, the posterior portions 3822A, 3822B of the flange 3822 can be disposed adjacent one or more posteriorly-located teeth, such as one or more molars and/or one or more bicuspids. In this manner, the posterior portions 3822A, 3822B are useful for treating tissue in the narrower/smaller posterior areas of the oral cavity that cannot otherwise be reached by virtue of the presence of the bite tray 3812, such as in the region of the molars, in the region of the second molar, and/or the like. In some embodiments, each posterior portion 3822A, 3822B of the flange 3822 extends distally beyond the respective posterior end 3812A, 3812B of the bite tray 3812 by any suitable distance such as, but not limited to, a non-zero distance that is less than about 1 cm, about 1cm, about 2 cm, about 3 cm, about 4 cm, including all subranges and values in between.

Figure 156D:
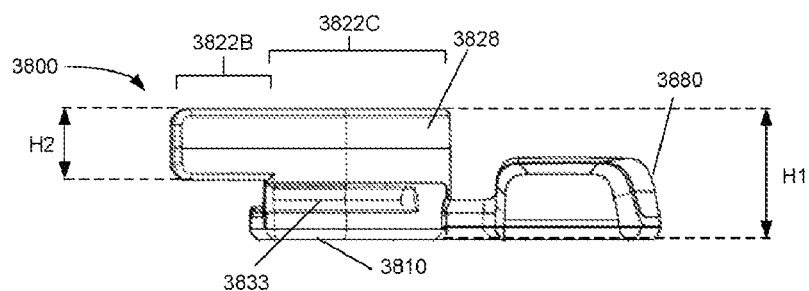

In some embodiments, as illustrated in FIGS. 156C-156D, the anterior portion 3822C of the flange 3822 has a height HI, and the posterior portions 3822A, 3822B each have a height H2. In some embodiments, the height H2 of the posterior portions 3822A, 3822B is less than the height HI of the anterior portion 3822C. In some embodiments, the height HI of the anterior portion 3822C of the flange 3822 can be about 20 mm, about 25 mm, about 30 mm, about 35 mm, including all subranges and values in between. In some embodiments, the height H2 of each of the posterior portions 3822A, 3822B of the flange 3822 can be about 15 mm, about 12 mm, about 10 mm, about 8 mm, about 5 mm, including all subranges and values in between. While shown in FIG. 156D as a sharp decrease in height from H2 to HI, in other embodiments, any suitable transition in height between the anterior portion and the posterior portions is possible including, but not limited to, a stepwise transition, a gradual (e.g., sloped or curved) transition, and/or the like. In this manner, the narrowing of the flange 3822 in the posterior portions 3822C enhances quality of fit and use of the apparatus 3800.

The flange 3822 is configured to be disposed between the buccal tissue and the alveolar mucosa. Thus, in use, the flange 3822 displaces oral soft tissue to maintain the desired position of the light emitters 3844 relative to the anatomy of the patient. More specifically, the flange 3822 is configured to displace buccal tissue away from the patient's alveolar mucosa. In one or more embodiments, an inner face 3826 of the flange 3822 can be spaced apart from the patient's alveolar tissue when the mouthpiece 3810 is disposed within the patient's mouth and the flange 3822 is displacing the buccal tissue.

In one or more embodiments, at least a portion of the inner face 3826 of the flange 3822 can contact the patient's alveolar tissue when the mouthpiece 3810 is disposed within the patient's mouth and the flange 3822 is displacing the buccal tissue.

The flange 3822 of the mouthpiece 3810 is configured to be flexible and/or deformable. Similarly stated, the flange 3822 is constructed from a material and have geometrical dimensions and/or configurations to provide the desired flexibility, as described herein. In this manner, the mouthpiece 3810 can be easily disposed within the oral cavity for a variety of different patients having a variety of different anatomical structures, as described herein.

In some embodiments, the flexibility of the anterior portion 3822C is different than that of the posterior portions 3822A, 3822B. Stated another way, the flange 3822 can have differential flexibility from the anterior portion to the posterior portions, and vice versa. In some embodiments, the posterior portions 3822A, 3822B can exhibit greater flexibility than the anterior portion 3822C, while in other embodiments, the anterior portion 3822C has greater flexibility than the posterior portions 3822A, 3822B. In some embodiments, the change in flexibility between the anterior portion 3822C and the posterior portions 3822A, 3822B can be discrete at the boundary therebetween. For example, the anterior portion 3822C can be composed of a first material having a first measure of flexibility (e.g., of flexural modulus), and the posterior portions 3822A, 3822B can be composted of a second material having a second measure of flexibility different than the first measure of flexibility. As another example, both the anterior portion 3822C and the posterior portions 3822A, 3822B can be made of the same material, but have different densities. In some embodiments, the change in flexibility between the anterior portion 3822C and the posterior portions 3822A, 3822B can be continuous and/or gradual, i.e., the rate of change of flexibility from one portion to another can be below a predetermined threshold. For example, both the anterior portion 3822C and the posterior portions 3822A, 3822B can be made of the same materials, and a density gradient exists that results in a gradient in flexibility from one portion to another.

In some embodiments, the flexibility of the posterior portions 3822A, 3822B can be greater than that of the anterior portion 3822C. In some embodiments, the flexibility of the posterior portions 3822A, 3822B permits deflection of the posterior portions 3822A, 3822B in multiple ways, including: a) in a manner similar to that of the anterior portion 3822C deflecting towards and away from the bite tray 3812 (movement denoted by arrow Fct in FIG. 156A); b) in a torsional/twistable manner (e.g., up to a torsion angle of about 30 degrees), about the point of attachment/coupling/formation with the anterior portion 3822C (movement denoted by arrow F1 in FIG. 156A); and/or c) in a "flapping"/flappable manner (e.g. up to an angle of about 30 degrees), towards or away from a midline of the oral cavity (or away from the tongue towards buccal tissue) of the patient during use (movement denoted by arrow Frin FIG. 156A). In this manner, the posterior portions 3822A, 3822B provide enhanced flexibility for conforming to the patient's mouth in the relatively narrow reaches of the posterior portions of the patient's mouth, near and/or posterior to the molars.

The mouthpiece 3810 defines at least one groove 3832, 3833 defined by a lower outer (or front) surface of the flange 3822. For example, the mouthpiece 3810 comprises the first groove 3832 and the second groove 3833, each defined by the outer, anterior, or front surface 3828 of the mouthpiece 3810. The grooves 3832, 3833 can each be similar in many respects, or identical, to grooves 2532, 2533 described with respect to mouthpiece 2510 and FIGS. 84-113. In some embodiments, the grooves 3832, 3833 are each disposed at a height between the bite pad 3814 and a lower edge of a flexible circuit board disposed within the flange 3822, discussed in more detail below (not shown in FIGS. 156A-156D). Stated another way, the grooves 3832, 3833 can be defined by a base portion the flanges 3822. The grooves 3832, 3833 each extend about the outer surface 3828 of the mouthpiece 3810 between the posterior end portion of the mouthpiece 3810 and an anterior portion of the mouthpiece 3810. As illustrated, in some embodiments, the grooves 3832, 3833 are formed on the anterior portion 3822C of the flange 3822A, 3822B and are absent from the posterior portions 3822A, 3822B. In other embodiments, however, the grooves 3832, 3833 can be formed in a manner where they are defined by or extend at least partially along their respective posterior portions 3822A, 3822B. In some embodiments, a portion of the grooves 3832, 3833 formed in the posterior portions 3822A, 3822B can be relatively narrower and/or have a different cross-sectional profile than a portion of the grooves 3832, 3833 formed in the anterior portion 3822C.

As best seen in FIG. 156D, the grooves 3832, 3833 can be spaced apart at the anterior end portion of the mouthpiece 3810. In other words, the grooves 3832, 3833 do not necessarily meet at the anterior end of the mouthpiece 3810. For example, a first portion of the anterior portion 3822C of the flange 3822 can exclude the grooves 3832, 3833 and a second portion of the anterior portion 3822C of the flange 3822 can comprise the grooves 3832, 3833. The grooves 3832, 3833 can be noncontiguous and/or may not share a common boundary. The grooves 3832, 3833 can have any suitable shape, including, for example, that of a semi-circle or U-shape. The grooves 3832, 3833 produce a hinge-like structure (i.e., a "living hinge") about which the flange 3822 can rotate, bend and/or deflect. In this manner, the grooves 3832 permits the flanges 3122, 3124 to deflect inwardly (e.g., generally towards a midline of the apparatus 3800, or more specifically towards a midline of the bite tray 3812), for example, in response to pressure from the patient's lip or inner cheek.

As such, the groove 3832 facilitates the transition of the mouthpiece 3810 between a first configuration and a second configuration. When the mouthpiece 3810 is in the first configuration, the angle formed between the anterior portion 3822A, 3822B of the flange 3822 and the bite pad 3814 (the "outer flange angle") has a first value. When the mouthpiece 3810 is in the second configuration, the outer flange angle has a second value that is different from the first value. In particular, the mouthpiece 3810 can be moved to the second configuration when disposed within the patient's mouth. In one or more embodiments, the second value is less than the first value (i.e., the anterior portion 3822C of the flange 3822 "tips" inwardly toward the bite plate 3812 when the mouthpiece 3810 is inserted into the mouth). In one or more embodiments, the outer flange angle is approximately 90 degrees when the mouthpiece is in the first configuration and is acute when the mouthpiece is in the second configuration. In one or more embodiments, the outer flange angle is about 80 degrees (e.g., the flange 3822 tips inward toward the bite plate 3812 by about 10 degrees) when the mouthpiece is in the second configuration. In other embodiments, the outer flange angle is between about 75 degrees and about 80 degrees (e.g., the flange 3822 tips inward toward the bite plate 3812 by between about 10 degrees and 15 degrees). In yet other embodiments, the outer flange angle is about 85 degrees, about 75 degrees, about 70 degrees, or about 65 degrees (e.g., the flange 3822 tips inward toward the bite plate by about 5 degrees, about 15 degrees, about 20 degrees and about 25 degrees, respectively) when the mouthpiece is in the second configuration.

The flexibility of the mouthpiece 3810, and the differential flexibility of the various portions of the flange 3822 in particular, provides significant advantages. For example, in contrast to mouthpieces constructed of a hard plastic and/or with a permanent set (or shape), the current arrangement allows for easier insertion and better conformance to the oral tissue of the patient. The flexibility of the mouthpiece 3810 also accommodates variation in patient anatomy (whether between two different patients or for the same patient as that patient's anatomy changes over time). For example, some patients have a pronounced overbite and may need more or less than a 10 degree inward deflection (or "tip-in"). In such instances, the mouthpiece 3810 can conform to the internal structure and/or anatomy within the patient's mouth. As another example, over the course of orthodontic treatment, the patient's dental anatomy is expected to change.

Accordingly, the mouthpiece 3810 can conform to the internal structure and/or anatomy within the patient's mouth to accommodate such change without requiring new mouthpiece moldings or the like. Further, the flexible design of the mouthpiece 3810 provides greater comfort for the patient than would be provided by mouthpieces constructed of a hard plastic.

Additionally, the flexible nature of the mouthpiece 3810 and/or the flange 3822 provides manufacturing benefits. In particular, fabrication and/or molding of a mouthpiece having an acute angle between the bite surface and the side surface of the flange (i.e., the internal angle of the flange or the "flange angle") can be difficult. The design of the mouthpiece 3810, however, allows for the molding and/or fabrication to be performed with a flange angle of approximately ninety degrees (or greater), while allowing for an in-use inner flange angle that is acute (e.g., when the mouthpiece 3810 is in the second configuration, as described above).

The mouthpiece 3810 of the light therapy apparatus 3800 can comprise an electronic assembly. The electronics assembly is disposed primarily in the flange 3822, and comprises a flexible circuit board (not shown) and comprises or is otherwise coupled to the one or more light emitters 3844. The one or more light emitters 3844 are coupled to the flange 3844 of the mouthpiece 3810. In some embodiments, one or more light emitters 3844 are disposed on, disposed in, or embedded in the flange 3822, as described in more detail herein. In some embodiments, light emitter(s) 3844 protrude through and/or are generally visible on a posterior (or lingual-facing) surface of the flange 3822.

In some embodiments, and as illustrated in FIGS. 156A-156D, the one or more light emitters 3844 can comprise multiple light emitters disposed on or at least partially in each of the posterior portions 3822A, 3822B and the anterior portion 3822C of the flange. In other embodiments, the light emitters 3844 can be disposed on the anterior portion 3822C, and be absent from the posterior portions 3822A, 3822B. In some embodiments, at least one light emitter 3844 is disposed on one or more of the posterior portions 3822A, 3822B. In some embodiments, the light emitter(s) disposed on the posterior portions 3822A, 3822B are not co-linear with the light emitter(s) disposed on the anterior portion 3822C (as illustrated), but are offset in a direction towards or away from the bite tray 3812. For example, the light emitter(s) coupled to the posterior portions 3822A, 3822B of the flange 3822 can be arranged in one or more rows that are parallel to, but not co-linear to, the one or more rows of light emitter(s) 3844 coupled to the anterior portion 3822C of the flange 3822.

The light emitter(s) can be any suitable light emitter described herein, such as a plurality of LEDs. The light emitters 3844 are electrically and/or physically coupled to the flexible circuit board, which in turn electrically couples the light emitters 3844 to electronic circuitry outside of the mouthpiece 3810 (e.g., in the extra-oral housing 3880 or via electrical connectors to an external controller, not shown). In this manner, the light emitters 3844 can receive power and/or a signal to produce the desired light, as described herein. The light emitters may be disposed on the flexible circuit board in a manner as already described for FIG. 131, and will not be further detailed herein. In this manner, the light emitters 3844 are configured to emit light toward a patient's teeth and/or adjacent oral tissue when the mouthpiece 3810 is disposed within the patient's mouth. Stated another way, the light emitters 3844 are configured to emit light towards the anterior root area of an upper and/or lower jaw and/or the buccal alveolar soft tissue.

The light emitters 3844 can be configured to emit light at any suitable intensity, wavelength and/or frequency described herein. For example, in one or more embodiments, the light emitters 3844 can be configured to emit light in the red, the infrared, or near infrared wavelength range. For example, in one or more embodiments, the light emitters 3844 are configured to emit light at a wavelength of about 850 nm. In one or more embodiments, the light emitters 3844 are configured to emit light at a wavelength of 850 nm±5 nm. In some embodiments, one or more of the light emitters 3844 are configured to emit light at a first wavelength, and the remainder of the light emitters 3844 are configured to emit light at a second wavelength. In some embodiments, the first wavelength is about 850 nm, and the second wavelength is about 625 nm.

In some embodiments, at least about 10%, at least about 20%, at least about 30%, at least about 40%, at least about 60%, at least about 80%, at least about 90% of the light emitters 3844 emit light at the first wavelength (including all values and sub ranges in between), and the remainder emit light at the second wavelength. In some embodiments, about two-thirds of the light emitters 3844 can emit light at the first wavelength, and the remaining one-third of the light emitters 3844 can emit light at the second wavelength. It is understood that while explained herein with reference to the light emitters emitting two different wavelengths, any suitable number of wavelengths may be employed in this manner.

The light emitters 3844 can be configured to emit light sufficient deliver light energy to the patient's bone to facilitate and/or perform any of the methods described herein. The light emitters 3844 can be configured to emit light at less than 150 mW/cm$^2$.

In some embodiments, the light emitters 3844 are coupled to the electronics assembly such that zones of the light emitters are individually addressable or controllable. One or more of the light emitters 3844 (e.g., one or more LEDs) can constitute a zone of light emitters. In one or more embodiments, from about 1 to about 20, from about 1 to about 15, from about 1 to about 10, or from about 1 to about 9, or from about 1 to about 8, or from about 1 to about 7, or from about 1 to about 6, or from about 1 to about 5, or from about 1 to about 4 light emitters are included in a zone of light emitters. It will be understood by one of skill in the art that the number of light emitters that actually irradiate light during light therapy will vary depending on patient presentation and ultimate treatment protocol. In some embodiments, light emitters disposed on each posterior portion 8422A can constitute one or more zones of light emitters, and light emitters disposed on the anterior portion 8422B can constitute a separate zone or zones of light emitters. In some embodiments, light emitters disposed on the anterior portion 8422B can constitute two or more zones of light emitters. In some embodiments, each zone is independently and selectively operable, such that any of the following example scenarios is possible: 1) a first zone of light emitters can emit light at a first time, and a second zone of light emitters can emit light at a second time that may or may not overlap with the first time; and 2) multiples zones of light emitters may be operated to emit light in a predetermined sequence and/or pattern. In some embodiments, the light emitters within a zone can emit light at a wavelength (e.g., at about 850 nm) that is different than that emitted by light emitters in a different zone (e.g., at about 625 nm). In other embodiments, the light emitters within a single zone can emit light at two or more different wavelengths.

The light emitters 3844 can provide any suitable power density effective for treatment. In some embodiments, the power density is from about 30 mW/cm 2 to about 150 mW/cm 2, including all values and sub ranges in between. In some embodiments, the light emitters 3844 can provide a power density of about 60 mW/cm 2. In some embodiments, the light emitters 3844 can provide a power density of about 120 mW/cm 2.

The light emitters 3844 can be disposed on the mouthpiece 3810 in any suitable configuration, including any configuration described herein. For example, in one or more embodiments, the light emitters 3844 comprise LEDs disposed in one or more parallel rows and/or columns. In one or more embodiments, at least some of the light emitters 3844 are disposed on the mouthpiece 3810 in a single row, as illustrated in FIGS. 156A-156C. In some embodiments, the mouthpiece 3810 comprises additional light emitters e.g., structurally and/or functionally similar to the light emitters 3050, 3052.

Although the light emitters 3844 are shown as being evenly spaced on the flange 3822, in other embodiments, the light emitters can be unevenly spaced. For example, in one or more embodiments, a mouthpiece can comprise a series of light emitters that are spaced apart by a first distance in or near the anterior portion of the mouthpiece and spaced apart by a second, different distance in or near the posterior portion of the mouthpiece.

The mouthpiece 3810 can be constructed of any suitable material, including, for example, any material described herein with respect to mouthpiece 2510, and thus such material is not described in detail with respect to mouthpiece 3810. For example, the mouthpiece 3110 can be constructed of an elastomeric material (e.g., a soft silicone). In another example, the mouthpiece 3810 can be fabricated from medical-grade injection-molded, highly flexible and very low durometer silicone. In another example, the silicone and/or portions of the mouthpiece 3810 are substantially transparent, such that one or more components embedded within the silicone are visible through the silicone. Moreover, in this manner, the mouthpiece 3810 can provide suitable optical properties for allowing the light produced and/or conveyed by the light emitters 3844 to pass through the mouthpiece 3810 to the desired target tissue. In one or more embodiments, the mouthpiece 3810 and/or the flange 3822 can comprise one or more components configured to filter, focus and/or otherwise act upon the light produced by the light emitters 3844. In other embodiments, the mouthpiece 3810 can comprise air gaps between the light emitters 3844 and the surface of the flange 3822 to facilitate focusing of the light. The mouthpiece 3810 can constructed such that the light emitters 3844 are fully encapsulated or embedded within the molded silicone such that no space or air gap exists between the silicone material and the emitters 844. Similarly stated, the mouthpiece 3810 can exclude an air gap between the light emitters 3844 and the material of the mouthpiece 3810, thus no air gap lensing is needed to produce the desired optical properties of the light produced by the light emitters 3844.

Figure 157A:
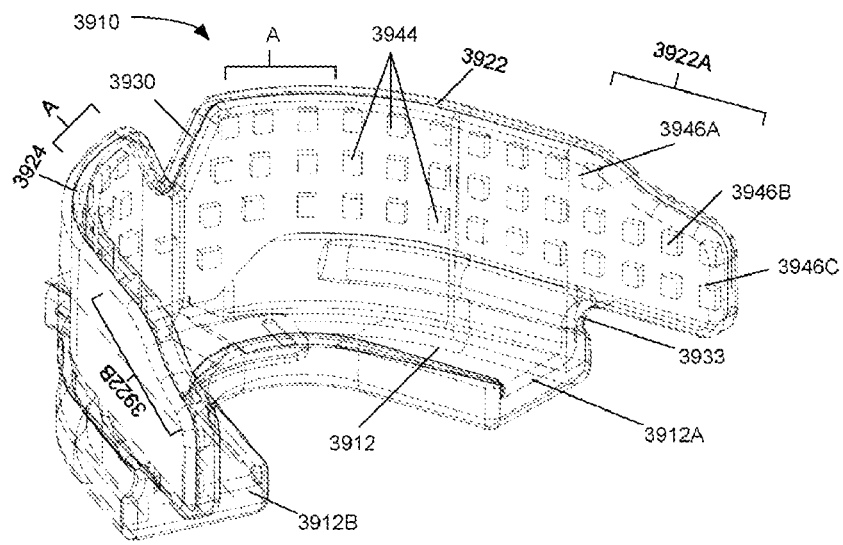
Figure 157B:
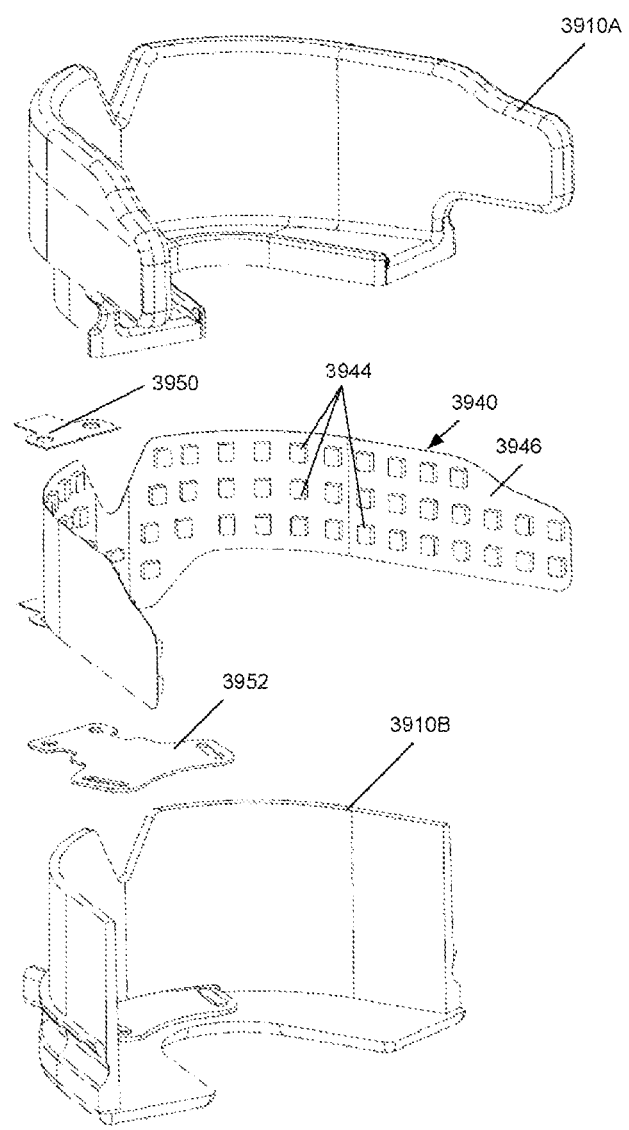

An intra-oral housing 3910 (also referred to herein as a "mouthpiece") according to an embodiment, being sized and/or shaped to be fully or substantially fully disposed within a patient's mouth, is illustrated in FIGS. 157A-157B. Unless explicitly noted otherwise, components of the mouthpiece 3910 can be structurally and/or functionally similar or identical to similarly named and numbered components of the mouthpiece 3810, or any intra-oral housing or mouthpiece described herein. For example, the intra-oral housing 3910 can comprise light emitters 3944 that can be similar to the light emitters 3844, the intra-oral housing 3910 can comprise a posterior end 3912A of a bite tray 3912 that can be similar to the posterior end 3812A of the bite tray 3812, and so on. As shown in FIG. 157A, the bite tray 3912 includes two posterior ends—3912A and 3912B.

As illustrated in FIG. 157A, the mouthpiece 3910 can comprise a notch 3930, which can be similar to the notch 2530, described herein with respect to FIG. 90, or to notch 3130, described herein with respect to FIG. 130. The notch 3930 can be V-shaped, generally dividing the anterior portion of the mouthpiece into two flanges 3922, 3924, compared to the flange 3822, which has a continuous top edge with no notch formed therein. In this manner, the deflectability (e.g., with respect to the bite tray) of the flanges 3922, 3924 can be enhanced (e.g., as described herein with respect to FIG. 90).

In some embodiments, the deflectability of the flange 3922 can be different than the deflectability of the flange 3924.

The light emitters 3944 are disposed along multiple rows and columns, in contrast to the light emitters 3844, which are illustrated as being disposed in a single row. In some embodiments, and as illustrated in FIG. 157A, one or more rows of light emitters 3944 are noncontiguous in the vicinity of the notch 3930, either by virtue of the presence of the notch, or by design. In some embodiments, one or more rows of light emitters 3944 can extend to different extents to the posterior portions 3922A, depending on the design of the posterior portion. For example, FIG. 157A illustrates a tapered design for the posterior portion 3922A, such that a row 3946A of light emitters extends into the posterior portion 3922A to a lesser degree than the rows 3946B, 3946C of light emitters. Stated another way, the number of light emitters in the row 3946A that are disposed in the posterior portion 3922A is fewer than the number of light emitters in the row 3946B of light emitters or in the row 3946C of light emitters that are disposed in the posterior portion 3922A. As shown in FIG. 157A, posterior portions of the flange (3922A and 3922B) extend (e.g., by a distance of from about 1 mm to about 24 mm, or about 10 mm to about 24 mm, or about 1 mm to about 12 mm, or about 12 mm to about 24 mm, or about 5 mm to about 15 mm, or about 5 mm to about 20 mm, or about 2 mm to about 18 mm, or about 5 mm to about 18 mm, or about 1 mm to about 5 mm, or about 5 mm to about 10 mm) beyond the posterior ends 3912A and 3912B (respectively) of the bite tray. One or both posterior portions of the flange (3922A and 3922B) can have a height (i.e., a measurement from a bottom edge thereof to a top edge thereof, as oriented in FIG. 157A and in a non-deflected state) that is less than a maximum height (i.e., a measurement from a bottom edge thereof to a top edge thereof, taken in a region other than the notched region) of an anterior portion ("A") of the flange. In some embodiments, a first posterior portion of the flange (3922A) is substantially perpendicular to a first posterior end of the bite tray (3912A) and/or a second posterior portion of the flange (3922B) is substantially perpendicular to a second posterior end of the bite tray (3912B).

In some embodiments, one or both of the posterior portions of the flange (3922A and 3922B) is twistable with respect to an anterior portion ("A") of the flange. Alternatively or in addition, one or both of the posterior portions of the flange (3922A and 3922B) is flappable with respect to an anterior portion ("A") of the flange. Although the posterior portions 3922A, 3922B shown and described with reference to FIG. 157A as being tapered or "sloped" (i.e., having a height that gradually reduces along a direction extending from an anterior portion "A" of the flange towards a posterior portion (3922A, 3922B) of the flange), other height variations are also contemplated. For example, the posterior portions 3922A, 3922B can each have a height that changes in a stepwise manner along a direction extending from an anterior portion of the flange towards the posterior portion of the flange. The height variation can occur along an entire flange (i.e., spanning the distance from a front/anterior of the overall mouthpiece to a rear/posterior of the overall mouthpiece), or may be confined to the posterior portions (3922A, 3922B) of the flange.

The light emitters 3944 can provide any suitable power density effective for treatment. In some embodiments, the power density is from about 30 mW/cm$^2$ to about 150 mW/cm$^2$, including all values and sub ranges in between. In some embodiments, the light emitters 3844 can provide a power density of about 60 mW/cm$^2$. In some embodiments, the light emitters 3844 can provide a power density of about 120 mW/cm$^2$.

FIG. 157B is an exploded view showing components of the mouthpiece 3910.

The mouthpiece 3910 comprises an inner layer 3910A, an electronic assembly 3940, and an outer layer 3910B. The mouthpiece also comprises connectors 3950, 3952 with slots formed therein for coupling the layers 3910A, 3910B, and the electronic assembly 3940, as well as for electrical/electronic coupling of the mouthpiece 3910 to an external housing (not shown).

The electronics assembly 3940 comprises a flexible circuit board 3946, and the light emitters 3944. The flexible circuit board 3946 can be formed of any suitable material as any flexible circuit board described herein, such as flexible circuit boards 2546, 3046, 3146, and 3646. The light emitters 3944 can be any suitable light source described herein, including, for example, LEDs.

The inner layer 3910A of the mouthpiece 3910 and the outer layer 3910B of the mouthpiece 3910, in some embodiments, can be formed of substantially the same material such as, for example, any material described herein (e.g., with respect to mouthpiece 2510), and thus such material is not described in detail with respect to mouthpiece 3810. For example, the layers 3910A, 3910B can be constructed of an elastomeric material (e.g., a soft silicone, a silicone rubber such as the Silbione® liquid silicone rubber, and/or the like). In another example, the layers 3910A, 3910B can be fabricated from medical-grade injection-molded, highly flexible and very low durometer silicone. In some embodiments, the layers 3910A, 3910B can be made of the same material but have differing flexibility/rigidity. In some embodiments, the layers 3910A, 3910B can be made of different materials but have substantially the same flexibility/rigidity. In some embodiments, the layers 3910A, 3910B can be made of different materials having differing flexibility/rigidity.

As a non-limiting example of manufacture and assembly of the mouthpiece 3910, in some embodiments, the inner layer 3910 can be formed via injection molding of an elastomeric material. The flexible circuit board 3946 can then be placed inside a volume formed by the inner layer 3910 via an opening in the inner layer 3910. Thereafter, additional elastomeric material can be poured into any residual volume in the inner layer 3910, and can also be used to create the bite tray 3912. The outer layer 3910B can then be coupled to the inner layer 3910A via the connectors 3950, 3952 as described herein.

FIG. 157C is a top view of a light therapy apparatus according to an embodiment. FIGS. 157D-G are perspective, first side, rear, and second side views, respectively, of the light therapy apparatus of FIG. 157C. As shown in FIG. 157C, the light therapy apparatus 3960 includes a bite tray 3961 having a first posterior end 3961A and a second posterior end 3961B. Visible in each of FIGS. 157D-157G are first and second posterior flange portions 3962A and 3962B, which are similar to posterior portions 3922A, 3922B of FIG. 157A in that they protrude beyond the posterior ends of the bite tray (3961A and 3961B, respectively, but differ in that they have a tapered or "sloped" bottom portion as well as top portion. In some such implementations, a first (upper/top) edge of each of the posterior portions has a taper, shape or contour that mirrors (i.e., has the same shape as, but is inverted with respect to) a taper, shape or contour of a corresponding second (lower/bottom) edge of each of the posterior portions. In alternative implementations, a first (upper/top) edge of each of the posterior portions has a taper, shape or contour that is different from a taper, shape or contour of a corresponding second (lower/bottom) edge of each of the posterior portions. Although the posterior portions 3962A, 3962B shown and described with reference to FIGS. 157D-G as being tapered or "sloped" (i.e., having a height that gradually reduces along a direction extending from an anterior end of the flange towards a posterior end of the flange), other height variations are also contemplated. For example, each of the posterior portions 3962A, 3962B can each have a first (upper/top) edge that reduces in height (with respect to a midline of the light therapy apparatus when viewed as shown in FIG. 157D) in a stepwise manner along a direction extending from an anterior end of the flange towards the posterior end of the flange, in which case the corresponding second (lower/bottom) edge of each of the posterior portions can have a shape that either mirrors that of the first edge, or that differs from that of the first edge. For example, the first edge may taper (e.g., downward) in a stepwise manner, while the second edge tapers (e.g., upward) in a sloped manner.

In some embodiments, a method of regulating tooth movement includes administering light (e.g., using a light therapy apparatus similar to that of shown in any of FIGS. 157A-157G) to a region of alveolar mucosa overlying a root of a tooth (e.g., a molar) of a patient such that a rate of movement of the tooth is increased (in the presence of the light), relative to a rate of movement of the tooth in the absence of the light. The region of alveolar mucosa can include alveolar mucosa overlying a tooth root of a tooth such as a molar. In some such embodiments, the tooth is a first tooth, and the rate of movement is associated with a movement of the first tooth relative to a second tooth of the patient. The method can also include removably coupling an orthodontic appliance to the tooth.

Figure 157I:
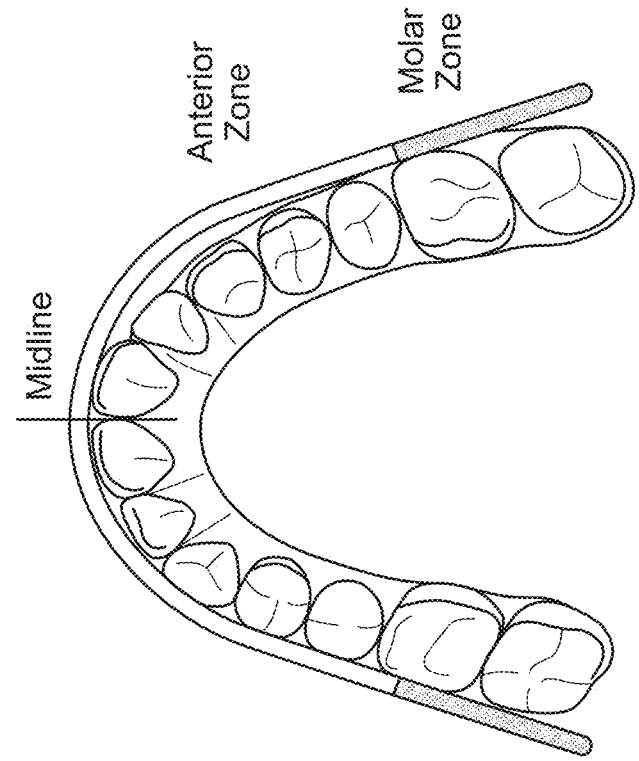
Figure 157H:
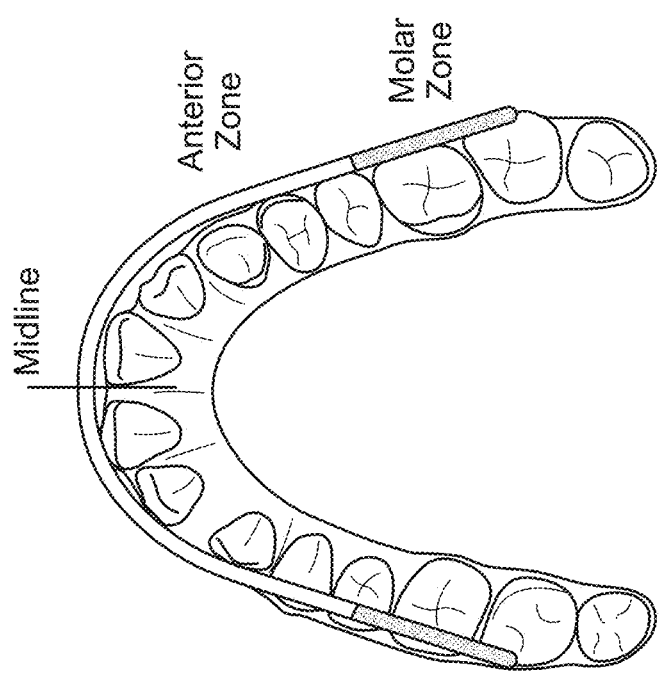

FIGS. 157H-I show example views of a patient's mouth (upper dental arch and lower arch), with an overlaid outline of a light therapy apparatus disposed therein, and illustrating the positioning of a midline, an anterior zone, and a molar zone of the light therapy apparatus. The light therapy apparatus of FIGS. 157H and 157I can be any intra-oral light therapy apparatus described herein. A "molar zone" can include one or more light emitters, and in some implementations, one or both of the molar zone regions of the light therapy apparatus can be controlled separately from other light-emitting portions of the light therapy apparatus. The precise positioning of the light therapy apparatus within the patient's mouth can vary, depending, for example, of the patient's anatomy (e.g., tooth size, age, etc.), however, as shown in FIGS. 157H and 157I, the molar zone of the light therapy apparatus can span at least the entirety of the length of a first molar and a portion (e.g., at least 50% coverage) of the second molar, such that, during use, light from the light therapy apparatus is directed to alveolar mucosa overlying tooth roots of the associated molars. Such embodiments can enhance clinical efficacy in terms of inducing accelerated movement of the teeth orthodontic ally, as compared with treatments that do not involve such illumination. In some embodiments, light emitted from the molar zone to alveolar mucosa overlying tooth roots of the associated molars can spread in the jaw bone.

In some embodiments, a light therapy apparatus (or a flange thereof) includes two controllable light-emitting zones: a molar zone (e.g., as described above with reference to FIGS. 157H-I), and an anterior zone that excludes the molars (or associated alveolar mucosa). The molar zone can include one or more light emitters (e.g., LEDs) configured to emit light toward a patient's molars or anatomy associated with the molars (e.g., to alveolar mucosa overlying tooth root associated with molars), for example, for aligner treatments and/or to distalize molars (i.e., sequentially move molars posteriorly) for the treatment of malocclusion. The controllability of the light-emitting zones can be accomplishes, for example, via a Bluetooth connection and/or one of a mobile software application ("app") or web-based app. In some implementations, the light therapy is controllable remotely (e.g., via an application programing interface, "API"), for example via the mobile or web-based app, such that the molar zone and anterior zone can be programmed to emit light according to a predetermined schedule, such as a tooth movement plan./

In some embodiments, each molar zone resides solely within a posterior portion, such as posterior portions 3922A, 3922B of FIG. 157A. In other embodiments, each molar zone resides partially within a posterior portion of an associated flange of the light therapy apparatus, such as posterior portions 3922A, 3922B of FIG. 157A, and partially within another portion of the associated flange. In other words, the molar zones can each "straddle" protruding and non-protruding portion of the flange. The molar zones can be configured to emit light to molar area (i.e., portions of the patient's mouth associated with the molars, such as alveolar mucosa overlying a tooth root of a molar, and/or the molars themselves), for example to accelerate distalization or any other significant molar movement that is planned as part of an orthodontic treatment plan. In some embodiments, the posterior portions 3922A, 3922B of the flange can one or more of: improve the positioning of the light therapy apparatus within a patient's mouth during use, reduce the need for a patient to bite down on the bite tray for positioning purposes, or increase a surface area of regions within the patient's mouth that are illuminated during treatment with the light therapy apparatus.

It is understood that although apparatuses or portions thereof (e.g., apparatus 2100, 2500, 3000, 3100, 3300, 3600, 3700, 3800, mouthpiece 3910) are each separately described herein via different figures, aspects of any of the apparatuses, or portions thereof, (e.g., apparatus 2100, 2500, 3000, 3100, 3300, 3600, 3700, 3800, and mouthpiece 3910) can be combined with one or more aspects of any one or more of another of apparatus (e.g., apparatus 2100, 2500, 3000, 3100, 3300, 3600, 3700, 3800, and mouthpiece 3910). For example, the signal processing described for apparatus 2500 may be included or used in apparatus 3100 and/or 3600 as well. In another example, one or more sensors (e.g., the light emitters 3050, 3052) described with respect to apparatus 3000 may be included in apparatus 3800 or mouthpiece 3910.

In some embodiments, a method of the invention can comprise intra-orally administering, to one or more teeth of a patient in need thereof, an effective amount of light from one or more light emitters of a light therapy apparatus (e.g., apparatus 2100, 2500, 3000, 3100, 3300, 3600, 3700, 3800, mouthpiece 3910). In some embodiments, the one or more light emitters can be associated with the one or more teeth during use of the light therapy apparatus. For example, a user or practitioner can specify that the one or more light emitters can substantially overlay the one or more teeth of the patient. The one or more light emitters can be selectively employed to deliver the light therapy to the targeted teeth.

The light emitters can provide any suitable power density effective for treatment, as described herein. In some embodiments, the power density is from about 30 mW/cm 2 to about 150 mW/cm 2, including all values and subranges in between. In some embodiments, the light emitters can provide a power density of about 60 mW/cm 2. In some embodiments, the light emitters can provide a power density of about 120 mW/cm 2.

In some embodiments, the one or more light emitters can constitute a first zone of illumination of a plurality of zones of illumination (e.g., two, three, four or more zones of illumination) of the light therapy apparatus (as generally described herein with respect to the mouthpiece 3810). In some embodiments, the one or more light emitters in the first zone of illumination can be at least partly or wholly disposed on a posterior portion of a flange of a mouthpiece of the apparatus that posteriorly extends from or beyond a posterior end of a bite tray of the mouthpiece. For example, as described herein with reference to the apparatus 3800, the light emitters 3844 can comprise multiple light emitters disposed on the posterior portion 3822A that extends beyond the posterior end of the bite tray 3812. In this manner, the light emitters in the first zone of illumination are configured to overlay and emit light towards one or more of: a targeted region of alveolar mucosa, or a targeted region of a tooth or teeth, such as one or more molars. Each zone of illumination can be independently controlled by a controller of an electronics assembly of the light therapy apparatus. In some such implementations, the electronics assembly can be configured to receive and/or store (e.g., in memory) an indication (e.g., identifiers, a mapping, etc.) of a plurality of zones of illumination associated with the light therapy apparatus, each zone of illumination comprising a subset of light emitters from a plurality of light emitters of the overall light therapy apparatus. The electronics assembly can be further configured to independently control an operational state (e.g., on, off, standby, sleep mode) of all light emitters (collectively) within a given zone of illumination from the plurality of zones of illumination. As used herein, a "zone of illumination" can refer to a region or portion of the light therapy apparatus that is configured to emit light to a region within a mouth of patient (e.g., to alveolar mucosa above the patient's gums).

It is understood that while described herein with respect to light emitters in a first zone of illumination affecting rate of tooth movement in some teeth, the approach is extendible to treating any desirable tooth or teeth, using one or more zones of illumination.

In some embodiments, the methods of the invention comprise administering the effective amount of light via one or more light emitters in the first zone of illumination in conjunction with the use of one or more orthodontic appliances, such as transparent aligner(s). In some embodiments, the methods comprise administering light using the light therapy apparatus for a predetermined time period. More specifically, during a particular session of a treatment program, the patient (or other administrator or healthcare professional) can use the light therapy apparatus to administer light therapy via one or more light emitters (e.g., in the first or a different zone of illumination) for a predetermined duration of time, i.e., the predetermined time period. In other words, the predetermined time period can be associated with an individual treatment session. In some embodiments, the predetermined time period is less than I minute, is about 1 minute, is about 2 minutes, is about 4 minutes, is about 6 minutes, is about 8 minutes, is about IO minutes, including all values and sub ranges in between. In some embodiments, the predetermined time period is about 5 minutes. In some embodiments, the predetermined time period is about 2.5 minutes. In some embodiments, the methods comprise administering light via a light therapy apparatus during a first session having a first predetermined time period and a during a second session having a second predetermined time period, where the second session is non-consecutive with the first session, and the duration of the first predetermined time period is independent of the duration of the second predetermined time period (note that the first predetermined time period can have a duration the same as or different from a duration of the second predetermined time period).

In some embodiments, the power density of the LED emitters, for example, during a particular treatment session or portion thereof, is about 60 mW/cm$^2$, and the predetermined time period is about 5 minutes. In some embodiments, the power density of the LED emitters is about 120 mW/cm$^2$, and the predetermined time period is about 5 minutes. In some embodiments, the power density of the LED emitters is about 60 mW/cm$^2$, and the predetermined time period is about 2.5 minutes. In some embodiments, the power density of the LED emitters is about 120 mW/cm$^2$, and the predetermined time period is about 2.5 minutes.

Administering Light Treatment

Light can be administered to the patient using an intra-oral apparatus (including, but not limited to, any intra-oral apparatus or light therapy apparatus, such as apparatus 2500, 3500, described herein) in any of the following ways.

Light can be administered to a region of the patient's mouth. Some examples of these regions include, but are not limited to, one or more teeth (e.g., incisor, canine, premolar, or molar, such as a maxillary central incisor, maxillary lateral incisor, maxillary canine, maxillary first premolar, maxillary second premolar, maxillary first molar, maxillary second molar, maxillary third molar, mandibular central incisor, mandibular lateral incisor, mandibular canine, mandibular first premolar, mandibular second premolar, mandibular first molar, mandibular second molar, or mandibular third molar), a root of one or more teeth (e.g., wherein a root of a tooth may include a portion of one or more roots supporting the tooth, one root supporting the tooth, a plurality of roots supporting the tooth, or all of the roots supporting the tooth), tissue supporting one or more teeth, a portion of the maxilla (e.g., portion of the patient's maxillary alveolar bone), a portion of the mandible (e.g., portion of the patient's mandibular alveolar bone), alveolus, basal tissue, gingiva (e.g., alveolar soft tissue), periodontal ligaments, cementum, periodontium, a region of a jaw bone or tissue, or at least a portion of the patient's other oral soft tissue or bone tissue. The region can be located on a left side or right side of the patient's mouth. In one or more embodiments, one or more regions are located on both the left and right side of the patient's mouth. In one or more embodiments, the region can be located in the front of the patient's mouth. The region can include one, two, three, four, five, six, seven, eight, or more teeth, or tissue surrounding or supporting the teeth. The region can include one or more roots of one, two, three, four, five, six, seven, eight, or more teeth, or periodontium of teeth. Regions can include tissue (e.g., alveolar or basal tissue) surrounding or supporting any of the teeth specifically described with or without including the tooth itself. Regions can include teeth or tissue supported by the maxilla or teeth supported by the mandible. One or more regions can be adjacent to one another, continuous with one another, or separate from one another. Any description herein of regions or examples of regions can apply to any other region or examples of treatment regions provided herein.

In one or more embodiments, light irradiates a region that can include a portion of tissue (e.g., bone tissue, or soft tissue) or other regions within the patient's oral cavity without irradiating one or more other portions of the patient's oral cavity. For example, light can irradiate the mandibular first molar on the right side of the patient's oral cavity without irradiating the mandibular third molar that is also located on the right side of the patient's oral cavity. In one or more embodiments, light is administered to one or more roots of only one tooth root and to only one periodontium. Alternatively, light is administered to one or more roots of a plurality of teeth and to a plurality of periodontia. Light can be administered to one or more roots of all or less than all the teeth and periodontia in the patient's oral cavity. One or more selected teeth, roots or periodontia can be irradiated with light. For example, the mandibular first molar and the mandibular third molar on the right side of the patient's oral cavity can be irradiated without the mandibular second molar being irradiated.

In one or more embodiments, light is administered to a patient's alveolar soft tissue, wherein an effective amount of light is irradiated from one or more emitters of an apparatus of the invention. In one or more embodiments, the alveolar soft tissue is alveolar mucosa.

In one or more embodiments, light from an intra-oral apparatus can irradiate a region that includes a portion of tissue (e.g., bone tissue, or soft tissue) at a much greater intensity than it irradiates other portions of the patient's tissue within the mouth. For example, light can irradiate a first tissue region (e.g., the region of tissue covered by panel 2 shown in FIG. 23) at an intensity that is 3×, 5×, 10×, 20×, 50×, or 100× greater than the intensity that irradiates any other region or portion of the patient's tissue (e.g., the regions of tissue covered by remaining panels 1 and 3-6 shown in FIG. 23). In one or more embodiments, light can irradiate a portion of a patient's alveolar soft tissue at a greater intensity than that of light that irradiates any of the patient's teeth. In another embodiment, light can irradiate or be focused with a greater intensity on the one or more teeth upon which heavy forces are optionally applied (that are desired to be moved), relative to the one or more teeth on which heavy forces are not exerted. Teeth with lower forces or anchorage teeth can be selectively shielded from light or irradiated at lower light intensity so that they can move less and the anchorage effect can be enhanced. In one or more embodiments, this is achieved by applying to the intra-oral apparatus, or adjusting within the intra-oral apparatus, one or more masks that shield from light one or more non-regions, as described with respect to FIG. 27. In one or more embodiments, light reaching a region can have an intensity that is greater than a threshold value. In one or more embodiments, this is achieved by applying to the intra-oral apparatus, or adjusting within the intra-oral apparatus, the density of emitters adjacent one or more regions, as described with respect to FIG. 41. In one or more embodiments, the threshold value can have an intensity as described elsewhere herein.

In one or more embodiments, the region can be close to a surface within the patient's mouth, or within a soft tissue or bone tissue. The region can be at a depth from the surface within the patient's mouth. For example, the region can be about 1 µm, about 1 µm, about 10 µm, about 50 µm, about 100 µm, about 200 µm, about 300 µm, about 500 µm, about 750 µm, about 1 mm, about 2 mm, about 3 mm, about 4 mm, about 5 mm, about 7 mm, about 10 mm, about 15 mm, about 20 mm, about 25 mm, about 30 mm, about 40 mm, about 50 mm, about 60 mm, or about 70 mm from the surface within the patient's mouth. Light can irradiate a region, which can have an area greater than, less than, or about 1 nm$^2$, about 1 µm$^2$, about 0.1 mm$^2$, about 0.2 mm$^2$, about 0.3 mm$^2$, about 0.4 mm$^2$, about 0.5 mm$^2$, about 0.7 mm$^2$, about 1 mm$^2$, about 10 mm$^2$, about 0.2 cm$^2$, about 0.5 cm$^2$, about 1 cm$^2$, about 2 cm$^2$, about 3 cm$^2$, about 5 cm$^2$, about 7 cm$^2$, about 10 cm$^2$, about 15 cm$^2$, about 20 cm$^2$, about 25 cm$^2$, about 30 cm$^2$, about 35 cm$^2$, about 40 cm$^2$, about 50 cm$^2$, about 60 cm$^2$, about 80 cm$^2$, about 100 cm$^2$, about 120 cm$^2$, about 140 cm$^2$, about 160 cm$^2$, about 180 cm$^2$ or about 200 cm$^2$. Light can irradiate one area, a plurality of areas, a point, or a plurality of points. In one or more embodiments, light irradiates a particular area without irradiating with significant intensity surrounding areas.

For example, light can irradiate a particular tooth or set of teeth without significant amounts of light irradiating adjacent teeth. In one or more embodiments, irradiating a tooth comprises irradiating an exposed surface of the tooth, a tooth root, or a periodontium of the tooth (see, for example, FIG. 26 and associated description).

The light administered by an intra-oral apparatus can be emitted from multiple light sources (e.g., emitters 32 shown in FIG. 25A). Light can irradiate a continuous region or one or more discrete regions based on the location of the light sources or emitters within the intra-oral apparatus, as described herein. Light can irradiate various regions from different directions. For example, light can be administered from a right side of a patient's mouth (e.g., from panel 1 shown in FIG. 23) and from a left side of a patient's mouth (e.g., from panel 3 shown in FIG. 23). The light sources or emitters can be adjusted within an intra-oral apparatus such that the administered light is angled upward toward a region, or angled downward to toward a region. The light source or emitters can be displaced, can be angled, can be rotated, or any combination thereof within the intra-oral apparatus.

As described herein, an effective amount of light can be administered via the intra-oral apparatus. An effective amount of light is an amount of light that is effective for regulating tooth-movement; reducing, preventing or minimizing tooth-root resorption; reducing bone resorption, inflammatory dentin resorption or cementum resorption; preventing or minimizing inflammation, or remodeling of tissue surrounding one or more teeth upon which heavy forces are or were exerted; regenerating maxillary or mandibular alveolar bone; or for other methods disclosed herein. The light's properties can include, but are not limited to: its intensity, wavelength, coherency, range, peak wavelength of emission, energy density, continuity, pulsing, duty cycle, frequency or duration.

In one or more embodiments, a method for regulating tooth movement can further comprise determining an effective amount of light. The determination can be based on an intended tooth movement regulation effect. The method can further comprise selecting one or more light properties to provide the effective amount of light. The method can further comprise receiving instructions from a controller, and emitting light having particular properties. The controller can be, for example, controller 430 shown in FIG. 29, the external electronic device described with respect to FIG. 39, or any other controller described herein. The controller can implement any of the steps described herein.

Light can be administered from one or more light source within an intra-oral apparatus capable of irradiating light having intended properties. As described herein, the intra-oral apparatus can emit light from one or more light emitters, such as emitters 32, 132, 232, and/or 332. In one or more embodiments, the intra-oral apparatus comprises about 10 to about 15 emitters, about 15 to about 20 emitters, about 20 to about 30 emitters, about 30 to about 40 emitters, about 40 to about 50 emitters, about 50 to about 70 emitters, or about 70 emitters to about 100 emitters. For example, light can be administered from one or more of the following emitters: a light-emitting diode (LED), which can be present in an array; and a laser, for example, a vertical cavity surface emitting laser (VCSEL) or other suitable light emitter such as an Indium-Gallium-Aluminum-Phosphide (InGaAIP) laser, a Gallium-Arsenic Phosphide/Gallium Phosphide (GaAsP/GaP) laser, or a Gallium-Aluminum-Arsenide/Gallium-Aluminum-Arsenide (GaAIAs/GaAs) laser. In one or more embodiments, the intra-oral apparatus comprises a plurality of lasers. A plurality of light emitters can emit light at one or more different wavelengths. Alternatively, one or more light emitters can emit light at the same wavelength. The one or more light emitters can be arranged on or within the intra-oral apparatus in any manner, such as a linear array or another arrangement described herein.

An effective amount of light can have an intensity that is effective for regulating tooth movement. In one or more embodiments, the light intensity is at least about 10 mW/cm$^2$. In other embodiments, the light intensity is about 1 mW/cm$^2$ or greater, about 3 mW/cm$^2$ or greater, about 5 mW/cm$^2$ or greater, about 7 mW/cm$^2$ or greater, about 12 mW/cm$^2$ or greater, about 15 mW/cm$^2$ or greater, about 20 mW/cm$^2$ or greater, about 30 mW/cm$^2$ or greater, about 50 mW/cm$^2$ or greater, about 75 mW/cm$^2$ or greater, about 100 mW/cm$^2$ or greater, about 200 mW/cm$^2$ or greater, about 500 mW/cm$^2$ or greater, or about 1 W/cm$^2$ or greater. In other embodiments, the light intensity is about 20 mW/cm$^2$ or less, about 30 mW/cm$^2$ or less, about 50 mW/cm$^2$ or less, about 75 mW/cm$^2$ or less, about 100 mW/cm$^2$ or less, about 200 mW/cm$^2$ or less, about 500 mW/cm$^2$ or less, about 1 W/cm$^2$ or less, about 2 W/cm$^2$ or less, about 5 W/cm$^2$ or less, or about 10 W/cm² or less. In one or more embodiments the light intensity ranges from about 1 mW/cm² to about 10 W/cm². In another embodiment, the light intensity's lower range is about 3 mW/cm², about 5 mW/cm², about 7 mW/cm², about 12 mW/cm², about 15 mW/cm², about 20 mW/cm², about 30 mW/cm², about 50 mW/cm², about 75 mW/cm², about 100 mW/cm², about 200 mW/cm², about 500 mW/cm² or about 1 W/cm².

In another embodiment, the light intensity's upper range is about 20 mW/cm², about 30 mW/cm², about 50 mW/cm², about 75 mW/cm², about 100 mW/cm², about 200 mW/cm², about 500 mW/cm², about 1 W/cm², about 2 W/cm² about 5 W/cm² or about 10 W/cm², another embodiment, the light intensity is at 15 mW/cm². Light can be administered having an intensity having a range determined by any of the intensities described herein. In one or more embodiments, the intensity is an average intensity. In one or more embodiments, the light has an intensity in the range of about 10 mW/cm² to about 60 mW/cm², or about 20 mW/cm² to about 60 mW/cm². In such embodiments, the peak light intensity can about 50 mW/cm² or greater. A peak wavelength is the wavelength at which the highest intensity of light is emitted. In one or more embodiments, light can be pulsed. In other embodiments, the output of light is continuous. In one or more embodiments, the light intensity can vary over time in a cyclical or non-cyclical fashion. The light intensity can vary with or without pulsing. In one or more embodiments, pulsewidth modulation can be useful for affecting a desired light intensity. If one or more wavelengths of light are administered, then each wavelength can be administered at its own intensity. In one or more embodiments, an effective amount or dosage of light can comprise administering light having an intensity of about 15 mW/cm² for less than or up to three minutes duration. Additional details regarding effective amounts or dosages of light are described herein.

In one or more embodiments, an effective amount of light can include light having a wavelength that is of a particular range, or light of a range of wavelengths. The light is not necessarily visible light. For example, the light can include infrared light or near-infrared light. The light can also be provided in the visible light region. Light can administered having one or more wavelengths ranging from about 620 nm to about 1000 nm.

In one or more embodiments, administered light has one or more wavelengths ranging from about 585 nm to about 665 nm, about 815 nm to about 895 nm, about 640 nm to about 680 nm, or about 740 nm to about 780 nm, or any particular wavelength or range of wavelengths, such as, for example, about 625 nm or about 855 nm, or about 605 nm to about 645 nm, or about 835 nm to about 875 nm. In one or more embodiments, the administered light has one or more wavelengths from about 605 nm to about 645 nm, or from about 835 nm to about 875 nm. In one or more embodiments, the administered light has one or more wavelengths from about 615 nm to about 635 nm, or from about 845 nm to about 865 nm. In one or more embodiments, the wavelengths of the administered light are about 625 nm or about 855 nm. In additional embodiments, the administered light has one or more wavelengths ranging from about 400 nm to about 1200 nm. In particular embodiments, the administered light has one or more wavelengths ranging from about 500 nm to about 700 nm, about 585 nm to about 665 nm, about 605 nm to about 630 nm, about 620 nm to about 680 nm, about 815 nm to about 895 nm, about 820 nm to about 890 nm, about 640 nm to about 680 nm, or about 740 nm to about 780 nm. In one or more the administered light has one or more wavelengths in one or both of the following wavelength ranges: about 820 to about 890 nm and about 620 to about 680 nm. In one or more embodiments, the administered light has one or more wavelengths in the ranges of about 820 to about 890 nm and about 620 nm to about 680 nm. In one or more embodiments, the administered light has one or more wavelengths in the ranges of about 815 to about 895 nm and about 585 to about 665 nm. The administered light can alternatively have one or more wavelengths in one or more of the following ranges: about 613 nm to about 624 nm, about 667 nm to about 684 nm, about 750 nm to about 773 nm, about 812 nm to about 846 nm.

In one or more embodiments, the light wavelength's lower range is about 400 nm, about 450 nm, about 500 nm, about 550 nm, about 585 nm, about 595 nm, about 605 nm, about 613 nm, about 615 nm, about 620 nm, about 624 nm, about 625 nm, about 640 nm, about 650 nm, about 667 nm, about 680 nm, about 710 nm, about 740 nm, about 750 nm, about 770 nm, about 812 nm, about 815 nm, about 820 nm, about 835 nm, about 845 nm, or about 860 nm. In another embodiment, the light wavelength's upper range is about 585 nm, about 605 nm, about 624 nm, about 630 nm, about 635 nm, about 645 nm, about 655 nm, about 660 nm, about 665 nm, about 680 nm, about 684 nm, about 700 nm, about 725 nm, about 755 nm, about 773 nm, about 780 nm, about 795 nm, about 815 nm, about 830 nm, about 846 nm, about 855 nm, about 865 nm, about 875 nm, about 890 nm, about 895 nm, about 935 nm, about 975 nm, about 1000 nm, about 1050 nm, about 1100 nm, or about 1200 nm.

The wavelengths of light administered comprise or consist of the wavelength values described herein.

For example, in one or more embodiments, light administered to a region does not comprise one or more wavelengths exceeding one or more of the following: about 585 nm, about 605 nm, about 624 nm, about 630 nm, about 635 nm, about 645 nm, about 655 nm, about 660 nm, about 665 nm, about 680 nm, about 684 nm, about 700 nm, about 725 nm, about 755 nm, about 773 nm, about 780 nm, about 795 nm, about 815 nm, about 830 nm, about 846 nm, about 855 nm, about 865 nm, about 875 nm, about 890 nm, about 895 nm, about 905 nm, about 910 nm, about 915 nm, about 920 nm, about 935 nm, about 975 nm, about 1000 nm, about 1050 nm, about 1100 nm, or about 1200 nm. For example, in one or more embodiments, no light exceeding about 585 nm, about 605 nm, about 624 nm, about 630 nm, about 635 nm, about 645 nm, about 655 nm, about 660 nm, about 665 nm, about 680 nm, about 684 nm, about 700 nm, about 725 nm, about 755 nm, about 773 nm, about 780 nm, about 795 nm, about 815 nm, about 830 nm, about 846 nm, about 855 nm, about 865 nm, about 875 nm, about 890 nm, about 895 nm, about 905 nm, about 910 nm, about 915 nm, about 920 nm, about 935 nm, about 975 nm, about 1000 nm, about 1050 nm, about 1100 nm, or about 1200 nm is administered to a selected region.

In one or more embodiments, light administered to a region does not comprise one or more wavelengths below one or more of the following: about 400 nm, about 450 nm, about 500 nm, about 550 nm, about 585 nm, about 595 nm, about 605 nm, about 613 nm, about 615 nm, about 620 nm, about 624 nm, about 625 nm, about 640 nm, about 650 nm, about 667 nm, about 680 nm, about 710 nm, about 740 nm, about 750 nm, about 770 nm, about 812 nm, about 815 nm, about 820 nm, about 835 nm, about 845 nm, or about 860 nm. For example, in one or more embodiments, no light below about 400 nm, about 450 nm, about 500 nm, about 550 nm, about 585 nm, about 595 nm, about 605 nm, about 613 nm, about 615 nm, about 620 nm, about 624 nm, about 625 nm, about 640 nm, about 650 nm, about 667 nm, about 680 nm, about 710 nm, about 740 nm, about 750 nm, about 770 nm, about 812 nm, about 815 nm, about 820 nm, about 835 nm, about 845 nm, or about 860 nm is administered to a selected region. In one or more embodiments, the light administered does not comprise a wavelength of about 600 nm or less. In one or more embodiments, the light administered does not comprise a wavelength of about 1000 nm or greater. In one or more embodiments, the light administered does not comprise a wavelength of about 600 nm or less and does not comprise a wavelength of about 1000 nm or greater.

In one or more embodiments, light administered to a region with a sufficient intensity to be an effective amount in the present methods does not comprise one or more wavelengths exceeding one or more of the following: about 585 nm, about 605 nm, about 624 nm, about 630 nm, about 635 nm, about 645 nm, about 655 nm, about 660 nm, about 665 nm, about 680 nm, about 684 nm, about 700 nm, about 725 nm, about 755 nm, about 773 nm, about 780 nm, about 795 nm, about 815 nm, about 830 nm, about 846 nm, about 855 nm, about 865 nm, about 875 nm, about 890 nm, about 895 nm, about 905 nm, about 910 nm, about 915 nm, about 920 nm, about 935 nm, about 975 nm, about 1000 nm, about 1050 nm, about 1100 nm, or about 1200 nm. For example, in one or more embodiments, no light having a sufficient intensity to be an effective amount for oral or maxillofacial bone remodeling and exceeding about 585 nm, about 605 nm, about 624 nm, about 630 nm, about 635 nm, about 645 nm, about 655 nm, about 660 nm, about 665 nm, about 680 nm, about 684 nm, about 700 nm, about 725 nm, about 755 nm, about 773 nm, about 780 nm, about 795 nm, about 815 nm, about 830 nm, about 846 nm, about 855 nm, about 865 nm, about 875 nm, about 890 nm, about 895 nm, about 905 nm, about 910 nm, about 915 nm, about 920 nm, about 935 nm, about 975 nm, about 1000 nm, about 1050 nm, about 1100 nm, or about 1200 nm is administered to a selected region. In one or more embodiments, light administered to a region with a sufficient intensity to be an effective amount in the present methods does not comprise one or more wavelengths exceeding one or more of the following: about 400 nm, about 450 nm, about 500 nm, about 550 nm, about 585 nm, about 595 nm, about 605 nm, about 613 nm, about 615 nm, about 620 nm, about 624 nm, about 625 nm, about 640 nm, about 650 nm, about 667 nm, about 680 nm, about 710 nm, about 740 nm, about 750 nm, about 770 nm, about 812 nm, about 815 nm, about 820 nm, about 835 nm, about 845 nm, or about 860 nm. For example, in one or more embodiments, no light having a sufficient intensity to be an effective amount in the present methods and below about 400 nm, about 450 nm, about 500 nm, about 550 nm, about 585 nm, about 595 nm, about 605 nm, about 613 nm, about 615 nm, about 620 nm, about 624 nm, about 625 nm, about 640 nm, about 650 nm, about 667 nm, about 680 nm, about 710 nm, about 740 nm, about 750 nm, about 770 nm, about 812 nm, about 815 nm, about 820 nm, about 835 nm, about 845 nm, or about 860 nm is administered to a selected region.

In one or more embodiments, the light administered does not comprise a wavelength of about 600 nm or less having a sufficient intensity to be an effective amount for the present methods. In one or more embodiments, the light administered does not comprise a wavelength of about 1000 nm or greater having a sufficient intensity to be an effective amount for the present methods. In one or more embodiments, the light administered does not comprise a wavelength of about 600 nm or less having a sufficient intensity to be an effective amount for the present methods and does not comprise a wavelength of about 1000 nm or greater having a sufficient intensity to be an effective amount for the present methods.

In one or more embodiments, particular treatments respond better to specific wavelength ranges. For example, in one or more embodiments, tooth movement (or, more particularly, rapid tooth movement) is more effective when the amount of light administered has a wavelength from about 700 nm to about 900 nm. For example, the effective amount of light can have a wavelength of about 850 nm. In one or more embodiments, the intra-oral apparatus irradiates light having a wavelength of about 850 nm and with an intensity of less than 100 mW/cm$^2$ continuous wave. In one or more embodiments, bone healing or bone grafting is more effective when the amount of light administered has a wavelength from about 600 nm to about 700 nm.

In one or more embodiments, light is administered at a wavelength sufficient to produce a bactericidal and/or bacteriostatic effect on the patient's teeth and/or oral mucosa. In other words, light can be administered at a wavelength sufficient to kill and/or prevent reproduction of bacteria on the patient's teeth and/or oral mucosa. For example, the light can be administered at a blue or similar wavelength, such as a wavelength of from about 450 nm to about 495 nm. In one or more embodiments, the bactericidal- and/or bacteriostatic-effective light can be administered concurrently with administration of light effective to accelerate tooth movement. For example, in one or more embodiments, light can concurrently be administered to the patient at a blue wavelength, for the resulting bactericidal and/or bacteriostatic effect, and at a red to infrared wavelength to accelerate tooth movement (e.g., towards alignment). In one or more embodiments, the bactericidal- and/or bacteriostatic-effective light can be administered prior to administration of light effective to accelerate tooth movement. In one or more embodiments, the bactericidal- and/or bacteriostatic-effective light can be administered subsequent to administration of light effective to accelerate tooth movement.

In one or more embodiments, light is administered at one, two, or more of the light ranges described. In some instances, light is not administered outside of one, two, or more of the light ranges described. In other embodiments, administered light has other wavelengths, as desired for a particular application. In one or more embodiments, light having a first set of characteristics (e.g., wavelength, intensity, pulsing, timing) can be administered to a first region (e.g., the region at the panel I shown in FIG. 23), and light with a second set of characteristics can be administered to a second region (e.g., the region at panel 3 shown in FIG. 23). The first region and the second region can be the same region, can partially overlap, or can not overlap. The first set of characteristics can be the same as the second set of characteristics, can partially overlap with the second set, or can all be different from the second set. In one or more embodiments, one region of a jaw can receive light having a wavelength of a first wavelength range, while another region of the jaw can receive light having a wavelength of a second wavelength range.

The first and second wavelengths can overlap. Alternatively, in other embodiments, the first and second wavelengths do not overlap.

In one or more embodiments, one or more wavelengths of light can be sequentially or simultaneously administered to the patient. For example, an intra-oral apparatus of the invention can comprise a first emitter that emits light having a wavelength of about 850 nm and a second emitter that sequentially or simultaneously emits light having a wavelength of about 620 nm. In one or more embodiments, the first emitter can be configured to emit light during a first period of time and the second emitter can be configured to emit light during a second period of time following the first period of time. Stated another way, the second emitter emits light having a wavelength of about 850 nm after the first emitter begins emitting light having a wavelength of about 620 nm, or the second emitter emits light having a wavelength of about 620 nm after the first emitter begins emitting light having a wavelength of about 850 nm. In one or more embodiments, light having a wavelength of about 850 nm is administered daily to a patient until one or more of the following orthodontic treatment phases are complete or almost complete: the alignment phase, the space-closure phase, the finishing-or-detailing phase or the retention phase. Once one or more of these phases are complete or almost complete, the patient can begin receiving a blended light treatment, which comprises administering light having a wavelength of, e.g., about 850 nm and about 620 nm. The about 850 nm wavelength of light can be administered to the patient sequentially or simultaneously with the about 620 nm wavelength of light. Once the teeth have moved into their final position, the passive stage of orthodontic treatment can begin and the patient can begin receiving light having a wavelength of about 620 nm only.

Although examples of light wavelength ranges are provided below for different applications, light having any other light wavelength value, which can comprise those described herein, can be administered for those applications.

In one or more embodiments, the light can be administered to at least a portion of a patient's alveolar soft tissue or other oral tissue, or to it entirely. Alternatively, using an intra-oral apparatus, light of one or more particular wavelengths can be administered to different selected regions of a patient's alveolar soft tissue in order to effect movement of teeth (e.g. anchor (no movement), bodily, or tipped) in one or more regions of a patient's mouth. For example, one or more regions in which it is desired that the teeth not be moved, or that the teeth serve as an anchor to facilitate movement of teeth in other selected regions of a patient's jaw, can be optionally screened or masked such that they receive no light, as described herein with reference to FIG. 5. Alternatively, the one or more regions in which it is desired that the teeth not be moved, or that the teeth serve as an anchor to facilitate movement of teeth in other selected regions of a patient's jaw, do not receive light as the light emitters over such regions are turned off Regions in which it is desired that the teeth be moved bodily can be administered with light having a wavelength in the range of about 585 nm to about 665 nm, in the range of about 605 nm to about 645 nm, about 615 nm to about 635 nm, or about 625 nm. Regions in which it is desired to increase tooth movement but permit some tipped movement of the teeth can be administered with light having a wavelength in the range of about 815 nm to about 895 nm, about 835 nm to about 875 nm, about 845 nm to about 865 nm, or about 855 nm.

Tooth movement can be selectively regulated by administering an effective amount of light having one wavelength to one or more selected regions of a patient's alveolar soft tissue, and by administering an effective amount of light having a different wavelength to one or more different selected regions of the mucosa.

In one or more embodiments, light can be administered at a wavelength of a narrow range of wavelengths (e.g., 50 nm or less, 30 nm or less, 20 nm or less, 10 nm or less, 5 nm or less), or at a single wavelength. In one or more embodiments, light is administered at a limited wavelength range (e.g., 1000 nm or less, 700 nm or less, 600 nm or less, 500 nm or less, 400 nm or less, 300 nm or less, 250 nm or less, 200 nm or less, 150 nm or less, 100 nm or less, or 75 nm or less). In one or more embodiments, the light administered does not include wavelengths beyond the narrow or limited range of wavelengths. The narrow or limited range of wavelengths can have any of the upper or lower limits of wavelength as described previously. In one or more embodiments, however, the light administered does not include light having a sufficient intensity to constitute an effective amount having wavelengths beyond the narrow or limited range of wavelengths.

In one or more embodiments, light can be emitted at one, two, or more peak wavelengths of emission. A peak wavelength is the wavelength at which the highest intensity of light is emitted. In one or more embodiments, light can be administered at a range of wavelengths that includes a peak wavelength having the highest intensity of the range. In one or more embodiments, a peak wavelength can be at about 620 nm, about 640 nm, about 650 nm, about 655 nm, about 660 nm, about 665 nm, about 670 nm, about 680 nm, about 690 nm, about 800 nm, about 820 nm, about 830 nm, about 835 nm, about 840 nm, about 845 nm, about 850 nm, about 860 nm, about 870 nm, about 890 nm, about 910 or about 930 nm. In one or more embodiments, the administered light does not have wavelengths that vary from the peak wavelength by more than about 1 nm, about 2 nm, about 3 nm, about 5 nm, about 10 nm, about 15 nm, about 20 nm, about 30 nm, about 40 nm, about 50 nm, about 75 nm, about 100 nm, about 150 nm, about 200 nm, about 250 nm, about 300 nm, about 400 nm, or about 500 nm.

Where two or more light wavelengths are administered, the light can be administered at any ratio of each wavelength's intensity. For example, light administered at a first wavelength can have an intensity that is about I.Ix, 1.2x, 1.3x, 1.5x, 1.7x, 2.0x, 2.5x, 3.0x, 3.5x, 4.0x, 5.0x, I Ox, 12x, 15x, 20x, 30x, 50x, lOOx that of light administered at a second wavelength. In one or more embodiments, the administered light is emitted from one or more light emitters, in another embodiment, from one or more light emitters having a first set of properties and, optionally, from a second set of light emitters having a second set of properties. In other embodiments, the number of light emitters having a first set of characteristics exceeds that of the light emitters having a second set of characteristics. For example, the number of light emitters having the first set of characteristics can be about I. Ix, 1.2x, 1.3x, 1.5x, 1.7x, 2.0x, 2.5x, 3.0x, 3.5x, 4.0x, 5.0x, I Ox, 12x, 15x, 20x, 30x, 50x, lOOx the number of light emitters having the second set of characteristics, or vice versa.

The light can optionally be monochrome or substantially monochrome, e.g., having a wavelength from about IO nm less than to about IO nm greater than a specific wavelength. When light is "substantially monochrome" it has a single wavelength, or comprises light of the single and light of one or more other wavelengths that are emitted at an intensity that is ineffective in the present methods, including for regulating oral or maxillofacial bone remodeling when administered to the oral or maxillofacial bone, muscle, or soft tissue, or one or more teeth of a patient, with or without allowing a functional appliance to exert a force on oral or maxillofacial bone, muscle, or soft tissue, or one or more teeth of the patient. In one or more embodiments, substantially monochrome light is emitted at a narrow range of wavelengths without being emitted at other wavelengths outside the range or without an effective intensity of light being emitted at other wavelengths outside the range. In one or more embodiments, substantially monochrome light includes light of wavelengths within about 5 nm, about IO nm, or about 20 nm of a specific wavelength, and either (1) does not include light of other wavelengths outside such a range, or (1) does not include an effective intensity of light of other wavelengths outside the range. By way of example, substantially monochrome 850 nm light can include light of wavelengths ranging from about 830 nm to about 870 nm. Administering light from light emitters that emit at multiple wavelengths can allow for irradiation over multiple wavelengths or greater selectivity and precision in administration. The light can optionally comprise incoherent light. In one or more embodiments, light can be administered at a single frequency, light can have a phase that drifts relatively quickly, a pulse of light waves can have an amplitude that changes quickly, or a light wave can encompass a broad range of frequencies.

Light can be administered directly from a light emitter to a region in the patient's mouth. In one or more embodiments, light can be modified by optics before reaching or traveling through the surface within the patient's mouth (e.g., the alveolar soft tissue).

For example, light can be diffused, focused, parallel, reflected, redirected, or filtered after it is emitted and before it reaches or travels through the surface within the patient's mouth. Such modification can be achieved, for example, by using a foil or other suitable material with the intra-oral apparatus, such as the reflective backing 20 depicted in FIG. 3A. In one or more embodiments, light of one or more wavelengths can be selectively blocked or partially filtered before reaching the surface within the patient's mouth. In one or more embodiments, light can diverge or converge from an emission source before reaching the region. For example, light can diverge in a beam having an included angle 8 in the range of about 45-60°. The emitted light diverge to have an included angle 8 of 0 to about 15°, 0 to about 30°, 0 to about 45°, 0 to about 60°, 0 to about 75°, 0 to about 90°, or 0 to about 120°.

In one or more embodiments, industry standard LEDs are used to produce the light. The LEDs can include one or more emitter arrays arranged on a series of treatment arrays to cover the target area of the alveolus of both the maxilla and mandible.

Light that irradiates the region can optionally have the same or about the same characteristics as light that is emitted. In one or more embodiments, light that reaches the region does not have the same characteristics as the light that is emitted. One or more of the light characteristics can optionally be altered prior to administration or when it passes through the oral tissue of the patient. One or more of the light characteristics can optionally be altered when it passes through optics, such as one or more lenses or mirrors that are coupled to or disposed within the intra-oral apparatus. For example, one or more of the light characteristics can be altered in the range of about ±20% or less, about ±15% or less, about ±10% or less, about ±5% or less, about ±3% or less, about ±1% or less, about ±0.5% or less, or about ±0.1% or less.

The dosage or effective amount of light that irradiates from, for example, the light emitters, can range from about 24 J/cm$^2$ to about 200 J/cm$^2$. The effective dosage of light can be administered once or repetitively. In one or more embodiments, the effective amount can have an irradiated light energy density that is from about 30 J/cm$^2$ to about 100 J/cm$^2$. In other embodiments, the effective amount can be about 5 J/cm$^2$ or less, about 10 J/cm$^2$ or less, about 20 J/cm$^2$ or less, about 30 J/cm$^2$ or less, about 50 J/cm$^2$ or less, about 75 J/cm$^2$ or less, about 100 J/cm$^2$ or less, about 125 J/cm$^2$ or less, about 150 J/cm$^2$ or less, about 175 J/cm$^2$ or less, or about 200 J/cm$^2$ or less. The effective amount of irradiated light can be about 1 J/cm$^2$ or more, about 5 J/cm$^2$ or more, about 10 J/cm$^2$ or more, about 20 J/cm$^2$ or more, about 25 J/cm$^2$ or more, about 30 J/cm$^2$ or more, about 40 J/cm$^2$ or more, about 50 J/cm$^2$ or more, about 60 J/cm$^2$ or more, about 75 J/cm$^2$ or more, about 100 J/cm$^2$ or less, about 125 J/cm$^2$ or more, about 150 J/cm$^2$ or more, or about 175 J/cm$^2$ or more. The effective amount of irradiated light can be in a range bounded by any of the energy density values described herein. The effective amount of irradiated light can be increased, for example, by using a light source that emits light having a relatively higher average intensity, or by increasing the duration of administration of light.

An effective amount of light can have an energy density that reaches a region, such as the mandibular bone or maxillary bone. For example, an effective amount of light that reaches a region can be from about 0.5 J/cm$^2$ to about 100 J/cm$^2$. The effective amount of light that reaches the region can be administered once or repetitively. In some other embodiments, the effective amount has an irradiated light energy density that is from about 1 J/cm$^2$ to about 50 J/cm$^2$. In other embodiments, the effective amount of light is about 0.5 J/cm$^2$ or less, about 1 J/cm$^2$ or less, about 2 J/cm$^2$ or less, about 5 J/cm$^2$ or less, about 10 J/cm$^2$ or less, about 15 J/cm$^2$ or less, about 20 J/cm$^2$ or less, about 30 J/cm$^2$ or less, about 40 J/cm$^2$ or less, about 50 J/cm$^2$ or less, about 70 J/cm$^2$ or less, about 80 J/cm$^2$ or less, about 90 J/cm$^2$ or less, or about 100 J/cm$^2$ or less. The effective amount of light can be about 0.5 J/cm$^2$ or more, about 1 J/cm$^2$ or more, about 2 J/cm$^2$ or more, about 3 J/cm$^2$ or more, about 5 J/cm$^2$ or more, about 10 J/cm$^2$ or more, about 15 J/cm$^2$ or more, about 20 J/cm$^2$ or more, about 30 J/cm$^2$ or more, about 40 J/cm$^2$ or more, about 50 J/cm$^2$ or less, about 60 J/cm$^2$ or more, about 70 J/cm$^2$ or more, or about 80 J/cm$^2$ or more. The effective amount of light that reaches the region can be in a range bounded by any of the energy density values described herein.

The duration over which the effective amount, which is optionally repetitive, is administered via the intra-oral apparatus can range from about 10 to about 40 minutes. In other embodiments, dosage can be administered in a period of time of about 30 seconds or more, about 1 minute or more, about 2 minutes or more, about 3 minutes or more, about 5 minutes or more, about 7 minutes or more, about 10 minutes or more, about 15 minutes or more, about 20 minutes or more, about 25 minutes or more, about 30 minutes or more, about 40 minutes or more, about 50 minutes or more, about 1 hour or more, about 1 hour 15 minutes or more, about 1 hour 30 minutes or more, or about 2 hours or more. The effective amount can be administered in a period of time of about 3 minutes or less, about 5 minutes or less, about 10 minutes or less, about 15 minutes or less, about 20 minutes or less, about 25 minutes or less, about 30 minutes or less, about 35 minutes or less, about 40 minutes or less, about 50 minutes or less, about 1 hour or less, about 1 hour 15 minutes or less, about 1 hour 30 minutes or less, about 2 hours or less, or about 4 hours or less. The effective amount can be administered for a range of time based on any of the time values described herein. In one or more embodiments, one or more light blocking masks or shades can be used with the intra-oral apparatus. An oral mask can block one or more wavelengths of light, or can reduce the intensity of one or more wavelengths of light, from reaching a region covered by the oral mask. This can include an upper arch (e.g., maxillary teeth), or lower arch (e.g., mandibular teeth). In one or more embodiments, the oral mask contacts oral tissue or one or more teeth of a patient.

Any time period can be provided between dosages of light. For example, the time period between dosages can be on the order of seconds, minutes, hours, days, weeks, months, quarter of a year, or years.

The effective amount, which in one or more embodiments is repetitive, can be administered with any desired frequency, e.g., four times daily, three times daily, twice daily, daily, every second day, weekly, biweekly, monthly, or quarterly. In one or more embodiments, dosage can be administered at regular intervals (e.g., daily), while in other embodiments, the dosage is not administered at regular intervals (e.g., administration can occur 2 times a week at any time during the week). In one or more embodiments, light can be administered in the morning and at night. Light can be administered throughout the time period that a patient is undergoing bone remodeling or tooth movement. In one or more embodiments, a patient undergoes orthodontic treatment in addition to undergoing bone remodeling or tooth movement. Orthodontic treatment can occur prior to, subsequent to, or concurrently with oral or maxillofacial bone remodeling. Light can be administered throughout the time period that a patient is undergoing orthodontic treatment, or following treatment to stabilize tooth movement. For example, light can be administered after a functional appliance or an orthodontic appliance is applied, removed, adjusted, after an appointment, or after an active stage, as described herein. It can be desirable to administer light with greater frequency, e.g. four times daily, three times daily, twice daily, daily or every second day, while a patient is undergoing orthodontic treatment. Where light is being administered, for example, to stabilize tooth movement or reduce tooth-root resorption, treatments of reduced frequency, e.g. weekly, biweekly, monthly, or quarterly, can be used to minimize inconvenience to patients. In one or more embodiments, the effective amount of light maintains the ATP energy levels of tissue cells, e.g., ischemic tissue cells, to prevent cell death, as described herein. In one or more embodiments, light is administered no less than about every second day. In one or more embodiments, a patient receives light treatment at least three or four times a week.

Light can be administered for any length of time. In one or more embodiments, light can be administered on the order of seconds, minutes, hours, days, weeks, months, quarters, or years. For example, light can be administered while an orthodontic appliance or a functional appliance exerts a force. One or more dosages of light can be administered over a period of time during which a patient is undergoing oral or maxillofacial bone remodeling during which an orthodontic appliance or a functional appliance exerts a force. In one or more embodiments, one or more dosages of light can be administered over a period of time during which a force is exerted on one or more teeth, during which a patient is wearing an orthodontic appliance that itself can exert a force, such as a heavy force, or during which a patient is undergoing orthodontic treatment during which a force, such as a heavy force may be applied. In one or more embodiments, while a patient is undergoing orthodontic treatment or is wearing a secondary appliance, the patient is administered with light via the intra-oral apparatus. For example, a portion of the intra-oral apparatus (e.g., a mouthpiece) can be configured to be disposed over the orthodontic appliance, such as an orthodontic appliance that can exert a force effective to move one or more teeth, during the light administration. In other embodiments, the intra-oral apparatus exerts a heavy force on one or more teeth such that no secondary appliance is necessary. Administration of light, which can include regular, irregular, continuous or discontinuous administration of light, can be on the order of days, weeks, months, quarters, or years. In one or more embodiments, light is administered over a plurality of days, weeks, months, quarters, or years. In one or more embodiments, light is administered over a plurality of sessions. In one or more embodiments, one or more hours, days, weeks, months, quarters, or years occur between sessions.

If the light emitters are pulsed, then their duty cycle can be adjusted as desired; e.g., light can be administered with a duty cycle of about 10%, about 20%, about 30%, about 40%, about 50%, about 60%, about 70%, about 80%, or about 90%. The pulsing can occur with any frequency. For example, light can be pulsed every picosecond, nanosecond, microsecond, millisecond, second, multiple seconds, or minutes.

Frequencies can include, but are not limited to, about 1 mHz, about 10 mHz, about 50 mHz, about 100 mHz, about 500 mHz, about 1 Hz, about 2 Hz, about 5 Hz, about 10 Hz, about 15 Hz, about 20 Hz, about 25 Hz, about 30 Hz, about 35 Hz, about 40 Hz, about 50 Hz, about 70 Hz, about 100 Hz, about 200 Hz, about 500 Hz, or about 1 kHz. Any of the aforementioned characteristics of light emission (e.g., whether the light is on or off, continuous or pulsed, duty cycle, frequency, intensity, wavelength) can be varied or maintained. Where the light is emitted from a source having a controller, any characteristics of light emission can be varied or maintained in accordance with instructions from its controller.

In one or more embodiments, the emitters of the intra-oral apparatus can be controlled so that the number of lights that are on or off at a given period can be individually controllable. For example, a light source or emitter can be turned on or off relative to other light sources or emitters (such as, e.g., the apparatus depicted in FIG. 40C). Various light sources can be modulated individually (e.g., one or more properties of a particular light source can be varied) or otherwise individually controlled, to expose individual sections of a patient's alveolar soft tissue or other regions to a desired energy density. This can be desirable when it is desirable to administer light to different regions (e.g., via the various panels of the intra-oral apparatus). Thus, the position of light being administered can be varied. In another embodiment, different types of light sources can be turned on or off relative to other light emitters. For example, at some times, light emitted in a first wavelength range can be turned on while light emitted in a second wavelength range can be turned off, vice versa, or both types of light emitters can be turned on or off Thus, the wavelength of light being administered can be varied. In one or more embodiments, the intensity of light being administered can be varied (e.g., by turning some light sources on or off, or varying the intensity emitted by the light sources).

In one or more embodiments, particularly where infrared light is administered to a patient, the present methods further comprise providing emission of a visible light. In one or more embodiments the visible light is bright enough to aid in the apparatus's positioning if performed by a person other than the patient. The visible light can be, but is not necessarily, of a wavelength or wavelength range that is beneficial for light treatment or regulation of tooth movement. In one or more embodiments, the ratio of the intensities of the visible and infrared components of the light is 1 part or less visible light to 5 parts or more infrared light. In other embodiments, the ratio of the intensities of visible and infrared components is about 1 part or more visible light to 5 parts or more infrared light, I part or more visible light to 3 parts infrared light, I part or more visible light to 2 parts infrared light, I part or more visible light to I part infra-red light, 2 parts or more visible light to I part infrared light, 3 parts or more visible light to I part infrared light, 5 parts or more visible light to I part infrared light, IO parts or more visible light to I part infrared light, or no infrared light. In one or more embodiments, light can be emitted at a range can include wavelengths less than an order of magnitude relative to one another. Alternatively, the range can include wavelengths emitted at one, two, three or more orders of magnitude relative to one another.

The region and desired light characteristics can vary from patient to patient. A physician, dentist, other health-care provider or patient can determine a light treatment regimen for a patient wearing an intra-oral apparatus.

In some instances, it can be desirable to administer light to less than all regions of the patient's alveolar soft tissue, for example, if it is desired that teeth in other regions do not need to be moved (e.g. it can be desired to regulate the movement of only the upper teeth of a patient, or only the lower teeth, or to use particular teeth as an anchor when regulating the movement of other teeth by administering no light to, e.g., blocking light from, the anchor teeth). Administering light to selected regions of the patient's alveolar soft tissue can comprise causing light to irradiate one or more selected tooth roots through the tissue or mucosa.

In one or more embodiments, light is selectively administered to less than all regions of the patient's alveolar soft tissue before, during, or after the exertion of heavy forces. In one or more embodiments, light is not administered to an anchor tooth. In this embodiment, a secondary appliance, such as a functional appliance, is located between the anchor region or tooth and one or more selected bone region sought to be remodeled. The secondary appliance can exert a force on the selected bone region, for example, on another tooth. In one or more embodiments, the force is a heavy force. In one or more embodiments, an effective amount of light is administered to the selected bone region or other tooth and not to the anchor region or anchored tooth via the intra-oral apparatus.

The administration of light can increase the rate of the selected bone remodeling region or velocity (or rate of movement) of the other tooth and reduce, minimize, or prevent root resorption of the other tooth, while not increasing the rate of bone remodeling of the non-selected regions or velocity of the anchor tooth.

It can also be desirable to administer light of different wavelengths to different regions of the patient's alveolar soft tissue, if it is desired to differentially manipulate the movement of a patient's teeth, as described herein. For example, light of a first wavelength can be administered to a first region and light of a second wavelength can be administered to a second region. The first and second wavelengths can include any wavelengths described elsewhere herein, such as for example, about 585 nm to about 665 nm, or about 815 nm to about 895 nm.

Light can be administered over an area (also referred to herein as a "light irradiation area"). For example, light can be administered to a region with an area. In one or more embodiments, light characteristics (e.g., light intensity) can remain uniform over the area. In other embodiments, light characteristics can vary over the area. For example, light intensity can be uniform or can vary over an area of a region. The area of light administration can have any shape or size.

Light can be administered to a light irradiation area of any size and shape. For example, a region, such as a specified region of the patient's alveolar soft tissue, can have any size or shape. The light irradiation area can have one or more dimensions (e.g., length, width, diameter) that range from about 1 to about 80 mm or from about 1 to about 70 mm. In one or more embodiments, one or more dimensions (e.g., length, width, diameter) of a light irradiation area can range from about 1 to about 3 mm, about 3 to about 5 mm, about 5 to about 7 mm, about 7 to about 10 mm, about 10 to about 15 mm, about 15 to about 20 mm, about 20 to about 25 mm, about 25 to about 30 mm, about 30 to about 35 mm, about 35 to about 40 mm, about 40 to about 50 mm, about 50 to about 60 mm, or about 60 to about 80 mm.

A light-irradiation area can have any shape, which can include, but is not limited to, a rectangular shape, square shape, triangular shape, hexagonal shape, octagonal shape, trapezoidal shape, circular shape, elliptical shape, crescent shape, cylindrical shape or half-circle. In one or more embodiments, the dimensions of a light emitter can be about the same as dimensions for a light irradiation area. In other embodiments, the dimensions of a light source can be greater than the dimensions of a light irradiation area.

Alternatively, the dimensions of a light source can be less than the dimensions of the light irradiation area. The relative areas of a light source and light irradiation area can depend on any angle, which can be a parallel, convergence, or divergence angle, at which light is emitted.

In one or more embodiments, an effective amount of light can be provided in a treatment regimen using the intra-oral apparatus. The treatment regimen can be used in the present methods.

In one or more embodiments, a typical treatment regimen provides a dose of light daily. Each of the daily doses of light can be administered over a period lasting from a few minutes to about an hour when the patient is using the intra-oral apparatus. For example, daily ½ hour doses of light can be effective and are not unduly inconvenient for patients. A single daily dose can be as effective as dividing the same dose into multiple sessions administered at different times during the day. Some treatment regimens can comprise administering light in 5 treatments per week for 12 weeks. Each treatment can last ½ hour and irradiate the patient's oral tissue with light having wavelengths of 660 nm and 840 nm. The 660 nm light can have an intensity of about 20 mW/cm$^2$ at the skin's surface. The 840 nm light can have an intensity of about 10 mW/cm$^2$ at the skin's surface. These treatment regimens can enhance bone density.

Other treatment regimens can comprise administering light in daily treatments for 21 days. Each treatment lasts from about 20 minutes to about one hour and illuminates the tissues of a patient's mouth with light having a wavelength of 618 nm and an intensity of 20 mW/cm$^2$ at the skin's surface. These treatment regimens can accelerate healing of bone grafts.

Another treatment regimen can include a twice-daily administration of light for six months. Light can be administered, via the intra-oral apparatus, at a wavelength of about 660 nm or about 840 nm, or at both wavelengths. The intensity of the light can be about 20 mW/cm$^2$ at the target surface within the patient's mouth.

The present methods can further comprise controlling temperature of the apparatus of the invention, the patient's mouth, the patient's alveolar soft tissue or of any light source that is directed at or that contacts the patient's mouth or region thereof. As described herein, the intra-oral apparatus can include a temperature sensor (or other like sensor) that monitors the temperature of the patient's mouth, the patient's alveolar soft tissue and/or light emitters. The method can comprise cooling, heating, or maintaining the temperature at a patient's mouth. A patient's mouth, for example, the patient's alveolar soft tissue, can be contacted with a temperature control mechanism, which can cause the removal or provision of heat. In one or more embodiments, such a temperature control mechanism is coupled to or disposed within the intra-oral apparatus. In one or more embodiments, the temperature of the light source can be controlled. The temperature control mechanism can communicate with the light source. Heat can be removed from or provided to the light source. Any embodiments for temperature regulation described herein can be employed in the method. The method can further comprise measuring a temperature of the patient's mouth, measuring a temperature at a particular surface region within the patient's mouth, e.g., the alveolar soft tissue, or measuring a temperature at one or more of the light emitters. Temperature regulation can optionally occur in response to one or more temperature measurements made.

In one or more embodiments, the dosage or effective amount of light has a density that ranges from about 24 $J/cm^2$ to about 200 $J/cm^2$, and has a wavelength in the range of about 585 nm to about 665 nm, or about 815 nm to about 895 nm. Administration of light having a wavelength in the range of about 585 nm to about 665 nm can be useful in the present methods. Administration of light having a wavelength in the range of 815 nm to about 895 nm, can also be useful in the present methods. In some other embodiments, an effective dosage of light can have any of the light characteristics as described anywhere herein. Light is administered directly to a specific region of the patient's mouth, e.g., the patient's alveolar soft tissue, using the intra-oral apparatus, as described herein.

In one or more embodiments, the present methods comprise administering to a patient in need thereof, via an intra-oral apparatus, an effective amount of light having a first wavelength to a selected first region of the patient's mouth (e.g., a first region of the alveolar soft tissue), and further comprise administering, via the intra-oral apparatus, an effective amount of light having a second wavelength to a selected second region of the patient's mouth (e.g., a second region of the alveolar soft tissue). In one or more embodiments the effective amount of light having a first wavelength is a repetitive dosage. In another embodiment the effective amount of light having a second wavelength is a repetitive dosage. Regions other than alveolar soft tissue can receive the first or second wavelength of light. In one or more embodiments, the effective amount of light can be in the range of 24 $J/cm^2$ to 200 $J/cm^2$. The first wavelength can be in the range of about 585 nm to about 665 nm, and the second wavelength can be in the range of about 815 nm to about 895 nm. In other embodiments, an effective amount of light can have any light characteristics as described anywhere herein.

One aspect of the invention provides for a light treatment kit comprising an intra-oral light-therapy apparatus as described herein and instructions for use in the present methods. The kit can further comprise a light source that is separate from the intra-oral light-therapy apparatus. The separate light source and/or the light sources of the intra-oral light-therapy apparatus can be removable and disposable, so that they can be easily replaced after a given amount of use. In one or more embodiments, a light-therapy apparatus and separate light sources can be individually packaged or can be packaged together. The separate light source can operate in combination with the light sources of the intra-oral light-therapy apparatus to aid in light administration. The separate light sources can emit light in any manner described herein and can further have any wavelength of characteristic described herein.

The kit can also comprise a programmable controller as described herein. The kit can further comprise any components useful for the controller to operate. For example, the kit can comprise a component to power the controller or the intra-oral light-therapy apparatus. The kit can also comprise a component that allows the controller to operably connect with an intra-oral light-therapy apparatus.

The kit can also comprise software, an algorithm, or one or more computer readable media that can provide instructions to a controller. The software, algorithm, or set of computer readable media can be provided on a memory medium. The memory medium can be a removable or portable, such as a CD, USB flash drive, or external hard drive The kit can be conveniently packaged and can be commercially available. The kit can also include written instructions for use or maintenance of items therein.

As described herein, a light therapy apparatus according to embodiments of the invention can be electronically linked, or paired, with an external device, such as a mobile phone, including smartphones (e.g., an iPhone® or an Android™ based device), personal digital assistance, computer, tablet, portable electronic device, or the like. In this manner, the apparatus can be configured for at least one of wireless uni-directional or wireless bi-directional communication with the external device, such as via a Bluetooth® or other wireless connection. In one or more embodiments, the apparatus (e.g., apparatus 2500) is configured to transmit data associated with a patient's compliance with a prescribed treatment program, during which the patient is to use the apparatus to administer light therapy to the patient's teeth, to the external device. As such, in one or more embodiments, a light therapy system includes the external device. The external device can be used, for example, by a dental practitioner to receive, store, and analyze the patient compliance data, in addition to other patient information, as described herein.

The external device in one or more embodiments, is used by a patient to track progress through a light therapy regimen.

Referring to FIGS. 115-124, the external device can be configured to execute code to at least one of receive, store, or process the patient compliance data transmitted by the light therapy apparatus. For example, an application including the executable code can be loaded onto the external device. The executable code can be configured to display one or more screens on the external device to enable the dental practitioner to enter information associated with one or more patients and access the patient compliance data.

Figure 115:
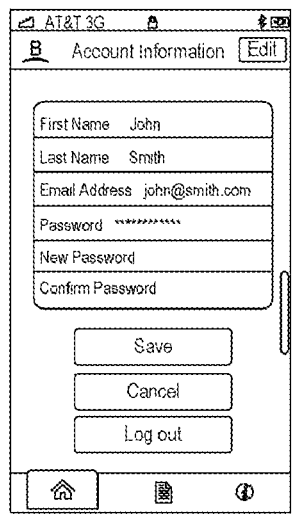
FIGS. 115-125 are images of sample display screens of an external electronic device according to an embodiment.
Figure 116:
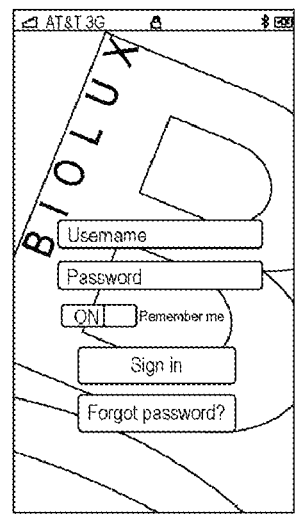

The external device can be configured for the practitioner (or a designated compliance administrator) to create a new account. For example, as shown in FIG. 115, the external device can require entry of the practitioner's name, an email address, and a password (and can include password reset capabilities). As shown in FIG. 116, the external device can be configured to require entry of log-in credentials to access the application, such as via a long-in screen, to maintain security of the patient information.

Figure 117:
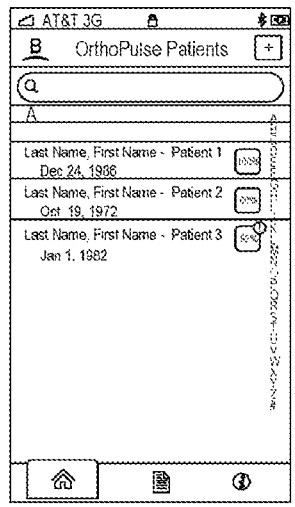

As shown in FIG. 117, the external device can be configured to display a list of patients for whom patient information has been entered onto the external device.

Figure 118:
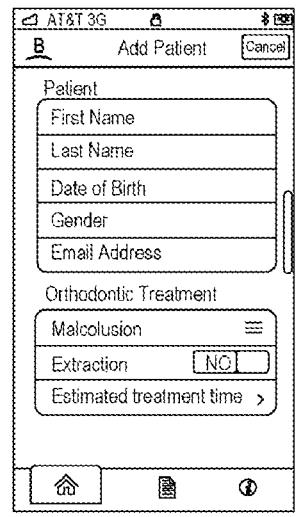
Figure 119:
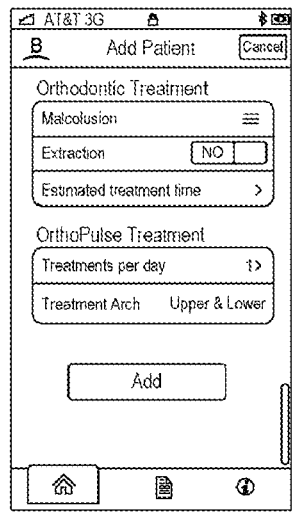
Figure 120:
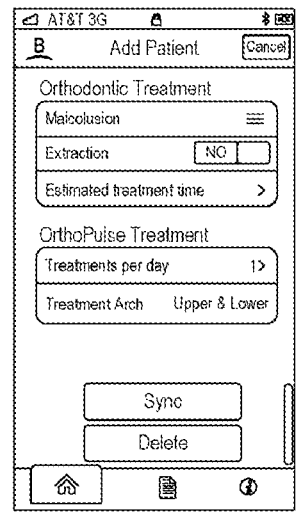

As shown in FIGS. 118-120, the external device can be configured to display a screen via which information associated with a new patient or an existing patient can be added to the external device. For example, external device can be configured to receive patient information such as the patient's name, date of birth, gender, contact information (e.g., an email address). The external device can also be configured to receive information associated with an orthodontic treatment program for the patient. For example, the external device can be configured to receive information about the patient's malocclusion, whether the patient's orthodontic treatment includes tooth extraction, and the patient's estimated treatment time and/or treatment prescription, e.g., number of aligners and the amount of time per aligner. In one or more embodiments, the external device is configured to receive information about the patient's light therapy treatment program, including the number of treatment sessions to be administered per day, and the arch or arches (i.e., upper, lower, or upper and lower arches) to which light therapy is to be administered during the treatment session. In one or more embodiments, the external device is accessed by a clinician to alter a patient's light therapy treatment program. The external device in another embodiment is used to program the light therapy apparatus, for example, the number of light emitters to use for a particular treatment, and/or the number of distinct light emitter zones to use. As described herein, a zone can include one or more light emitters (e.g., one or more LEDs).

Figure 97:
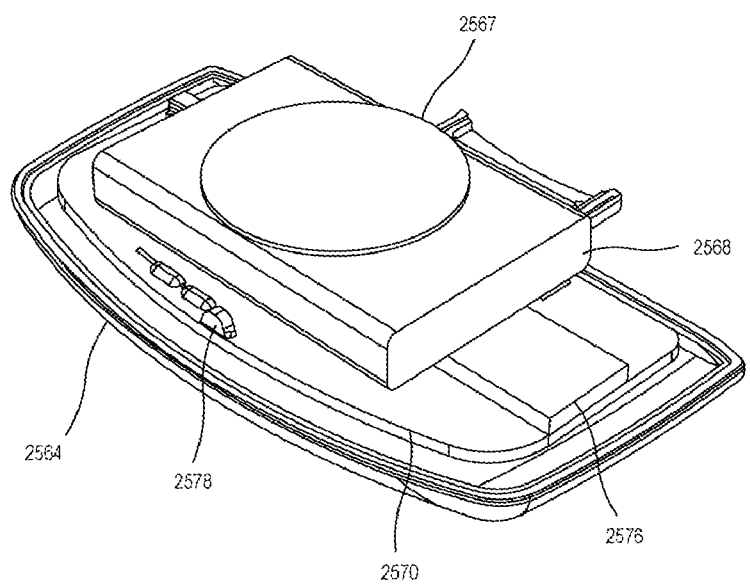
FIG. 97 is a perspective view of a portion of the light therapy apparatus of FIG. 84.
Figure 121:
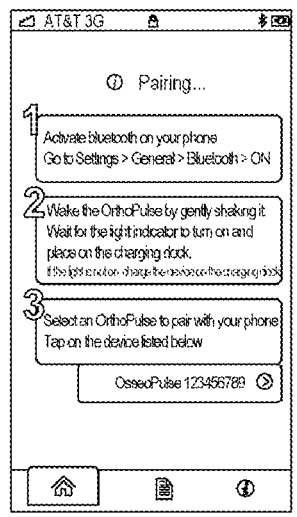
Figure 122:
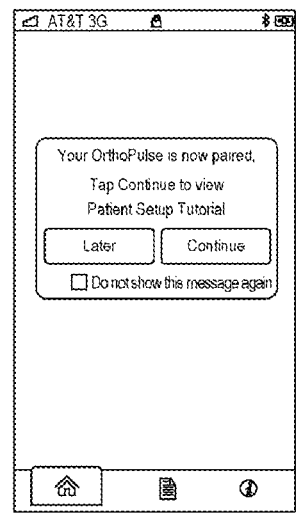

As shown in FIG. 121, the external device is configured to be paired with a light therapy apparatus, e.g., a light therapy apparatus according to an embodiment described herein. In one or more embodiments, the external device is configured to display instructions on a pairing screen for pairing the external device and the light therapy apparatus. The external device can be configured to display a confirmation indicating whether or not the external device and the light therapy apparatus were successfully paired, as shown in FIG. 122. The external device can also be configured to provide a tutorial, for example, to assist the practitioner with entering the patient information as shown in FIGS. 96-98. The external device can be configured to be paired with the light therapy apparatus before or after the patient information is entered into the external device. After the external device and light therapy apparatus are paired, the external device can receive the patient compliance data from the light therapy apparatus.

Figure 123:
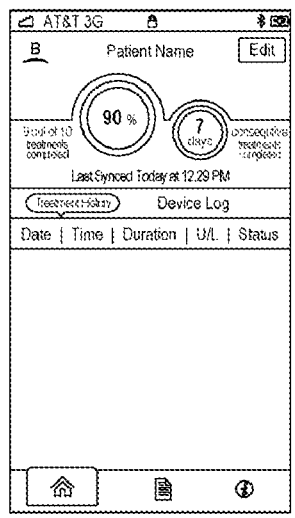
Figure 124:
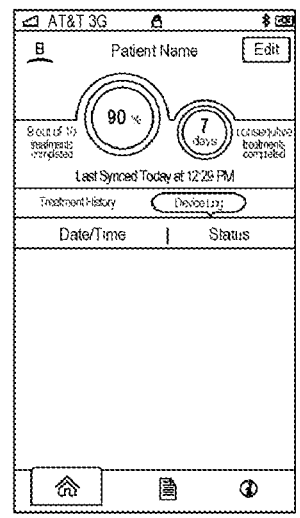

The external device can be configured to display at least a portion of the patient compliance data. For example, as shown in FIGS. 123 and 124, the external device can be configured to display a number of treatments sessions completed by and prescribed for the patient (e.g., "9 out of 10") and/or a percentage of the total number of prescribed treatments sessions completed by the patient (e.g., 90%). The external device can be configured to display a number of consecutive treatment sessions completed by the patient (e.g., "7 days of consecutive treatments completed"). The external device can be configured to display the last incidence (e.g., date and time) patient compliance data was received from the light therapy apparatus. In other words, the external device can display when the patient compliance data stored on the external device was last synced with the patient compliance data stored on the light therapy apparatus. As shown in FIG. 120, the external device can be configured to synchronize patient compliance data with the light therapy apparatus, if, for example, such synchronization was not already initiated by the light therapy apparatus itself The clinician in one or more embodiments reassesses the patient's treatment protocol depending on the compliance data. For example, the clinician determines based on the compliance data whether to advance the patient to another aligner, to turn on different light emitter zones during light therapy, to increase the number of light emitters turned on in a zone during a light therapy session, etc.

Figure 125:
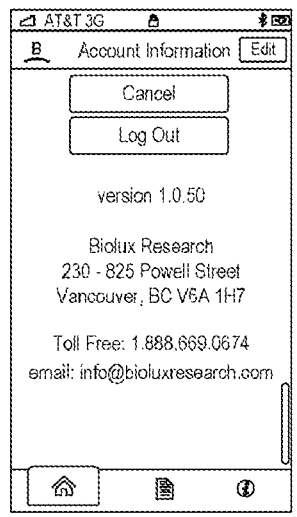

The external device can also be configured to display a log of the patient's usage of the light therapy apparatus, including a listing of one or more of the date a treatment session was administered using the light therapy apparatus, the time of the treatment session, the duration of the treatment session, whether the treatment session was administered with respect to the patient's upper or lower arch, and a status of the treatment session or light therapy apparatus. As shown in FIG. 124, the external device can also be configured to display a log associated with the light therapy apparatus itself, including a status of the apparatus and a date and time of the status. The status log can, for example, list the light therapy apparatus' status history indicating each time the apparatus was in one or more of the apparatus statuses (or states), such as sleep, ready, charge, communication, or error statuses, described herein. Finally, as shown in FIG. 125, the external device can be configured to provide a log out option to exit the application. The external device can also be configured to display contact information, such as for a manufacturer of the light therapy apparatus, as shown in FIG. 125.

One or more embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code disclosed herein.

One or more embodiments and/or methods described herein can be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) can be expressed in a variety of software languages (e.g., computer code), including C, C++, Java®, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

While various embodiments of the invention have been described herein, it should be understood that they have been presented by way of example only, and not limitation.

For example, although apparatus (e.g., apparatus 2100) have been described herein as including a gyroscope, in other embodiments, an apparatus can include any suitable mechanism for detecting tilt and/or spatial orientation of the apparatus such that the mechanism can help determine whether the apparatus is in an upright or inverted position.

In another example, although apparatus (e.g., apparatus 2100) have been illustrated and described herein as including an intra-oral housing configured to be positioned within the patient's mouth for administration of light to one of the upper jaw and the lower jaw at a time, in other embodiments, an apparatus includes an intra-oral housing with upper and lower flanges, each including an LED array coupled to or embedded therein. In this manner, the apparatus is configured to concurrently administer light therapy with respect to each of the upper and lower jaws.

Although the bite pad 2514 is described above as having a thickness that varies from the anterior portion (thinner) to the posterior portion (thicker), in other embodiments, the anterior portion of the bite pads shown and described herein can be thicker than that of the posterior portion. Moreover, in one or more embodiments, a thickness of any of the bite pads shown herein can vary along any direction, for example, from a lingual (or inside portion) to the buccal (or cheek-side) portion.

Although the mouthpiece 2510 is shown as including a notch 2530, a first groove 2532 and a second groove 2534, in other embodiments, any of the mouthpieces shown and described herein can include any suitable geometric features and/or combinations of materials to produce the desired flexibility for placement of the light array. For example, in one or more embodiments, the mouthpiece 2510 and any of the mouthpieces shown and described herein can include a series of notches along the upper portion of the flanges 2522, 2524, a series of circumferential perforations about the buccal portion (i.e., the cheek-side) and/or the lingual (i.e., inside) portion, or the like.

The invention is further described with reference to the following specific examples, which are not meant to limit the invention, but rather to further illustrate it.

EXAMPLE

Example 1: Effects of Light Therapy on Pituitary Adenoma

The effect of light therapy on a human female subject suffering from pituitary macroadenoma was evaluated. The subject had refused a radical surgery treatment option.

The subject used an ORTHOPULSE™ (Biolux Research, Vancouver, Canada) light therapy apparatus to intra-orally self-administer light. The intraorally administered light had a wavelength of 850 nm, a power density of 65 mw/cm² and energy density of 19.5 J/cm². The ORTHOPULSE™ irradiated the subject's maxillary and mandibular alveolar mucosa. Each of the maxillary and mandibular alveolar mucosa was irradiated for about 5 minutes to about 10 minutes per day three times per week for a period of three months. The intra-oral light irradiated mesenchymal stem cells in the subject's alveolar bone marrow.

The subject was also administered extra-oral light therapy for a period of 3 months, three times per week. The extra-oral light therapy was intermittently interspersed with the intra-oral light therapy. Each extra-oral-administration session lasted approximately 15 minutes. The light irradiated from LED (light emitting diode) light sources located on the inner surface of a helmet worn on the subject's head and was extra-orally administered directly to the surface of the subject's forehead. The light had a wavelength of 660-670 nm, power density of about 88 mW/cm² and energy density of 40 J/cm².

The subject was highly responsive to the light therapy. Repeated brain magnetic resonance imaging (MRI) during the course of treatment showed a reduction of the subject's pituitary macroadenoma tumor load from 4.05 cm3 before treatment to 2.16 cm3 following treatment. Biochemical analysis of the subject's blood revealed a reduction of prolactin level from 891.5 mIU/L before treatment to 782.3 mIU/L following treatment.

All publications, patents and patent applications are herein incorporated by reference in their entirety to the same extent as if each individual publication, patent or patent application was specifically and individually indicated to be incorporated by reference in its entirety.

What is claimed is:

1. A method for preferentially activating oral stem cells, comprising:
    positioning an intra-oral device within the oral cavity of a subject; and
    intra-orally administering a first effective amount of light at a first wavelength to a first selected region of the oral cavity of the subject; and
    intra-orally administering a second effective amount of light at a second wavelength to a second selected region of the oral cavity in need thereof such that a directional migration of the oral stem cells into blood vessels is enhanced and the oral cavity is differentially treated, wherein the first wavelength is different from the second wavelength and the first selected region is different from the second selected region of the oral cavity.

2. The method of claim 1, wherein intra-orally administering the first effective amount of light proliferates or differentiates the oral stem cells.

3. The method of claim 1, wherein the oral stem cells are adult stem cells.

4. The method of claim 1, wherein the oral stem cells are mesenchymal stem cells.

5. The method of claim 1 wherein the oral stem cells are dental stem cells or non-dental stem cells.

6. The method of claim 1, wherein the oral stem cells are dental pulp stem cells, stem cells of the apical papilla, periodontal ligament stem cells, dental follicle stem cells, tooth germ progenitor cells, oral epithelial stem cells, gingival-derived mesenchymal stem cells, inflamed periapical progenitor cells, periosteal stem cells, jaw bone marrow stem cells, alveolar bone marrow mesenchymal stem cells or salivary gland stem cells.

7. The method of claim 1, wherein the oral stem cells are inside a mouth of the subject.

8. The method of claim 1, wherein the oral stem cells are in a bone marrow of the subject's maxilla and/or mandible.

9. The method of claim 1, wherein the oral stem cells are not cancer stem cells.

10. The method of claim 1, wherein the administering the first effective amount of light comprises irradiating the light directly to the subject's alveolar mucosa, buccal mucosa, labial mucosa, masticatory mucosa, tooth, gum or tongue.

11. The method of claim 1, wherein the first effective amount of light has a wavelength ranging from about 600 nm to about 1,200 nm.

12. The method of claim 1, wherein the first effective amount of light has a power density ranging from about 20 mW/cm$^2$ to about 200 mW/cm$^2$.

13. The method of claim 1, wherein the first effective amount of light has an energy density ranging from about 5 J/cm$^2$ to about 50 J/cm$^2$.

14. The method of claim 1, further comprising extra-orally administering the first effective amount of light.

15. The method of claim 14, wherein the extra-orally administering is by an extra-oral device.

16. The method of claim 1, wherein the first effective amount of light is a first light and wherein the second effective amount of light is a second light administered to the subject's skin.

17. The method of claim 16, wherein the skin is the skin of the subject's scalp, face or neck.

18. The method of claim 16, wherein the second light is administered extra-orally to the subject's skin.

19. The method of claim 18, wherein the second light is administered extra-orally by an extra-oral device.

* * * * *